United States Patent
Nirogi et al.

(10) Patent No.: US 11,040,026 B2
(45) Date of Patent: Jun. 22, 2021

(54) MUSCARINIC M1 RECEPTOR POSITIVE ALLOSTERIC MODULATORS

(71) Applicant: SUVEN LIFE SCIENCES LIMITED, Telangana (IN)

(72) Inventors: Ramakrishna Nirogi, Telangana (IN); Anil Karbhari Shinde, Telangana (IN); Abdul Rasheed Mohammed, Telangana (IN); Rajesh Kumar Badange, Telangana (IN); Pradeep Jayarajan, Telangana (IN); Gopinadh Bhyrapuneni, Telangana (IN); Venkateswarlu Jasti, Telangana (IN)

(73) Assignee: Suven Life Sciences Limited, Hyperabad (IN)

( * ) Notice: Subject to any disclaimer, the term of this patent is extended or adjusted under 35 U.S.C. 154(b) by 172 days.

(21) Appl. No.: 16/327,742

(22) PCT Filed: Aug. 31, 2017

(86) PCT No.: PCT/IB2017/055238
§ 371 (c)(1),
(2) Date: Feb. 22, 2019

(87) PCT Pub. No.: WO2018/042362
PCT Pub. Date: Mar. 8, 2018

(65) Prior Publication Data
US 2019/0343812 A1 Nov. 14, 2019

(30) Foreign Application Priority Data

Sep. 2, 2016 (IN) ............................ 201641030062
Apr. 13, 2017 (IN) ............................ 201741013343

(51) Int. Cl.
| | | |
|---|---|---|
| A61K 31/437 | (2006.01) |
| A61P 25/28 | (2006.01) |
| A61K 31/13 | (2006.01) |
| A61K 31/325 | (2006.01) |
| A61K 31/436 | (2006.01) |
| A61K 31/4375 | (2006.01) |
| A61K 31/445 | (2006.01) |
| A61K 31/473 | (2006.01) |
| A61K 31/5383 | (2006.01) |
| A61K 31/55 | (2006.01) |
| C07D 471/04 | (2006.01) |
| C07D 491/056 | (2006.01) |
| C07D 498/04 | (2006.01) |

(52) U.S. Cl.
CPC ............ *A61K 31/437* (2013.01); *A61K 31/13* (2013.01); *A61K 31/325* (2013.01); *A61K 31/436* (2013.01); *A61K 31/4375* (2013.01); *A61K 31/445* (2013.01); *A61K 31/473* (2013.01); *A61K 31/5383* (2013.01); *A61K 31/55* (2013.01); *A61P 25/28* (2018.01); *C07D 471/04* (2013.01); *C07D 491/056* (2013.01); *C07D 498/04* (2013.01)

(58) Field of Classification Search
None
See application file for complete search history.

(56) References Cited

U.S. PATENT DOCUMENTS 8,940,765 B2 * 1/2015 Kuduk ................. C07D 401/06
514/314

FOREIGN PATENT DOCUMENTS

| WO | 2011084368 | 7/2011 |
| WO | 2011149801 | 12/2011 |
| WO | 2011159554 | 12/2011 |
| WO | 2013055577 | 4/2013 |
| WO | 2015110370 | 7/2015 |
| WO | 2016029454 | 3/2016 |
| WO | 2017143041 | 8/2017 |

OTHER PUBLICATIONS

Langmead et al., "Muscarinic acetylcholine receptors as CNS drug targets" Pharmacol and Therap. 117:232-243 (2008).
Levey, "Immunological Localization of m1-m5 Muscarinic Acetylcholine Receptors in Peripheral Tissues and Brain" Life Sci 52:441-448 (1993).
Levey, "Muscarinic acetylcholine receptor expression in memory circuits: Implications for treatment of Alzheimer's disease" PNAS 93:13541-13546 (1996).
Shirey et al., "A Selective Allosteric Potentiator of the M1 Muscarinic Acetylcholine Receptor Increases Activity of Medial Prefrontal Cortical Neurons and Restores Impairments in Reversal Learning" J. Neurosci 29(45):14271-14286.
Uslaner et al., "The muscaranic M1 receptor positive allosteric modulator PQCA improves cognitive measures in rats, cynomolgus macaque, and rhesus macaque." Psychopharmacol. 225:21-30 (2013).
Wess, "Molecular Biology of Muscarinic Acetylcholine Receptors" Crit. Rev. Neurobiol. 10(1):69-99 (1996).
European Patent Office, "International Search Report" dated Mar. 20, 2018 in PCT Appln. No. PCT/IB2017/055238.
European Patent Office, "Revised International Search Report" dated May 3, 2018 in PCT Appln. No. PCT/IB2017/055238.
European Patent Office, "Written Opinion" dated Mar. 20, 2018 in PCT Appln. No. PCT/IB2017/055238.
European Patent Office, "International Preliminary Report on Patentability" dated Aug. 21, 2018 in PCT Appln. No. PCT/IB2017/055238, with Response to Written Opinion dated Mar. 31, 2018 and claim amendments submitted in PCT Appln. No. PCT/IB2017/055238.

* cited by examiner

*Primary Examiner* — Zinna Northington Davis
(74) *Attorney, Agent, or Firm* — IpHorgan Ltd.

(57) ABSTRACT

The present invention relates to compounds of formula (I), or their isotopic forms, stereoisomers, tautomers or pharmaceutically acceptable salt(s) thereof as muscarinic M1 receptor positive allosteric modulators (M1 PAMs). The present invention describes the preparation, pharmaceutical composition and the use of compound formula (I).

16 Claims, 1 Drawing Sheet

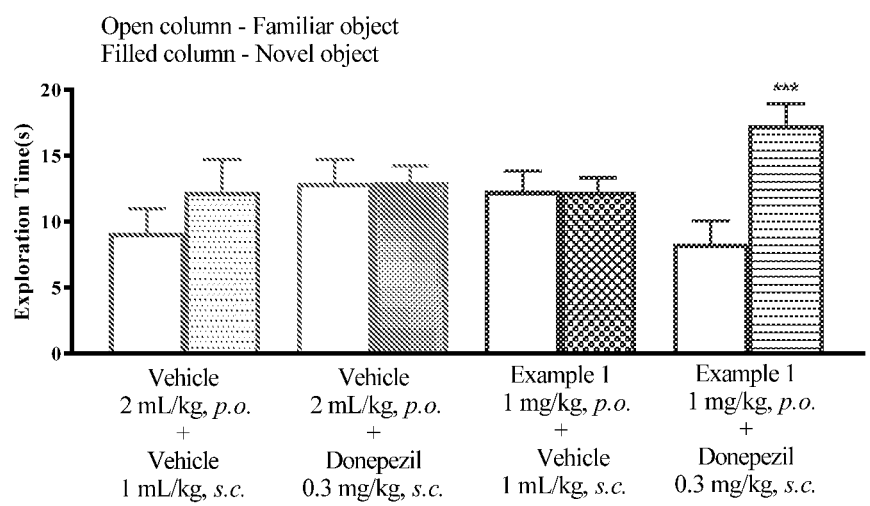
Data represents mean ± SEM of exploration time (***P<0.001 vs familiar object, Students paired 't' test) n=7-11

MUSCARINIC M1 RECEPTOR POSITIVE ALLOSTERIC MODULATORS

CROSS REFERENCE TO RELATED APPLICATIONS

This application is a national stage completion application of PCT Application No. PCT/IB2017/055238, filed Aug. 31, 2017, and claims priority from India Application No. 201641030062, filed Sep. 2, 2016, and India Application No. 201741013343, filed Apr. 13, 2017. Each of these applications is incorporated by reference herein in its entirety.

FIELD OF INVENTION

The present invention relates to compounds of formula (I), or their isotopic forms, stereoisomers, tautomers or pharmaceutically acceptable salt (s) thereof as muscarinic M1 receptor positive allosteric modulators (M1 PAMs). The present invention describes the preparation, pharmaceutical composition and the use of such compounds.

BACKGROUND OF THE INVENTION

Muscarinic acetylcholine receptors (mAChRs) which belong to the class A family of G protein-coupled receptors (GPCRs), are widely expressed throughout the body. Five subtypes termed M1 through M5 that respond to the endogenous neurotransmitter acetylcholine (ACh) has been identified till date. They play key role in regulating the activity of many important functions of the central and peripheral nervous system including cognitive function. M1, M3 and M5 couple to Gq, whereas M2 and M4 couple via Gi/o to downstream signaling pathways and associated effector systems (*Critical Reviews in Neurobiology*, 1996, 10, 69-99; *Pharmacology & Therapeutics*, 2008, 117, 232-243). M2 and M3 are highly expressed in the periphery and are known to be involved in gastrointestinal (GI) motility and parasympathetic responses such as salivation (*Life Sciences*, 1993, 52, 441-448). The muscarinic M1 receptor is predominantly expressed in the brain regions such as cortex, hippocampus and amygdala which are involved in cognition, and therefore selective activation of the muscarinic M1 receptor would be expected to boost cognitive performance (*Proc. Natl. Acad. Sci. USA* 1996, 93, 13541-13546).

There is a high degree of conservation between muscarinic receptor subtypes at their orthosteric acetylcholine ligand binding sites which makes it difficult to identify a selective muscarinic M1 receptor agonist. To circumvent this issue, an alternative approach was adopted which consists of developing M1 PAMs that act at the less conserved allosteric binding site which exhibits less sequence homology. The M1 PAM, PQCA, (1-{[4-cyano-4-(pyridine-2-yl) piperidin-1-yl] methyl}-4-oxo-4H-quinolizine-3-carboxylic acid) is reported to be highly selective for muscarinic M1 receptor over the other muscarinic receptor subtypes and efficacious in several preclinical models of cognition (*Psychopharmacology*, 2013, 225(1), 21-30) with no gastrointestinal side effects at doses equal to or less than a fivefold margin from the minimum effective dose required to improve cognition. In preclinical studies, it was demonstrated that M1 activation increases neurotransmitter acetylcholine concentration in brain. Moreover, the M1 activation has potential as disease-modifying therapy for Alzheimer's disease (AD) by both shifting the β-amyloid precursor protein (βAPP) processing towards the non-amyloidogenic α-secretase pathway and by decreasing the tau hyper-phosphorylation. M1 PAMs have demonstrated to increase the generation of sAPPα in in-vitro system (*The Journal of Neuroscience*, 2009, 29, 14271-14286). Therefore, M1 PAMs provide an approach to target both symptomatic and disease-modifying treatment of cognitive disorders.

PCT patent application publications, WO2015110370, WO2011084368, WO2011159554 and WO2011149801 have disclosed M1 PAM compounds. While several M1 PAMs have been disclosed in the literature till date, no drug acting as M1 PAM is launched in the market. Therefore, there remains an unmet need for developing novel and more effective M1 PAMs that modulate muscarinic M1 receptors to treat M1 mediated diseases such as Alzheimer's disease and others as described herein.

SUMMARY OF THE INVENTION

In first aspect, the present invention relates to M1 PAMs of compound of formula (I),

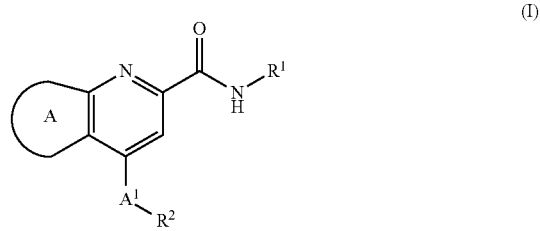

wherein:
ring A is 5- to 8-membered saturated, partially saturated or unsaturated monocyclic or bridged bicyclic ring system containing one or two heteroatom selected from nitrogen, oxygen and sulphur; wherein the ring is optionally substituted with —$(C_{1-4})$-alkyl, —$(C_{3-6})$-cycloalkyl, —$(C_{1-4})$-alkyl-$(C_{3-6})$-cycloalkyl or halo$(C_{1-4})$-alkyl;
$A^1$ is $CH_2$, CHF or $CF_2$;
$R^1$ is —$(C_{1-6})$-alkyl, —$(C_{5-7})$-cycloalkyl, —$(C_{5-7})$-heterocycloalkyl, or —$(C_{6-10})$-aryl; each of which is optionally substituted with one or more groups selected from halogen, hydroxy, $NH_2$, $CH_2OH$ and $(C_{1-4})$-alkyl;
$R^2$ is —$(C_{6-10})$-aryl or —$(C_{5-10})$-heteroaryl; each of which is optionally substituted with one or more substituents selected from halogen, —OH, —O—$(C_{1-4})$-alkyl, —S—$(C_{1-4})$-alkyl, —N($CH_3$)$_2$, —$(C_{1-4})$-alkyl, —$(C_{3-6})$-cycloalkyl, halo $(C_{1-4})$-alkyl, —$NH_2$, —CN and $R^{2a}$;
$R^{2a}$ is —$(C_{6-10})$-aryl or $(C_{5-10})$-heteroaryl; each of which is optionally substituted with one or more substituents selected from the group consisting of halogen, —OH, —$NH_2$, —CN, —O—$(C_{1-2})$-alkyl, —S—$(C_{1-2})$-alkyl, —$(C_{1-2})$-alkyl and $(C_{3-6})$-cycloalkyl;
or an isotopic form, a stereoisomer, a tautomer or a pharmaceutically acceptable salt thereof.

In another aspect, the present invention relates to M1 PAMs of compound of formula (I),

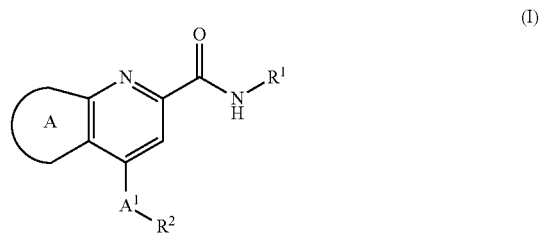

wherein:
ring A is selected from,

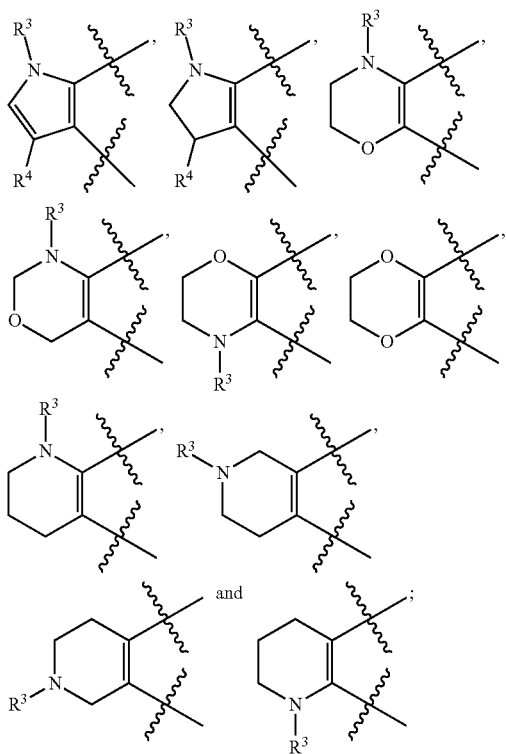

$A^1$ is $CH_2$, CHF or $CF_2$;
$R^1$ is —$(C_{1-6})$-alkyl, —$(C_{5-7})$-cycloalkyl, —$(C_{5-7})$-heterocycloalkyl, or —$(C_{6-10})$-aryl; each of which is optionally substituted with one or more groups selected from halogen, hydroxy, $NH_2$, $CH_2OH$ and $(C_{1-4})$-alkyl;
$R^2$ is —$(C_{6-10})$-aryl or —$(C_{5-10})$-heteroaryl; each of which is optionally substituted with one or more substituents selected from halogen, —OH, —O—$(C_{1-4})$-alkyl, —S—$(C_{1-4})$-alkyl, —$N(CH_3)_2$, —$(C_{1-4})$-alkyl, —$(C_{3-6})$-cycloalkyl, halo $(C_{1-4})$-alkyl, —$NH_2$, —CN and $R^{2a}$;
$R^{2a}$ is —$(C_{6-10})$-aryl or —$(C_{5-10})$-heteroaryl; each of which is optionally substituted with one or more substituents selected from the group consisting of halogen, —OH, —$NH_2$, —CN, —O—$(C_{1-2})$-alkyl, —S—$(C_{1-2})$-alkyl, —$(C_{1-2})$-alkyl and $(C_{3-6})$-cycloalkyl;
or an isotopic form, a stereoisomer, a tautomer or a pharmaceutically acceptable salt thereof.

In another aspect, the present invention relates to the processes for preparing the compound of formula (I), or a stereoisomer or a pharmaceutically acceptable salt thereof.

In yet another aspect, the present invention relates to pharmaceutical composition containing a therapeutically effective amount of at least one compound of formula (I), or a stereoisomer or a pharmaceutically acceptable salt thereof and pharmaceutically acceptable excipients or carriers.

In yet another aspect, the present invention relates to a combination of compound of formula (I), with other therapeutic agents selected from acetylcholinesterase inhibitors and NMDA receptor antagonist.

In yet another aspect, the present invention relates to compound of formula (I), or a stereoisomer or a pharmaceutically acceptable salt thereof, for use as muscarinic M1 receptor positive allosteric modulators.

In yet another aspect, the present invention relates to compound of formula (I), or a stereoisomer or a pharmaceutically acceptable salt thereof, for use in the treatment of disease or disorders selected from cognitive, pain or sleep disorders.

In yet another aspect, the present invention relates to compound of formula (I), or a stereoisomer or a pharmaceutically acceptable salt thereof, for use in the treatment of disease or disorders selected from Alzheimer's disease, schizophrenia or insomnia.

In another aspect, the present invention relates to a method for the treatment of disease or disorders related to muscarinic M1 receptor, comprising administering to a patient in need thereof, a therapeutically effective amount of a compound of formula (I), or a stereoisomer or a pharmaceutically acceptable salt thereof.

In yet another aspect, the present invention relates to use of the compound of formula (I), or a stereoisomer or a pharmaceutically acceptable salt thereof, for the manufacture of a medicament for the treatment of disease or disorders related to muscarinic M1 receptors.

In yet another aspect, the present invention relates to compound of formula (I) or a stereoisomer or a pharmaceutically acceptable salt thereof, for use in positive allosteric modulation of muscarinic M1 receptor.

BRIEF DESCRIPTION OF THE DRAWINGS

FIG. 1 depicts the results of the effect of a co-treatment of example 1 with donepezil on cognition enhancing properties using object recognition task model.

DETAILED DESCRIPTION OF THE INVENTION

Unless otherwise stated, the following terms used in the specification and claims have the meanings given below:

The term, "$(C_{1-4})$-alkyl" as used herein refers to branched or straight chain aliphatic hydrocarbon containing 1 to 4 carbon atoms. Examples of $(C_{1-4})$-alkyl include methyl, ethyl, n-propyl, isopropyl, n-butyl, isobutyl, sec-butyl and tert-butyl. Preferably $(C_{1-4})$-alkyl is methyl, ethyl or isopropyl.

The term, "$(C_{1-2})$-alkyl" as used herein refers to straight chain aliphatic hydrocarbon containing 1 to 2 carbon atoms. Examples of $(C_{1-2})$-alkyl include methyl or ethyl.

The term, "halogen" or "halo" as used herein refers to fluorine, chlorine, bromine or iodine. Preferably, halogen is fluorine, chlorine or bromine. More preferably halogen is fluorine or chlorine.

The term "halo$(C_{1-4})$-alkyl" as used herein refers to $(C_{1-4})$-alkyl as defined above wherein one or more hydrogen of the same or different carbon atom is substituted with same or different halogens. Examples of halo$(C_{1-4})$-alkyl include fluoromethyl, chloromethyl, fluoroethyl, difluoromethyl, dichloromethyl, trifluoromethyl, difluoroethyl and the like.

The term, "$(C_{3-6})$-cycloalkyl" as used herein refers to saturated monocyclic hydrocarbon ring containing from three to six carbon atoms. Examples of $(C_{3-6})$-cycloalkyl group include cyclopropyl, cyclobutyl, cyclopentyl and cyclohexyl.

The term, "$(C_{5-7})$-cycloalkyl" as used herein refers to saturated monocyclic hydrocarbon ring containing from five to seven carbon atoms. Examples of $(C_{5-7})$-cycloalkyl group include cyclopentyl, cyclohexyl, cycloheptyl and the like.

The term, "($C_{6-10}$)-aryl" used herein refers to aromatic hydrocarbon rings containing six to ten carbon atoms. Examples of ($C_{6-10}$)-aryl group include phenyl or naphthyl.

The term "($C_{5-7}$)-heterocycloalkyl" used herein refers to saturated hydrocarbon rings containing one or two heteroatoms selected from oxygen, nitrogen and sulphur. Examples of ($C_{5-7}$)-heterocycloalkyl group include tetrahydropyran, tetrahydrothiopyran, piperidine, azepane, morpholine, thiomorpholine, tetrahydrofuran, pyrrolidine or tetrahydrothiophene.

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include $^2$H (deuterium) and $^3$H (tritium).

The term, "stereoisomers" as used herein refers to isomers of compound of formula (I) that differ in the arrangement of their atoms in space. Compounds disclosed herein may exist as single stereoisomer, racemates and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The term, "cognitive disorder" as used herein refers to a group of mental health disorders that principally affect learning, memory, perception, and problem solving, and include amnesia, dementia, and delirium. Cognitive disorders can result due to disease, disorder, ailment or toxicity. Preferably the cognitive disorder is dementia. Example of dementia includes but not limited to, dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, senile dementia and dementia in general medical conditions.

EMBODIMENTS

The present invention encompasses all the compounds described by the compound of formula (I) without any limitation, however, preferred aspects and elements of the invention are discussed herein in the form of the following embodiments.

In second aspect, the present invention relates to M1 PAMs of compound of formula (I),

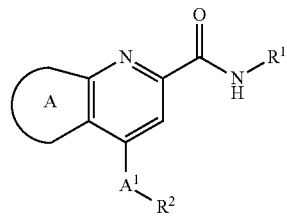

wherein:

ring A is selected from,

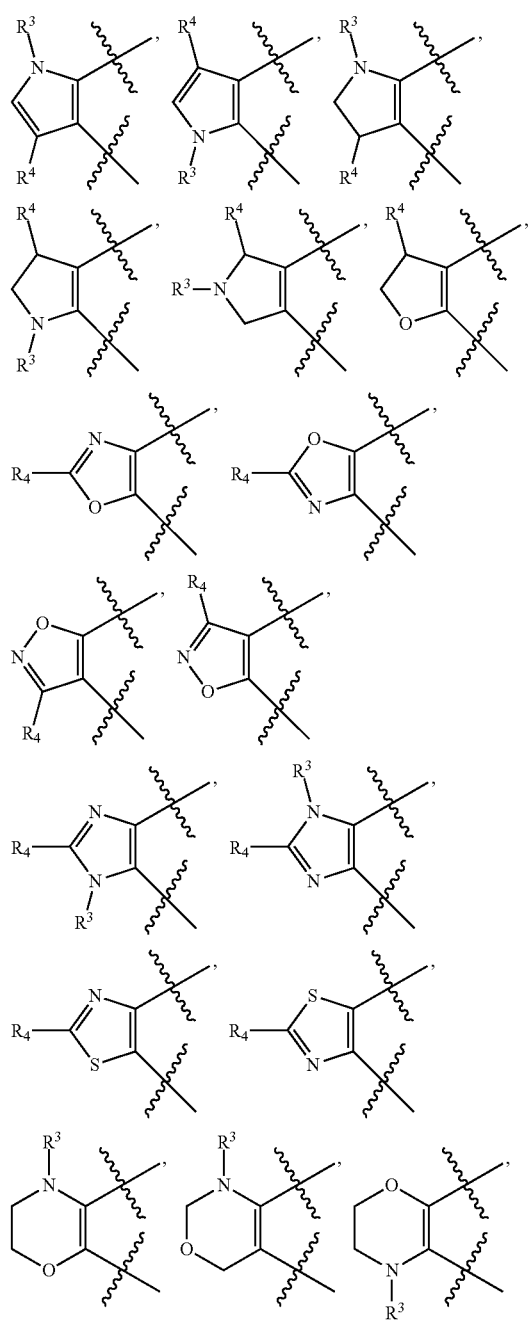

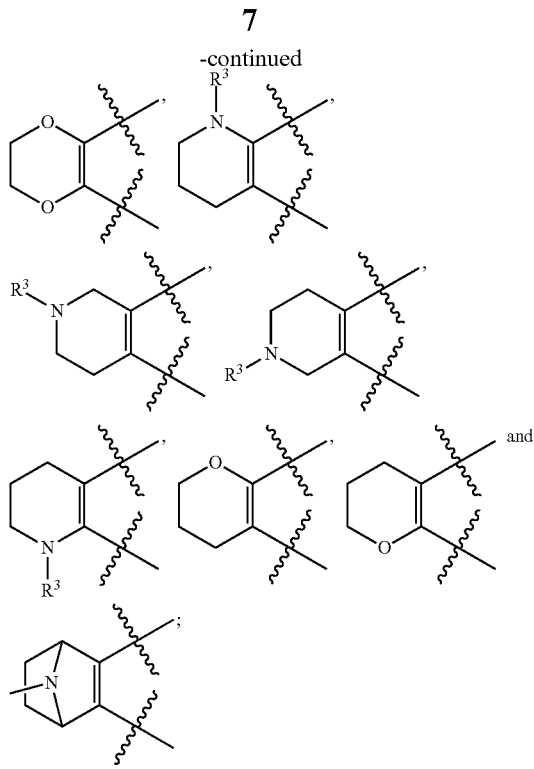

$A^1$ is $CH_2$, CHF or $CF_2$;
$R^1$ is selected from the group consisting of:

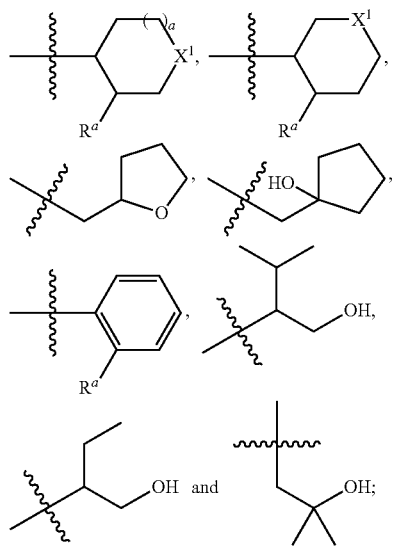

$R^a$ is independently selected from OH, F and $CH_2OH$;
$X^1$ is independently selected from $CH_2$, O and NH;
a is 0 or 1;
$R^2$ is selected from the group consisting of:

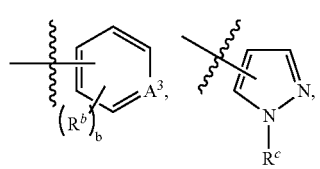

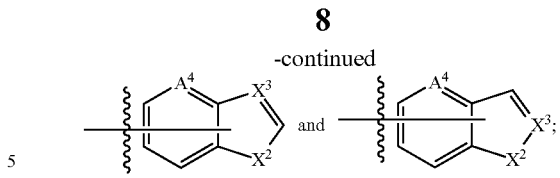

$A^3$ is N or CH;
$A^4$ is CH or CF;
$R^b$ at each occurrence is independently selected from halogen, —O—$(C_{1-4})$-alkyl, —S—$(C_{1-4})$-alkyl, —N$(CH_3)_2$, —$(C_{1-4})$-alkyl, —$(C_{3-6})$-cycloalkyl, halo$(C_{1-4})$-alkyl, —OH, —$NH_2$, —CN, phenyl, pyridyl, pyrazolyl, thiazolyl and oxazolyl; wherein phenyl, pyridyl, pyrazolyl, thiazolyl and oxazolyl are optionally substituted with one or more substituents selected from the group consisting of halogen, —OH, —$NH_2$, —CN, —O—$(C_{1-2})$-alkyl, —S—$(C_{1-2})$-alkyl, —$(C_{1-2})$-alkyl and —$(C_{3-6})$-cycloalkyl;
$R^c$ is hydrogen or —$(C_{1-4})$-alkyl;
$X^2$ is independently selected from NH, —N—$(C_{1-2})$-alkyl, O and S;
$X^3$ is independently selected from CH and N;
b is 0, 1 or 2;
~~~ represents point of attachment;
$R^3$ is —$(C_{1-4})$-alkyl, —$(C_{3-6})$-cycloalkyl, —$(C_{1-4})$-alkyl-$(C_{3-6})$-cycloalkyl, halo$(C_{1-4})$-alkyl or hydrogen; and
$R^4$ is hydrogen, —$(C_{1-4})$-alkyl or halo$(C_{1-4})$-alkyl;
or an isotopic form, a stereoisomer, a tautomer or a pharmaceutically acceptable salt thereof.

In another aspect, the present invention relates to M1 PAMs of compound of formula (I),

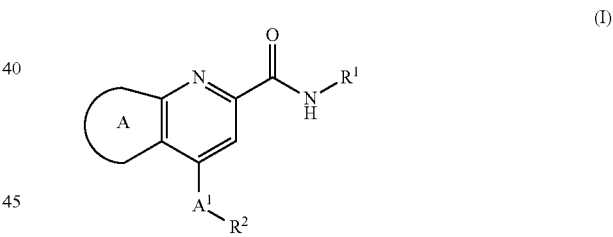

wherein:
ring A is selected from,

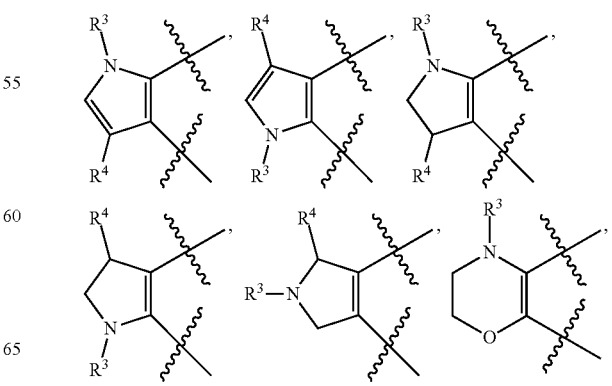

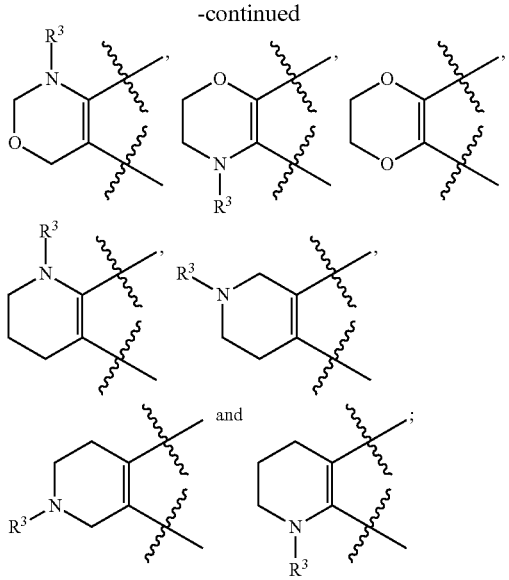

$A^1$ is $CH_2$;
$R^1$ is selected from the group consisting of:
$R^a$ is

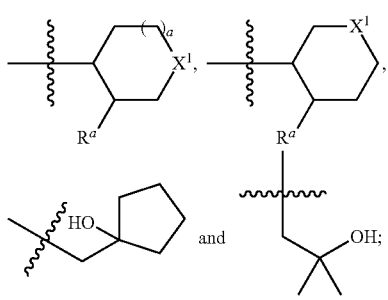

$X^1$ is independently selected from $CH_2$ and O;
a is 0 or 1;
$R^2$ is selected from the group consisting of:

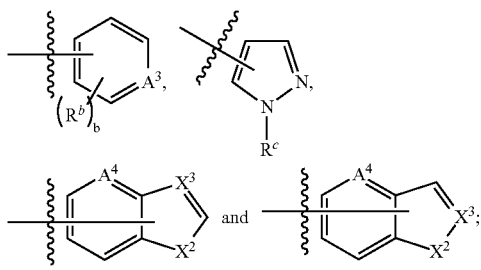

$A^3$ is N or CH;
$A^4$ is CH or CF;
$R^b$ at each occurrence is independently selected from halogen, —O—$(C_{1-4})$-alkyl, —S—$(C_{1-4})$-alkyl, —N$(CH_3)_2$, —$(C_{1-4})$-alkyl, —$(C_{3-6})$-cycloalkyl, halo$(C_{1-4})$-alkyl, —OH, —NH$_2$, —CN, phenyl, pyridyl, pyrazolyl, thiazolyl and oxazolyl; wherein phenyl, pyridyl, pyrazolyl, thiazolyl and oxazolyl are optionally substituted with one or more substituents selected from the group consisting of halogen, —OH, —NH$_2$, —CN, —O—$(C_{1-2})$-alkyl, —S—$(C_{1-2})$-alkyl, —$(C_{1-2})$-alkyl and —$(C_{3-6})$-cycloalkyl;
$R^c$ is hydrogen or —$(C_{1-4})$-alkyl;
$X^2$ is independently selected from NH, —N—$(C_{1-2})$-alkyl, O and S;
$X^3$ is independently selected from CH and N;
b is 0, 1 or 2;
"〜〜〜" represents point of attachment;
$R^3$ is —$(C_{1-4})$-alkyl, halo$(C_{1-4})$-alkyl or hydrogen; and
$R^4$ is hydrogen, —$(C_{1-4})$-alkyl or halo$(C_{1-4})$-alkyl;
or an isotopic form, a stereoisomer, a tautomer or a pharmaceutically acceptable salt thereof.

In one embodiment, the present invention relates to the compound of formula (I), wherein: ring A is selected from,

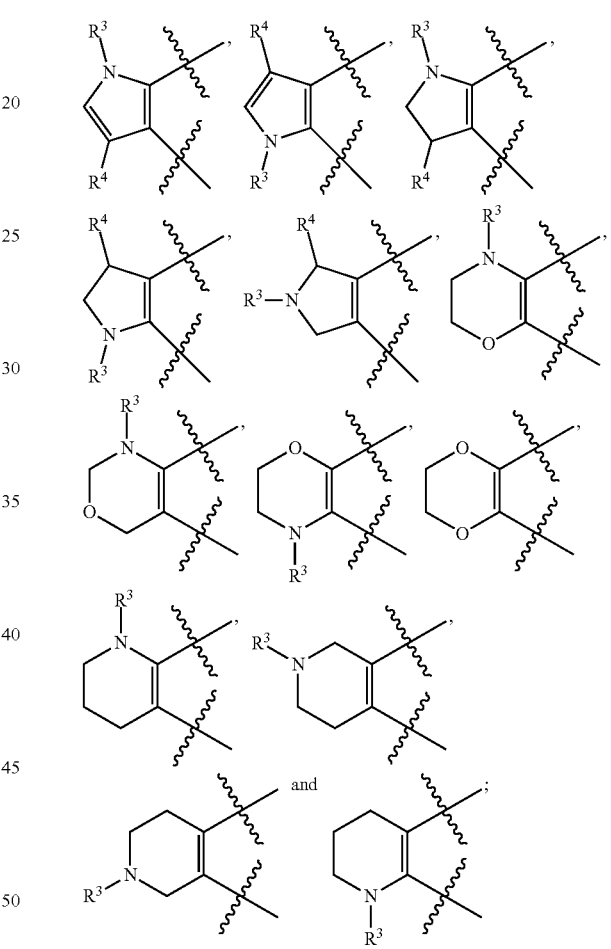

wherein $R^3$ and $R^4$ are as defined in the first aspect; or an isotopic form, a stereoisomer or a pharmaceutically acceptable salt thereof.

In one embodiment, the present invention relates to the compound of formula (I), wherein:
$R^1$ is

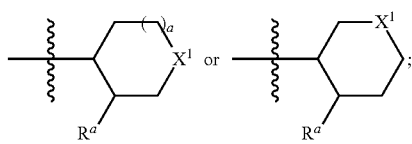

wherein $X^1$, $R^a$ and a are as defined in the first aspect; or an isotopic form, a stereoisomer or a pharmaceutically acceptable salt thereof.

In another embodiment, the present invention relates to the compound of formula (I), wherein:

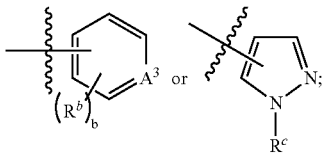

wherein $A^3$, $R^b$, $R^c$ and b are as defined in the first aspect; or an isotopic form, a stereoisomer or a pharmaceutically acceptable salt thereof.

In another embodiment, the present invention relates to the compound of formula (I), wherein:
$R^2$ is

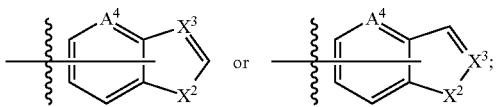

wherein $X^2$, $X^3$ and $A^4$ are as defined in the first aspect; or an isotopic form, a stereoisomer or a pharmaceutically acceptable salt thereof.

In another embodiment, the present invention relates to the compound of formula (I), wherein:
$R^2$ is

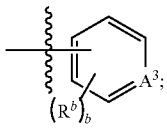

wherein $A^3$, $R^b$ and b are as defined in the first aspect; or an isotopic form, a stereoisomer or a pharmaceutically acceptable salt thereof.

In another embodiment, the present invention relates to the compound of formula (I), wherein: $A^1$ is $CH_2$; or an isotopic form, a stereoisomer or a pharmaceutically acceptable salt thereof.

In another embodiment, the preferred compound of the invention is selected from the group consisting of:

N-[(1S,2S)-2-Hydroxycyclohexyl]-4-(2-fluoropyridin-4-ylmethyl)-1-methyl-1H-pyrrolo[2,3-b]pyridine-6-carboxamide;

N-[(1S,2S)-2-Hydroxycyclohexyl]-4-(2-methoxypyridin-5-ylmethyl)-1-methyl-1H-pyrrolo[2,3-b]pyridine-6-carboxamide;

N-[(1S,2S)-2-Hydroxycyclohexyl]-4-(2-fluoropyridin-5-ylmethyl)-1-methyl-1H-pyrrolo[2,3-b]pyridine-6-carboxamide;

N-[(1S,2S)-2-Hydroxycyclohexyl]-4-(4-fluorobenzyl)-1-methyl-1H-pyrrolo[2,3-b]pyridine-6-carboxamide;

N-[(1S,2S)-2-Hydroxycyclohexyl]-4-(4-thiazol-4-ylbenzyl)-1-methyl-1H-pyrrolo[2,3-b]pyridine-6-carboxamide;

N-[(1S,2S)-2-Hydroxycyclohexyl]-4-(4-pyrazol-1-ylbenzyl)-1-methyl-1H-pyrrolo[2,3-b]pyridine-6-carboxamide;

N-[(1S,2S)-2-Hydroxycyclohexyl]-4-[4-(1-methyl-1H-pyrazol-4-yl)benzyl]-1-methyl-1H-pyrrolo[2,3-b]pyridine-6-carboxamide;

N-[(1S,2S)-2-Hydroxycyclohexyl]-4-[2-fluoro-4-(1-methyl-1H-pyrazol-4-yl)benzyl]-1-methyl-1H-pyrrolo[2,3-b]pyridine-6-carboxamide;

N-[(1S,2S)-2-Hydroxycyclohexyl]-4-(2-methylpyridin-5-ylmethyl)-1-methyl-1H-pyrrolo[2,3-b]pyridine-6-carboxamide;

N-[(1S,2S)-2-Hydroxycyclohexyl]-4-(2-chloropyridin-4-ylmethyl)-1-methyl-1H-pyrrolo[2,3-b]pyridine-6-carboxamide;

N-[(1S,2S)-2-Hydroxycyclohexyl]-4-(2,5-difluoropyridin-4-ylmethyl)-1-methyl-1H-pyrrolo[2,3-b]pyridine-6-carboxamide;

N-[(1S,2S)-2-Hydroxycyclohexyl]-4-(benzothiazol-6-ylmethyl)-1-methyl-1H-pyrrolo[2,3-b]pyridine-6-carboxamide;

N-[(1S,2S)-2-Hydroxycyclohexyl]-4-(2'-fluoro-[2,5]bipyridinyl-5-ylmethyl)-1-methyl-1H-pyrrolo[2,3-b]pyridine-6-carboxamide;

N-[(1S,2S)-2-Hydroxycyclohexyl]-4-(pyridin-4-ylmethyl)-1-methyl-1H-pyrrolo[2,3-b]pyridine-6-carboxamide;

N-[(1S,2S)-2-Hydroxycyclohexyl]-4-[2-(1-methyl-1H-pyrazol-4-yl)pyridin-5-ylmethyl]-1-methyl-1H-pyrrolo[2,3-b]pyridine-6-carboxamide;

N-[(1S,2S)-2-Hydroxycyclohexyl]-4-(2,3-difluorobenzyl)-1-methyl-1H-pyrrolo[2,3-b]pyridine-6-carboxamide;

N-[(1S,2S)-2-Hydroxycyclohexyl]-4-(2-methylpyridin-4-ylmethyl)-1-methyl-1H-pyrrolo[2,3-b]pyridine-6-carboxamide;

N-[(1S,2S)-2-Hydroxycyclohexyl]-4-(2-chloropyridin-5-ylmethyl)-1-methyl-1H-pyrrolo[2,3-b]pyridine-6-carboxamide;

N-[(1S,2S)-2-Hydroxycyclohexyl]-4-(4-methoxybenzyl)-1-methyl-1H-pyrrolo[2,3-b]pyridine-6-carboxamide;

N-[(1S,2S)-2-Hydroxycyclohexyl]-4-(2-methylsulfanylpyridin-5-ylmethyl)-1-methyl-1H-pyrrolo[2,3-b]pyridine-6-carboxamide;

N-[(1S,2S)-2-Hydroxycyclohexyl]-4-[4-(2-methylpyridin-3-yl)benzyl]-1-methyl-1H-pyrrolo[2,3-b]pyridine-6-carboxamide;

N-[(1S,2S)-2-Hydroxycyclohexyl]-4-(1-methyl-1H-benzimidazol-4-ylmethyl)-1-methyl-1H-pyrrolo[2,3-b]pyridine-6-carboxamide;

N-[(1S,2S)-2-Hydroxycyclohexyl]-4-(2-chloropyridin-5-ylmethyl)-1-(2-fluoroethyl)-1H-pyrrolo[2,3-b]pyridine-6-carboxamide;

N-(2-Hydroxy-2-methylpropyl)-4-[4-(thiazol-4-yl)benzyl]-1-methyl-1H-pyrrol[2,3-b]pyridine-6-carboxamide;

N-[(1S,2S)-2-Hydroxycyclohexyl]-4-(3-fluorobenzyl)-1-methyl-1H-pyrrolo[2,3-b]pyridine-6-carboxamide;

N-(1-Hydroxycyclopentylmethyl)-4-[4-(thiazol-4-yl)benzyl]-1-methyl-1H-pyrrolo[2,3-b]pyridine-6-carboxamide;

N-[(1S,2S)-2-Hydroxycyclohexyl]-4-(pyridin-3-ylmethyl)-1-methyl-1H-pyrrolo[2,3-b]pyridine-6-carboxamide;

N-[(1S,2S)-2-Hydroxycyclohexyl]-4-(2-cyclopropylpyridin-5-ylmethyl)-1-methyl-1H-pyrrolo[2,3-b]pyridine-6-carboxamide;

N-[(1S,2S)-2-Hydroxycyclohexyl]-4-(2-fluoropyridin-4-ylmethyl)-1-ethyl-1H-pyrrolo[2,3-b]pyridine-6-carboxamide;

N-[(1S,2S)-2-Hydroxycyclohexyl]-4-(2-fluoropyridin-4-ylmethyl)-1-isopropyl-1H-pyrrolo[2,3-b]pyridine-6-carboxamide;

N-[(1S,2S)-2-Hydroxycyclohexyl]-4-(2,3-difluorophenylmethyl)-1,3-dimethyl-1H-pyrrolo[2,3-b]pyridine-6-carboxamide;

Racemic trans-N-(3-Hydroxytetrahydropyran-4-yl)-4-(4-fluorobenzyl)-1-methyl-1H-pyrrolo[2,3-b]pyridine-6-carboxamide;

trans-N-(3-Hydroxytetrahydropyran-4-yl)-4-(4-fluorobenzyl)-1-methyl-1H-pyrrolo[2,3-b]pyridine-6-carboxamide (Isomer-I);

trans-N-(3-Hydroxytetrahydropyran-4-yl)-4-(4-fluorobenzyl)-1-methyl-1H-pyrrolo[2,3-b]pyridine-6-carboxamide (Isomer-II);

Racemic cis-N-(3-Hydroxytetrahydropyran-4-yl)-4-(4-fluorobenzyl)-1-methyl-1H-pyrrolo[2,3-b]pyridine-6-carboxamide;

cis-N-(3-Hydroxytetrahydropyran-4-yl)-4-(4-fluorobenzyl)-1-methyl-1H-pyrrolo[2,3-b]pyridine-6-carboxamide (Isomer-I);

cis-N-(3-Hydroxytetrahydropyran-4-yl)-4-(4-fluorobenzyl)-1-methyl-1H-pyrrolo[2,3-b]pyridine-6-carboxamide (Isomer-II);

Racemic trans-N-(3-Hydroxytetrahydropyran-4-yl)-4-(2-fluoropyridin-4-ylmethyl)-1-methyl-1H-pyrrolo[2,3-b]pyridine-6-carboxamide;

trans-N-(3-Hydroxytetrahydropyran-4-yl)-4-(2-fluoropyridin-4-ylmethyl)-1-methyl-1H-pyrrolo[2,3-b]pyridine-6-carboxamide (Isomer-I);

trans-N-(3-Hydroxytetrahydropyran-4-yl)-4-(2-fluoropyridin-4-ylmethyl)-1-methyl-1H-pyrrolo[2,3-b]pyridine-6-carboxamide (Isomer-II);

Racemic cis-N-(3-Hydroxytetrahydropyran-4-yl)-4-(3,4-difluorobenzyl)-1-methyl-1H-pyrrolo[2,3-b]pyridine-6-carboxamide;

cis-N-(3-Hydroxytetrahydropyran-4-yl)-4-(3,4-difluorobenzyl)-1-methyl-1H-pyrrolo[2,3-b]pyridine-6-carboxamide (Isomer-I);

cis-N-(3-Hydroxytetrahydropyran-4-yl)-4-(3,4-difluorobenzyl)-1-methyl-1H-pyrrolo[2,3-b]pyridine-6-carboxamide (Isomer-II);

Racemic trans-N-(3-Hydroxytetrahydropyran-4-yl)-4-(2,3-difluorobenzyl)-1-methyl-1H-pyrrolo[2,3-b]pyridine-6-carboxamide;

trans-N-(3-Hydroxytetrahydropyran-4-yl)-4-(2,3-difluorobenzyl)-1-methyl-1H-pyrrolo[2,3-b]pyridine-6-carboxamide (Isomer-I);

trans-N-(3-Hydroxytetrahydropyran-4-yl)-4-(2,3-difluorobenzyl)-1-methyl-1H-pyrrolo[2,3-b]pyridine-6-carboxamide (Isomer-II);

Racemic cis-N-(3-Hydroxytetrahydropyran-4-yl)-4-(2,3-difluorobenzyl)-1-methyl-1H-pyrrolo[2,3-b]pyridine-6-carboxamide;

cis-N-(3-Hydroxytetrahydropyran-4-yl)-4-(2,3-difluorobenzyl)-1-methyl-1H-pyrrolo[2,3-b]pyridine-6-carboxamide (Isomer-I);

cis-N-(3-Hydroxytetrahydropyran-4-yl)-4-(2,3-difluorobenzyl)-1-methyl-1H-pyrrolo[2,3-b]pyridine-6-carboxamide (Isomer-II);

Racemic cis-N-(3-Hydroxytetrahydropyran-4-yl)-4-(2-fluoropyridin-4-ylmethyl)-1-methyl-1H-pyrrolo[2,3-b]pyridine-6-carboxamide;

cis-N-(3-Hydroxytetrahydropyran-4-yl)-4-(2-fluoropyridin-4-ylmethyl)-1-methyl-1H-pyrrolo[2,3-b]pyridine-6-carboxamide (Isomer-I);

cis-N-(3-Hydroxytetrahydropyran-4-yl)-4-(2-fluoropyridin-4-ylmethyl)-1-methyl-1H-pyrrolo[2,3-b]pyridine-6-carboxamide (Isomer-II);

Racemic cis-N-(3-Hydroxytetrahydropyran-4-yl)-4-(2-chloropyridin-5-ylmethyl)-1-methyl-1H-pyrrolo[2,3-b]pyridine-6-carboxamide;

cis-N-(3-Hydroxytetrahydropyran-4-yl)-4-(2-chloropyridin-5-ylmethyl)-1-methyl-1H-pyrrolo[2,3-b]pyridine-6-carboxamide (Isomer-I);

cis-N-(3-Hydroxytetrahydropyran-4-yl)-4-(2-chloropyridin-5-ylmethyl)-1-methyl-1H-pyrrolo[2,3-b]pyridine-6-carboxamide (Isomer-II);

Racemic trans-N-(3-Hydroxytetrahydropyran-4-yl)-4-(2-chloropyridin-5-ylmethyl)-1-methyl-1H-pyrrolo[2,3-b]pyridine-6-carboxamide;

trans-N-(3-Hydroxytetrahydropyran-4-yl)-4-(2-chloropyridin-5-ylmethyl)-1-methyl-1H-pyrrolo[2,3-b]pyridine-6-carboxamide (Isomer-I);

trans-N-(3-Hydroxytetrahydropyran-4-yl)-4-(2-chloropyridin-5-ylmethyl)-1-methyl-1H-pyrrolo[2,3-b]pyridine-6-carboxamide (Isomer-II);

Racemic trans-N-(3-Hydroxytetrahydropyran-4-yl)-4-(3,4-difluorobenzyl)-1-methyl-1H-pyrrolo[2,3-b]pyridine-6-carboxamide;

trans-N-(3-Hydroxytetrahydropyran-4-yl)-4-(3,4-difluorobenzyl)-1-methyl-1H-pyrrolo[2,3-b]pyridine-6-carboxamide (Isomer-I);

trans-N-(3-Hydroxytetrahydropyran-4-yl)-4-(3,4-difluorobenzyl)-1-methyl-1H-pyrrolo[2,3-b]pyridine-6-carboxamide (Isomer-II);

Racemic trans-N-(3-Hydroxytetrahydropyran-4-yl)-4-[4-(thiazol-4-yl)benzyl]-1-methyl-1H-pyrrolo[2,3-b]pyridine-6-carboxamide;

trans-N-(3-Hydroxytetrahydropyran-4-yl)-4-[4-(thiazol-4-yl)benzyl]-1-methyl-1H-pyrrolo[2,3-b]pyridine-6-carboxamide (Isomer-I);

trans-N-(3-Hydroxytetrahydropyran-4-yl)-4-[4-(thiazol-4-yl)benzyl]-1-methyl-1H-pyrrolo[2,3-b]pyridine-6-carboxamide (Isomer-II);

Racemic cis-N-(3-Hydroxytetrahydropyran-4-yl)-4-[4-(thiazol-4-yl)benzyl]-1-methyl-1H-pyrrolo[2,3-b]pyridine-6-carboxamide;

cis-N-(3-Hydroxytetrahydropyran-4-yl)-4-[4-(thiazol-4-yl)benzyl]-1-methyl-1H-pyrrolo[2,3-b]pyridine-6-carboxamide (Isomer-I);

cis-N-(3-Hydroxytetrahydropyran-4-yl)-4-[4-(thiazol-4-yl)benzyl]-1-methyl-1H-pyrrolo[2,3-b]pyridine-6-carboxamide (Isomer-II);

Racemic trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide;

trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-I);

trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-II);

Racemic cis-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide;

cis-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-I);

cis-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-II);

Racemic trans-N-(3-Hydroxytetrahydropyran-4-yl)-4-(4-methoxybenzyl)-1-methyl-1H-pyrrolo[2,3-b]pyridine-6-carboxamide;

trans-N-(3-Hydroxytetrahydropyran-4-yl)-4-(4-methoxybenzyl)-1-methyl-1H-pyrrolo[2,3-b]pyridine-6-carboxamide (Isomer-I);

trans-N-(3-Hydroxytetrahydropyran-4-yl)-4-(4-methoxybenzyl)-1-methyl-1H-pyrrolo[2,3-b]pyridine-6-carboxamide (Isomer-II);

Racemic cis-N-(3-Hydroxytetrahydropyran-4-yl)-4-(4-methoxybenzyl)-1-methyl-1H-pyrrolo[2,3-b]pyridine-6-carboxamide;

cis-N-(3-Hydroxytetrahydropyran-4-yl)-4-(4-methoxybenzyl)-1-methyl-1H-pyrrolo[2,3-b]pyridine-6-carboxamide (Isomer-I);

cis-N-(3-Hydroxytetrahydropyran-4-yl)-4-(4-methoxybenzyl)-1-methyl-1H-pyrrolo[2,3-b]pyridine-6-carboxamide (Isomer-II);

Racemic trans-N-(3-Hydroxytetrahydropyran-4-yl)-4-(3-fluorobenzyl)-1-methyl-1H-pyrrolo[2,3-b]pyridine-6-carboxamide;

trans-N-(3-Hydroxytetrahydropyran-4-yl)-4-(3-fluorobenzyl)-1-methyl-1H-pyrrolo[2,3-b]pyridine-6-carboxamide (Isomer-I);

trans-N-(3-Hydroxytetrahydropyran-4-yl)-4-(3-fluorobenzyl)-1-methyl-1H-pyrrolo[2,3-b]pyridine-6-carboxamide (Isomer-II);

Racemic cis-N-(3-Hydroxytetrahydropyran-4-yl)-4-(3-fluorobenzyl)-1-methyl-1H-pyrrolo[2,3-b]pyridine-6-carboxamide;

cis-N-(3-Hydroxytetrahydropyran-4-yl)-4-(3-fluorobenzyl)-1-methyl-1H-pyrrolo[2,3-b]pyridine-6-carboxamide (Isomer-I);

cis-N-(3-Hydroxytetrahydropyran-4-yl)-4-(3-fluorobenzyl)-1-methyl-1H-pyrrolo[2,3-b]pyridine-6-carboxamide (Isomer-II);

Racemic cis-N-(4-Hydroxytetrahydropyran-3-yl)-4-(4-fluorobenzyl)-1-methyl-1H-pyrrolo[2,3-b]pyridine-6-carboxamide;

cis-N-(4-Hydroxytetrahydropyran-3-yl)-4-(4-fluorobenzyl)-1-methyl-H-pyrrolo[2,3-b]pyridine-6-carboxamide (Isomer-I);

cis-N-(4-Hydroxytetrahydropyran-3-yl)-4-(4-fluorobenzyl)-1-methyl-H-pyrrolo[2,3-b]pyridine-6-carboxamide (Isomer-II);

Racemic trans-N-(4-Hydroxytetrahydropyran-3-yl)-4-(4-fluorobenzyl)-1-methyl-1H-pyrrolo[2,3-b]pyridine-6-carboxamide;

trans-N-(4-Hydroxytetrahydropyran-3-yl)-4-(4-fluorobenzyl)-1-methyl-1H-pyrrolo[2,3-b]pyridine-6-carboxamide (Isomer-I);

trans-N-(4-Hydroxytetrahydropyran-3-yl)-4-(4-fluorobenzyl)-1-methyl-1H-pyrrolo[2,3-b]pyridine-6-carboxamide (Isomer-II);

Racemic cis-N-(4-Hydroxytetrahydropyran-3-yl)-4-(4-methoxybenzyl)-1-methyl-1H-pyrrolo[2,3-b]pyridine-6-carboxamide;

cis-N-(4-Hydroxytetrahydropyran-3-yl)-4-(4-methoxybenzyl)-1-methyl-1H-pyrrolo[2,3-b]pyridine-6-carboxamide (Isomer-I);

cis-N-(4-Hydroxytetrahydropyran-3-yl)-4-(4-methoxybenzyl)-1-methyl-1H-pyrrolo[2,3-b]pyridine-6-carboxamide (Isomer-II);

Racemic trans-N-(4-Hydroxytetrahydropyran-3-yl)-4-(4-methoxybenzyl)-1-methyl-1H-pyrrolo[2,3-b]pyridine-6-carboxamide;

trans-N-(4-Hydroxytetrahydropyran-3-yl)-4-(4-methoxybenzyl)-1-methyl-1H-pyrrolo[2,3-b]pyridine-6-carboxamide (Isomer-I);

trans-N-(4-Hydroxytetrahydropyran-3-yl)-4-(4-methoxybenzyl)-1-methyl-1H-pyrrolo[2,3-b]pyridine-6-carboxamide (Isomer-II);

Racemic cis-N-(4-Hydroxytetrahydropyran-3-yl)-4-(2-methylpyridin-5-ylmethyl)-1-methyl-1H-pyrrolo[2,3-b]pyridine-6-carboxamide;

cis-N-(4-Hydroxytetrahydropyran-3-yl)-4-(2-methylpyridin-5-ylmethyl)-1-methyl-1H-pyrrolo[2,3-b]pyridine-6-carboxamide (Isomer-I);

cis-N-(4-Hydroxytetrahydropyran-3-yl)-4-(2-methylpyridin-5-ylmethyl)-1-methyl-1H-pyrrolo[2,3-b]pyridine-6-carboxamide (Isomer-II);

Racemic trans-N-(4-Hydroxytetrahydropyran-3-yl)-4-(2-methylpyridin-5-ylmethyl)-1-methyl-1H-pyrrolo[2,3-b]pyridine-6-carboxamide trans-N-(4-Hydroxytetrahydropyran-3-yl)-4-(2-methylpyridin-5-ylmethyl)-1-methyl-1H-pyrrolo[2,3-b]pyridine-6-carboxamide (Isomer-I);

trans-N-(4-Hydroxytetrahydropyran-3-yl)-4-(2-methylpyridin-5-ylmethyl)-1-methyl-1H-pyrrolo[2,3-b]pyridine-6-carboxamide (Isomer-II);

(3S,4S)—N-(4-Hydroxytetrahydropyran-3-yl)-4-(4-fluorobenzyl)-1-methyl-1H-pyrrolo[2,3-b]pyridine-6-carboxamide;

(3S,4S)—N-(4-Hydroxytetrahydropyran-3-yl)-4-(4-methoxybenzyl)-1-methyl-1H-pyrrolo[2,3-b]pyridine-6-carboxamide;

(3S,4S)—N-(4-Hydroxytetrahydropyran-3-yl)-4-(2-methylpyridin-5-ylmethyl)-1-methyl-1H-pyrrolo[2,3-b]pyridine-6-carboxamide;

N-[(1S,2S)-2-Hydroxycyclohexyl]-4-(2-chloropyridin-5-ylmethyl)-1-methyl-2,3-dihydro-1H-pyrrolo[2,3-b]pyridine-6-carboxamide;

N-[(1S,2S)-2-Hydroxycyclohexyl]-4-(2-fluoropyridin-4-ylmethyl)-1-methyl-2,3-dihydro-1H-pyrrolo[2,3-b]pyridine-6-carboxamide;

N-[(1S,2S)-2-Hydroxycyclohexyl]-4-(2-fluoropyridin-5-ylmethyl)-1-methyl-2,3-dihydro-1H-pyrrolo[2,3-b]pyridine-6-carboxamide;

N-[(1S,2S)-2-Hydroxycyclohexyl]-1-methyl-(6-methylpyridin-3-ylmethyl)-2,3-dihydro-1H-pyrrolo[2,3-b]pyridine-6-carboxamide;

N-[(1S,2S)-2-Hydroxycyclohexyl]-4-(4-fluorobenzyl)-1-methyl-2,3-dihydro-1H-pyrrolo[2,3-b]pyridine-6-carboxamide;

N-[(1S,2S)-2-Hydroxycyclohexyl]-4-(4-methoxybenzyl)-1-methyl-2,3-dihydro-1H-pyrrolo[2,3-b]pyridine-6-carboxamide;

N-[(1S,2S)-2-Hydroxycyclohexyl]-4-(2'-fluoro-[2,5]bipyridinyl-5-ylmethyl)-1-methyl-2,3-dihydro-1H-pyrrolo[2,3-b]pyridine-6-carboxamide;

N-[(1S,2S)-2-Hydroxycyclohexyl]-4-(2,3-difluorobenzyl)-1-methyl-2,3-dihydro-1H-pyrrolo[2,3-b]pyridine-6-carboxamide;

N-[(1S,2S)-2-Hydroxycyclohexyl]-4-(2-methyl-4-pyridinylmethyl)-1-methyl-2,3-dihydro-1H-pyrrolo[2,3-b]pyridine-6-carboxamide;

cis-N-(4-Hydroxytetrahydropyran-3-yl)-4-(4-fluorobenzyl)-1-methyl-2,3-dihydro-1H-pyrrolo[2,3-b]pyridine-6-carboxamide (Isomer-I);

cis-N-(4-Hydroxytetrahydropyran-3-yl)-4-(4-fluorobenzyl)-1-methyl-2,3-dihydro-1H-pyrrolo[2,3-b]pyridine-6-carboxamide (Isomer-II);

Racemic cis-N-(4-Hydroxytetrahydropyran-3-yl)-4-(4-methoxybenzyl)-1-methyl-2,3-dihydro-1H-pyrrolo[2,3-b]pyridine-6-carboxamide;

(3S,4S)—N-(4-Hydroxytetrahydropyran-3-yl)-4-(4-fluorobenzyl)-1-methyl-2,3-dihydro-1H-pyrrolo[2,3-b]pyridine-6-carboxamide;
(3S,4S)—N-(4-Hydroxytetrahydropyran-3-yl)-4-(4-methoxybenzyl)-1-methyl-2,3-dihydro-1H-pyrrolo[2,3-b]pyridine-6-carboxamide;
(3S,4S)—N-(4-Hydroxytetrahydropyran-3-yl)-4-(2-methylpyridin-5-ylmethyl)-1-methyl-2,3-dihydro-1H-pyrrolo[2,3-b]pyridine-6-carboxamide;
N-[(1S,2S)-2-Hydroxycyclohexyl]-4-(4-fluorobenzyl)-5,6,7,8-tetrahydro[1,7]naphthyridine-2-carboxamide Hydrochloride;
N-[(1S,2S)-2-Hydroxycyclohexyl]-4-(4-fluorobenzyl)-5,6,7,8-tetrahydro[1,7]naphthyridine-2-carboxamide;
N-[(1S,2S)-2-Hydroxycyclohexyl]-4-(4-chlorobenzyl)-5,6,7,8-tetrahydro[1,7]naphthyridine-2-carboxamide Hydrochloride;
N-[(1S,2S)-2-Hydroxycyclohexyl]-4-(4-chlorobenzyl)-5,6,7,8-tetrahydro[1,7]naphthyridine-2-carboxamide;
N-[(1S,2S)-2-Hydroxycyclohexyl]-4-(3-fluorobenzyl)-5,6,7,8-tetrahydro[1,7]naphthyridine-2-carboxamide Hydrochloride;
N-[(1S,2S)-2-Hydroxycyclohexyl]-4-(3-fluorobenzyl)-5,6,7,8-tetrahydro[1,7]naphthyridine-2-carboxamide;
N-[(1S,2S)-2-Hydroxycyclohexyl]-4-[4-(1-methyl-1H-pyrazol-4-yl)-benzyl]-5,6,7,8-tetrahydro[1,7]naphthyridine-2-carboxamide Hydrochloride;
N-[(1S,2S)-2-Hydroxycyclohexyl]-4-[4-(1-methyl-1H-pyrazol-4-yl)-benzyl]-5,6,7,8-tetrahydro[1,7]naphthyridine-2-carboxamide;
N-[(1S,2S)-2-Hydroxycyclohexyl]-4-(2-fluoropyridin-5-ylmethyl)-5,6,7,8-tetrahydro[1,7]naphthyridine-2-carboxamide Hydrochloride;
N-[(1S,2S)-2-Hydroxycyclohexyl]-4-(2-fluoropyridin-5-ylmethyl)-5,6,7,8-tetrahydro[1,7]naphthyridine-2-carboxamide;
N-[(1S,2S)-2-Hydroxycyclohexyl]-4-(4-methoxybenzyl)-5,6,7,8-tetrahydro[1,7]naphthyridine-2-carboxamide Hydrochloride;
N-[(1S,2S)-2-Hydroxycyclohexyl]-4-(4-methoxybenzyl)-5,6,7,8-tetrahydro[1,7]naphthyridine-2-carboxamide;
N-[(1S,2S)-2-Hydroxycyclohexyl]-4-(2-fluoropyridin-4-ylmethyl)-5,6,7,8-tetrahydro[1,7]naphthyridine-2-carboxamide Hydrochloride;
N-[(1S,2S)-2-Hydroxycyclohexyl]-4-(2-fluoropyridin-4-ylmethyl)-5,6,7,8-tetrahydro[1,7]naphthyridine-2-carboxamide;
N-[(1S,2S)-2-Hydroxycyclohexyl]-4-(4-pyrazol-1-ylbenzyl)-5,6,7,8-tetrahydro[1,7]naphthyridine-2-carboxamide Hydrochloride;
N-[(1S,2S)-2-Hydroxycyclohexyl]-4-(4-pyrazol-1-ylbenzyl)-5,6,7,8-tetrahydro[1,7]naphthyridine-2-carboxamide;
N-[(1S,2S)-2-Hydroxycyclohexyl]-4-(4-fluorobenzyl)-7-methyl-5,6,7,8-tetrahydro[1,7]naphthyridine-2-carboxamide;
N-[(1S,2S)-2-Hydroxycyclohexyl]-4-(4-fluorobenzyl)-7-ethyl-5,6,7,8-tetrahydro[1,7]naphthyridine-2-carboxamide;
trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-II);
Racemic cis-N-(3-Hydroxytetrahydropyran-4-yl)-4-[4-(thiazol-4-yl)benzyl]-5,6,7,8-tetrahydro[1,7]naphthyridine-2-carboxamide Hydrochloride;
cis-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-I);
cis-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-II)
Racemic trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride;
trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-I);
Racemic cis-N-(3-Hydroxytetrahydropyran-4-yl)-4-[4-(thiazol-4-yl)benzyl]-5,6,7,8-tetrahydro[1,7]naphthyridine-2-carboxamide;
cis-N-(3-Hydroxytetrahydropyran-4-yl)-4-[4-(thiazol-4-yl)benzyl]-5,6,7,8-tetrahydro[1,7]naphthyridine-2-carboxamide (Isomer-I);
cis-N-(3-Hydroxytetrahydropyran-4-yl)-4-[4-(thiazol-4-yl)benzyl]-5,6,7,8-tetrahydro[1,7]naphthyridine-2-carboxamide (Isomer-II);
Racemic trans-N-(3-Hydroxytetrahydropyran-4-yl)-4-[4-(thiazol-4-yl)benzyl]-5,6,7,8-tetrahydro[1,7]naphthyridine-2-carboxamide;
trans-N-(3-Hydroxytetrahydropyran-4-yl)-4-[4-(thiazol-4-yl)benzyl]-5,6,7,8-tetrahydro[1,7]naphthyridine-2-carboxamide (Isomer-I);
trans-N-(3-Hydroxytetrahydropyran-4-yl)-4-[4-(thiazol-4-yl)benzyl]-5,6,7,8-tetrahydro[1,7]naphthyridine-2-carboxamide (Isomer-II);
trans-N-(3-Hydroxytetrahydropyran-4-yl)-4-(4-fluorobenzyl)-5,6,7,8-tetrahydro[1,7]naphthyridine-2-carboxamide Hydrochloride (Isomer-II);
Racemic cis-N-(3-Hydroxytetrahydropyran-4-yl)-4-(4-fluorobenzyl)-5,6,7,8-tetrahydro[1,7]naphthyridine-2-carboxamide Hydrochloride;
cis-N-(3-Hydroxytetrahydropyran-4-yl)-4-(4-fluorobenzyl)-5,6,7,8-tetrahydro[1,7]naphthyridine-2-carboxamide Hydrochloride (Isomer-I);
cis-N-(3-Hydroxytetrahydropyran-4-yl)-4-(4-fluorobenzyl)-5,6,7,8-tetrahydro[1,7]naphthyridine-2-carboxamide Hydrochloride (Isomer-II);
Racemic trans-N-(3-Hydroxytetrahydropyran-4-yl)-4-(4-fluorobenzyl)-5,6,7,8-tetrahydro[1,7]naphthyridine-2-carboxamide Hydrochloride;
trans-N-(3-Hydroxytetrahydropyran-4-yl)-4-(4-fluorobenzyl)-5,6,7,8-tetrahydro[1,7]naphthyridine-2-carboxamide Hydrochloride (Isomer-I);
Racemic cis-N-(3-Hydroxytetrahydropyran-4-yl)-4-(4-fluorobenzyl)-5,6,7,8-tetrahydro[1,7]naphthyridine-2-carboxamide;
cis-N-(3-Hydroxytetrahydropyran-4-yl)-4-(4-fluorobenzyl)-5,6,7,8-tetrahydro[1,7]naphthyridine-2-carboxamide (Isomer-I);
cis-N-(3-Hydroxytetrahydropyran-4-yl)-4-(4-fluorobenzyl)-5,6,7,8-tetrahydro[1,7]naphthyridine-2-carboxamide (Isomer-II);
Racemic trans-N-(3-Hydroxytetrahydropyran-4-yl)-4-(4-fluorobenzyl)-5,6,7,8-tetrahydro[1,7]naphthyridine-2-carboxamide;
trans-N-(3-Hydroxytetrahydropyran-4-yl)-4-(4-fluorobenzyl)-5,6,7,8-tetrahydro[1,7]naphthyridine-2-carboxamide (Isomer-I);
trans-N-(3-Hydroxytetrahydropyran-4-yl)-4-(4-fluorobenzyl)-5,6,7,8-tetrahydro[1,7]naphthyridine-2-carboxamide (Isomer-II);

trans-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-II);

Racemic trans-N-(3-Hydroxytetrahydropyran-4-yl)-4-(4-pyrazol-1-ylbenzyl)-5,6,7,8-tetrahydro[1,7]naphthyridine-2-carboxamide Hydrochloride;

trans-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-I);

Racemic cis-N-(3-Hydroxytetrahydropyran-4-yl)-4-(4-pyrazol-1-ylbenzyl)-5,6,7,8-tetrahydro[1,7]naphthyridine-2-carboxamide Hydrochloride;

cis-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-I);

cis-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-II);

Racemic trans-N-(3-Hydroxytetrahydropyran-4-yl)-4-(4-pyrazol-1-ylbenzyl)-5,6,7,8-tetrahydro[1,7]naphthyridine-2-carboxamide;

trans-N-(3-Hydroxytetrahydropyran-4-yl)-4-(4-pyrazol-1-ylbenzyl)-5,6,7,8-tetrahydro[1,7]naphthyridine-2-carboxamide (Isomer-I);

trans-N-(3-Hydroxytetrahydropyran-4-yl)-4-(4-pyrazol-1-ylbenzyl)-5,6,7,8-tetrahydro[1,7]naphthyridine-2-carboxamide (Isomer-II);

Racemic cis-N-(3-Hydroxytetrahydropyran-4-yl)-4-(4-pyrazol-1-ylbenzyl)-5,6,7,8-tetrahydro[1,7]naphthyridine-2-carboxamide;

cis-N-(3-Hydroxytetrahydropyran-4-yl)-4-(4-pyrazol-1-ylbenzyl)-5,6,7,8-tetrahydro[1,7]naphthyridine-2-carboxamide (Isomer-I);

cis-N-(3-Hydroxytetrahydropyran-4-yl)-4-(4-pyrazol-1-ylbenzyl)-5,6,7,8-tetrahydro[1,7]naphthyridine-2-carboxamide (Isomer-II);

cis-N-(4-Hydroxytetrahydropyran-3-yl)-4-(4-fluorobenzyl)-5,6,7,8-tetrahydro[1,7]naphthyridine-2-carboxamide Hydrochloride (Isomer-I);

cis-N-(4-Hydroxytetrahydropyran-3-yl)-4-(4-fluorobenzyl)-5,6,7,8-tetrahydro[1,7]naphthyridine-2-carboxamide Hydrochloride (Isomer-II);

Racemic cis-N-(4-Hydroxytetrahydropyran-3-yl)-4-(4-fluorobenzyl)-5,6,7,8-tetrahydro[1,7]naphthyridine-2-carboxamide Hydrochloride;

Racemic trans-N-(4-Hydroxytetrahydropyran-3-yl)-4-(4-fluorobenzyl)-5,6,7,8-tetrahydro[1,7]naphthyridine-2-carboxamide Hydrochloride;

trans-N-(4-Hydroxytetrahydropyran-3-yl)-4-(4-fluorobenzyl)-5,6,7,8-tetrahydro[1,7]naphthyridine-2-carboxamide Hydrochloride (Isomer-I);

trans-N-(4-Hydroxytetrahydropyran-3-yl)-4-(4-fluorobenzyl)-5,6,7,8-tetrahydro[1,7]naphthyridine-2-carboxamide Hydrochloride (Isomer-II);

Racemic cis-N-(4-Hydroxytetrahydropyran-3-yl)-4-(4-fluorobenzyl)-5,6,7,8-tetrahydro[1,7]naphthyridine-2-carboxamide;

cis-N-(4-Hydroxytetrahydropyran-3-yl)-4-(4-fluorobenzyl)-5,6,7,8-tetrahydro[1,7]naphthyridine-2-carboxamide (Isomer-I);

cis-N-(4-Hydroxytetrahydropyran-3-yl)-4-(4-fluorobenzyl)-5,6,7,8-tetrahydro[1,7]naphthyridine-2-carboxamide (Isomer-II);

Racemic trans-N-(4-Hydroxytetrahydropyran-3-yl)-4-(4-fluorobenzyl)-5,6,7,8-tetrahydro[1,7]naphthyridine-2-carboxamide;

trans-N-(4-Hydroxytetrahydropyran-3-yl)-4-(4-fluorobenzyl)-5,6,7,8-tetrahydro[1,7]naphthyridine-2-carboxamide (Isomer-I);

trans-N-(4-Hydroxytetrahydropyran-3-yl)-4-(4-fluorobenzyl)-5,6,7,8-tetrahydro[1,7]naphthyridine-2-carboxamide (Isomer-II);

Racemic cis-N-(4-Hydroxytetrahydropyran-3-yl)-4-(4-pyrazol-1-ylbenzyl)-5,6,7,8-tetrahydro[1,7]naphthyridine-2-carboxamide Hydrochloride;

cis-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-I);

cis-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-II);

Racemic trans-N-(4-Hydroxytetrahydropyran-3-yl)-4-(4-pyrazol-1-ylbenzyl)-5,6,7,8-tetrahydro[1,7]naphthyridine-2-carboxamide Hydrochloride;

trans-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-I);

trans-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-II);

Racemic cis-N-(4-Hydroxytetrahydropyran-3-yl)-4-(4-pyrazol-1-ylbenzyl)-5,6,7,8-tetrahydro[1,7]naphthyridine-2-carboxamide;

cis-N-(4-Hydroxytetrahydropyran-3-yl)-4-(4-pyrazol-1-ylbenzyl)-5,6,7,8-tetrahydro[1,7]naphthyridine-2-carboxamide (Isomer-I);

cis-N-(4-Hydroxytetrahydropyran-3-yl)-4-(4-pyrazol-1-ylbenzyl)-5,6,7,8-tetrahydro[1,7]naphthyridine-2-carboxamide (Isomer-II);

Racemic trans-N-(4-Hydroxytetrahydropyran-3-yl)-4-(4-pyrazol-1-ylbenzyl)-5,6,7,8-tetrahydro[1,7]naphthyridine-2-carboxamide;

trans-N-(4-Hydroxytetrahydropyran-3-yl)-4-(4-pyrazol-1-ylbenzyl)-5,6,7,8-tetrahydro[1,7]naphthyridine-2-carboxamide (Isomer-I);

trans-N-(4-Hydroxytetrahydropyran-3-yl)-4-(4-pyrazol-1-ylbenzyl)-5,6,7,8-tetrahydro[1,7]naphthyridine-2-carboxamide (Isomer-II);

N-[(1S,2S)-2-Hydroxycyclohexyl]-8-(4-fluorobenzyl)-2,3-dihydro-[1,4]dioxino[2,3-b]pyridine-6-carboxamide;

N-[(1S,2S)-2-Hydroxycyclohexyl]-8-(4-methoxybenzyl)-2,3-dihydro-[1,4]dioxino[2,3-b]pyridine-6-carboxamide;

N-[(1S,2S)-2-Hydroxycyclohexyl]-8-(2-chloropyridin-5-ylmethyl)-2,3-dihydro-[1,4]dioxino[2,3-b]pyridine-6-carboxamide;

N-[(1S,2S)-2-Hydroxycyclohexyl]-8-[4-(1-methyl-1H-pyrazol-4-yl)-benzyl]-2,3-dihydro-[1,4]dioxino[2,3-b]pyridine-6-carboxamide;

N-[(1S,2S)-2-Hydroxycyclohexyl]-8-(2,3-difluorobenzyl)-2,3-dihydro-[1,4]dioxino[2,3-b]pyridine-6-carboxamide;

N-[(1S,2S)-2-Hydroxycyclohexyl]-8-(1-methyl-1H-pyrazol-4-ylmethyl)-2,3-dihydro-[1,4]dioxino[2,3-b]pyridine-6-carboxamide;

N-[(1S,2S)-2-Hydroxycyclohexyl]-8-[4-(pyrazol-1-yl)benzyl]-2,3-dihydro-[1,4]dioxino[2,3-b]pyridine-6-carboxamide;

N-[(1S,2S)-2-Hydroxycyclohexyl]-8-(2-methylpyridin-5-ylmethyl)-2,3-dihydro-[1,4]dioxino[2,3-b]pyridine-6-carboxamide;

N-[(1S,2S)-2-Hydroxycyclohexyl]-8-(2-fluoropyridin-5-ylmethyl)-2,3-dihydro-[1,4]dioxino[2,3-b]pyridine-6-carboxamide;

N-[(1S,2S)-2-Hydroxycyclohexyl]-8-(2-fluoropyridin-4-yl-methyl)-2,3-dihydro-[1,4]dioxino[2,3-b]pyridine-6-carboxamide;

trans-N-(3-Hydroxytetrahydropyran-4-yl)-8-(4-fluorobenzyl)-2,3-dihydro-[1,4]dioxino[2,3-b]pyridine-6-carboxamide (Isomer-II);

cis-N-(3-Hydroxytetrahydropyran-4-yl)-8-(4-fluorobenzyl)-2,3-dihydro-[1,4]dioxino[2,3-b]pyridine-6-carboxamide (Isomer-II);

Racemic cis-N-(3-Hydroxytetrahydropyran-4-yl)-8-(4-fluorobenzyl)-2,3-dihydro-[1,4]dioxino[2,3-b]pyridine-6-carboxamide;

cis-N-(3-Hydroxytetrahydropyran-4-yl)-8-(4-fluorobenzyl)-2,3-dihydro-[1,4]dioxino[2,3-b]pyridine-6-carboxamide (Isomer-I);

Racemic trans-N-(3-Hydroxytetrahydropyran-4-yl)-8-(4-fluorobenzyl)-2,3-dihydro-[1,4]dioxino[2,3-b]pyridine-6-carboxamide;

trans-N-(3-Hydroxytetrahydropyran-4-yl)-8-(4-fluorobenzyl)-2,3-dihydro-[1,4]dioxino[2,3-b]pyridine-6-carboxamide (Isomer-I);

(3S,4S)—N-(4-Hydroxytetrahydropyran-3-yl)-8-(4-methoxybenzyl)-2,3-dihydro-[1,4]dioxino[2,3-b]pyridine-6-carboxamide;

(3S,4S)—N-(4-Hydroxytetrahydropyran-3-yl)-8-(4-fluorobenzyl)-2,3-dihydro-[1,4]dioxino[2,3-b]pyridine-6-carboxamide;

(3S,4S)—N-(4-Hydroxytetrahydropyran-3-yl)-8-(2-chloropyridin-5-ylmethyl)-2,3-dihydro-[1,4]dioxino[2,3-b]pyridine-6-carboxamide;

(3S,4S)—N-(4-Hydroxytetrahydropyran-3-yl)-8-(2-methylpyridin-5-ylmethyl)-2,3-dihydro-[1,4]dioxino[2,3-b]pyridine-6-carboxamide;

Racemic cis-N-(4-Hydroxytetrahydropyran-3-yl)-8-(4-fluorobenzyl)-2,3-dihydro-[1,4]dioxino[2,3-b]pyridine-6-carboxamide;

Racemic cis-N-(4-Hydroxytetrahydropyran-3-yl)-8-(4-methoxybenzyl)-2,3-dihydro-[1,4]dioxino[2,3-b]pyridine-6-carboxamide;

N-[(1S,2S)-2-Hydroxycyclohexyl]-8-(4-fluorobenzyl)-4-methyl-2H-pyrido[3,2-b][1,4]oxazine-6-carboxamide;

N-[(1S,2S)-2-Hydroxycyclohexyl]-8-(3-fluorobenzyl)-4-methyl-2H-pyrido[3,2-b][1,4]oxazine-6-carboxamide;

N-[(1S,2S)-2-Hydroxycyclohexyl]-8-[4-(1-methyl-1H-pyrazol-4-yl)benzyl]-4-methyl-2H-pyrido[3,2-b][1,4]oxazine-6-carboxamide;

N-[(1S,2S)-2-Hydroxycyclohexyl]-8-(2-fluoropyridin-4-ylmethyl)-4-methyl-2H-pyrido[3,2-b][1,4]oxazine-6-carboxamide;

trans-N-(3-Hydroxytetrahydropyran-4-yl)-8-(4-fluorobenzyl)-4-methyl-2H-pyrido[3,2-b][1,4]oxazine-6-carboxamide (Isomer-II);

Racemic cis-N-(3-Hydroxytetrahydropyran-4-yl)-8-(4-fluorobenzyl)-4-methyl-2H-pyrido[3,2-b][1,4]oxazine-6-carboxamide;

cis-N-(3-Hydroxytetrahydropyran-4-yl)-8-(4-fluorobenzyl)-4-methyl-2H-pyrido[3,2-b][1,4]oxazine-6-carboxamide (Isomer-I);

Racemic trans-N-(3-Hydroxytetrahydropyran-4-yl)-8-(4-fluorobenzyl)-4-methyl-2H-pyrido[3,2-b][1,4]oxazine-6-carboxamide;

trans-N-(3-Hydroxytetrahydropyran-4-yl)-8-(4-fluorobenzyl)-4-methyl-2H-pyrido[3,2-b][1,4]oxazine-6-carboxamide (Isomer-I);

trans-N-(3-Hydroxytetrahydropyran-4-yl)-8-(4-fluorobenzyl)-4-methyl-2H-pyrido[3,2-b][1,4]oxazine-6-carboxamide (Isomer-II);

trans-N-(3-Hydroxytetrahydropyran-4-yl)-8-(4-methoxybenzyl)-4-methyl-2H-pyrido[3,2-b][1,4]oxazine-6-carboxamide (Isomer-II);

Racemic trans-N-(3-Hydroxytetrahydropyran-4-yl)-8-(4-methoxybenzyl)-4-methyl-2H-pyrido[3,2-b][1,4]oxazine-6-carboxamide;

trans-N-(3-Hydroxytetrahydropyran-4-yl)-8-(4-methoxybenzyl)-4-methyl-2H-pyrido[3,2-b][1,4]oxazine-6-carboxamide (Isomer-I);

Racemic cis-N-(3-Hydroxytetrahydropyran-4-yl)-8-(4-methoxybenzyl)-4-methyl-2H-pyrido[3,2-b][1,4]oxazine-6-carboxamide;

cis-N-(3-Hydroxytetrahydropyran-4-yl)-8-(4-methoxybenzyl)-4-methyl-2H-pyrido[3,2-b][1,4]oxazine-6-carboxamide (Isomer-I);

cis-N-(3-Hydroxytetrahydropyran-4-yl)-8-(4-methoxybenzyl)-4-methyl-2H-pyrido[3,2-b][1,4]oxazine-6-carboxamide (Isomer-II);

N-[(1S,2S)-2-Hydroxycyclohexyl]-8-(2-chloropyridin-5-ylmethyl)-4-methyl-2H-pyrido[3,2-b][1,4]oxazine-6-carboxamide;

N-[(1S,2S)-2-Hydroxycyclohexyl]-8-(4-methoxybenzyl)-4-methyl-2H-pyrido[3,2-b][1,4]oxazine-6-carboxamide;

N-[(1S,2S)-2-Hydroxycyclohexyl]-8-(2-methylpyridin-5-ylmethyl)-4-methyl-2H-pyrido[3,2-b][1,4]oxazine-6-carboxamide;

N-[(1S,2S)-2-Hydroxycyclohexyl]-8-[4-pyrazol-1-ylbenzyl]-4-methyl-2H-pyrido[3,2-b][1,4]oxazine-6-carboxamide;

N-[(1S,2S)-2-Hydroxycyclohexyl]-4-methyl-8-(1-methyl-1H-pyrazol-4-ylmethyl)-2H-pyrido[3,2-b][1,4]oxazine-6-carboxamide;

Racemic cis-N-(4-Hydroxytetrahydropyran-3-yl)-8-(4-fluorobenzyl)-4-methyl-2H-pyrido[3,2-b][1,4]oxazine-6-carboxamide;

Racemic cis-N-(4-Hydroxytetrahydropyran-3-yl)-8-(4-methoxybenzyl)-4-methyl-2H-pyrido[3,2-b][1,4]oxazine-6-carboxamide;

(3S,4S)—N-(4-Hydroxytetrahydropyran-3-yl)-8-(4-fluorobenzyl)-4-methyl-2H-pyrido[3,2-b][1,4]oxazine-6-carboxamide;

(3S,4S)—N-(4-Hydroxytetrahydropyran-3-yl)-8-(4-methoxybenzyl)-4-methyl-2H-pyrido[3,2-b][1,4]oxazine-6-carboxamide;

(3S,4S)—N-(4-Hydroxytetrahydropyran-3-yl)-8-(4-pyrazol-1-ylbenzyl)-4-methyl-2H-pyrido[3,2-b][1,4]oxazine-6-carboxamide;

(3S,4S)—N-(4-Hydroxytetrahydropyran-3-yl)-4-methyl-8-(1-methyl-1H-pyrazol-4-ylmethyl)-2H-pyrido[3,2-b][1,4]oxazine-6-carboxamide;

N-[(1S,2S)-2-Hydroxycyclohexyl]-7-(4-fluorobenzyl)-1-methyl-1H-pyrrolo[3,2-b]pyridine-5-carboxamide;

Racemic cis-N-(3-Hydroxytetrahydropyran-4-yl)-7-(2-chloropyridin-5-ylmethyl)-1-methyl-1H-pyrrolo[3,2-b]pyridine-5-carboxamide;

cis-N-(3-Hydroxytetrahydropyran-4-yl)-7-(2-chloropyridin-5-ylmethyl)-1-methyl-1H-pyrrolo[3,2-b]pyridine-5-carboxamide (Isomer-I);

cis-N-(3-Hydroxytetrahydropyran-4-yl)-7-(2-chloropyridin-5-ylmethyl)-1-methyl-1H-pyrrolo[3,2-b]pyridine-5-carboxamide (Isomer-II);

Racemic trans-N-(3-Hydroxytetrahydropyran-4-yl)-7-(2-chloropyridin-5-ylmethyl)-1-methyl-1H-pyrrolo[3,2-b]pyridine-5-carboxamide;

trans-N-(3-Hydroxytetrahydropyran-4-yl)-7-(2-chloropyridin-5-ylmethyl)-1-methyl-1H-pyrrolo[3,2-b]pyridine-5-carboxamide (Isomer-I);

trans-N-(3-Hydroxytetrahydropyran-4-yl)-7-(2-chloropyridin-5-ylmethyl)-1-methyl-1H-pyrrolo[3,2-b]pyridine-5-carboxamide (Isomer-II);

N-[(1S,2S)-2-Hydroxycyclohexyl]-7-(2-chloropyridin-5-ylmethyl)-1-methyl-1H-pyrrolo[3,2-b]pyridine-5-carboxamide;

Racemic cis-N-(4-Hydroxytetrahydropyran-3-yl)-7-(4-methoxybenzyl)-1-methyl-1H-pyrrolo[3,2-b]pyridine-5-carboxamide;

(3S,4S)—N-(4-Hydroxytetrahydropyran-3-yl)-7-(4-fluorobenzyl)-1-methyl-1H-pyrrolo[3,2-b]pyridine-5-carboxamide; and (3S,4S)—N-(4-Hydroxytetrahydropyran-3-yl)-7-(4-methoxybenzyl)-1-methyl-1H-pyrrolo[3,2-b]pyridine-5-carboxamide;

or a pharmaceutically acceptable salt thereof.

EXPERIMENTAL PROCEDURE

Scheme-1 depicts processes for the preparation of compound of formula (I), wherein: $A^1$ is $CH_2$; $R^1$, $R^2$, $R^3$ and $R^4$ are as defined above.

Step 1: Preparation of Compound of Formula B

The compound of formula A is reacted with potassium hydroxide in water at reflux temperature for 5-8 hours to obtain the compound of formula B.

Step 2: Preparation of Compound of Formula C

The compound of formula B obtained in step 1 is reacted with alkyl iodide selected from methyl iodide or ethyl iodide in presence of base such as sodium hydride, sodium tert-butoxide, potassium tert-butoxide or cesium carbonate in a solvent selected from DMF, THF or acetonitrile at the temperature range of 60-70° C. for 8-10 hours to obtain the compound of formula C.

Step 3: Preparation of Compound of Formula D

The compound of formula C obtained in step 2 is reacted with bis(pinacolato)diboron and 1,1'-bis(diphenylphosphino)ferrocenepalladium(II)dichloride dichloromethane complex in presence of potassium acetate in a solvent selected from toluene or 1,4-dioxane at the temperature range of 90-110° C. for 7-9 hours to obtain the compound of formula D.

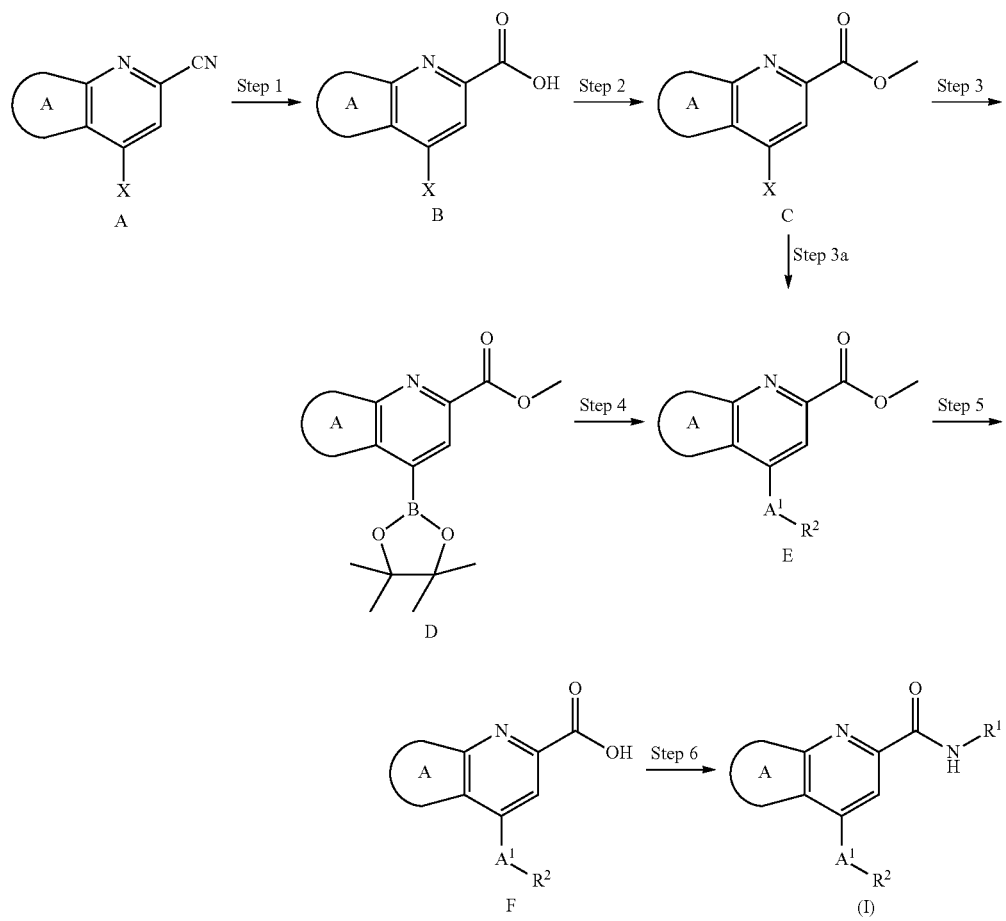

X is haolgen

Step 3a: Preparation of Compound of Formula E

The compound of formula C obtained in step 2 is reacted with 4-fluorobenzylzinc chloride in presence of bis(tritert-butylphosphine)palladium in a solvent selected from THF, DMF or acetonitrile under reflux temperature for 2-5 hours to obtain the compound of formula E.

Step 4: Preparation of Compound of Formula E

The compound of formula D obtained in step 3 is reacted with compound of formula 1c, $R^2$-$A^1$-X (wherein X is halogen; $A^1$ is $CH_2$) in presence of base such as cesium carbonate, potassium carbonate, or sodium carbonate; potassium iodide, sodium iodide or lithium iodide and [1,1'-bis(diphenylphosphino)ferrocene] di chloropalladium (II), 1:1 complex with dichloromethane in a mixture of solvents selected from THF, 1,4-dioxane and water in a microwave at the temperature range of 70-80° C. for 1-2 hours to obtain the compound of formula E.

Step 5: Preparation of Compound of Formula F

The compound of formula E obtained in step 3a or step 4 is hydrolyzed using a base selected from sodium hydroxide or potassium hydroxide in a solvent selected from $H_2O$, THF, ethanol and methanol at the temperature range of 50-100° C. for 2-4 hours to obtain the compound of formula F.

Step 6: Preparation of Compound of Formula (I)

The compound of formula F obtained in step 5 is coupled with amine $R^1$—$NH_2$.HCl in presence of coupling reagent, HATU, DCC or EDC and a base such as triethylamine, DIPEA, or DABCO in a solvent selected from DMF, THF, dichloromethane or 1,4-dioxane at RT for 6-16 hours to obtain the compound of formula (I) (wherein $A^1$ is $CH_2$). The amines of $R^1$—$NH_2$, such as (1S,2S)-trans-2-aminocyclohexanol hydrochloride (CAS No. 13374-30-6), (1R,2R)-2-aminocyclohexanol (CAS No. 931-16-8), 1-amino-2-methyl-2-propanol, 2-amino-3-methyl-1-butanol, 2-aminobenzyl alcohol, and (1R,2R)-trans-2-aminocyclopentanol (CAS No. 68327-11-7) were procured from commercial sources.

Preparation of Compound of Formula (I) (Wherein $A^1$ is CHF or $CF_2$)

The compound of formula (I) (wherein $A^1$ is $CH_2$) is reacted with a brominating agent such as N-Bromosuccinimide (NBS) in the presence of a radical initiator such as azobisisobutyronitrile (AIBN) followed by hydrolysis under aqueous conditions to furnish an intermediate biarylmethanol/biarylketone derivative. The intermediate compound containing hydroxyl/oxo group is reacted with a fluorinating agent selected from HF-amine complex such as HF-pyridine, DAST or triethylamine trihydrofluoride and activating agent such as 1,1,2,2,3,3,4,4,4-nonafluorobutane-1-sulfonyl fluoride in the presence of triethylamine trihydrofluoride to obtain the compound of formula (I) (wherein $A^1$ is CHF or $CF_2$).

Preparation of Pharmaceutically Acceptable Salt of Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric & phosphoric acid or organic acids e.g., oxalic, succinic, maleic, acetic, fumaric, citric, malic, tartaric, benzoic, p-toluic, p-toluenesulfonic, benzenesulfonic acid, methanesulfonic or naphthalenesulfonic acid.

Alternatively the compound of formula (I) can also be prepared by scheme 1a as given below:

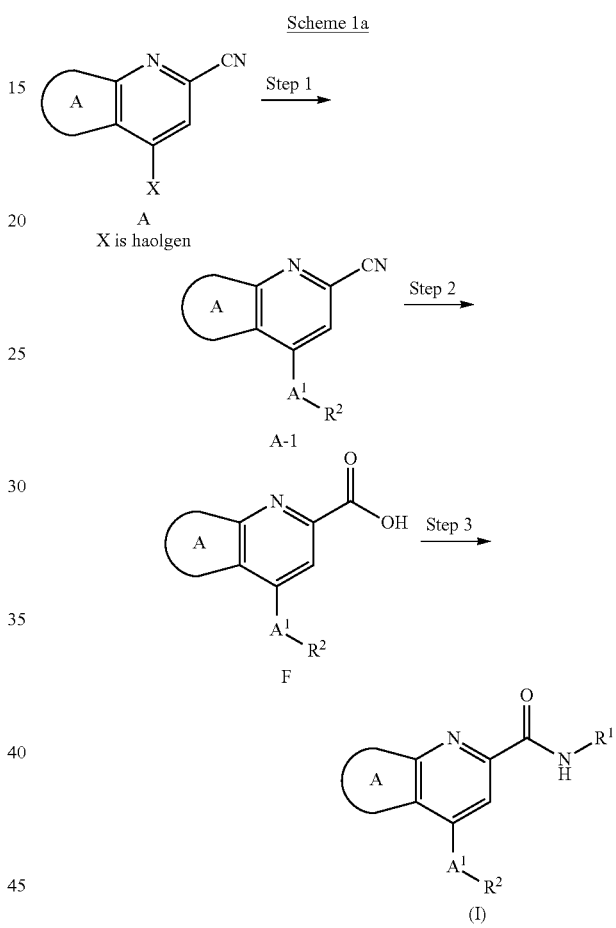

Scheme 1a

Step 1: Preparation of Compound of Formula A-1

The compound of formula A is reacted with 4-fluorobenzylzinc chloride in presence of bis(tri-tert-butylphosphine) palladium in a solvent selected from THF, DMF or acetonitrileunder reflux temperature for 2-5 hours to obtain the compound of formula A-1.

Step 2: Preparation of Compound of Formula F

The compound of formula A-1 obtained from step 1 is hydrolyzed using a base selected from sodium hydroxide or potassium hydroxide in a solvent selected from $H_2O$, THF, ethanol or methanol at the temperature range of 50-100° C. for 2-4 hours to obtain the compound of formula F.

Step 3: Preparation of Compound of Formula (I)

The compound of formula F obtained in step 2 is coupled with amine $R^1$—$NH_2$.HCl in presence of coupling reagent, HATU, DCC or EDC and a base, DIPEA in a solvent selected from DMF, THF, dichloromethane or 1,4-dioxane at RT overnight to obtain the compound of formula (I) (wherein $A^1$ is $CH_2$). The amines of $R^1$—$NH_2$, such as (1S,2S)-trans-2-aminocyclohexanol (CAS No. 13374-30-6), (1R,2R)-2-aminocyclohexanol (CAS No. 931-16-8), 1-amino-2-methyl-2-propanol, 2-amino-3-methyl-1-butanol, 2-aminobenzyl alcohol, and (1R,2R)-trans-2-aminocyclopentanol (CAS No. 68327-11-7) were procured from commercial sources.

Scheme 1b depicts the alternate process for the preparation of compound of formula (I), wherein ring A is 5- to 8-membered saturated ring containing nitrogen atom (s).

hydroxide or potassium hydroxide in a solvent selected from $H_2O$, THF, methanol or ethanol at the temperature range of 50-100° C. for 2-4 hours to obtain the compound of formula 3.

Step 3: Preparation of Compound of Formula 4

The compound of formula 3 obtained in step 2 is coupled with amine $R^1$—$NH_2$.HCl in presence of coupling reagent, HATU, DCC or EDC and a base such as triethylamine, DIPEA and DABCO in a solvent selected from DMF, THF, dichloromethane or 1,4-dioxane at RT overnight to obtain the compound of formula 4 (wherein $A^1$ is $CH_2$). The amines Scheme 1b

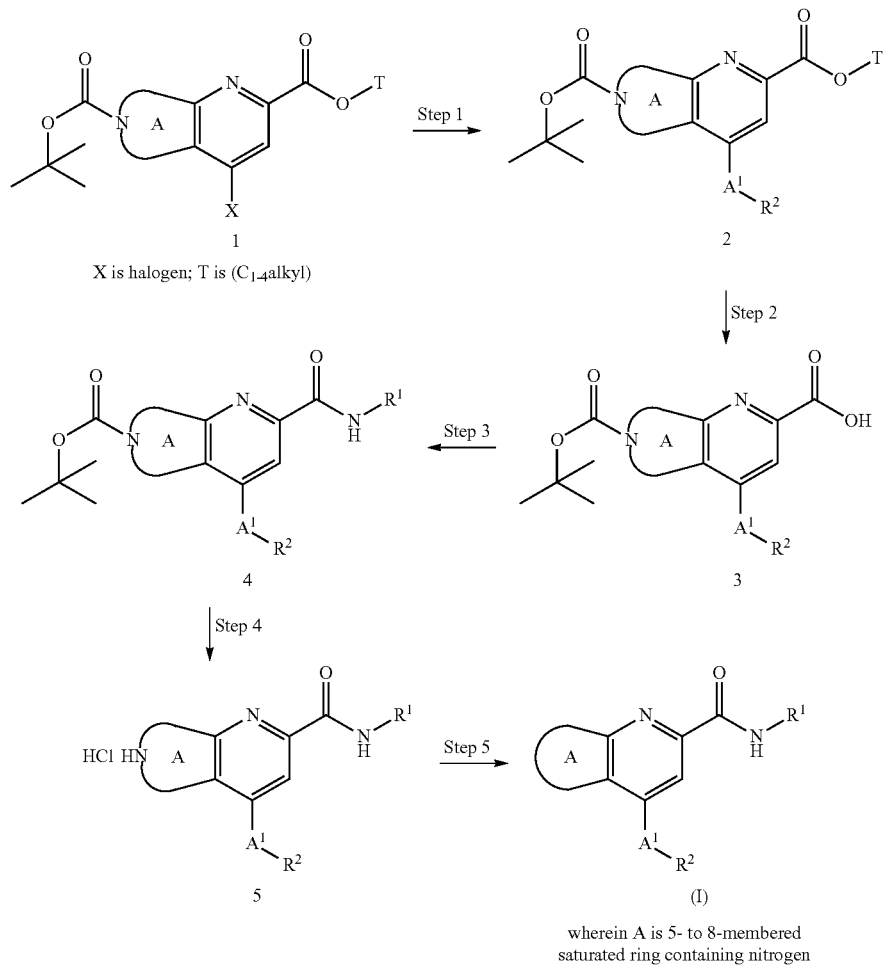

X is halogen; T is ($C_{1-4}$alkyl)

wherein A is 5- to 8-membered
saturated ring containing nitrogen

Step 1: Preparation of Compound of Formula 2

The compound of formula 1 is reacted with 4-fluorobenzylzinc chloride in presence of bis(tri-tert-butylphosphine) palladium in a solvent selected from THF, DMF or acetonitrile under reflux temperature for 2-5 hours to obtain the compound of formula 2.

Step 2: Preparation of Compound of Formula 3

The compound of formula 2 obtained in step 2 is hydrolyzed using a base selected from lithium hydroxide, sodium of $R^1$—$NH_2$, such as (1S,2S)-trans-2-aminocyclohexanol (CAS No. 13374-30-6), (1R,2R)-2-aminocyclohexanol (CAS No. 931-16-8), 1-amino-2-methyl-2-propanol, 2-amino-3-methyl-1-butanol, 2-aminobenzyl alcohol, and (1R,2R)-trans-2-aminocyclopentanol (CAS No. 68327-11-7) were procured from commercial sources.

Step 4: Preparation of Compound of Formula 5

The compound of formula 4 obtained in step 3 is reacted with IPA.HCl at a temperature in the range of 25-30° C. for 4-6 hours to obtain the compound of formula 5.

Step 5: Preparation of Compound of Formula (I)

The compound of formula 5 is basified using bases such as aqueous ammonia, sodium bicarbonate, sodium hydroxide to obtain the compound of formula (I) (wherein ring A is 5- to 8-membered saturated ring containing nitrogen atom (s)).

Preparation of Stereoisomers of Compound of Formula (I)

The stereoisomers of compounds of formula (I) may be prepared by one or more conventional ways presented below:
a. One or more of the reagents may be used in their optically active form.
b. Optically pure catalyst or chiral ligands along with metal catalyst may be employed in the reduction process. The metal catalyst may be rhodium, ruthenium, indium and the like. The chiral ligands may preferably be chiral phosphines.
c. The mixture of stereoisomers may be resolved by conventional methods such as forming diastereomeric salts with chiral acids or chiral amines or chiral amino alcohols, or chiral amino acids. The resulting mixture of diastereomers may then be separated by methods such as fractional crystallization, chromatography and the like, which is followed by an additional step of isolating the optically active product from the resolved material/salt.
d. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

Scheme-2 depicts processes for the preparation of the intermediates of compound of formula 1.

Scheme 2

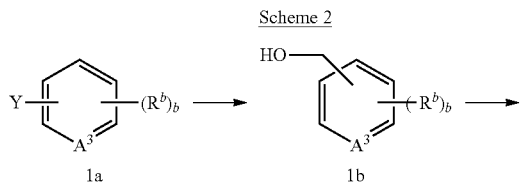

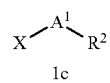

1c

Reduction of compound of formula 1a (wherein Y is COOCH$_3$ or CHO; A$^1$ is CH$_2$, A$^3$, R$^b$ and b is as defined in first aspect) using LAH, NaBH$_4$ in a solvent selected from THF, alcohol selected from methanol, ethanol and IPA at the temperature range of 25-30° C. for 2-5 hours gives the compound of formula 1b.

The compound of formula 1b is reacted with halogenating agents selected from SOCl$_2$, SOBr$_2$, PCl$_3$, PBr$_3$, CBr$_4$/PPh$_3$ and CCl$_4$/PPh$_3$ in presence of solvents such as DCM and at a temperature range of 25-30° C. for 2-5 hours to obtain the compound of formula 1c (wherein X is halogen; A$^1$ is CH$_2$ and R$^2$ is

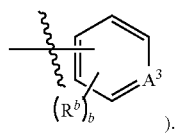
).

Scheme-3 depicts processes for the preparation of the intermediates of compound of formula 1a.

Scheme 3

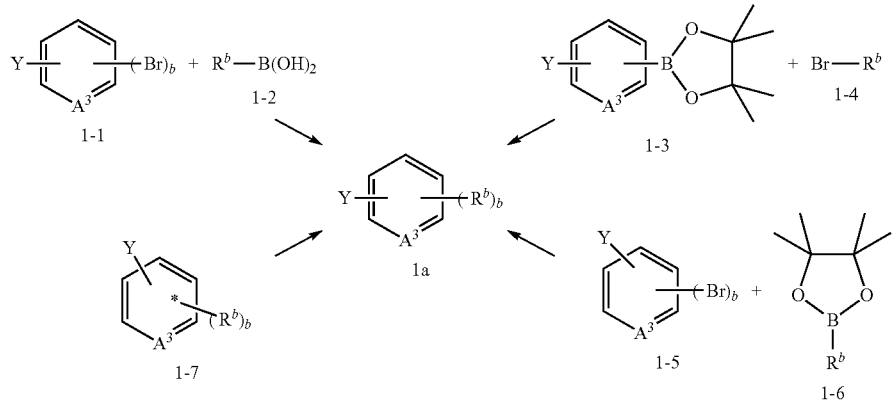

The compound of formula 1-1 is reacted with compound of formula 1-2 (wherein R$^b$ is pyridinyl) in presence of tetrakis(triphenylphosphine)palladium(0) in mixture of solvents selected from DME and water under reflux for 11 to 14 hours to obtain the compound of formula 1a.

The compound of formula 1-3 is reacted with compound of formula 1-4 (wherein R$^b$ is pyridinyl, thiazolyl and isoxazolyl) in presence of Pd(dppf)Cl$_2$.CH$_2$Cl$_2$ and base selected from sodium carbonate and potassium carbonate in a mixture of solvents selected from water and 1,4-dioxane at a temperature range of 70-100° C. for 5-7 hours to obtain the compound of formula 1a.

The compound of formula 1-5 is reacted with compound of formula 1-6 (wherein R$^b$ is pyrazolyl) in presence of Pd(dppf)Cl$_2$.CH$_2$Cl$_2$ and base selected from sodium carbonate and potassium carbonate in a mixture of solvents selected from water and 1,4-dioxane at a temperature range of 70-100° C. for 5-7 hours to obtain the compound of formula 1a.

The compound of formula 1-7 (wherein Y is COOH, $R^b$ is S—CH$_3$) is reacted with (trimethylsilyl)diazomethane in a mixture of solvents selected from DCM and methanol at the temperature range of 25-30° C. for 24-27 hours to obtain the compound of formula 1a.

In another embodiment, the suitable pharmaceutically acceptable salt includes hydrochloride, hydrobromide, oxalate, fumarate, tartrate, maleate and succinate.

In another aspect of the present invention, the compound of formula (I) are muscarinic M1 positive alloseteric modulators.

In another aspect, the present invention relates to a method of treatment of Alzheimer's diseases comprising administering to a patient in need thereof, a therapeutically effective amount of compounds of formula (I) or a pharmaceutically acceptable salt thereof.

In another aspect, the present invention relates to a method of treatment of Alzheimer's diseases including mild Alzheimer's disease, moderate Alzheimer's disease, severe Alzheimer's disease, mild to moderate Alzheimer's disease or moderate to severe Alzheimer's disease, comprising administering to a patient in need thereof, a therapeutically effective amount of compounds of formula (I) or a pharmaceutically acceptable salt thereof.

In yet another aspect, the present invention relates to compound of formula (I) for use in the treatment of disease or disorder selected from cognitive disorder, pain or sleep disorder.

In yet another aspect, the present invention relates to use of the compound of formula (I) in the manufacture of medicament for the treatment of diseases or disorder selected from cognitive disorder, pain or sleep disorder.

In yet another aspect, the present invention relates to use of the compound of formula (I) in the manufacture of medicament for the treatment of diseases or disorder selected from cognitive disorder.

In yet another aspect, the present invention relates to use of the compound of formula (I) in the manufacture of medicament for the treatment of Alzheimer's disease.

In yet another embodiment, the present invention relates to the combination of compound of formula (I) with one or more other therapeutic agents acetylcholinesterase inhibitors and NMDA receptor antagonist.

In another embodiment, the compound of formula (I) of the present invention may be used in combination with one or more other therapeutic agents in the treatment of diseases or disorders for which the compound of formula (I) of the present invention have utility. Examples of the combinations of the compounds of present invention include combination with the therapeutic agents for the treatment of Alzheimer's disease, for example acetylcholinesterase inhibitors such as galantamine, rivastigmine, donepezil, and tacrine; and NMDA receptor antagonist such as memantine.

In yet another embodiment, the present invention relates to combination of compound of formula (I) with at least one therapeutic agents selected from galantamine, rivastigmine, donepezil, tacrine and memantine.

In yet another embodiment the present invention relates to the combination of compound of formula (I) with one or more other therapeutic agents acetylcholinesterase inhibitors and NMDA receptor antagonist for use in the treatment of cognitive disorder, schizophrenia, pain and sleep disorder.

In yet another aspect, the present invention relates to the pharmaceutical composition of the compound of formula (I). In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like. Excipients are selected from microcrystalline cellulose, mannitol, lactose, pregelatinized starch, sodium starch glycolate, corn starch or derivatives thereof, povidone, crospovidone, calcium stearate, glyceryl monostearate, glyceryl palmitostearate, talc, colloidal silicone dioxide, magnesium stearate, sodium lauryl sulfate, sodium stearyl fumarate, zinc stearate, stearic acid or hydrogenated vegetable oil, gum arabica, magnesia, glucose, fats, waxes, natural or hardened oils, water, physiological sodium chloride solution or alcohols, for example, ethanol, propanol or glycerol, sugar solutions, such as glucose solutions or mannitol solutions and the like or a mixture of the various excipients.

In yet another aspect, the active compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In yet another aspect, the pharmaceutical composition of the instant invention contains 1 to 90%, 5 to 75% and 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg or from about 5 mg to about 400 mg or from about 5 mg to about 250 mg or from about 7 mg to about 150 mg or in any range falling within the broader range of 1 mg to 500 mg.

The dose of the active compounds can vary depending on factors such as age and weight of patient, nature and severity of the disease to be treated and such other factors. Therefore, any reference regarding pharmacologically effective amount of the compounds of general formula (I), stereoisomers and pharmaceutically acceptable salts thereof refers to the aforementioned factors.

The following abbreviations are used herein:
AMP: Adenosine monophosphate
AUC: Area under the curve
CBr$_4$: Carbon tetrabromide
CCl$_4$: Carbon tetrachloride
C$_{max}$: Maximum concentration
CDCl$_3$: Deuterated chloroform
DAST: Diethylaminosulfur trifluoride
DABCO: 1,4-Diazabicyclo[2.2.2]octane
DCM: Dichloromethane
DCC: N,N'-Dicyclohexylcarbodiimide
DEA: Diethylamine
DIPEA: N,N-Diisopropylethylamine
DME: Dimethoxyethane
DMF: N,N-Dimethylformamide DMSO: Dimethyl sulfoxide
$EC_{50}$: Half maximal effective concentration
EDC: Ethylene dichloride
HATU: 2-(7-Aza-1H-benzotriazole-1-yl)-1,1,3,3-tetramethyluronium hexafluorophosphate
HCl: Hydrochloric acid
$H_2O$: Water
IPA: Isopropyl alcohol
$K_2CO_3$: Potassium carbonate
LC-MS/MS: Liquid chromatography-Mass spectrometry/Mass spectrometry
MeOH: Methanol
MeOD: Deutrated methanol
$NaBH_4$: Sodium borohydride
NaOH: Sodium hydroxide
$Na_2SO_4$: Sodium sulphate
$PBr_3$: Phosphorus tribromide
$PCl_3$: Phosphorus trichloride
$Pd(dppf)Cl_2.CH_2C_2$: [1,1'-Bis(diphenylphosphino)ferrocene]dichloro palladium(II)
$PPh_3$: Triphenylphosphine
RT: Room temperature (25-30° C.)
ROA: Route of Administration
S.E.M.: Standard error of the mean
$SOBr_2$: Thionyl bromide
$SOCl_2$: Thionyl chloride
T: Temperature
THF: Tetrahydrofuran
$T_{1/2}$: Half-life time

EXAMPLES

The compounds of the present invention were prepared according to the following experimental procedures, using appropriate materials and conditions. The following examples are provided by way of illustration only but not to limit the scope of present invention.

Preparation 1: 4-Bromomethyl-2-fluoropyridine
(I-1)

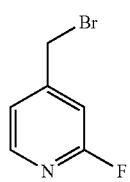

To a solution of 2-fluoro-4-methylpyridine (2.5 g, 0.022 mole) in $CCl_4$ (75 mL) under $N_2$ atmosphere at 25° C. was added N-bromosuccinimide (4.4 g, 0.024 mole) and benzoyl peroxide (0.81 g, 0.003 mole). Reaction mixture was heated to 85° C. for 5 hours, cooled to RT, filtered under vacuum and washed with $CCl_4$ (40 mL). The filtrate was concentrated under vacuum to obtain the crude compound, which was further purified by flash chromatography using ethyl acetate:n-hexane (02:98) to afford the title compound.

Yield: 1.1 g; $^1$H-NMR ($CDCl_3$, 400 MHz) δ ppm: 4.71 (s, 2H), 7.27 (s, 1H), 7.42-7.43 (d, J=4.9 Hz, 1H), 8.24-8.25 (d, J=5.1 Hz, 1H); Mass (m/z): 190.0, 192.1 (M+H)$^+$.

Preparation 2: 5-Bromomethyl-2-fluoropyridine
(I-2)

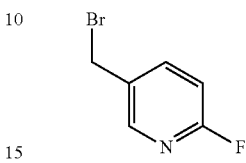

The title compound, 5-bromomethyl-2-fluoropyridine was synthesized from 2-fluoro-5-methylpyridine by the procedure as described in preparation 1.

$^1$H-NMR ($CDCl_3$, 400 MHz) δ ppm: 4.75 (s, 2H), 7.18-7.21 (dd, J=2.7, 8.4 Hz, 1H), 8.04-8.09 (m, 1H), 8.32-8.33 (d, J=1.5 Hz, 1H); Mass (m/z): 190.0, 192.2 (M+H)$^+$.

Preparation 3: 5-Bromomethyl-2-chloropyridine I-3)

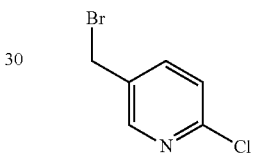

Step-1

A solution of 6-chloronicotinic acid (2.0 g, 0.012 mole) in DMF (5 mL) was added to a suspension of sodium hydride (0.76 g, 0.015 mole) in DMF (3 mL) under $N_2$ at 25° C. and stirred for 1 hour. Methyl iodide (1.5 mL, 0.025 mole) was added at RT and warmed to 50° C. for 2 hours. Reaction mixture was cooled to RT, quenched in to ice cold water (50 mL) and extracted with ethyl acetate (50 mL×3). Organic layer was washed with brine solution (50 mL), dried over $Na_2SO_4$ and concentrated under vacuum to obtain methyl 6-chloronicotinate.

Yield: 1.6 g; Mass (m/z): 172.0, 174.0 (M+H)$^+$.

Step-2

To a solution of methyl 6-chloronicotinate (1.08 g, 0.009 mole) in THF (30 mL) at 0° C. under $N_2$, was added lithium aluminum hydride (1 M in THF, 7.5 mL, 0.0075 mole) drop wise. Reaction mixture was warmed to RT and stirred for 3 hours. The reaction mixture was cooled to 0° C., diluted with ethyl acetate and treated with water (2 mL). The mixture was filtered through celite bed and concentrated under vacuum to obtain the crude compound which was further purified by flash chromatography using ethyl acetate:n-hexane (40:60) to afford 2-chloro-5-hydroxymethylpyridine.

Yield: 0.55 g; $^1$H-NMR ($CDCl_3$, 400 MHz) δ ppm: 2.09 (bs, 1H), 4.72 (s, 2H), 7.31-7.34 (d, J=8.1 Hz, 1H), 7.68-7.71 (dd, J=2.2, 8.4 Hz, 1H), 8.36 (s, 1H); Mass (m/z): 144.1, 146.0 (M+H)$^+$.

Step-3

To a solution of 2-chloro-5-hydroxymethylpyridine (0.45 g, 0.003 mole) in DCM (10 mL) at 0° C. under N₂, was added phosphorus tribromide (0.44 mL, 0.0037 mole) drop wise. Reaction mixture was warmed to RT and stirred for 1.5 hours. The reaction mixture was diluted with DCM (75 mL), treated with saturated aqueous sodium bicarbonate (20 mL). Organic layer was washed with water (20 mL), brine solution (20 mL) and dried over Na₂SO₄ and concentrated under vacuum to obtain the title compound.

Yield: 0.49 g; ¹H-NMR (CDCl₃, 400 MHz) δ ppm: 4.35 (s, 2H), 7.32-7.34 (d, J=8.2 Hz, 1H), 7.69-7.71 (dd, J=2.2, 7.9 Hz, 1H), 8.40-8.41 (d, J=1.7 Hz, 1H); Mass (m/z): 205.9, 208.0 (M+H)⁺.

Preparation 4: 5-(Chloromethyl)-2-methoxypyridine (I-4)

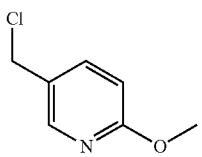

Step-1

2-Methoxypyridine-5-carboxylic acid was converted to 2-methoxy-5-hydroxymethylpyridine similar to the procedure as described in step-2 of preparation 3.

Yield: 0.72 g; Mass (m/z): 140.1 (M+H)⁺.

Step-2

To a solution of 2-methoxy-5-hydroxymethylpyridine (0.71 g, 0.005 mole) in DCM (5 mL) at 0° C. under N₂, was added thionyl chloride (0.7 mL, 0.009 mole) drop wise. The reaction mixture was warmed to RT and stirred for 2 hours. The reaction mixture was diluted with DCM (50 mL) and treated with saturated aqueous sodium bicarbonate (10 mL). Organic layer was washed with water (20 mL), brine solution (20 mL), dried over Na₂SO₄ and concentrated under vacuum to obtain the title compound.

Yield: 0.58 g; ¹H-NMR (CDCl₃, 400 MHz) δ ppm: 3.94 (s, 3H), 4.55 (s, 2H), 6.75-6.77 (d, J=8.5 Hz, 1H), 7.61-7.64 (dd, J=2.2, 8.5 Hz, 1H), 8.14 (s, 1H); Mass (m/z): 158.0-160.0 (M+H)⁺.

Preparation 5: 5-Chloromethyl-2-methylpyridine (I-5)

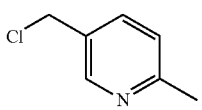

The title compound, 5-chloromethyl-2-methylpyridine was synthesized from 6-methyl-nicotinic acid by the procedure as described in preparation 4.

Yield: 1.7 g; ¹H-NMR (CDCl₃, 400 MHz) δ ppm: 2.58 (s, 3H), 4.56 (s, 2H), 7.16-7.18 (d, J=7.9 Hz, 1H), 7.61-7.64 (dd, J=1.6, 7.8 Hz, 1H), 8.49 (s, 1H); Mass (m/z): 142.0, 144.1 (M+H)⁺.

Preparation 6: 4-Chloromethyl-2-methylpyridine (I-6)

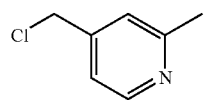

The title compound, 4-chloromethyl-2-methylpyridine was synthesized from 2-methylisonicotinic acid by the procedure as described in preparation 4.

Yield: 0.47 g; ¹H-NMR (CDCl₃, 400 MHz) δ ppm: 2.58 (s, 3H), 4.51 (s, 2H), 7.12-7.13 (d, J=4.8 Hz, 1H), 7.19 (s, 1H), 8.48-8.50 (d, J=5.1 Hz, 1H); Mass (m/z): 142.0, 144.0 (M+H)⁺.

Preparation 7: 4-Bromomethyl-2,5-difluoropyridine-7)

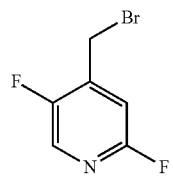

The title compound, 4-bromomethyl-2,5-difluoropyridine was synthesized from 2,5-difluoropyridine-4-carboxylic acid by the procedure as described in preparation 3.

Yield: 0.23 g; ¹H-NMR (DMSO-d₆, 400 MHz) δ ppm: 4.68 (s, 2H), 7.20 (s, 1H), 8.16 (s, 1H); Mass (m/z): 208.1, 210.1 (M+H)⁺.

Preparation 8: 4-Bromomethyl-2-chloropyridine (I-8)

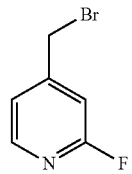

The title compound, 4-bromomethyl-2-chloropyridine was synthesized from 2-chloroisonicotinic acid by the procedure as described in preparation 3.

Yield: 0.49 g; ¹H-NMR (CDCl₃, 400 MHz) δ ppm: 4.35 (s, 2H), 7.36 (s, 1H), 8.37-8.38 (d, J=4.9 Hz, 1H); Mass (m/z): 205.9, 208.0 (M+H)⁺.

Preparation 9: 4-Chloromethylpyridine (I-9)

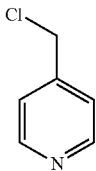

Step-1

Thionyl chloride (0.7 mL, 0.009 mole) was added drop wise to a stirred suspension of isonicotinic acid (5 g, 0.04 mole) in methanol (50 mL) under $N_2$ at 0-5° C. The reaction mixture was then refluxed for 3 hours to obtain a clear solution. The reaction mass was cooled to RT and concentrated to obtain a residue that was diluted with water (20 mL) and extracted with ethyl acetate (100 mL×3). The organic extracts were combined, washed with aqueous sodium bicarbonate (10 mL), brine (20 mL) dried over anhydrous $Na_2SO_4$ and concentrated under vacuum to obtain the crude compound that was further purified by flash chromatography using ethyl acetate:hexane (40:60) to obtain methyl isonicotinate.

Yield: 2.82 g; $^1$H-NMR (CDCl$_3$, 400 MHz) δ ppm: 3.96 (s, 3H); 7.83-7.85 (d, J=5.3 Hz, 2H), 8.77-8.78 (d, J=5.2 Hz, 2H); Mass (m/z): 138.0 (M+H)$^+$.

Step-2

Methyl isonicotinate was reacted with lithium aluminium hydride as described in step-2 of preparation 3 to obtain crude 4-hydroxymethylpyridine that was further purified by chromatography using ethyl acetate:hexane (80:20) to obtain the pure compound.

Yield: 3.05 g; $^1$H-NMR (CDCl$_3$, 400 MHz) δ ppm: 4.74 (s, 2H), 7.29-7.30 (d, J=5.3 Hz, 2H), 8.51-8.52 (d, J=5.5 Hz, 2H); Mass (m/z): 110.0 (M+H)$^+$.

Step-3

4-Hydroxymethylpyridine was reacted with thionyl chloride as described in step-2 of preparation 4 to obtain the title compound, 4-chloromethylpyridine.

Yield: 0.35 g; $^1$H-NMR (MeOH, 400 MHz) δ ppm: 4.71 (s, 2H), 7.51-7.53 (d, J=5.7 Hz, 2H), 8.56-8.58 (d, J=5.9 Hz, 2H); Mass (m/z): 128.0, 130.0 (M+H)$^+$.

Preparation 10: 4-(4-Bromomethylphenyl)-1-methyl-1H-pyrazole (I-10)

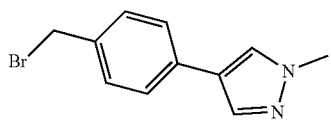

Step-1

To a solution of 4-bromobenzaldehyde (0.50 g, 0.0027 mole) in a mixture of 1,4-dioxane (18 mL) and water (5 mL) under $N_2$, was added 1-methyl-4-(4,4,5,5-tetramethyl-[1,3,2]dioxaborolan-2-yl)-1H-pyrazole (1.12 g, 0.0054 mole), sodium carbonate (0.85 g, 0.0081 mole) and [1,1'-bis(diphenylphosphino)ferrocene] dichloro-palladium (II), 1:1 complex with dichloromethane (0.043 g, 0.00013 mole). The reaction mixture was heated at 80° C. for 4 hours, cooled to RT, filtered through celite and washed with ethyl acetate (30 mL). The filtrate was concentrated under vacuum to obtain the crude compound which was further purified by flash chromatography using ethyl acetate:n-hexane (40:60) to get 4-(1-methyl-1H-pyrazol-4-yl)benzaldehyde.

Yield: 0.49 g; $^1$H-NMR (CDCl$_3$, 400 MHz) δ ppm: 3.96 (s, 3H), 7.60-7.62 (d, J=8.0 Hz, 2H), 7.72 (s, 1H), 7.84-7.87 (m, 3H), 9.97 (s, 1H); Mass (m/z): 187.2 (M+H)$^+$.

Step-2

To a cooled solution of 4-(1-methyl-1H-pyrazol-4-yl) benzaldehyde (0.49 g, 0.0026 mole) in methanol (10 mL) under $N_2$, was added sodium borohydride (0.12 g, 0.0032 mole) in portion wise. The reaction mixture was warmed to RT and stirred for 2 hours. The reaction mixture was concentrated under vacuum, dissolved in ice cold water (50 mL) and extracted with ethyl acetate (50 mL×3). Organic layer was washed with brine solution (50 mL), dried over $Na_2SO_4$ and concentrated under vacuum to get 4-(4-hydroxymethylphenyl)-1-methyl-1H-pyrazole.

Yield: 0.45 g; $^1$H-NMR (CDCl$_3$, 400 MHz) δ ppm: 3.85 (s, 3H), 4.46-4.47 (d, J=5.7 Hz, 2H), 5.11-5.14 (t, J=5.7 Hz, 1H), 7.27-7.29 (d, J=7.9 Hz, 2H), 7.49-7.51 (d, J=8.0 Hz, 2H), 7.82 (s, 1H), 8.09 (s, 1H); Mass (m/z): 189.1 (M+H)$^+$.

Step-3

4-(4-Hydroxymethylphenyl)-1-methyl-1H-pyrazole was converted to the title compound using similar procedure as described in step-3 of preparation 3.

Yield: 0.17 g; $^1$H-NMR (DMSO-d$_6$, 400 MHz) δ ppm: 3.85 (s, 3H), 5.27 (s, 2H), 7.41-7.43 (d, J=8.0 Hz, 2H), 7.53-7.55 (d, J=8.0 Hz, 2H), 7.87 (s, 1H), 8.15 (s, 1H); Mass (m/z): 251.0, 253.0 (M+H)$^+$.

Preparation 11: 4-(4-Chloromethyl-3-fluorophenyl)-1-methyl-1H-pyrazole (I-11)

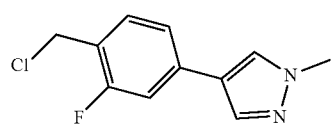

Step-1

4-(4-Hydroxymethyl-3-fluorophenyl)-1-methyl-1H-pyrazole was synthesized from 2-fluoro-4-bromo benzaldehyde by procedure as described in step-1 and step-2 of preparation 10. The crude compound obtained was further purified by flash chromatography using ethyl acetate:n-hexane (70:30) to get pure compound.

Yield: 0.95 g; $^1$H-NMR (CDCl$_3$, 400 MHz) δ ppm: 3.94 (s, 3H), 4.75 (s, 2H), 7.13-7.16 (m, 1H), 7.23-7.24 (d, J=1.2 Hz, 1H), 7.37-7.41 (t, J=7.8 Hz, 1H), 7.61 (s, 1H), 7.74 (s, 1H); Mass (m/z): 207.2 (M+H)$^+$.

Step-2

4-(4-Hydroxymethyl-3-fluorophenyl)-1-methyl-1H-pyrazole was converted to the title compound using similar procedure as described in step-2 of preparation 4.

Yield: 0.13 g; $^1$H-NMR (CDCl$_3$, 400 MHz) δ ppm: 3.95 (s, 3H), 4.64 (s, 2H), 7.15-7.17 (m, 1H), 7.23-7.24 (m, 1H), 7.36-7.40 (m, 1H), 7.61 (s, 1H), 7.74 (s, 1H); Mass (m/z): 225.2 (M+H)$^+$.

Preparation 12: 5-Bromomethyl-2'-fluoro-[2,5'] bipyridinyl (I-12)

Step-1

Methyl iodide (1.06 g, 0.007 mole) was added at 0-5° C. to a stirred suspension of 6-bromonicotinic acid (1.0 g, 0.004 mol) and K$_2$CO$_3$ (2.06 g, 0.014 mole) in DMF (15 mL) at 25-30° C. and then reaction mass was warmed to 55° C. for 4 hours. The reaction mixture was poured on to cold water (50 mL) and extracted with ethyl acetate (50 mL×3). The combined organic layers were washed with brine solution (50 mL) and dried over anhydrous Na$_2$SO$_4$ and concentrated under vacuum to obtain methyl 6-bromonicotinate.

Yield: 0.909 g; $^1$H-NMR (DMSO-d$_6$, 400 MHz) δ ppm: 3.89 (s, 3H), 7.83-7.85 (d, J=8.3 Hz, 1H), 8.18-8.21 (dd, J=2.3, 8.2 Hz, 1H), 8.87-8.88 (d, J=2.3 Hz, 1H); Mass (m/z): 216.1 (M+H)$^+$.

Step-2

Pd(PPh$_3$)$_4$ was added to a stirred mixture of methyl 6-bromonicotinate (0.70 g, 0.003 mole), 6-fluoropyridine-3-boronic acid (0.505 g, 0.003 mole) and K$_2$CO$_3$ (0.9 g, 0.006 mole) in a mixture of DME and water (12 mL, 5:1) and reaction mixture was refluxed for 12 hours. The reaction mixture was then cooled to RT, filtered through celite and washed the residue with ethyl acetate. The filtrate was dried over anhydrous Na$_2$SO$_4$ and concentrated under vacuum to obtain methyl 2'-fluoro-[2, 5'] bipyridinyl-5-carboxylate.

Yield: 0.38 g; $^1$H-NMR (DMSO-d$_6$, 400 MHz) δ ppm: 3.9 (s, 3H), 7.36-7.39 (m, 1H), 8.23-8.25 (d, J=8.3 Hz, 1H), 8.39-8.42 (m, 1H), 8.72-8.73 (d, J=2.2 Hz, 1H), 9.02-9.02 (d, J=1.8, 1H) 9.18-9.19 (d, J=1.5, 1H); Mass (m/z): 233.2 (M+H)$^+$.

Step-3

Methyl 2'-fluoro-[2, 5'] bipyridinyl-5-carboxylate was reacted with lithium aluminium hydride by the procedure as described in step 2 of preparation 3 to obtain 5-hydroxymethyl-2'-fluoro-[2, 5'] bipyridine.

Yield: 0.294 g; $^1$H-NMR (DMSO-d$_6$, 400 MHz) δ ppm: 4.59 (s, 2H), 5.38-5.41 (t, 1H), 7.29-7.32 (d, J=8.0 Hz, 1H), 7.84-7.86 (d, J=1.8 Hz, 1H), 8.02-8.04 (d, J=8.2 Hz, 1H), 8.61-8.65 (m, 2H) 8.92-8.92 (d, J=1.8, 1H); Mass (m/z): 205.1 (M+H)$^+$.

Step-4

5-Hydroxymethyl-2'-fluoro-[2, 5']bipyridine was reacted with phosphorus tribromide by the procedure as described in step 3 of preparation 3 to obtain the title compound, 5-bromomethyl-2'-fluoro-[2, 5'] bipyridinyl.

Yield: 0.150 g; $^1$H-NMR (CDCl$_3$, 400 MHz) δ ppm: 4.53 (s, 2H), 7.04-7.07 (m, 1H), 7.72-7.74 (d, J=8.0 Hz, 1H), 7.86-7.88 (d, J=7.2 Hz, 1H), 8.47-8.50 (m, 1H), 8.773 (s, 1H), 8.80-8.80 (d, J=1.84 Hz, 1H); Mass (m/z): 267.0, 269.0 (M+H)$^+$.

Preparation 13: 5-Bromomethyl-2-(1-methyl-1H-pyrazol-4-yl)pyridine (I-13)

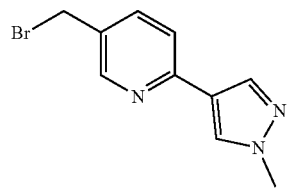

Step-1

Pd(dppf)Cl$_2$.CH$_2$Cl$_2$ (0.13 gm, 0.0001 mole) was added to a stirred mixture of 6-bromopyridine-3-carboxaldehyde (0.6 g, 0.003 mole), sodium carbonate (1.02 g, 0.0096 mole) and 1-methyl-4-(4,4,5,5-tetramethyl-[1,3,2]dioxaborolan-2-yl)-1H-pyrazole (1.34 g, 0.006 mole) in a mixture 1,4-dioxane and water (25 mL, 4:1). The reaction mixture was heated to 70-80° C. and maintained for 6 hours, cooled to RT, diluted with H$_2$O (10 mL), extracted with ethyl acetate (25 mL×3). The organic extracts were combined, dried over anhydrous Na$_2$SO$_4$ and concentrated under vacuum to obtain the crude compound that was further purified by flash chromatography using ethyl acetate:hexane (60:40) to obtain 6-(1-methyl-1H-pyrazol-4-yl)pyridine-3-carboxaldehyde.

Yield: 0.54 g; $^1$H-NMR (CDCl$_3$, 400 MHz) δ ppm: 3.98 (s, 3H), 7.57-7.59 (d, J=8.2 Hz, 1H), 8.03-8.04 (d, J=3.44 Hz, 2H), 8.11-8.14 (m, 1H), 8.96-8.96 (d, J=1.0 Hz, 1H), 10.04 (s, 1H); Mass (m/z): 188.0 (M+H)$^+$.

Step-2

6-(1-Methyl-1H-pyrazol-4-yl)pyridine-3-carboxaldehyde was reacted with NaBH$_4$ by the procedure as described in step 2 of preparation 3 to obtain 5-hydroxymethyl-2-(1-methyl-1H-pyrazol-4-yl)pyridine.

Yield: 0.50 g; $^1$H-NMR (DMSO-d$_6$, 400 MHz) δ ppm: 3.87 (s, 3H), 4.48-4.50 (d, J=5.52 Hz, 2H), 5.24-5.27 (m, 1H), 7.58-7.60 (d, J=8.04 Hz, 1H), 7.68-7.69 (d, J=1.56 Hz, 1H), 7.96 (s, 1H), 8.24 (s, 1H), 8.43 (s, 1H); Mass (m/z): 190.1 (M+H)$^+$.

Step-3

A solution of 5-hydroxymethyl-2-(1-methyl-1H-pyrazol-4-yl)pyridine (0.4 g, 0.002 mole) in DCM (20 mL) was added to a stirred solution of carbon tetrabromide (0.84 g, 0.0025 mole) and triphenyl phosphine (1.6 g, 0.006 mole) in DCM (25 mL) at 0-5° C. and then stirred at RT for 2 hours. The reaction mixture was poured on to water (50 mL) and separated the organic layer. The organic layer was washed with aq. sodium bicarbonate solution (25 mL), dried over anhydrous $Na_2SO_4$ and concentrated under vacuum to obtain the crude compound that was further purified by flash chromatography using ethyl acetate:hexane (60:40) to obtain 5-bromomethyl-2-(1-methyl-1H-pyrazol-4-yl)pyridine that was used immediately for further reaction.

Preparation 14: 4-(4-Bromomethylphenyl)thiazole (I-14)

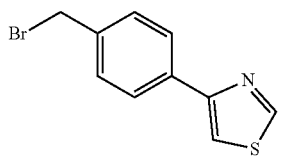 [SMILES: BrCc1ccc(-c2cscn2)cc1]

Step-1

$Pd(dppf)Cl_2.CH_2Cl_2$ (0.65 g, 0.0008 mol) was added to a sealed tube containing a mixture of 4-bromobenzaldehyde (1.51 g, 0.008 mole), potassium acetate (1.96 g, 0.02 mole) and bis(pinacolato)diboron (2.6 g, 0.01 mole) in toluene (20 mL) and the contents were heated to 90-100° C. for 6 hours and then cooled to room temperature. The reaction mass was filtered through a pad of celite and washed with ethyl acetate (20 mL×2). The filtrate was concentrated under vacuum to obtain the crude compound that was further purified by flash chromatography using ethyl acetate:hexanes (10:90) to obtain 4-(4,4,5,5-tetramethyl-[1,3,2]dioxaborolan-2-yl)benzaldehyde.

Yield: 1.77 g; $^1$H-NMR ($CDCl_3$, 400 MHz) δ ppm: 1.36 (s, 12H), 7.85-7.89 (d, J=7.8 Hz, 2H), 7.95-7.97 (d, J=7.8 Hz, 2H), 10.04 (s, 1H).

Step-2

$Pd(dppf)Cl_2.CH_2Cl_2$ (0.17 g, 0.0002 mole) was added to a stirred mixture of 4-bromothiazole (0.7 g, 0.004 mol), sodium carbonate (1.3 g, 0.012 mole) and 4-(4,4,5,5-tetramethyl-[1,3,2]dioxaborolan-2-yl)benzaldehyde (1.89 g, 0.008 mole) in a mixture of 1,4-dioxane and water (25 mL, 4:1). The reaction mixture was heated to 80° C. and maintained for 6 hours, cooled to RT, diluted with $H_2O$ (10 mL), extracted with ethyl acetate (25 mL×3). The organic extracts were combined, dried over anhydrous $Na_2SO_4$ and concentrated under vacuum to obtain the crude 4-(thiazol-4-yl) benzaldehyde that was used as such for further reaction.

Step-3

4-(Thiazol-4-yl) benzaldehyde was reacted with $NaBH_4$ to obtain 4-(4-hydroxymethylphenyl)thiazole by the procedure as described in step-2 of preparation 10.

Yield: 0.58 g; $^1$H-NMR ($CDCl_3$, 400 MHz) δ ppm: 1.76-1.79 (m, 1H), 4.73-4.74 (d, J=5.0 Hz, 2H), 4.73-4.74 (d, J=8.0 Hz, 2H), 7.54-7.54 (d, J=1.8 Hz, 1H), 7.92-7.94 (d, J=8.2 Hz, 2H), 8.87-8.88 (d, J=1.5 Hz, 1H); Mass (m/z): 192.1 $(M+H)^+$.

Step-4

4-(4-Hydroxymethylphenyl)thiazole was reacted with phosphorus tribromide by the procedure as described in step-3 of preparation 3 to obtain the title compound, 4-(4-bromomethylphenyl)thiazole.

Yield: 0.42 g; $^1$H-NMR ($CDCl_3$, 400 MHz) δ ppm: 4.54 (s, 2H), 7.46-7.48 (d, J=8.02 Hz, 2H), 7.56-7.56 (d, J=1.44 Hz, 1H), 7.90-7.92 (d, J=8.24 Hz, 2H), 8.89-8.89 (d, J=1.36 Hz, 1H); Mass (m/z): 253.8, 255.9 $(M+H)^+$.

Preparation 15:
1-(4-Bromomethylphenyl)-1H-pyrazole (I-15)

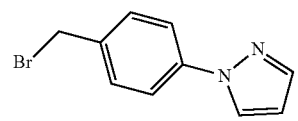

Step-1

To a solution of 4-bromobenzaldehyde (2.0 g, 0.010 mole) in DMF 20 mL under $N_2$ at 25° C., was added 1H-pyrazole (0.668 g, 0.0098 mole), copper iodide (0.185 g, 0.0009 mole), L-proline (0.224 g, 0.0019 mole) and cesium carbonate (6.4 g, 0.0196 mole). The reaction mixture was heated at 120° C. for 20 hours, cooled to RT, filtered through celite and washed with ethyl acetate (50 mL). The filtrate was concentrated under vacuum to obtain the crude compound which was further purified by flash chromatography using ethyl acetate:n-hexane (40:60) to obtain 4-(pyrazol-1-yl)benzaldehyde.

Yield: 1.0 g; $^1$H-NMR (DMSO-$d_6$, 400 MHz) δ ppm: 6.62 (s, 1H), 7.84 (s, 1H), 8.01-8.03 (d, J=8.4 Hz, 2H), 8.07 (d, J=8.4 Hz, 2H), 8.67 (s, 1H), 10.00 (s, 1H); Mass (m/z): 173.1 $(M+H)^+$.

Step-2

1-(4-Hydroxymethylphenyl)-1H-pyrazole was synthesized from 4-(pyrazol-1-yl)benzaldehyde by the procedure described in step-2 of preparation 10.

Yield: 0.5 g; $^1$H-NMR (DMSO-$d_6$, 400 MHz) δ ppm: 4.52-4.53 (d, J=5.6 Hz, 2H), 5.23-5.26 (t, J=5.7 Hz, 1H), 6.52 (s, 1H), 7.41-7.43 (d, J=8.3 Hz, 2H), 7.72 (s, 1H), 7.77-7.79 (d, J=8.3 Hz, 2H), 8.09 (d, J=2.3 Hz, 1H); Mass (m/z): 175.1 $(M+H)^+$.

Step-3

The title compound was synthesized from 1-(4-hydroxymethylphenyl)-1H-pyrazole by the procedure described in step-3 of preparation 3.

Yield: 0.33 g; $^1$H-NMR (DMSO-$d_6$, 400 MHz) δ ppm: 4.76 (s, 2H), 6.55 (s, 1H), 7.56-7.58 (d, J=8.5 Hz, 2H), 7.75 (s, 1H), 7.82-7.84 (d, J=8.4 Hz, 2H), 8.51-8.52 (d, J=2.4 Hz, 1H); Mass (m/z): 237.0 $(M+H)^+$, 238.9 $(M+H)^+$.

Preparation 16:
5-Chloromethyl-2-methylsulfanylpyridine (I-16)

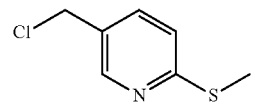

Step 1

To a solution of 6-chloronicotinic acid (0.5 g, 0.0031 mole) in DMSO (10 mL) under $N_2$ at 25° C., was added sodium methane thiolate (0.55 g, 0.0079 mole). The reaction mixture was warmed to 80° C. for 2 hours, cooled to RT, treated with 2.2 mL of HCl and stirred for 15 minutes. Then the reaction mixture was diluted with ethyl acetate (30 mL) and concentrated under vacuum to obtain 6-methylsulfanyl nicotinic acid.

Yield: 0.46 g; Mass (m/z): 168.3 $(M-H)^-$.

Step 2

To a solution of 6-methylsulfanyl nicotinic acid (0.53 g, 0.0031 mole) in a mixture of DCM (10 mL) and methanol (5 mL) under $N_2$ at 25° C., was added (trimethylsilyl) diazomethane (2.0 M in n-hexane, 16 mL, 0.0314 mole). Reaction mixture was stirred for 26 hours at RT, quenched in to ice cold water (20 mL) and extracted with ethyl acetate (50 mL×3). Organic layer was washed with brine solution (20 mL), dried over $Na_2SO_4$ and concentrated under vacuum to obtain methyl 6-methylsulfanyl nicotinate.

Yield: 0.56 g; $^1$H-NMR (DMSO-$d_6$, 400 MHz) δ ppm: 2.58-2.60 (s, 3H), 3.73-3.77 (s, 3H), 7.42-7.44 (d, J=8.0 Hz, 1H), 8.06-8.08 (d, J=8.4 Hz, 1H), 8.90 (s, 1H); Mass (m/z): 184.3 $(M+H)^+$.

Step-3

To solution of methyl 6-methylsulfanyl nicotinate (0.76 g, 0.00415 mole) in a mixture of diethyl ether (8 mL) and DCM (8 mL) at 0° C. under $N_2$ was added lithium borohydride (2.0M in n-hexane, 4.1 mL, 0.008 mole) drop-wise followed by methanol (0.25 mL, 0.008 mole). The mass was stirred for 5 minutes and then warmed to RT, stirred for 3 hours, additional lithium borohydride (2.0 M in n-hexane, 4.1 mL, 0.008 mole) and methanol (0.25 mL, 0.008 mole) were added and further stirred for 15 hours at RT. Then the reaction mixture was treated with saturated solution of sodium bicarbonate and extracted with DCM (50 mL×3). Organic layer was washed with water (50 mL), brine solution (50 mL), dried over $Na_2SO_4$ and concentrated under vacuum to obtain (2-methylsulfanylpyridin-5-yl)methanol.

Yield: 0.47 g; $^1$H-NMR (DMSO-$d_6$, 400 MHz) δ ppm: 2.44-2.48 (s, 3H), 4.50-4.55 (s, 2H), 4.88-4.91 (t, 1H), 7.26-7.28 (d, J=8.2 Hz, 1H), 7.53-7.56 (d, J=8.1 Hz, 1H), 8.35 (s, 1H); Mass (m/z): 156.0 $(M+H)^+$.

Step-4

(2-Methylsulfanylpyridin-5-yl) methanol was converted into 5-chloromethyl-2-methylsulfanylpyridine by the procedure as described in step-2 preparation 4.

Yield: 0.17 g; $^1$H-NMR (DMSO-$d_6$, 400 MHz) δ ppm: 3.25-3.27 (s, 3H), 4.76 (s, 2H), 7.30-7.32 (d, J=8.2 Hz, 1H), 7.69-7.71 (d, J=8.1 Hz, 1H), 8.47 (s, 1H); Mass (m/z): 173.9, 176.2 $(M+H)^+$.

Preparation 17: 6-Bromomethylbenzothiazole (I-17)

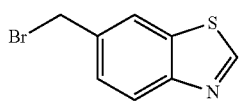 [SMILES: BrCc1ccc2ncsc2c1]

The title compound was synthesized from benzothiazole-6-carboxylic acid by the procedure described in preparation 3.

Yield: 0.19 g; $^1$H-NMR (CDCl$_3$, 400 MHz) δ ppm: 4.65 (s, 2H), 7.54-7.55 (d, J=8.0 Hz, 1H), 8.0 (s, 1H), 8.10-8.12 (d, J=8.4 Hz, 1H), 9.02 (s, 1H); Mass (m/z): 228.0, 229.8 $(M+H)^+$.

Preparation 18: 4-Bromomethyl-1-methyl-1H-benzimidazole hydrobromide (I-18)

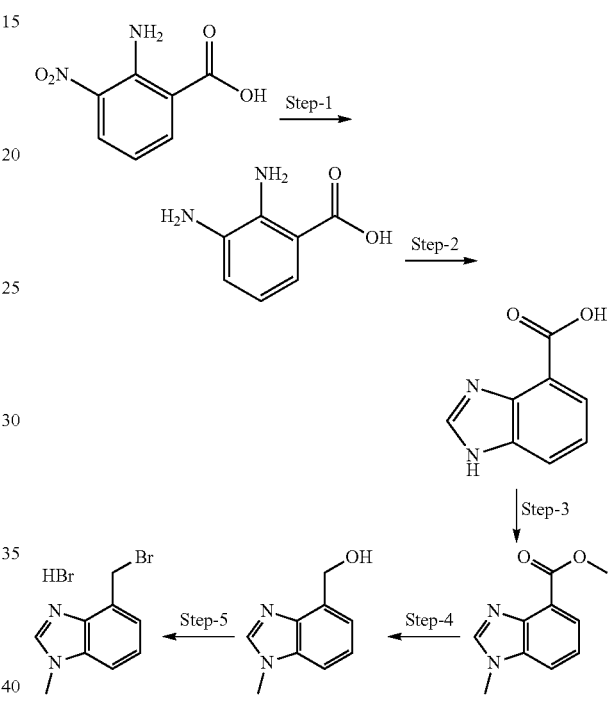

Step-1

To a solution of 2-amino-3-nitrobenzoic acid (2.0 g, 0.01092 mole) in methanol (30 mL) at 25° C., was added Pd/C (2.0 g) and stirred for 15 hours under $H_2$ gas atmosphere. Reaction mixture was filtered through celite, washed with methanol (50 mL) and filtrate was concentrated under vacuum to obtain 2,3-diaminobenzoic acid.

Yield: 1.5 g; $^1$H-NMR (DMSO-$d_6$, 400 MHz) δ ppm: 4.92-5.22 (m, 4H), 6.34-6.35 (t, J=7.6 Hz, 1H), 6.66-6.68 (d, J=7.3 Hz, 1H), 7.08-7.10 (d, J=7.9 Hz, 1H), 8.12 (m, 1H); Mass (m/z): 153.2 $(M+H)^+$.

Step-2

To a solution of 2,3-diaminobenzoic acid (1.4 g, 0.0092 mole) in 6N HCl (18.2 mL), formic acid (1.2 mL, 0.028 mole) was added, temperature raised to 105° C. and maintained there for 18 hours. Reaction mixture was treated with aqueous ammonia to pH 4.5, filtered through celite, washed with water (50 mL), n-hexane (50 mL), dissolved in methanol and concentrated under vacuum to obtain 1H-benzimidazole-4-carboxylic acid.

Yield: 1.37 g; $^1$H-NMR (DMSO-d$_6$, 400 MHz) δ ppm: 4.00-4.10 (m, 1H), 7.27-7.46 (m, 1H); 7.90-7.91 (d, J=2.2 Hz, 2H), 8.38 (m, 1H), 13.5 (bs, 1H); Mass (m/z): 163.1 (M+H)$^+$.

Step-3

1-Methyl-1H-benzimidazole-4-carboxylate was synthesized by the procedure as described in step-1 of preparation 3.

Yield: 0.38 g; $^1$H-NMR (DMSO-d$_6$, 400 MHz) δ ppm: 3.88 (s, 6H), 7.35-7.39 (t, 1H), 7.78-7.80 (d, J=7.9 Hz, 1H), 7.85-7.87 (d, J=2.4 Hz, 1H); 8.31 (s, 1H); Mass (m/z): 191.1 (M+H)$^+$.

Step-4

4-Hydroxymethyl-1-methyl-1H-benzimidazole was synthesized by the procedure as described in step-2 of preparation 3.

Yield: 0.40 g; $^1$H-NMR (DMSO-d$_6$, 400 MHz) δ ppm: 3.84 (s, 3H), 4.90-4.91 (d, 2H); 5.13-5.15 (t, 1H), 7.24-7.25 (d, J=6.9 Hz, 2H), 7.41-7.43 (d, J=8.4 Hz, 1H), 8.12 (s, 1H); Mass (m/z): 163.0 (M+H)$^+$.

Step-5

To a solution of 4-hydroxymethyl-1-methyl-1H-benzimidazole (0.45 g, 0.003 mole) in DCM (10 mL) at 0° C. under N$_2$, was added thionyl bromide (0.44 mL, 0.0037 mole) drop-wise. The reaction mixture was warmed to RT and stirred for 3 hours. The reaction mixture was concentrated under vacuum to obtain the title compound.

Yield: 0.18 g; $^1$H-NMR (DMSO-d$_6$, 400 MHz) δ ppm: 3.99 (s, 3H), 5.05 (s, 2H), 7.56-7.58 (d, J=7.8 Hz, 1H), 7.65-7.67 (d, J=7.3 Hz, 1H), 7.89-7.91 (d, J=8.2 Hz, 1H), 9.43 (s, 1H); Mass (m/z): 225.0, 226.9 (M+H)$^+$.

Preparation 19:
3-(4-Chloromethylphenyl)-2-methylpyridine (I-19)

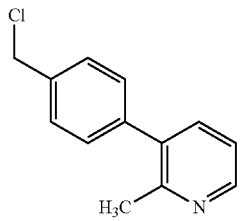

Step-1

Pd(dppf)Cl$_2$.CH$_2$Cl$_2$ (0.48 g, 0.0005 mole) was added to a sealed tube containing a mixture of 4-bromobenzaldehyde (1 g, 0.005 mole), potassium acetate (1.31 g, 0.013 mole) and bis(pinacolato)diboron (1.6 g, 0.006 mole) in toluene (20 mL) and the contents were heated at 90-100° C. for 6 hours and then cooled to room temperature. The reaction mass filtered through a pad of celite and washed with ethyl acetate (20 mL×2). The filtrate was concentrated under vacuum to obtain the crude compound that was further purified by flash chromatography using ethyl acetate: hexanes (10:90) to obtain 4-(4,4,5,5-tetramethyl-[1,3,2]dioxaborolan-2-yl)benzaldehyde.

Yield: 1.12 g; $^1$H-NMR (CDCl$_3$, 400 MHz) δ ppm: 1.36 (s, 12H), 7.85-7.87 (d, J=7.72 Hz, 2H), 7.95-7.97 (d, J=7.8 Hz, 2H), 10.05 (s, 1H); Mass (m/z): 233.0 (M+H)$^+$.

Step-2

4-(4,4,5,5-Tetramethyl-[1,3,2]dioxaborolan-2-yl)benzaldehyde was reacted with 3-bromo-2-methylpyridine by the procedure as described in step 2 of preparation 14 to obtain the title compound, 4-(2-methylpyridin-3-yl) benzaldehyde.

Yield: 0.19 g; $^1$H-NMR (CDCl$_3$, 400 MHz) δ ppm: 2.52 (s, 3H), 7.06 (s, 1H), 7.50-7.53 (m, 3H), 7.96-7.98 (d, J=8.04 Hz, 2H), 8.56-8.57 (d, J=1.24 Hz, 1H), 10.09 (s, 1H); Mass (m/z): 198.0 (M+H)$^+$.

Step-3

4-(2-Methylpyridin-3-yl)benzaldehyde was reacted with NaBH$_4$ to obtain 3-(4-hydroxymethylphenyl)-2-methylpyridine by the procedure as described in step-2 of preparation 10.

Yield: 0.17 g; $^1$H-NMR (CDCl$_3$, 400 MHz) δ ppm: 1.97 (m, 1H), 2.50 (s, 3H), 4.77 (s, 2H), 7.17-7.20 (m, 1H), 7.31-7.33 (d, J=7.96 Hz, 2H), 7.46-7.46 (d, J=7.86 Hz, 2H), 7.50-7.52 (m, 1H), 8.48-8.50 (m, 1H); Mass (m/z): 200.0 (M+H)$^+$.

Step-4

3-(4-Hydroxymethylphenyl)-2-methylpyridine was reacted with thionyl chloride by the procedure as described in step-2 of preparation 4 to obtain the title compound, 3-(4-chloromethylphenyl)-2-methylpyridine.

Yield: 0.14 g; $^1$H-NMR (CDCl$_3$, 400 MHz) δ ppm: 2.51 (s, 3H), 4.65 (s, 2H), 7.18-7.21 (m, 1H), 7.31-7.33 (d, J=8.04 Hz, 2H), 7.46-7.52 (m, 3H), 8.50-8.52 (m, 1H); Mass (m/z): 217.9, 220.0 (M+H)$^+$.

Preparation 20: cis-4-Aminotetrahydropyran-3-ol (I-20)

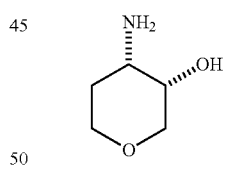

Step-1

To a solution of KOH (23.5 g, 0.419 mole) in methanol (230 mL) at 5° C., was added tetrahydropyran-4-one over a period of 20 minutes, a solution of iodine in methanol (300 mL) for 1 hour. After 30 minutes, the reaction mass was warmed to RT, stirred for 1 hour and diluted with toluene and concentrated to ⅓$^{rd}$ of its volume. Again toluene was added and concentrated to ⅓$^{rd}$ of its volume, filtered and diluted the filtrate with ethyl acetate. The organic layer was washed with water (100 mL), dried over Na$_2$SO$_4$ and concentrated under vacuum to get 4,4-dimethoxytetrahydropyran-3-ol.

Yield: 17.5 g; $^1$H-NMR (DMSO-d$_6$, 400 MHz) δ ppm: 1.57-1.60 (m, 1H), 1.75-1.82 (m, 1H), 3.09-3.10 (s, 6H), 3.21-3.31 (m, 1H), 3.43-3.45 (m, 1H), 3.48-3.51 (s, 1H), 3.56-3.59 (m, 2H), 4.47-4.75 (m, 1H).

Step-2

To a solution of above compound (17.5 g, 0.108 mole) in THF (170 mL) at 5° C. under $N_2$, was added sodium tert-butoxide (11.8 g, 0.123 mole) in one portion. Reaction mass was warmed to 35° C. for 1 hour and cooled to RT for 1 hour. tert-butyl ammonium iodide (1.99 g, 0.005 mole) and benzyl bromide were added at RT and warmed to 50° C. for 2 hours, cooled to RT, quenched in to water and extracted with ethyl acetate (100 mL×3). The organic layer was dried over $Na_2SO_4$ and concentrated under vacuum to obtain the crude residue which was further purified by flash chromatography using ethyl acetate:hexane (5:95) to afford 3-benzyloxy-4,4-dimethoxytetrahydropyran.

Yield: 15.5 g; $^1$H-NMR (DMSO-$d_6$, 400 MHz) δ ppm: 1.65-1.76 (m, 2H), 3.08-3.11 (d, 6H), 3.40-3.44 (m, 3H), 3.63-3.66 (m, 1H), 3.92-3.95 (m, 1H), 4.47-4.49 (m, 1H), 4.61-4.64 (m, 1H), 7.27-7.35 (m, 5H).

Step-3

To a solution of above compound (14.1 g, 0.056 mole) in THF (75 mL) at 25° C. under $N_2$, was added 2N HCl (75 mL) drop wise and stirred at RT for 1.5 hours. Reaction mixture was neutralized with saturated aqueous $K_2CO_3$ solution and extracted with ethyl acetate (100 mL×3). The organic layer was dried over $Na_2SO_4$ and concentrated under vacuum to obtain the crude compound which was further purified by flash chromatography using ethyl acetate:hexane (15:85) to afford 3-benzyloxytetrahydropyran-4-one.

Yield: 9.9 g; $^1$H-NMR (DMSO-$d_6$, 400 MHz) δ ppm: 2.32-2.37 (m, 1H), 2.61-2.67 (m, 1H), 3.39-3.43 (m, 1H), 3.57-3.63 (m, 1H), 4.02-4.06 (m, 1H), 4.09-4.16 (m, 2H), 4.75-4.50 (m, 1H), 4.69-4.72 (m, 1H), 7.21-7.36 (m, 5H).

Step-4

To a solution of above prepared compound (2.5 g, 0.012 mole) in DCM (50 mL) at 25° C. under $N_2$, was added benzylamine (1.4 g, 0.013 mole) in one portion and stirred for 1 hour. Then sodium triacetoxyborohydride (4.7 g, 0.022 mole) was added at 10° C. and stirred for 12 hours. Reaction mixture was quenched onto water and extracted with DCM (50 mL×3). The organic layer was dried over $Na_2SO_4$ and concentrated under vacuum to obtain the crude compound which was further purified by flash chromatography using methanol:chloroform (2:98) to afford N-benzyl(3-benzyloxytetrahydropyran-4-yl)amine.

Yield: 2.6 g; $^1$H-NMR (DMSO-$d_6$, 400 MHz) δ ppm: 1.49-1.53 (m, 1H), 1.59-1.62 (m, 1H), 1.84-1.87 (m, 1H), 2.73-2.75 (m, 1H), 3.24-3.32 (m, 2H), 3.55-3.63 (m, 3H), 3.73-3.76 (m, 1H), 3.88-3.92 (m, 1H), 4.41-4.44 (m, 1H), 4.55-4.58 (m, 1H), 7.20-7.33 (m, 10H); Mass (m/z): 298.2 (M+H)$^+$.

Step-5

To a solution of above compound (1.8 g, 0.06 mole) in methanol (50 mL), 10% Pd/C (1.8 g) was added in one portion and stirred for 6 hours under $H_2$ gas bubbling. Reaction mixture was filtered through celite and filtrate was concentrated under vacuum to obtain the title compound.

Yield: 0.65 g; $^1$H-NMR (DMSO-$d_6$, 400 MHz) δ ppm: 1.45-1.48 (m, 1H), 1.56-1.60 (m, 1H), 1.87 (m, 3H), 2.89- 2.90 (m, 1H), 3.16 (m, 1H), 3.27-3.34 (m, 1H), 3.47 (m, 1H), 3.60-3.63 (m, 1H), 3.69-3.72 (m, 1H); Mass (m/z): 118.1 (M+H)$^+$.

Preparation 21: trans-4-Aminotetrahydropyran-3-ol hydrochloride (I-21)

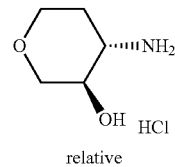

relative trans-4-Aminotetrahydropyran-3-ol was prepared by following the procedure as mentioned in WO2013/055577. This compound was converted into hydrochloride salt using the following procedure.

To a solution of the above compound (1.2 g, 0.01 moles) in DCM (10 mL) at 0-10° C. under $N_2$, was added IPA HCl (17% w/w, 2.9 g, 0.08 moles) slowly. After addition, reaction mass was allowed to 25° C. and stirred for 5 hours. Reaction mass was concentrated under vacuum. The reaction mass was triturated with diethyl ether (10 mL×2), decanted the solvent and solids were dried under vacuum to afford the title compound.

Yield: 1.5 g; $^1$H-NMR (DMSO-$d_6$, 400 MHz) δ ppm: 1.53-1.64 (m, 1H), 1.89-1.93 (m, 1H), 2.94-2.99 (m, 2H), 3.23-3.29 (m, 1H), 3.43-3.48 (m, 1H), 3.76-3.80 (m, 2H), 5.62-5.64 (d, J=4.6 Hz, 1H), 8.17 (bs, 3H); Mass (m/z): 118.1 (M+H)$^+$.

Preparation 22: trans-4-Aminotetrahydropyran-3-ol hydrochloride (Isomer-II) (I-22)

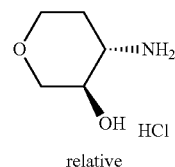

relative

Step-1: 4-Benzyloxycarbonylamino-3-hydroxy tetrahydropyran

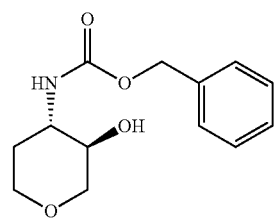 [SMILES: O=C(N[C@H]1CCOC[C@@H]1O)OCc1ccccc1]

To a solution of trans-4-aminotetrahydropyran-3-ol hydrochloride (preparation 21, 2.0 g, 0.013 mole) in water (50 mL) at 0° C., was added sodium carbonate (6.9 g, 0.06 mole) and stirred for 10 minutes. Benzyl chloroformate (6.7 g, 0.03 mole) was added at 0° C., reaction mixture was warmed to RT and stirred for overnight. Reaction mixture was diluted with water (50 mL) and extracted with ethyl acetate (100 mL×3). The organic layer was washed with brine solution (50 mL), dried over $Na_2SO_4$ and concentrated under vacuum to obtain the crude compound which was further purified by flash chromatography using ethyl acetate:n-hexane (50:50) to afford the title compound.

Yield: 1.4 g; $^1$H-NMR (DMSO-$d_6$, 400 MHz) δ ppm: 1.34-1.44 (m, 1H), 1.74-1.78 (m, 1H), 2.91-2.99 (m, 1H), 3.23-3.30 (m, 3H), 3.34-3.37 (m, 1H), 3.72-3.76 (m, 2H), 4.86-4.89 (d, J=4.6 Hz, 1H), 5.01 (s, 2H), 7.20-7.22 (d, J=7.5 Hz, 1H), 7.29-7.33 (m, 1H), 7.35-7.38 (m, 3H); Mass (m/z): 252.1 (M+H)$^+$.

The enantiomers were separated by chiral chromatography.

Isomer-I:
Chiral HPLC: 99.70%, Method: CHIRALPAK AD-H, 250×4.6 mm, 5 μm; Solvent=0.1% DEA in MeOH; Isocratic Flow=0.8 mL/min; T=25° C., retention time=7.64 min, wavelength=210 nm.

Isomer-II:
Chiral HPLC: 99.06%, Method: CHIRALPAK AD-H, 250×4.6 mm, 5 μm; Solvent=0.1% DEA in MeOH; Isocratic Flow=0.8 mL/min; T=25° C., retention time=7.99 min, wavelength=210 nm.

Step-2: trans-4-Aminotetrahydropyran-3-ol hydrochloride (Isomer-II)

To a solution of 4-benzyloxycarbonylamino-3-hydroxytetrahydropyran (Isomer-II, 0.52 g, 0.0009 mole) in methanol (25 mL) was added 10% palladium on carbon (0.03 g, 0.00002 mole) and stirred under hydrogen atmosphere for 3 hours and filtered the mass through celite. The filtrate was acidified with IPA HCl (5 volumes) and concentrated under vacuum to afford trans-4-aminotetrahydropyran-3-ol hydrochloride.

Yield: 0.15 g; $^1$H-NMR (DMSO-$d_6$, 400 MHz) δ ppm: 1.54-1.58 (m, 1H), 1.88-1.92 (m, 1H), 2.92-3.01 (m, 2H), 3.23-3.29 (m, 1H), 3.36-3.42 (m, 1H), 3.78-3.83 (m, 2H), 5.60 (bs, 1H), 8.03 (bs, 3H).

Preparation 23: cis-3-Aminotetrahydropyran-4-ol hydrochloride (I-23)

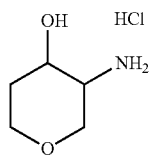

Step-1

4,4-Dimethoxydihydropyran-3-one was synthesized as per PCT/US2010/060007 by using 4,4-dimethoxytetrahydropyran-3-ol (preparation 20, step-1).

Yield: 4.1 g; $^1$H-NMR (DMSO-$d_6$, 400 MHz) δ ppm: 2.11-2.14 (m, 2H), 3.14 (s, 6H), 3.82-3.84 (m, 2H), 3.99 (s, 2H).

Step-2

N-Benzyl-(4,4-dimethoxytetrahydropyran-3-yl)-amine was synthesized by the procedure as described in step-4 of preparation 20 using 4,4-dimethoxydihydropyran-3-one (step-1) and EDC as solvent. Crude residue was further purified by flash chromatography using Methanol:DCM (1:99).

Yield: 3.4 g; $^1$H-NMR (DMSO-$d_6$, 400 MHz) δ ppm: 1.61-1.65 (m, 1H), 1.75-1.82 (m, 1H), 3.12 (s, 6H), 3.35-3.39 (m, 1H), 3.62-3.67 (m, 2H), 3.76-3.85 (m, 2H), 4.23-4.24 (d, 2H), 7.21-7.25 (m, 2H), 7.29-7.35 (m, 3H), 8.33 (bs, 1H); Mass (m/z): 252.2 (M+H)$^+$.

Step-3

To a solution of above compound (3.4 g, 0.014 mole) in THF (50 mL) at 10-15° C. under $N_2$, was added HCl (102 mL) dropwise and stirred at RT for overnight. Reaction mixture was neutralized with saturated aqueous $K_2CO_3$ solution and extracted with ethyl acetate (100 mL×4). The organic layer was dried over $Na_2SO_4$ and concentrated under vacuum to obtain the compound, 3-benzylaminotetrahydropyran-4-one.

Yield: 2.4 g; $^1$H-NMR (DMSO-$d_6$, 400 MHz) δ ppm: 1.49-1.55 (m, 1H), 1.71-1.78 (m, 1H), 3.39-3.45 (m, 2H), 3.62-3.66 (m, 2H), 3.76-3.78 (m, 2H), 4.47-4.49 (m, 1H), 7.23-7.25 (m, 2H), 7.30-7.33 (m, 3H), 8.34 (bs, 1H); Mass (m/z): 206.2 (M+H)$^+$.

Step-4

To a solution of 3-benzylaminotetrahydropyran-4-one (3.5 g, 0.165 mole) in THF (30 mL) at 0° C., under $N_2$, was added lithium aluminum hydride (1M in THF, 20 mL, 0.02 mole), stirred for 30 min at this temperature and warmed to RT for 1 hour. Reaction mixture was filtered through celite and filtrate was concentrated under vacuum to obtain the crude compound which was further purified by flash chromatography using methanol:chloroform (2:98) to afford 3-benzylaminotetrahydropyran-4-ol.

Yield: 0.85 g; $^1$H-NMR (DMSO-$d_6$, 400 MHz) δ ppm: 1.36-1.39 (m, 1H), 1.73-1.78 (m, 1H), 2.86-2.92 (m, 1H), 3.23-3.29 (m, 2H), 3.35-3.37 (m, 2H), 3.71-3.74 (m, 2H), 3.82-3.85 (m, 1H), 4.88-4.90 (m, 1H), 7.21-7.22 (m, 2H), 7.27-7.32 (m, 3H), 8.33 (bs, 1H); Mass (m/z): 208.2 (M+H)$^+$.

Step-5

To a solution of 3-benzylaminotetrahydropyran-4-ol (0.42 g, 0.002 mole) in methanol (50 mL), 10% palladium on carbon (0.42 g, 0.002 mole) was added in one portion and stirred for 6 hours under $H_2$ gas bubbling. Reaction mixture was filtered through celite, filtrate was concentrated under vacuum to $\frac{1}{3}^{rd}$ of its volume, was added IPA HCl (17% w/w, 0.58 g, 0.16 moles) slowly at 0° C. and concentrated under vacuum. The reaction mass was triturated with diethyl ether (10 mL×2), decant the solvent and solids were dried under vacuum to afford the title compound.

Yield: 0.16 g; $^1$H-NMR (DMSO-$d_6$, 400 MHz) δ ppm: 1.43-1.53 (m, 1H), 1.89-1.91 (m, 1H), 2.82-2.85 (m, 1H), 3.18-3.32 (m, 2H), 3.56-3.60 (m, 1H), 3.80-3.83 (m, 1H), 3.89-3.93 (m, 1H), 5.52-5.54 (bs, 1H), 7.99 (bs, 3H).

Example 1

N-[(1S,2S)-2-Hydroxycyclohexyl]-4-(2-fluoropyridin-4-ylmethyl)-1-methyl-1H-pyrrolo[2,3-b]pyridine-6-carboxamide

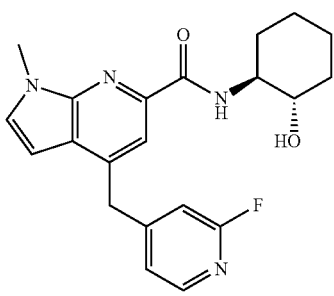 [SMILES: Cn1ccc2c(Cc3ccnc(F)c3)cc(C(=O)N[C@H]3CCCC[C@@H]3O)nc21]

Step-1: 4-Bromo-1H-pyrrolo[2,3-b]pyridine-7-oxide

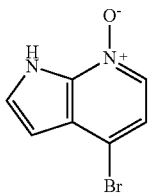

To a solution of 4-bromo-1H-pyrrolo[2,3-b]pyridine (10.1 g, 0.52 mole) in DCM (120 mL) at 0-5° C. under $N_2$, was added meta-chloroperoxybenzoic acid (13.5 g, 0.59 mole), warmed to RT and stirred for 20 hours. Reaction mixture was concentrated under vacuum to obtain the crude compound which was further purified by flash chromatography using DCM:methanol (98:2) to afford 4-bromo-1H-pyrrolo[2,3-b]pyridine-7-oxide.

Yield: 8.3 g; $^1$H-NMR (DMSO-$d_6$, 400 MHz) δ ppm: 6.50-6.51 (d, J=3.1 Hz, 1H), 7.32-7.33 (d, J=6.5 Hz, 1H), 7.56-7.57 (d, J=3.1 Hz, 1H), 8.07-8.08 (d, J=6.5 Hz, 1H), 12.88 (bs, 1H); Mass (m/z): 213.1 (M+H)+, 215.1 (M+H)$^+$.

Step-2: 4-Bromo-1H-pyrrolo[2,3-b]pyridine-6-carbonitrile

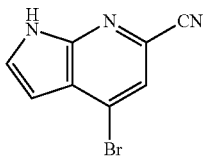

To a solution of 4-bromo-1H-pyrrolo[2,3-b]pyridine-7-oxide (8.1 g, 0.038 mole) in acetonitrile (80 mL) at 20-25° C. under $N_2$, was added trimethylsilyl cyanide (56.4 g, 0.57 mole), warmed to 85° C. and stirred for 20 hours. Reaction mixture was concentrated under vacuum to obtain the crude compound which was further purified by flash chromatography using ethyl acetate:n-hexane (30:70) to afford 4-bromo-6-cyano-1H-pyrrolo[2,3-b] pyridine.

Yield: 4.96 g; $^1$H-NMR (DMSO-$d_6$, 400 MHz) δ ppm: 6.60-6.61 (m, 1H), 7.97-7.98 (m, 1H), 8.02-8.3 (m, 1H), 12.67 (s, 1H); Mass (m/z): 222.0 (M+H)$^+$, 223.1 (M+H)$^+$.

Step-3: 4-Bromo-1H-pyrrolo[2,3-b]pyridine-6-carboxylic acid

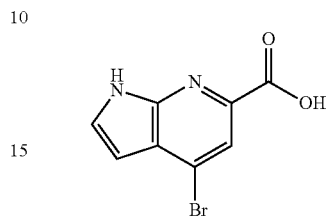

To a solution of potassium hydroxide (10.1 g, 0.18 mole) in water (130 mL) at 25° C., was added 4-bromo-6-cyano-1H-pyrrolo[2,3-b] pyridine (2 g, 0.009 mole) and warmed to 100° C. for 7 hours. Reaction mass was cooled to 2-5° C., acidified with diluted HCl, filtered the solids, dissolved in 200 mL of a mixture of DCM:methanol (80:20) and dried over $Na_2SO_4$. The organic phase was concentrated under vacuum to obtain 4-bromo-1H-pyrrolo[2,3-b] pyridine-6-carboxylic acid.

Yield: 2.0 g; $^1$H-NMR (DMSO-$d_6$, 400 MHz) δ ppm: 6.53 (s, 1H), 7.86-7.88 (m, 1H), 7.96 (s, 1H), 12.45 (s, 1H), 13.14 (bs, 1H); Mass (m/z): 241.1 (M+H)$^+$, 243.0 (M+H)$^+$.

Step-4: Methyl 4-bromo-1-methyl-1H-pyrrolo[2,3-b]pyridine-6-carboxylate

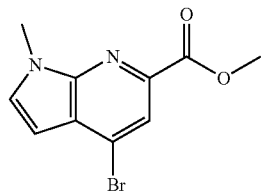

A solution of 4-bromo-1H-pyrrolo[2,3-b] pyridine-6-carboxylic acid (2.0 g, 0.0083 mole) in DMF (10 mL) under $N_2$ at 25° C., was added to suspension of sodium hydride (0.99 g, 0.024 mole) in DMF (10 mL) and stirred for 1 hour. Methyl iodide (1.6 mL, 0.025 mole) was added at RT and warmed to 65° C. for 6 hours. Reaction mixture was quenched onto ice water (75 mL) and extracted with ethyl acetate (50 mL×3). Organic layer was washed with water (50 mL), brine solution (50 mL), dried over $Na_2SO_4$ and concentrated under vacuum to obtain the crude compound which was further purified by flash chromatography using ethyl acetate:n-hexane (30:70) to obtain methyl 4-bromo-1-methyl-1H-pyrrolo[2,3-b]pyridine-6-carboxylate.

Yield: 1.51 g; $^1$H-NMR (DMSO-$d_6$, 400 MHz) δ ppm: 3.89 (s, 3H), 3.91 (s, 3H), 6.56-6.57 (d, J=3.45 Hz, 1H), 7.93-7.94 (d, J=3.4 Hz, 1H), 8.00 (s, 1H); Mass (m/z): 269.0, 271.1 (M+H)$^+$.

Step-5: Methyl 1-methyl-4-(4,4,5,5-tetramethyl-[1,3,2]dioxaborolan-2-yl)-1H-pyrrolo[2,3-b]pyridine-6-carboxylate

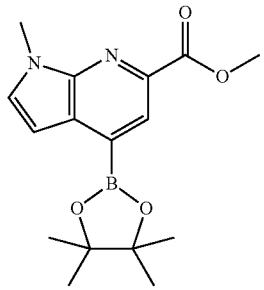 [SMILES: COC(=O)c1cc(B2OC(C)(C)C(C)(C)O2)c2ccn(C)c2n1]

To a solution of methyl 4-bromo-1-methyl-1H-pyrrolo[2,3-b]pyridine-6-carboxylate (0.49 g, 0.0018 mole) in toluene (15 mL) in a sealed tube under $N_2$ at 25° C., was added potassium acetate (0.57 g, 0.0058 mole), bis(pinacolato) diboron (0.57 g, 0.0023 mole) and 1,1-bis(diphenylphosphino)ferrocenepalladium(II) dichloride dichloromethane complex (0.10 g, 0.00012 mole). The reaction mixture was heated at 95° C. for 8 hours, cooled to RT, filtered through a pad of celite and washed with toluene (10 mL×2). The filtrate was concentrated under vacuum to obtain the crude compound which was further purified by flash chromatography using ethyl acetate:n-hexane (30:70) to obtain methyl 1-methyl-4-(4,4,5,5-tetramethyl-[1,3,2]dioxaborolan-2-yl)-1H-pyrrolo[2,3-b]pyridine-6-carboxylate.

Yield: 0.4 g; $^1$H-NMR (DMSO-$d_6$, 400 MHz) δ ppm: 1.36 (s, 12H), 3.88 (s, 3H), 3.90 (s, 3H), 6.74-6.75 (d, J=3.2 Hz, 1H), 7.85-7.86 (d, J=3.1 Hz, 1H), 8.09 (s, 1H); Mass (m/z): 317.2 (M+H)$^+$.

Step-6: Methyl 1-methyl-4-(2-fluoropyridin-4-ylmethyl)-1H-pyrrolo[2,3-b]pyridine-6-carboxylate

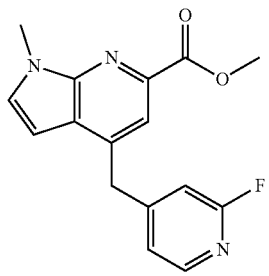 [SMILES: COC(=O)c1cc(Cc2ccnc(F)c2)c2ccn(C)c2n1]

To a solution of methyl 1-methyl-4-(4,4,5,5-tetramethyl-[1,3,2]dioxaborolan-2-yl)-1H-pyrrolo[2,3-b]pyridine-6-carboxylate (0.45 g, 0.0014 mole) in a mixture of 8 mL of THF and 0.8 mL of water under $N_2$, was added 4-bromomethyl-2-fluoropyridine (I-1, 0.3 g, 0.0017 mole), cesium carbonate (1.85 g, 0.0056 mole) and [1,1'-bis(diphenyl phosphino) ferrocene] dichloro-palladium (II), 1:1 complex with dichloromethane (0.116 g, 0.00014 mole). The mixture was irradiated in a microwave reactor at 75° C. for 60 minutes, cooled to RT, filtered through celite, and washed with ethyl acetate (30 mL×2). The filtrate was concentrated under vacuum to obtain the crude compound which was further purified by flash chromatography using ethyl acetate:n-hexane (30:70) to obtain the title compound.

Yield: 0.32 g; $^1$H-NMR (DMSO-$d_6$, 400 MHz) δ ppm: 3.85 (s, 3H), 3.88 (s, 3H), 4.40 (s, 2H), 6.70-6.71 (d, J=3.3 Hz, 1H), 7.15 (s, 1H), 7.25-7.26 (d, J=4.8 Hz, 1H), 7.76 (s, 1H), 7.77-7.78 (d, J=1.8 Hz, 1H), 8.11-8.12 (d, J=5.1 Hz, 1H); Mass (m/z): 300.0 (M+H).

Step-7: 1-Methyl-4-(2-fluoropyridin-4-ylmethyl)-1H-pyrrolo[2,3-b]pyridine-6-carboxylic acid

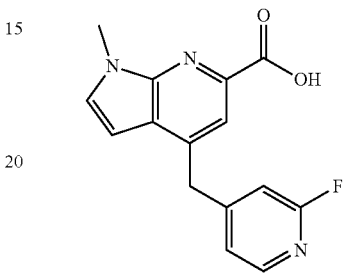

To a solution of methyl 1-methyl-4-(2-fluoropyridin-4-ylmethyl)-1H-pyrrolo[2,3-b]pyridine-6-carboxylate (0.25 g, 0.856 mole) in THF (6 mL) at 25° C., was added 2N aqueous sodium hydroxide (2.6 mL, 0.005 mole). Reaction mixture was warmed to 60° C. for 3 hours, then cooled to RT and acidified with 1N HCl and extracted with ethyl acetate (30 mL×3). The organic layer was washed with brine solution (30 mL), dried over $Na_2SO_4$ and concentrated under vacuum to obtain the title compound.

Yield: 0.05 g; $^1$H-NMR (DMSO-$d_6$, 400 MHz) δ ppm: 3.86 (s, 3H), 4.39 (s, 2H), 6.69-6.70 (d, J=3.2 Hz, 1H), 7.06 (s, 1H), 7.25-7.26 (d, J=4.8 Hz, 1H), 7.74-7.75 (d, J=2.2 Hz, 2H), 8.11-8.13 (d, J=5.1 Hz, 1H), 12.83 (bs, 1H); Mass (m/z): 286.0 (M+H)$^+$.

Step-8: N-[(1S,2S)-2-Hydroxycyclohexyl]-4-(2-fluoropyridin-4-ylmethyl)-1-methyl-1H-pyrrolo[2,3-b]pyridine-6-carboxamide To a solution of 1-methyl-4-(2-fluoropyridin-4-ylmethyl)-1H-pyrrolo[2,3-b]pyridine-6-carboxylic acid (0.23 g, 0.00081 mole) in DMF (10 mL) at 25° C. under $N_2$, was added HATU (0.372 g, 0.00009 mole) stirred for 10 minutes, followed by addition of (1S,2S)-2-amino cyclohexanol hydrochloride (0.136 g, 0.00089 mole) and DIPEA (0.6 mL, 0.0032 mole) in 10 minutes of time interval and stirred for 15 hours. Reaction mixture was quenched in to ice water (50 mL) and extracted with ethyl acetate (30 mL×3). Organic layer was washed with brine solution (50 mL) and dried over $Na_2SO_4$. Organic layer was concentrated under vacuum to obtain the crude compound which was further purified by flash chromatography using ethyl acetate:n-hexane (65:35) to afford the title compound.

Yield: 0.25 g; $^1$H-NMR (DMSO-$d_6$, 400 MHz) δ ppm: 1.25-1.27 (m, 4H), 1.64-1.67 (m, 2H), 1.89-1.95 (m, 2H), 3.47-3.48 (m, 1H), 3.60-3.62 (m, 1H), 3.91 (s, 3H), 4.39 (s, 2H), 4.71-4.72 (d, J=5.3 Hz, 1H), 6.67-6.68 (d, J=3.1 Hz, 1H), 7.14 (s, 1H), 7.23-7.24 (d, J=4.4 Hz, 1H), 7.68-7.69 (d, J=3.2 Hz, 1H), 7.72 (s, 1H), 8.11-8.12 (d, J=5.0 Hz, 1H), 8.28-8.30 (d, J=7.9 Hz, 1H); Mass (m/z): 383.4 (M+H)$^+$.

Examples 2 to 26

The compounds of Example 2 to 26 were prepared by following the experimental procedures as described in the Example 1, with some non-critical variations

| Example No. | Structure and IUPAC name | Characterization data |
|---|---|---|
| 2 | 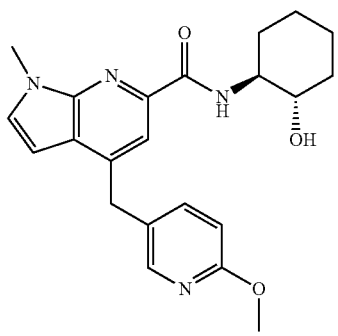<br>N-[(1S,2S)-2-Hydroxycyclohexyl]-4-(2-methoxypyridin-5-ylmethyl)-1-methyl-1H-pyrrolo[2,3-b]pyridine-6-carboxamide | $^1$H-NMR (CDCl$_3$, 400 MHz) δ ppm: 1.15-1.39 (m, 4H), 1.77-1.80 (m, 2H), 2.01-2.11 (m, 2H), 3.41-3.53 (m, 1H), 3.77-3.86 (m, 2H), 3.89 (s, 6H), 4.18 (s, 2H), 6.43-6.45 (m, 1H), 6.62-6.64 (m, 1H), 7.27-7.28 (m, 1H), 7.36-7.38 (d, J = 7.9 Hz, 1H), 7.86 (s, 1H), 8.02-8.04 (d, J = 6.5 Hz, 1H), 8.10 (s, 1H); Mass (m/z): 395.3 (M + H)$^+$. |
| 3 | 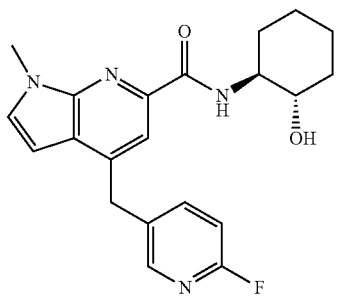<br>N-[(1S,2S)-2-Hydroxycyclohexyl]-4-(2-fluoropyridin-5-ylmethyl)-1-methyl-1H-pyrrolo[2,3-b]pyridine-6-carboxamide | $^1$H-NMR (CDCl$_3$, 400 MHz) δ ppm: 1.15-1.39 (m, 4H), 1.78-1.80 (m, 2H), 2.09-2.13 (m, 2H), 3.51-3.56 (m, 1H), 3.65-3.70 (m, 1H), 3.82-3.88 (m, 1H), 3.92 (s, 3H), 4.26 (s, 2H), 6.41-6.42 (d, J = 3.3 Hz, 1H), 6.80-6.83 (m, 1H), 7.29-7.30 (d, J = 3.30 Hz, 1H), 7.55-7.59 (m, 1H), 7.88 (s, 1H), 8.02-8.04 (d, J = 6.5 Hz, 1H), 8.15 (m, 1H); Mass (m/z): 383.4 (M + H)$^+$. |
| 4 | 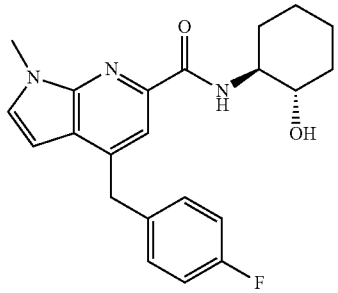<br>N-[(1S,2S)-2-Hydroxycyclohexyl]-4-(4-fluorobenzyl)-1-methyl-1H-pyrrolo[2,3-b]pyridine-6-carboxamide | $^1$H-NMR (CDCl$_3$, 400 MHz) δ ppm: 1.15-1.48 (m, 4H), 1.77-1.80 (m, 2H), 2.08-2.15 (m, 2H), 3.51-3.53 (m, 1H), 3.78-3.80 (m, 1H), 3.82-3.85 (m, 1H), 3.89 (s, 3H), 4.24 (s, 2H), 6.41-6.42 (d, J = 2.8 Hz, 1H), 6.92-6.99 (m, 2H), 7.16-7.19 (m, 2H), 7.27-7.28 (m, 1H), 7.87 (s, 1H), 8.04-8.05 (d, J = 6.7 Hz, 1H); Mass (m/z): 382.3 (M + H)$^+$. |

-continued

| Example No. | Structure and IUPAC name | Characterization data |
|---|---|---|
| 5 | 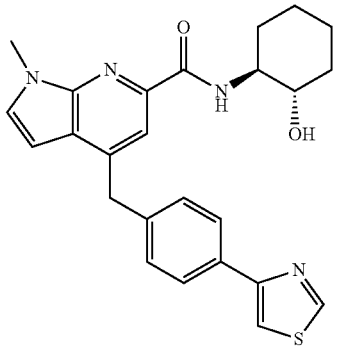<br>N-[(1S,2S)-2-Hydroxycyclohexyl]-4-(4-thiazol-4-ylbenzyl)-1-methyl-1H-pyrrolo[2,3-b]pyridine-6-carboxamide | $^1$H-NMR (DMSO-$d_6$, 400 MHz) δ ppm: 1.23-1.27 (m, 2H), 1.29-1.36 (m, 2H), 1.62-1.66 (m, 2H), 1.89-1.95 (m, 2H), 3.46-3.48 (m, 1H), 3.58-3.67 (m, 1H), 3.89-3.98 (s, 3H), 4.32 (s, 2H), 4.70-4.71 (d, 1H), 6.66-6.67 (d, J = 3.4 Hz, 1H), 7.35-7.37 (d, J = 8.08 Hz, 1H), 7.65-7.76 (d, J = 3.32 Hz, 2H), 7.68 (s, 1H), 7.89-7.91 (d, J = 8.04 Hz, 2H), 8.09-8.09 (d, J = 1.36 Hz, 1H), 8.26-8.28 (d, J = 7.92 Hz, 1H), 9.16-9.16 (d, J = 1.32 Hz, 1H); Mass (m/z): 447.0 (M + H)$^+$. |
| 6 | 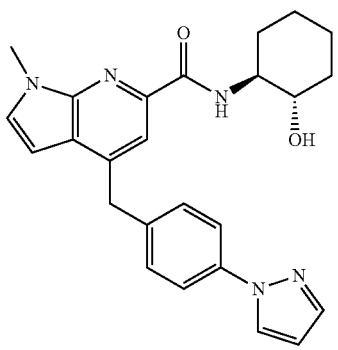<br>N-[(1S,2S)-2-Hydroxycyclohexyl]-4-(4-pyrazol-1-ylbenzyl)-1-methyl-1H-pyrrolo[2,3-b]pyridine-6-carboxamide | $^1$H-NMR (CDCl$_3$, 400 MHz) δ ppm: 1.15-1.45 (m, 4H), 1.77-1.80 (m, 2H), 2.09-2.15 (m, 2H), 3.51-3.56 (m, 1H), 3.64-3.68 (m, 1H), 3.80-3.83 (m, 1H), 3.90 (s, 3H), 4.31 (s, 2H), 6.43-6.44 (d, J = 2.1 Hz, 2H), 7.25-7.28 (m, 1H), 7.29-7.31 (d, J = 7.98 Hz, 2H), 7.57-7.59 (d, J = 8.1 Hz, 2H), 7.69 (s, 1H), 7.87 (s, 1H), 7.92 (s, 1H), 8.05-8.06 (m, 1H); Mass (m/z): 430.5 (M + H)$^+$. |
| 7 | 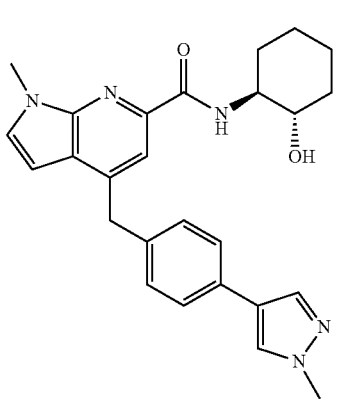<br>N-[(1S,2S)-2-Hydroxycyclohexyl]-4-[4-(1-methyl-1H-pyrazol-4-yl)benzyl]-1-methyl-1H-pyrrolo[2,3-b]pyridine-6-carboxamide | $^1$H-NMR (DMSO-$d_6$, 400 MHz) δ ppm: 1.25-1.29 (m, 4H), 1.63-1.66 (m, 2H), 1.89-1.93 (m, 2H), 3.37-3.41 (m, 1H), 3.46-3.47 (m, 1H), 3.58 (s, 3H), 3.92 (s, 3H), 4.26 (s, 2H), 4.70-4.72 (m, 1H), 6.66-6.67 (d, J = 3.25 Hz, 1H), 7.25-7.27 (d, J = 7.9 Hz, 2H), 7.44-7.46 (d, J = 7.9 Hz, 2H), 7.63-7.65 (s, 2H), 7.87 (s, 1H), 8.05 (s, 1H), 8.26-8.28 (d, J = 8.0 Hz, 1H); Mass (m/z): 444.2 (M + H)$^+$. |

| Example No. | Structure and IUPAC name | Characterization data |
|---|---|---|
| 8 | 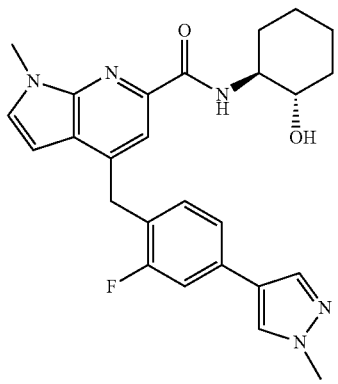<br>N-[(1S,2S)-2-Hydroxycyclohexyl]-4-[2-fluoro-4-(1-methyl-1H-pyrazol-4-yl)benzyl]-1-methyl-1H-pyrrolo[2,3-b]pyridine-6-carboxamide | $^1$H-NMR (DMSO-$d_6$, 400 MHz) δ ppm: 1.24-1.28 (m, 4H), 1.68-1.70 (m, 2H), 1.90-1.95 (m, 2H), 3.50-3.55 (m, 1H), 3.82-3.84 (m, 1H), 3.89 (s, 3H), 3.92 (s, 3H), 4.28 (s, 2H), 4.75-4.78 (m, 1H), 6.51-6.52 (d, J = 3.4 Hz, 1H), 7.11-7.18 (m, 3H), 7.27-7.28 (d, J = 3.9 Hz, 1H), 7.55-7.57 (m, 1H), 7.78-7.79 (m, 1H), 7.89 (s, 1H), 8.04-8.05 (d, J = 6.9 Hz, 1H); Mass (m/z): 462.4 (M + H)$^+$. |
| 9 | 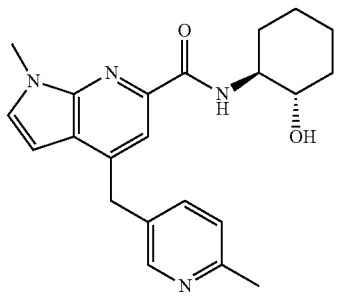<br>N-[(1S,2S)-2-Hydroxycyclohexyl]-4-(2-methylpyridin-5-ylmethyl)-1-methyl-1H-pyrrolo[2,3-b]pyridine-6-carboxamide | $^1$H-NMR (CDCl$_3$, 400 MHz) δ ppm: 1.18-1.37 (m, 4H), 1.75-1.80 (m, 2H), 2.01-2.11 (m, 2H), 2.50 (s, 3H), 3.52-3.53 (m, 1H), 3.83-3.87 (m, 2H), 3.91 (s, 3H), 4.23 (s, 2H), 6.42-6.43 (d, J = 3.40 Hz, 1H), 7.03-7.05 (d, J = 7.9 Hz, 1H), 7.27-7.28 (d, J = 3.50 Hz, 1H), 7.38-7.40 (dd, J = 1.7, 7.7 Hz, 1H), 7.86 (s, 1H), 8.03-8.05 (d, J = 7.0 Hz, 1H), 8.46 (s, 1H); Mass (m/z): 379.2 (M + H)$^+$. |
| 10 | 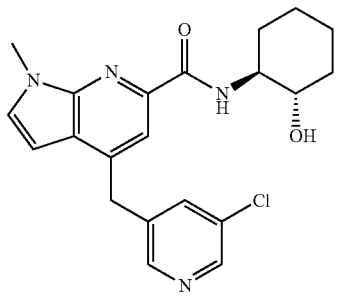<br>N-[(1S,2S)-2-Hydroxycyclohexyl]-4-(2-chloropyridin-4-ylmethyl)-1-methyl-1H-pyrrolo[2,3-b]pyridine-6-carboxamide | $^1$H-NMR (DMSO-$d_6$, 400 MHz) δ ppm: 1.25-1.27 (m, 4H), 1.64-1.67 (m, 2H), 1.90-1.92 (m, 2H), 3.46-3.48 (m, 1H), 3.51-3.62 (m, 1H), 3.91 (s, 3H), 4.36 (s, 2H), 4.70-4.72 (d, J = 5.3 Hz, 1H), 6.67-6.68 (d, J = 3.1 Hz, 1H), 7.30-7.32 (d, J = 4.8 Hz, 1H), 7.48 (s, 1H), 7.68-7.69 (d, J = 3.2 Hz, 1H), 7.71 (s, 1H), 8.28-8.30 (m, 2H); Mass (m/z): 399.2 (M + H)$^+$. |

| Example No. | Structure and IUPAC name | Characterization data |
|---|---|---|
| 11 | 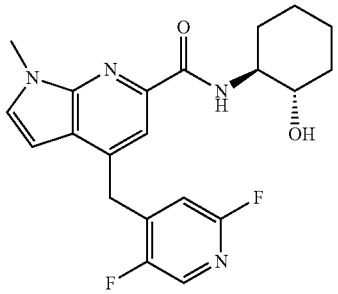<br>N-[(1S,2S)-2-Hydroxycyclohexyl]-4-(2,5-difluoropyridin-4-ylmethyl)-1-methyl-1H-pyrrolo[2,3-b]pyridine-6-carboxamide | $^1$H-NMR (DMSO-$d_6$, 400 MHz) δ ppm: 1.25-1.27 (m, 4H), 1.63-1.67 (m, 2H), 1.91-1.94 (m, 2H), 3.47-3.49 (m, 1H), 3.59-3.61 (m, 1H), 3.91 (s, 3H), 4.42 (s, 2H), 4.70-4.71 (d, J = 5.4 Hz, 1H), 6.66-6.66 (d, J = 3.3 Hz, 1H), 7.26 (s, 1H), 7.65 (s, 1H), 7.70-7.71 (d, J = 3.3 Hz, 1H), 8.21 (s, 1H), 8.28-8.30 (d, J = 7.9 Hz, 1H); Mass (m/z): 401.2 (M + H)$^+$. |
| 12 | 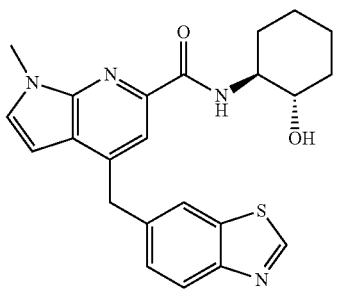<br>N-[(1S,2S)-2-Hydroxycyclohexyl]-4-(benzothiazol-6-ylmethyl)-1-methyl-1H-pyrrolo[2,3-b]pyridine-6-carboxamide | $^1$H-NMR (DMSO-$d_6$, 400 MHz) δ ppm: 1.24-1.26 (m, 4H), 1.62-1.66 (m, 2H), 1.89-1.94 (m, 2H), 3.48-3.49 (m, 1H), 3.58-3.60 (m, 1H), 3.89 (s, 3H), 4.44 (s, 2H), 4.71-4.72 (d, J = 5.2 Hz, 1H), 6.69-6.70 (d, J = 3.1 Hz, 1H), 7.45-7.47 (d, J = 8.3 Hz, 1H), 7.65-7.66 (d, J = 3.1 Hz, 1H), 7.68 (s, 1H), 7.97-7.99 (d, J = 8.3 Hz, 1H), 8.10 (s, 1H), 8.27-8.29 (d, J = 7.8 Hz, 1H), 9.31 (s, 1H); Mass (m/z): 421.0 (M + H)$^+$. |
| 13 | 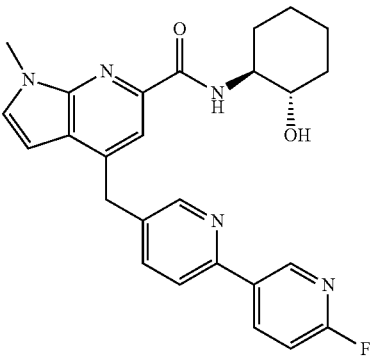<br>N-[(1S,2S)-2-Hydroxycyclohexyl]-4-(2'-fluoro-[2,5']bipyridinyl-5-ylmethyl)-1-methyl-1H-pyrrolo[2,3-b]pyridine-6-carboxamide | $^1$H-NMR (DMSO-$d_6$, 400 MHz) δ ppm: 1.25-1.27 (m, 4H), 1.63-1.66 (m, 2H), 1.89-1.95 (m, 2H), 3.43-3.47 (m, 1H), 3.59-3.61 (m, 1H), 3.91 (s, 3H), 4.38 (s, 2H), 4.70-4.71 (d, J = 5.3 Hz, 1H), 6.73-6.74 (d, J = 3.2 Hz, 1H), 7.27-7.30 (dd, J = 2.1, 8.4 Hz, 1H), 7.68-7.69 (d, J = 3.1 Hz, 1H), 7.71 (s, 1H), 7.80-7.82 (d, J = 7.8 Hz, 1H), 7.95-7.97 (d, J = 8.1 Hz, 1H), 8.27-8.29 (d, J = 7.9 Hz, 1H), 8.56-8.60 (m, 1H), 8.71 (s, 1H), 8.87 (s, 1H); Mass (m/z): 460.0 (M + H)$^+$. |

| Example No. | Structure and IUPAC name | Characterization data |
|---|---|---|
| 14 | 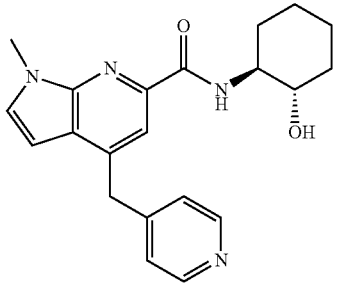 [SMILES: Cn1ccc2c(Cc3cccnc3)cc(C(=O)N[C@H]3CCCC[C@@H]3O)nc21]<br>N-[(1S,2S)-2-Hydroxycyclohexyl]-4-(pyridin-4-ylmethyl)-1-methyl-1H-pyrrolo[2,3-b]pyridine-6-carboxamide | $^1$H-NMR (DMSO-d$_6$, 400 MHz) δ ppm: 1.23-1.29 (m, 4H), 1.63-1.67 (m, 2H), 1.90-1.95 (m, 2H), 3.46-3.50 (m, 1H), 3.59-3.61 (m, 1H), 3.90 (s, 3H), 4.32 (s, 2H), 4.70-4.71 (d, J = 5.49 Hz, 1H), 6.64-6.65 (d, J = 3.44 Hz, 1H), 7.28-7.29 (d, J = 5.36 Hz, 2H), 7.67-7.68 (m, 2H), 8.26-8.28 (d, J = 7.96 Hz, 1H), 8.44-8.45 (d, J = 5.56 Hz, 2H); Mass (m/z): 365.1 (M + H)$^+$. |
| 15 | 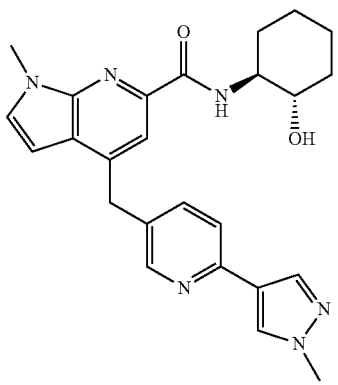<br>N-[(1S,2S)-2-Hydroxycyclohexyl]-4-[2-(1-methyl-1H-pyrazol-4-yl)pyridin-5-ylmethyl]-1-methyl-1H-pyrrolo[2,3-b]pyridine-6-carboxamide | $^1$H-NMR (DMSO-d$_6$, 400 MHz) δ ppm: 1.17-1.27 (m, 4H), 1.63-1.66 (m, 2H), 1.90-1.98 (m, 2H), 3.33-3.48 (m, 1H), 3.59-3.60 (m, 1H), 3.85 (s, 3H), 3.90 (s, 3H), 4.29 (s, 2H), 4.70-4.71 (d, J = 5.32 Hz, 1H), 6.68-6.69 (d, J = 3.08 Hz, 1H), 7.52-7.54 (d, J = 8.04 Hz, 1H), 7.61-7.63 (d, J = 8 Hz, 1H), 7.67 (s, 2H), 7.92 (s, 1H), 8.20 (s, 1H), 8.26-8.28 (d, J = 7.92 Hz, 1H), 8.50 (s, 1H); Mass (m/z): 445.0 (M + H)$^+$. |
| 16 | 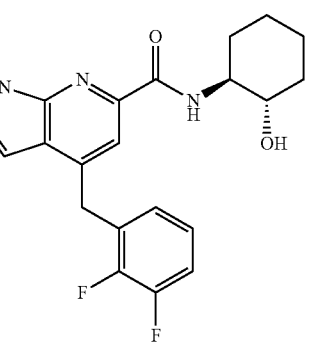<br>N-[(1S,2S)-2-Hydroxycyclohexyl]-4-(2,3-difluorobenzyl)-1-methyl-1H-pyrrolo[2,3-b]pyridine-6-carboxamide | $^1$H-NMR (DMSO-d$_6$, 400 MHz) δ ppm: 1.25-1.26 (m, 4H), 1.62-1.66 (m, 2H), 1.91 (m, 2H), 3.46-3.50 (m, 1H), 3.58-3.60 (m, 1H), 3.91 (s, 3H), 4.37 (s, 2H), 4.70-4.71 (d, J = 5.4 Hz, 1H), 6.63-6.63 (d, J = 3.12 Hz, 1H), 7.15-7.18 (m, 2H), 7.30-7.32 (m, 1H), 7.60 (s, 1H), 7.68-7.69 (d, J = 3.32 Hz, 1H), 8.27-8.29 (d, J = 7.88 Hz, 1H); Mass (m/z): 400.4 (M + H)$^+$. |

| Example No. | Structure and IUPAC name | Characterization data |
|---|---|---|
| 17 | 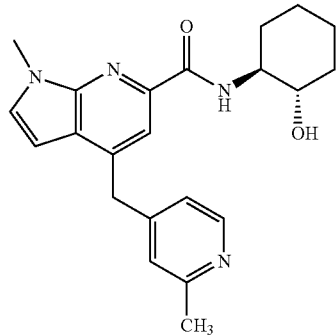<br>N-[(1S,2S)-2-Hydroxycyclohexyl]-4-(2-methylpyridin-4-ylmethyl)-1-methyl-1H-pyrrolo[2,3-b]pyridine-6-carboxamide | $^1$H-NMR (DMSO-d$_6$, 400 MHz) δ ppm; 1.23-1.27 (m, 4H), 1.60-1.67 (m, 2H), 1.91 (m, 2H), 2.38 (s, 3H), 3.46-3.49 (m, 2H), 3.90 (s, 3H), 4.24 (s, 2H), 4.70-4.71 (d, J = 5.4 Hz, 1H), 6.64-6.65 (d, J = 3.2 Hz, 1H), 7.07-7.08 (d, J = 4.5 Hz, 1H), 7.15 (s, 1H), 7.61-7.67 (m, 3H), 8.27-8.31 (m, 1H); Mass (m/z): 379.10 (M + H)$^+$. |
| 18 | 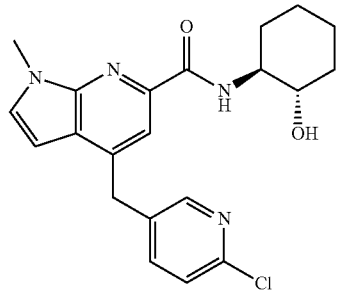<br>N-[(1S,2S)-2-Hydroxycyclohexyl]-4-(2-chloropyridin-5-ylmethyl)-1-methyl-1H-pyrrolo[2,3-b]pyridine-6-carboxamide | $^1$H-NMR (DMSO-d$_6$, 400 MHz) δ ppm: 1.22-1.26 (m, 4H), 1.61-1.65 (m, 2H), 1.88-1.94 (m, 2H), 3.46-3.47 (m, 1H), 3.58-3.60 (m, 1H), 3.89 (s, 3H), 4.32 (s, 2H), 4.68-4.69 (d, J = 5.3 Hz, 1H), 6.66-6.66 (d, J = 3.2 Hz, 1H), 7.39-7.41 (d, J = 8.1 Hz, 1H), 7.66-7.67 (d, J = 2.9 Hz, 1H), 7.70-7.73 (m, 1H), 8.25-8.29 (m, 2H), 8.43 (s, 1H); Mass (m/z): 399.6 (M + H)$^+$. |
| 19 | 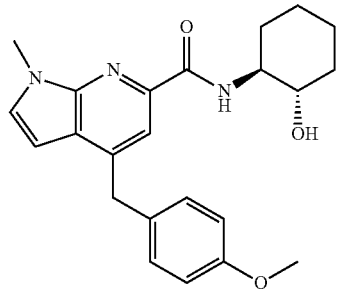<br>N-[(1S,2S)-2-Hydroxycyclohexyl]-4-(4-methoxybenzyl)-1-methyl-1H-pyrrolo[2,3-b]pyridine-6-carboxamide | $^1$H-NMR (CDCl$_3$, 400 MHz) δ ppm: 1.24-1.26 (m, 4H), 1.61-1.65 (m, 2H), 1.88-1.94 (m, 2H), 3.40-3.46 (m, 1H), 3.57-3.59 (m, 1H), 3.68 (s, 3H), 3.88 (s, 3H), 4.19 (s, 2H), 4.68-4.70 (d, J = 5.3 Hz, 1H), 6.62-6.63 (d, J = 3.1 Hz, 1H), 6.81-6.83 (d, J = 8.3 Hz, 2H), 7.17-7.19 (d, J = 8.3 Hz, 2H), 7.59-7.61 (m, 2H), 8.23-8.25 (d, J = 7.8 Hz, 1H); Mass (m/z): 394.3 (M + H)$^+$. |

| Example No. | Structure and IUPAC name | Characterization data |
|---|---|---|
| 20 | 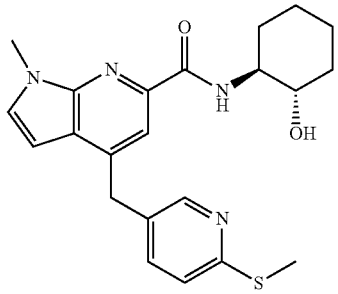<br>N-[(1S,2S)-2-Hydroxycyclohexyl]-4-(2-methylsulfanylpyridin-5-ylmethyl)-1-methyl-1H-pyrrolo[2,3-b]pyridine-6-carboxamide | $^1$H-NMR (DMSO-d$_6$, 400 MHz) δ ppm: 1.21-1.24 (m, 4H), 1.61-1.66 (m, 2H), 1.92-1.94 (m, 2H), 3.46-3.47 (m, 1H), 3.57-3.61 (m, 1H), 3.89 (s, 3H), 4.06 (s, 2H), 4.32 (s, 2H), 4.69-4.70 (d, J = 5.4 Hz, 1H), 6.66-6.67 (d, J = 3.3 Hz, 1H), 7.39-7.41 (m, 1H), 7.63 (s, 1H), 7.65-7.66 (d, J = 3.5 Hz, 1H), 7.97-8.00 (m, 1H), 8.24-8.26 (m, 1H), 8.39-8.40 (d, J = 3.9 Hz, 1H), 8.44 (s, 1H); Mass (m/z): 411.3 (M + H)$^+$. |
| 21 | 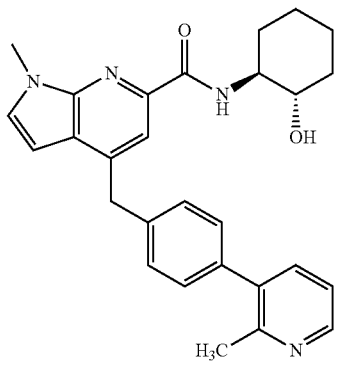<br>N-[(1S,2S)-2-Hydroxycyclohexyl]-4-[4-(2-methylpyridin-3-yl)benzyl]-1-methyl-1H-pyrrolo[2,3-b]pyridine-6-carboxamide | $^1$H-NMR (DMSO-d$_6$, 400 MHz) δ ppm: 1.23-1.27 (m, 4H), 1.63-1.66 (m, 2H), 1.90-1.92 (m, 2H), 2.39 (s, 3H), 3.34-3.37 (m, 2H), 3.39 (s, 3H), 4.35 (s, 2H), 4.71-4.72 (d, J = 5.52 Hz, 1H), 6.73-6.73 (d, J = 3.4 Hz, 1H), 7.26-7.29 (m, 1H), 7.29-7.31 (d, J = 8.04 Hz, 2H), 7.38-7.40 (d, J = 8.04 Hz, 2H), 7.57-7.57 (d, J = 1.12 Hz, 1H), 7.68-7.72 (m, 2H), 8.27-8.29 (d, J = 8.16 Hz, 1H), 8.42-8.42 (d, J = 1.2 Hz, 1H); Mass (m/z): 454.9 (M + H)$^+$. |
| 22 | 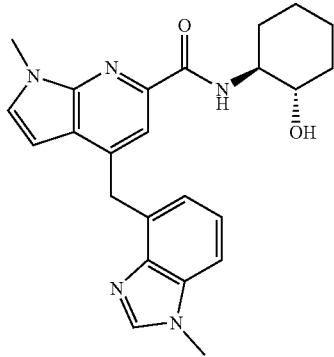<br>N-[(1S,2S)-2-Hydroxycyclohexyl]-4-(1-methyl-1H-benzimidazol-4-ylmethyl)-1-methyl-1H-pyrrolo[2,3-b]pyridine-6-carboxamide | $^1$H-NMR (DMSO-d$_6$, 400 MHz) δ ppm: 1.24-1.26 (m, 4H), 1.61-1.65 (m, 2H), 1.89-1.98 (m, 2H), 3.43-3.48 (m, 1H), 3.56-3.58 (m, 1H), 3.84 (s, 3H), 3.88 (s, 3H), 4.62 (s, 2H), 4.69 (bs, 1H), 6.70-6.71 (d, J = 3.3 Hz, 1H), 7.04-7.05 (d, J = 6.8 Hz, 1H), 7.16-7.18 (t, J = 6.8 Hz, 1H), 7.42-7.44 (d, J = 7.9 Hz, 1H), 7.61-7.62 (d, J = 3.1 Hz, 1H), 7.64 (s, 1H), 8.23-8.25 (d, J = 7.9 Hz, 1H); Mass (m/z): 418.2 (M + H)$^+$. |

-continued

| Example No. | Structure and IUPAC name | Characterization data |
|---|---|---|
| 23 | 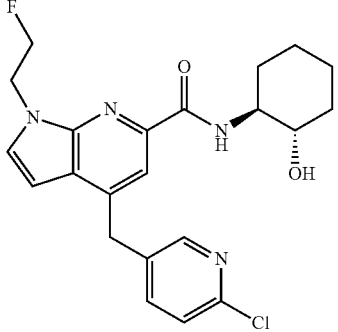<br>N-[(1S,2S)-2-Hydroxycyclohexyl]-4-(2-chloropyridin-5-ylmethyl)-1-(2-fluoroethyl)-1H-pyrrolo[2,3-b]pyridine-6-carboxamide | $^1$H-NMR (DMSO-d$_6$, 400 MHz) δ ppm: 1.25-1.27 (m, 4H), 1.61-1.65 (m, 2H), 2.03-2.05 (m, 2H), 3.46-3.48 (m, 1H), 3.58-3.60 (m, 1H), 4.33 (s, 2H), 4.64-4.67 (m, 2H), 4.68-4.76 (m, 2H), 4.87-4.89 (m, 1H), 6.17-6.72 (d, J = 3.3 Hz, 1H), 7.40-7.42 (d, J = 8.1 Hz, 1H), 7.69 (s, 1H), 7.73-7.74 (d, J = 3.5 Hz, 1H), 8.26-8.28 (d, J = 7.9 Hz, 1H), 8.44-8.45 (d, J = 1.6 Hz, 2H); Mass (m/z): 431.4 (M + H)$^+$. |
| 24 | 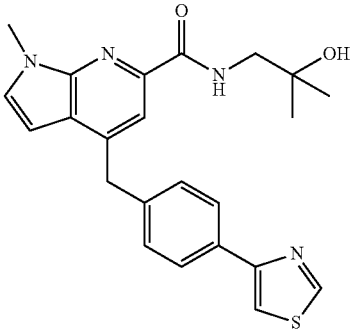<br>N-(2-Hydroxy-2-methylpropyl)-4-[4-(thiazol-4-yl)benzyl]-1-methyl-1H-pyrrolo[2,3-b]pyridine-6-carboxamide | $^1$H-NMR (CDCl$_3$, 400 MHz) δ ppm: 1.31 (s, 6H), 2.87 (bs, 1H), 3.52-3.53 (d, J = 6.37 Hz, 2H), 3.89 (s, 3H), 4.31 (s, 2H), 6.45-6.46 (d, J = 3.35 Hz, 1H), 7.27-7.28 (d, J = 3.14 Hz, 1H), 7.30-7.32 (d, J = 8.01 Hz, 2H), 7.47-7.47 (d, J = 1.64 Hz, 1H), 7.81-7.83 (d, J = 8.04 Hz, 2H), 7.93 (s, 1H), 8.44 (m, 1H), 8.85-8.85 (d, J = 1.58 Hz, 1H); Mass (m/z): 421.2 (M + H)$^+$. |
| 25 | 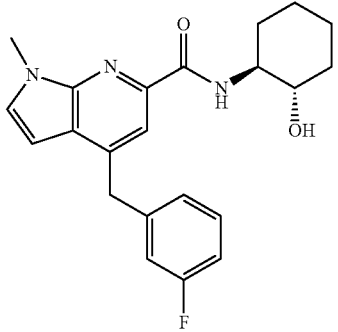<br>N-[(1S,2S)-2-Hydroxycyclohexyl]-4-(3-fluorobenzyl)-1-methyl-1H-pyrrolo[2,3-b]pyridine-6-carboxamide | $^1$H-NMR (DMSO-d$_6$, 400 MHz) δ ppm: 1.15-1.15 (m, 4H), 1.63-1.66 (m, 2H), 1.90-1.98 (m, 2H), 3.43-3.50 (m, 1H), 3.59-3.61 (m, 1H), 3.90 (s, 3H), 4.31 (s, 2H), 4.70-4.72 (d, J = 5.33 Hz, 1H), 6.68-6.67 (d, J = 3.22 Hz, 1H), 7.00-7.04 (m, 1H), 7.12-7.15 (m, 2H), 7.29-7.34 (m, 1H), 7.66 (s, 2H), 8.26-8.28 (d, J = 7.89 Hz, 1H); Mass (m/z): 382.4 (M + H)$^+$. |

| Example No. | Structure and IUPAC name | Characterization data |
|---|---|---|
| 26 | N-(1-Hydroxycyclopentylmethyl)-4-[4-(thiazol-4-yl)benzyl]-1-methyl-1H-pyrrolo[2,3-b]pyridine-6-carboxamide | $^1$H-NMR (DMSO-$d_6$, 400 MHz) δ ppm: 1.23-1.26 (m, 4H), 1.61-1.69 (m, 4H), 3.41-3.42 (m, 2H), 3.88 (s, 3H), 4.33 (s, 2H), 4.70 (s, 1H), 6.68-6.69 (d, J = 3.36 Hz, 1H), 7.37-7.39 (d, J = 8.08 Hz, 2H), 7.67-7.69 (d, J = 5.44 Hz, 2H), 7.89-7.91 (d, J = 8.08 Hz, 2H), 8.09-8.10 (d, J = 1.68 Hz, 1H), 8.49-8.52 (m, 1H), 9.16-9.16 (d, J = 1.64 Hz, 1H); Mass (m/z): 447.4 (M + H)$^+$. |

Example 27: N-[(1S,2S)-2-Hydroxycyclohexyl]-4-(pyridin-3-ylmethyl)-1-methyl-1H-pyrrolo[2,3-b]pyridine-6-carboxamide To a solution of N-[(1S,2S)-2-hydroxycyclohexyl]-4-(2-chloropyridin-5-ylmethyl)-1-methyl-1H-pyrrolo[2,3-b]pyridine-6-carboxamide (Example 18, 0.064 g, 0.06 mole) in a mixture of ethanol (1.5 mL), DMF (1.5 mL) and TEA (0.1 mL) at 25° C., was added 10% Pd/C (0.064 g) in one portion and stirred for 8 hours under H$_2$ gas bubbling. Reaction mixture was filtered through celite and filtrate was concentrated under vacuum to obtain the crude compound which was further purified by flash chromatography using methanolic ammonia:chloroform (3:97) to afford the title compound.

Yield: 0.027 g; $^1$H-NMR (DMSO-$d_6$, 400 MHz) δ ppm: 1.24-1.25 (m, 4H), 1.61-1.65 (m, 2H), 1.88-1.90 (m, 2H), 3.46-3.47 (m, 1H), 3.57-3.60 (m, 1H), 3.89 (s, 3H), 4.31 (s, 2H), 4.69-4.70 (d, J=5.4 Hz, 1H), 6.67-6.68 (d, J=3.3 Hz, 1H), 7.27-7.30 (m, 1H), 7.64-7.67 (m, 3H), 8.25-8.27 (d, J=7.9 Hz, 1H), 8.39-8.40 (d, J=3.9 Hz, 1H), 8.57 (s, 1H); Mass (m/z): 365.3 (M+H)$^+$.

Example 28

N-[(1S,2S)-2-Hydroxycyclohexyl]-4-(2-cyclopropylpyridin-5-ylmethyl)-1-methyl-1H-pyrrolo[2,3-b]pyridine-6-carboxamide To a suspension of N-[(1S,2S)-2-hydroxycyclohexyl]-4-(2-chloropyridin-5-ylmethyl)-1-methyl-1H-pyrrolo[2,3-b]pyridine-6-carboxamide (Example 18, 0.2 g, 0.0005 mole) in 5 mL at 25° C. under N$_2$, was added cyclopropylboronic acid pinacol ester (0.15 g, 0.0009 mole), Pd$_2$dba$_3$ (0.0046 g), PCy$_3$ (0.0035 g), aq.K$_3$PO$_4$ (1.7M, 0.373 g, 0.0017 mole). Reaction mixture was irradiated in a microwave reactor at 140° C. for 2 hours, cooled to RT, filtered through celite, washed with ethyl acetate. The filtrate was concentrated under vacuum to obtain the crude compound which was further purified by flash chromatography using methanolic ammonia:chloroform (1.4:98.6) to obtain the title compound.

Yield: 0.050 g; $^1$H-NMR (DMSO-$d_6$, 400 MHz) δ ppm: 1.21-1.26 (m, 8H), 1.62-1.65 (m, 2H), 1.74-1.91 (m, 3H), 3.45-3.46 (m, 1H), 3.58-3.61 (m, 1H), 3.89 (s, 3H), 4.31 (s, 2H), 4.68-4.70 (d, J=5.3 Hz, 1H), 6.66-6.67 (d, J=3.2 Hz, 1H), 7.17-7.28 (d, J=8.0 Hz, 1H), 7.65-7.73 (m, 3H), 8.24-8.25 (d, J=3.2 Hz, 1H), 8.30 (s, 1H); Mass (m/z): 405.3 (M+H)$^+$.

Example 29

N-[(1S,2S)-2-Hydroxycyclohexyl]-4-(2-fluoropyridin-4-ylmethyl)-1-ethyl-1H-pyrrolo[2,3-b]pyridine-6-carboxamide

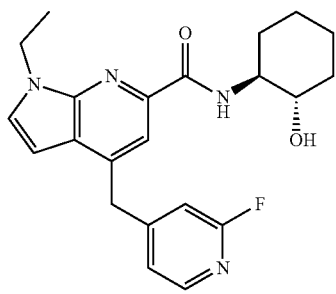 [SMILES: CCn1ccc2c(Cc3ccnc(F)c3)cc(C(=O)N[C@H]3CCCC[C@@H]3O)nc21]

This compound was synthesized using procedure similar to Example 1 except in step 4 where methyl iodide is replaced with ethyl iodide.

Yield: 0.054 g; $^1$H-NMR (DMSO-d$_6$, 400 MHz) δ ppm: 1.24-1.27 (m, 4H), 1.41-1.44 (t, 3H), 1.63-1.67 (m, 2H), 2.04-2.15 (m, 2H), 3.53-3.55 (m, 1H), 3.59-3.61 (m, 1H), 4.35-4.41 (t, 2H), 4.72-4.73 (d, J=5.5 Hz, 1H), 5.55 (s, 2H), 6.68-6.69 (d, J=3.4 Hz, 1H), 7.31 (s, 1H), 7.41 (s, 1H), 7.48-7.50 (d, J=4.8 Hz, 1H), 7.65-7.66 (d, J=3.3 Hz, 1H), 8.26-8.27 (d, J=3.7 Hz, 1H), 8.29 (s, 1H); Mass (m/z): 397.3 (M+H)$^+$.

Example 30

N-[(1S,2S)-2-Hydroxycyclohexyl]-4-(2-fluoropyridin-4-ylmethyl)-1-isopropyl-1H-pyrrolo[2,3-b]pyridine-6-carboxamide

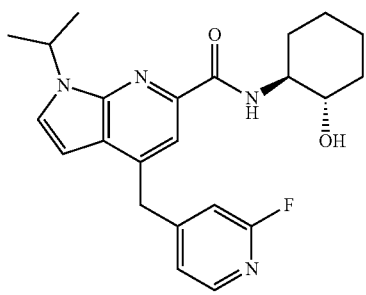 [SMILES: CC(C)n1ccc2c(Cc3ccnc(F)c3)cc(C(=O)N[C@H]3CCCC[C@@H]3O)nc21]

This compound was synthesized using procedure similar to Example 1 except in step 4 where methyl iodide is replaced with isopropyl iodide.

Yield: 0.027 g; $^1$H-NMR (DMSO-d$_6$, 400 MHz) δ ppm: 1.23-1.26 (m, 4H), 1.47-1.49 (t, 6H), 1.63-1.67 (m, 2H), 1.90-1.97 (m, 2H), 3.43-3.48 (m, 1H), 3.49-3.50 (m, 1H), 4.38 (s, 2H), 4.69-4.70 (d, J=5.4 Hz, 1H), 5.25-5.29 (m, 1H), 6.70-6.71 (d, J=3.6 Hz, 1H), 7.15 (s, 1H), 7.25-7.26 (d, J=4.7 Hz, 1H), 7.71 (s, 1H), 7.85-7.86 (d, J=2.3 Hz, 1H), 8.11-8.13 (d, J=5.1 Hz, 1H), 8.24-8.25 (d, J=7.9 Hz, 1H); Mass (m/z): 411.2 (M+H)$^+$.

Example 31

N-[(1S,2S)-2-Hydroxycyclohexyl]-4-(2,3-difluorophenylmethyl)-1,3-dimethyl-1H-pyrrolo[2,3-b]pyridine-6-carboxamide

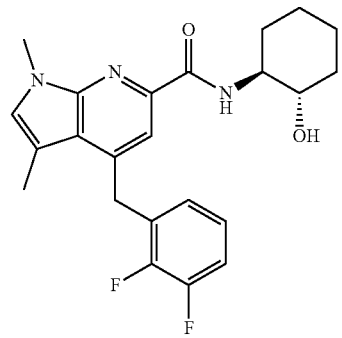 [SMILES: Cc1cn(C)c2nc(C(=O)N[C@H]3CCCC[C@@H]3O)cc(Cc3cccc(F)c3F)c12]

Step-1: 4-Bromo-1H-pyrrolo[2,3-b]pyridine-3-carboxaldehyde

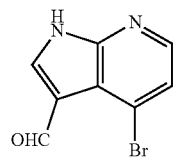 [SMILES: O=Cc1c[nH]c2nccc(Br)c12]

The title compound was synthesized as per literature procedure given in US2009/0298820A1

Yield: 0.21 g; $^1$H-NMR (DMSO-d$_6$, 400 MHz) δ ppm: 7.58-7.59 (d, J=5.08 Hz, 1H); 8.20-8.21 (d, J=5.12 Hz, 1H), 8.48 (s, 1H), 10.48-10.49 (d, J=6.2 Hz, 1H), 13.16 (s, 1H); Mass (m/z): 225.0 (M+H)$^+$.

Step-2: 4-Bromo-3-hydroxymethyl-1H-pyrrolo[2,3-b] pyridine

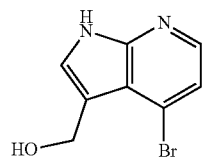

Sodium borohydride (0.098 g, 0.0026 mole) was added in portions to a stirred suspension of 4-bromo-1H-pyrrolo[2,3-b] pyridine-3-carboxaldehyde (0.4 g, 0.0017 mol) in methanol (15 mL) to obtain a clear solution. After completion of reaction, the reaction mixture was concentrated to obtain a residual mass that was diluted with water (25 mL) and extracted with ethyl acetate (25 mL×3). The organic extracts were combined, dried over anhydrous Na$_2$SO$_4$ and concentrated under vacuum to obtain the title compound.

Yield: 0.35 g; $^1$H-NMR (DMSO-d$_6$, 400 MHz) δ ppm: 4.76-4.77 (d, J=4.82 Hz, 2H), 4.86-(bs, 1H), 7.28-7.29 (d, J=5.04 Hz, 1H), 7.46-7.48 (d, J=8 Hz, 1H), 8.02-8.03 (d, J=5 Hz, 1H), 11.82 (s, 1H); Mass (m/z): 227.0 (M+H)$^+$.

Step-3: 4-Bromo-3-methyl-1H-pyrrolo[2,3-b]pyridine

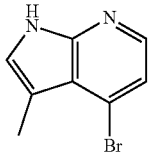

Triethylsilane (0.51 g, 0.004 mole) was added to a solution of 4-bromo-3-hydroxymethyl-1H-pyrrolo[2,3-b]pyridine (0.46 g, 0.002 mol) in trifluoroacetic acid (5 mL) at RT. The reaction mixture was heated at 65-70° C. for 2 hours, cooled to room temperature and poured onto cold water (20 mL), neutralized with NaHCO$_3$ and extracted with ethyl acetate (25 mL×3). The organic extracts were combined, washed with brine (15 mL), dried over anhydrous Na$_2$SO$_4$ and concentrated under vacuum to obtain the title compound.

Yield: 0.4 g; $^1$H-NMR (MeOD, 400 MHz) δ ppm: 2.53 (s, 3H), 7.30-7.32 (d, J=9.68 Hz, 1H), 7.40-7.41 (d, J=5.6 Hz, 1H), 8.02-8.03 (d, J=5.47 Hz, 1H); Mass (m/z): 211.0 (M+H)$^+$.

Step-4: 4-Bromo-3-methyl-1H-pyrrolo[2,3-b]pyridine-7-oxide

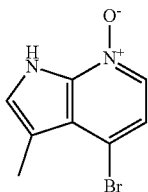

The title compound was synthesized from 4-bromo-3-methyl-1H-pyrrolo[2,3-b]pyridine following the procedure as described in step-1 of example 1.

Yield: 1.4 g; $^1$H-NMR (DMSO-d$_6$, 400 MHz) δ ppm: 2.4 (s, 3H), 7.23-7.25 (d, J=6.4 Hz, 1H), 7.30-7.32 (d, J=9.6 Hz, 1H), 7.9-8.0 (d, J=6.4 Hz, 1H), 12.43 (s, 1H); Mass (m/z): 227.0 (M+H)$^+$.

Step-5: 4-Bromo-3-methyl-1H-pyrrolo[2,3-b]pyridine-6-carbonitrile

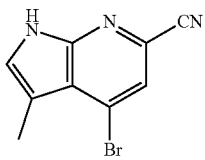

The title compound was synthesized from 4-bromo-3-methyl-1H-pyrrolo[2,3-b]pyridine-7-oxide following the procedure as described in step-2 of example 1.

Yield: 0.55 g; $^1$H-NMR (DMSO-d$_6$, 400 MHz) δ ppm: 2.53 (s, 3H), 7.38 (s, 1H), 7.61 (s, 1H), 9.53 (s, 1H); Mass (m/z): 236, 237.9 (M+H)$^+$.

Step-6: 4-Bromo-3-methyl-1H-pyrrolo[2,3-b]pyridine-6-carboxylic acid

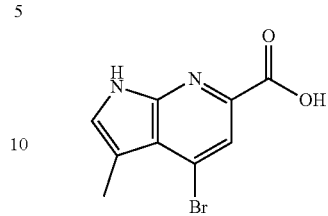

The title compound was synthesized from 4-bromo-3-methyl-1H-pyrrolo[2,3-b]pyridine-6-carbonitrile following the procedure as described in step-3 of example 1.

Yield: 0.073 g; $^1$H-NMR (DMSO-d$_6$, 400 MHz) δ ppm: 2.46 (s, 3H), 7.62 (s, 1H), 7.88 (s, 1H), 12.08 (s, 1H), 13.06 (bs, 1H); Mass (m/z): 255.0, 256.8 (M+H)$^+$.

Step-7: Methyl 4-bromo-1, 3-dimethyl-1H-pyrrolo[2,3-b] pyridine-6-carboxylate

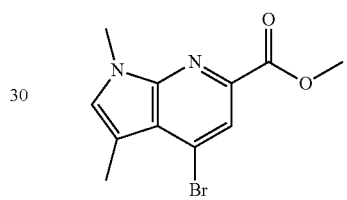

The title compound was synthesized from 4-bromo-3-methyl-1H-pyrrolo[2,3-b]pyridine-6-carboxylic acid following the procedure as described in step-4 of example 1.

Yield: 0.061 g; $^1$H-NMR (CDCl$_3$, 400 MHz) δ ppm: 2.5 (s, 3H), 3.89 (s, 3H), 4.01 (s, 3H), 7.17 (s, 1H), 8.06 (s, 1H); Mass (m/z): 282.8 (M+H)$^+$.

Step-8: Methyl 1,3-dimethyl-4-(4,4,5,5-tetramethyl-[1,3,2]dioxaborolan-2-yl)-1H-pyrrolo[2,3-b]pyridine-6-carboxylate

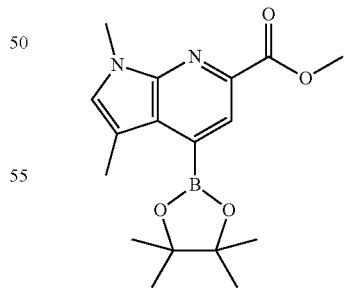

The title compound was synthesized from methyl 4-bromo-1,3-dimethyl-1H-pyrrolo[2,3-b]pyridine-6-carboxylate following the procedure as described in step-5 of example 1.

Yield: 0.047 g; $^1$H-NMR (CDCl$_3$, 400 MHz) δ ppm: 1.39 (s, 12H), 2.44 (s, 3H), 3.9 (s, 3H), 4.0 (s, 3H), 7.20 (s, 1H), 8.2 (s, 1H); Mass (m/z): 331 (M+1)$^+$.

Step-9: Methyl 4-(2,3-difluorobenzyl)-1,3-dimethyl-1H-pyrrolo[2,3-b]pyridine-6-carboxylate

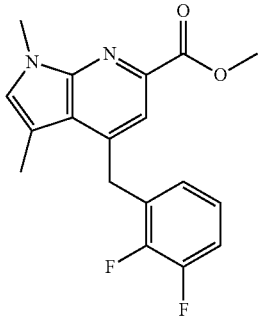 [SMILES: COC(=O)c1cc(Cc2cccc(F)c2F)c2c(C)cn(C)c2n1]

The title compound was synthesized from methyl 1,3-dimethyl-4-(4,4,5,5-tetramethyl-[1,3,2]dioxaborolan-2-yl)-1H-pyrrolo[2,3-b]pyridine-6-carboxylate following the procedure as described in step-6 of example 1.

Yield: 0.028 g (62%); $^1$H-NMR (CDCl$_3$, 400 MHz) δ ppm: 2.43 (s, 3H), 3.88 (s, 6H), 4.02 (s, 2H), 6.95 (s, 1H), 7.13-7.17 (m, 2H), 7.28-7.33 (m, 1H), 7.49 (s, 1H); Mass (m/z): 330.9 (M+1)$^+$.

Step-10: 4-(2,3-Difluorobenzyl)-1,3-dimethyl-1H-pyrrolo[2,3-b]pyridine-6-carboxylic acid

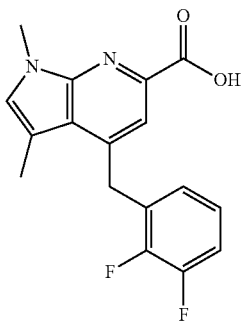 [SMILES: Cc1cn(C)c2nc(C(=O)O)cc(Cc3cccc(F)c3F)c12]

The title compound was synthesized from methyl 4-(2,3-difluorobenzyl)-1,3-dimethyl-1H-pyrrolo[2,3-b]pyridine-6-carboxylate following the procedure as described in step-7 of example 1. Yield: 0.019 g (70%); Mass (m/z): 317.1 (M+1)$^+$.

Step-11: N-[(1S,2S)-2-Hydroxycyclohexyl]-4-(2,3-difluorobenzyl)-1,3-dimethyl-1H-pyrrolo[2,3-b]pyridine-6-carboxamide

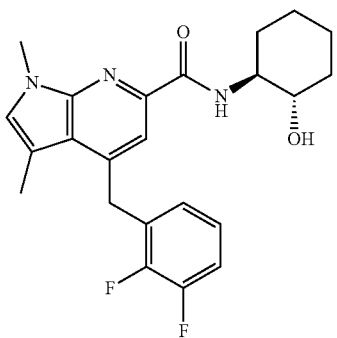 [SMILES: Cc1cn(C)c2nc(C(=O)N[C@H]3CCCC[C@@H]3O)cc(Cc3cccc(F)c3F)c12]

The title compound was synthesized from 4-(2,3-difluorobenzyl)-1,3-dimethyl-1H-pyrrolo[2,3-b]pyridine-6-carboxylic acid following the procedure as described in step-8 of example 1.

Yield: 0.010 g (40%); $^1$H-NMR (CDCl$_3$, 400 MHz) δ ppm: 1.29-1.43 (4H, m), 1.77-1.80 (2H, m), 2.03-2.11 (2H, m), 2.27 (3H, s), 3.51-3.53 (1H, m), 3.67-3.70 (1H, m), 3.84 (s, 3H), 4.46 (s, 2H), 6.60-6.62 (bs, 1H), 6.89 (s, 1H), 7.04-7.16 (m, 2H), 7.28-7.32 (m, 1H), 7.52 (s, 1H), 8.05-8.07 (bs, 1H); Mass (m/z): 414.0 (M+1)$^+$.

Example 32

Racemic trans-N-(3-Hydroxytetrahydropyran-4-yl)-4-(4-fluorobenzyl)-1-methyl-1H-pyrrolo[2,3-b]pyridine-6-carboxamide

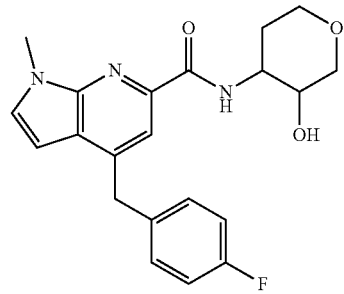 [SMILES: Cn1ccc2c(Cc3ccc(F)cc3)cc(C(=O)NC3CCOCC3O)nc21]

Step-1: Methyl 4-(4-fluorobenzyl)-1-methyl-1H-pyrrolo[2,3-b]pyridine-6-carboxylate

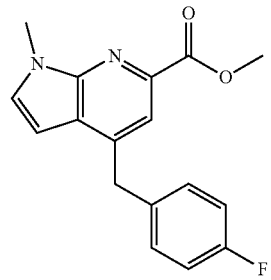 [SMILES: COC(=O)c1cc(Cc2ccc(F)cc2)c2ccn(C)c2n1]

Methyl 4-(4-fluorobenzyl)-1-methyl-1H-pyrrolo[2,3-b]pyridine-6-carboxylate was synthesized by the procedure described in step-6 of Example 1. The crude compound obtained was further purified by flash chromatography using ethyl acetate:n-hexane (20:80) to obtain the title compound.

Yield: 0.29 g; $^1$H-NMR (DMSO-d$_6$, 400 MHz) δ ppm: 3.84 (s, 3H), 3.86 (s, 3H), 4.28 (s, 2H), 6.67-6.68 (d, J=3.3 Hz, 1H), 7.08-7.12 (t, 2H), 7.32-7.38 (t, 2H), 7.76 (s, 1H), 7.73-7.74 (d, J=3.2 Hz, 1H); Mass (m/z): 299.0 (M+H)$^+$.

Step-2: 4-(4-Fluorobenzyl)-1-methyl-1H-pyrrolo[2,3-b]pyridine-6-carboxylic acid

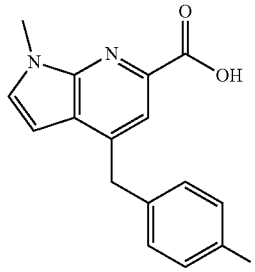

Methyl 4-(4-fluorobenzyl)-1-methyl-1H-pyrrolo[2,3-b]pyridine-6-carboxylate was converted in to 4-(4-fluorobenzyl)-1-methyl-1H-pyrrolo[2,3-b]pyridine-6-carboxylic acid by the procedure as described in step-7 of example 1.

Yield: 0.35 g; $^1$H-NMR (DMSO-$d_6$, 400 MHz) δ ppm: 3.86 (s, 3H), 4.27 (s, 2H), 6.66-6.67 (d, J=3.2 Hz, 1H), 7.08-7.13 (t, 2H), 7.33-7.35 (dd, J=2.4, 8.2 Hz, 2H), 7.65 (s, 1H), 7.71-7.72 (d, J=3.4 Hz, 1H), 12.02 (bs, 1H); Mass (m/z): 285.0 (M+H)$^+$.

Step-3: Racemic trans-N-(3-Hydroxytetrahydropyran-4-yl)-4-(4-fluorobenzyl)-1-methyl-1H-pyrrolo[2,3-b]pyridine-6-carboxamide The title compound was synthesized from 4-(4-fluorobenzyl)-1-methyl-1H-pyrrolo[2,3-b]pyridine-6-carboxylic acid by the procedure described in step 8 of example 1 using trans-4-aminotetrahydropyran-3-ol hydrochloride (I-21). The crude compound obtained was further purified by flash chromatography using methanol:dichloromethane (1:99) to afford the title compound.

Yield: 0.36 g (62%); $^1$H-NMR (DMSO-$d_6$, 400 MHz) δ ppm: 1.64-1.71 (m, 1H), 1.86-1.89 (m, 1H), 2.89-2.94 (m, 1H), 3.02-3.07 (m, 1H), 3.58-3.61 (m, 1H), 3.80-3.85 (m, 3H), 3.92 (s, 3H), 4.28 (s, 2H), 4.99-5.02 (m, d, J=5.7 Hz, 1H), 6.65-6.66 (d, J=3.4 Hz, 1H), 7.08-7.12 (m, 2H), 7.31-7.34 (m, 2H), 7.64-7.67 (m, 2H), 8.42-8.44 (d, J=8.1 Hz, 1H); Mass (m/z): 384.3 (M+H)$^+$.

Example 33 trans-N-(3-Hydroxytetrahydropyran-4-yl)-4-(4-fluorobenzyl)-1-methyl-1H-pyrrolo[2,3-b]pyridine-6-carboxamide (Isomer-I)

Yield: 0.12 g; $^1$H-NMR (DMSO-$d_6$, 400 MHz) δ ppm: 1.64-1.70 (m, 1H), 1.86-1.89 (m, 1H), 3.02-3.07 (m, 2H), 3.58-3.61 (m, 1H), 3.81-3.83 (m, 3H), 3.92 (s, 3H), 4.28 (s, 2H), 4.99-5.01 (d, J=5.6 Hz, 1H), 6.65-6.66 (d, J=3.4 Hz, 1H), 7.08-7.12 (m, 2H), 7.31-7.34 (m, 2H), 7.64-7.67 (m, 2H), 8.42-8.44 (d, J=8.1 Hz, 1H); Mass (m/z): 384.3 (M+H)$^+$.

Chiral HPLC: 99.46%, Method: CHIRALPAK AD-H 250×4.6 mm 5 μm; Solvent A=70.0% MeOH, B=30.0% IPA, C=0.1% DEA; Isocratic Flow=0.70 mL/min; T=25° C., retention time=7.25 min, wavelength=245 nm.

Example 34 trans-N-(3-Hydroxytetrahydropyran-4-yl)-4-(4-fluorobenzyl)-1-methyl-1H-pyrrolo[2,3-b]pyridine-6-carboxamide (Isomer-II)

Yield: 0.12 g; $^1$H-NMR (DMSO-$d_6$, 400 MHz) δ ppm: 1.64-1.71 (m, 1H), 1.86-1.89 (m, 1H), 3.02-3.07 (m, 2H), 3.58-3.64 (m, 1H), 3.77-3.85 (m, 3H), 3.92 (s, 3H), 4.28 (s, 2H), 4.99-5.01 (d, J=5.6 Hz, 1H), 6.65-6.66 (d, J=3.3 Hz, 1H), 7.08-7.12 (m, 2H), 7.31-7.34 (m, 2H), 7.64-7.67 (m, 2H), 8.42-8.44 (d, J=8.1 Hz, 1H); Mass (m/z): 384.3 (M+H)$^+$.

Chiral HPLC: 97.41%, Method: CHIRALPAK AD-H 250×4.6 mm 5 μm; Solvent A=70.0% MeOH, B=30.0% IPA, C=0.1% DEA; Isocratic Flow=0.70 mL/min; T=25° C., retention time=9.36 min, wavelength=245 nm.

Example 35

Racemic cis-N-(3-Hydroxytetrahydropyran-4-yl)-4-(4-fluorobenzyl)-1-methyl-H-pyrrolo[2,3-b]pyridine-6-carboxamide

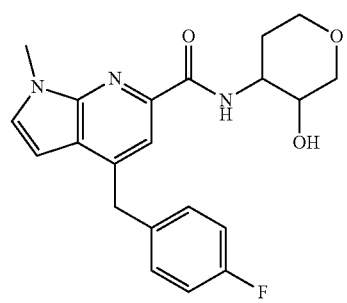 [SMILES: Cn1ccc2c(Cc3ccc(F)cc3)cc(C(=O)NC3CCOCC3O)nc21]

The title compound was prepared by the experimental procedure as described in the Example 32 using cis-4-aminotetrahydropyran-3-ol (I-20).

Yield: 0.092 g; $^1$H-NMR (DMSO-$d_6$, 400 MHz) δ ppm: 1.58-1.62 (m, 1H), 1.87-1.91 (m, 1H), 3.33-3.42 (m, 1H), 3.50-3.53 (m, 1H), 3.65 (m, 1H), 3.74-3.82 (m, 2H), 3.86 (s, 3H), 4.02-4.05 (m, 1H), 4.28 (s, 2H), 5.25-5.26 (d, J=5.1 Hz, 1H), 6.66-6.67 (d, J=3.3 Hz, 1H), 7.08-7.12 (m, 2H), 7.31-7.34 (m, 2H), 7.66 (s, 1H), 7.68-7.69 (d, J=3.3 Hz, 1H), 8.36-8.38 (d, J=8.3 Hz, 1H); Mass (m/z): 384.3 (M+H)$^+$.

Example 36 cis-N-(3-Hydroxytetrahydropyran-4-yl)-4-(4-fluorobenzyl)-1-methyl-1H-pyrrolo[2,3-b]pyridine-6-carboxamide (Isomer-I)

Yield: 0.033 g; $^1$H-NMR (DMSO-$d_6$, 400 MHz) δ ppm: 1.58-1.62 (m, 1H), 1.87-1.91 (m, 1H), 3.33-3.42 (m, 1H), 3.50-3.53 (m, 1H), 3.65 (m, 1H), 3.74-3.82 (m, 2H), 3.86 (s, 3H), 4.02-4.05 (m, 1H), 4.28 (s, 2H), 5.25-5.26 (d, J=5.1 Hz, 1H), 6.66-6.67 (d, J=3.3 Hz, 1H), 7.08-7.12 (m, 2H), 7.31-7.34 (m, 2H), 7.66 (s, 1H), 7.68-7.69 (d, J=3.3 Hz, 1H), 8.36-8.38 (d, J=8.3 Hz, 1H); Mass (m/z): 384.3 (M+H)$^+$.

Chiral HPLC: 99.58%, Method: CHIRALPAK AD-H, 250×4.6 mm, 5 μm; Solvent A=30.0% n-Heptane, B=40.0% MeOH, C=30.0% IPA, D=0.10% DEA; Isocratic Flow=0.7 mL/min; T=25° C., retention time=8.37 min, wavelength=245 nm.

Example 37 cis-N-(3-Hydroxytetrahydropyran-4-yl)-4-(4-fluorobenzyl)-1-methyl-1H-pyrrolo[2,3-b]pyridine-6-carboxamide (Isomer-II)

Yield: 0.031 g; $^1$H-NMR (DMSO-$d_6$, 400 MHz) δ ppm: 1.59-1.62 (m, 1H), 1.87-1.91 (m, 1H), 3.33-3.42 (m, 1H), 3.50-3.53 (m, 1H), 3.65 (m, 1H), 3.74-3.82 (m, 2H), 3.86 (s, 3H), 4.04-4.06 (m, 1H), 4.28 (s, 2H), 5.25-5.26 (d, J=5.1 Hz, 1H), 6.66-6.67 (d, J=3.3 Hz, 1H), 7.08-7.12 (m, 2H), 7.31-7.34 (m, 2H), 7.66 (s, 1H), 7.68-7.69 (d, J=3.3 Hz, 1H), 8.36-8.38 (d, J=8.3 Hz, 1H); Mass (m/z): 384.3 (M+H)⁺.

Chiral HPLC: 98.88%, Method: CHIRALPAK AD-H, 250×4.6 mm, 5 μm; Solvent A=30.0% n-Heptane, B=40.0% MeOH, C=30.0% IPA, D=0.10% DEA; Isocratic Flow=0.7 mL/min; T=25° C., retention time=10.31 min, wavelength=245 nm.

Examples 38 to 63

The compounds of Examples 38 to 63 were prepared by following the experimental procedures as described in the Examples 32-37, with some non-critical variations.

| Example No. | Structure and IUPAC name | Characterization data |
|---|---|---|
| 38 | 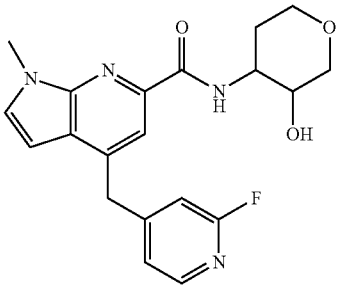<br>Racemic trans-N-(3-Hydroxytetrahydropyran-4-yl)-4-(2-fluoropyridin-4-ylmethyl)-1-methyl-1H-pyrrolo[2,3-b]pyridine-6-carboxamide | ¹H-NMR (DMSO-d₆, 400 MHz) δ ppm: 1.65-1.71 (m, 1H), 1.86-1.89 (m, 1H), 2.89-2.94 (m, 1H), 3.05-3.13 (m, 1H), 3.58-3.65 (m, 1H), 3.80-3.84 (m, 3H), 3.93 (s, 3H), 4.39 (s, 2H), 5.01-5.02 (d, J = 5.6 Hz, 1H), 6.67-6.68 (d, J = 3.3 Hz, 1H), 7.14 (s, 1H), 7.23-7.24 (d, J = 4.2 Hz, 1H), 7.69-7.69 (d, J = 3.2 Hz, 1H), 7.72 (s, 1H), 8.11-8.12 (d, J = 5.0 Hz, 1H), 8.45-8.47 (d, J = 8.1 Hz, 1H); Mass (m/z): 385.3 (M + H)⁺. |
| 39 | 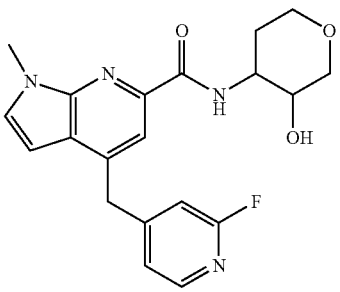<br>trans-N-(3-Hydroxytetrahydropyran-4-yl)-4-(2-fluoropyridin-4-ylmethyl)-1-methyl-1H-pyrrolo[2,3-b]pyridine-6-carboxamide (Isomer-I) | ¹H-NMR (DMSO-d₆, 400 MHz) δ ppm: 1.65-1.71 (m, 1H), 1.86-1.89 (m, 1H), 2.89-2.94 (m, 1H), 3.03-3.08 (m, 1H), 3.59-3.64 (m, 1H), 3.82-3.85 (m, 3H), 3.93 (s, 3H), 4.39 (s, 2H), 4.99-5.01 (d, J = 5.6 Hz, 1H), 6.68-6.69 (d, J = 3.3 Hz, 1H), 7.14 (s, 1H), 7.24-7.25 (d, J = 4.2 Hz, 1H), 7.69-7.70 (d, J = 3.2 Hz, 1H), 7.72 (s, 1H), 8.11-8.12 (d, J = 5.0 Hz, 1H), 8.45-8.47 (d, J = 8.1 Hz, 1H); Mass (m/z): 385.3 (M + H)⁺.<br>Chiral HPLC: 99.94%, Method: CHIRAL PAK IC, 250 × 4.6 mm, 5 μm; Solvent A = 60.0% MeOH, B = 40.0% IPA, C = 0.10% DEA; Isocratic Flow = 0.50 mL/min; T = 25° C., retention time = 13.13 min, wavelength = 300 nm. |
| 40 | 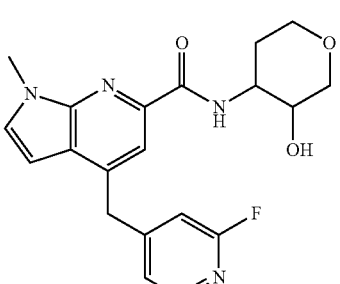<br>trans-N-(3-Hydroxytetrahydropyran-4-yl)-4-(2-fluoropyridin-4-ylmethyl)-1-methyl-1H-pyrrolo[2,3-b]pyridine-6-carboxamide (Isomer-II) | ¹H-NMR (DMSO-d₆, 400 MHz) δ ppm: 1.65-1.71 (m, 1H), 1.86-1.89 (m, 1H), 2.88-2.93 (m, 1H), 3.02-3.08 (m, 1H), 3.60-3.64 (m, 1H), 3.82-3.85 (m, 3H), 3.93 (s, 3H), 4.39 (s, 2H), 4.99-5.01 (d, J = 5.7 Hz, 1H), 6.68-6.69 (d, J = 3.3 Hz, 1H), 7.14 (s, 1H), 7.24-7.25 (d, J = 4.4 Hz, 1H), 7.69-7.70 (d, J = 3.3 Hz, 1H), 7.72 (s, 1H), 8.11-8.12 (d, J = 5.0 Hz, 1H), 8.45-8.47 (d, J = 8.1 Hz, 1H); Mass (m/z): 385.3 (M + H)⁺.<br>Chiral HPLC: 99.44%, Method: CHIRAL PAK IC, 250 × 4.6 mm, 5 μm; Solvent A = 60.0% MeOH, B = 40.0% IPA, C = 0.10% DEA; Isocratic Flow = 0.50 mL/min; T = 25° C., retention time = 15.54 min, wavelength = 300 nm. |

| Example No. | Structure and IUPAC name | Characterization data |
|---|---|---|
| 41 | cis-N-(3-Hydroxytetrahydropyran-4-yl)-4-(3,4-difluorobenzyl)-1-methyl-1H-pyrrolo[2,3-b]pyridine-6-carboxamide (Isomer-I) | $^1$H-NMR (DMSO-d$_6$, 400 MHz) δ ppm: 1.60-1.62 (m, 1H), 1.84-1.94 (m, 1H), 3.37-3.43 (m, 1H), 3.45-3.53 (m, 1H), 3.65 (m, 1H), 3.74-3.82 (m, 2H), 3.86 (s, 3H), 4.02-4.07 (m, 1H), 4.30 (s, 2H), 5.28 (m, 1H), 6.69-6.69 (d, J = 3.4 Hz, 1H), 7.14 (m, 1H), 7.30-7.43 (m, 2H), 7.69-7.70 (m, 2H), 8.36-8.38 (d, J = 8.4 Hz, 1H); Mass (m/z): 401.9 (M + H)$^+$. Chiral HPLC: 96.12%, Method: CHIRAL PAK AD-H, 250 × 4.6 mm, 5 μm; Solvent A = 30.0% n-Heptane, B = 40.0% MeOH, C = 30.0% IPA, D = 0.10% DEA; Isocratic Flow = 0.7 mL/min; T = 25° C., retention time = 8.65 min, wavelength = 245 nm. |
| 42 | cis-N-(3-Hydroxytetrahydropyran-4-yl)-4-(3,4-difluorobenzyl)-1-methyl-1H-pyrrolo[2,3-b]pyridine-6-carboxamide (Isomer-II) | $^1$H-NMR (DMSO-d$_6$, 400 MHz) δ ppm: 1.60-1.62 (m, 1H), 1.85-1.91 (m, 1H), 3.35-3.43 (m, 1H), 3.51-3.53 (m, 1H), 3.65 (m, 1H), 3.74-3.82 (m, 2H), 3.86 (s, 3H), 4.02-4.07 (m, 1H), 4.30 (s, 2H), 5.26 (s, 1H), 6.69-6.69 (d, J = 3.3 Hz, 1H), 7.14-7.14 (d, J = 2.0 Hz, 1H), 7.30-7.43 (m, 2H), 7.67-7.70 (m, 2H), 8.36-8.38 (d, J = 8.4 Hz, 1H); Mass (m/z): 402.0 (M + H)$^+$. Chiral HPLC: 99.01%, Method: CHIRAL PAK AD-H, 250 × 4.6 mm, 5 μm; Solvent A = 30.0% n-Heptane, B = 40.0% MeOH, C = 30.0% IPA, D = 0.10% DEA; Isocratic Flow = 0.7 mL/min; T = 25° C., retention time = 11.21 min, wavelength = 245 nm. |
| 43 | trans-N-(3-Hydroxytetrahydropyran-4-yl)-4-(2,3-difluorobenzyl)-1-methyl-1H-pyrrolo[2,3-b]pyridine-6-carboxamide (Isomer-I) | $^1$H-NMR (DMSO-d$_6$, 400 MHz) δ ppm: 1.64-1.67 (m, 1H), 1.85-1.89 (m, 1H), 3.00-3.07 (m, 2H), 3.61 (m, 1H), 3.79-3.85 (m, 3H), 3.93 (s, 3H), 4.37 (s, 2H), 4.99 (s, 1H), 6.63-6.64 (d, J = 3.4 Hz, 1H), 7.14-7.20 (m, 2H), 7.30-7.33 (m, 1H), 7.60 (s, 1H), 7.68-7.69 (d, J = 3.3 Hz, 1H), 8.43-8.45 (d, J = 8.2 Hz, 1H); Mass (m/z): 402.0 (M + H)$^+$. Chiral HPLC: 95.96%, Method: CHIRAL PAK AD-H, 250 × 4.6 mm, 5 μm; Solvent A = 30.0% n-Heptane, B = 40.0% MeOH, C = 30.0% IPA, D = 0.10% DEA; Isocratic Flow = 0.70 mL/min; T = 25° C., retention time = 6.82 min, wavelength = 245 nm. |

| Example No. | Structure and IUPAC name | Characterization data |
|---|---|---|
| 44 | trans-N-(3-Hydroxytetrahydropyran-4-yl)-4-(2,3-difluorobenzyl)-1-methyl-1H-pyrrolo[2,3-b]pyridine-6-carboxamide (Isomer-II) | $^1$H-NMR (DMSO-d$_6$, 400 MHz) δ ppm: 1.65-1.68 (m, 1H), 1.86-1.88 (m, 1H), 3.02-3.07 (m, 2H), 3.59-3.62 (m, 1H), 3.81-3.85 (m, 3H), 3.93 (s, 3H), 4.38 (s, 2H), 4.99-5.00 (d, J = 5.6 Hz, 1H), 6.63-6.64 (d, J = 3.3 Hz, 1H), 7.15-7.19 (m, 2H), 7.30-7.32 (m, 1H), 7.60 (s, 1H), 7.68-7.69 (d, J = 3.3 Hz, 1H), 8.43-8.45 (d, J = 8.1 Hz, 1H); Mass (m/z): 402.0 (M + H)$^+$. Chiral HPLC: 99.84%, Method: CHIRAL PAK AD-H, 250 × 4.6 mm, 5 μm; Solvent A = 30.0% n-Heptane, B = 40.0% MeOH, C = 30.0% IPA, D = 0.10% DEA; Isocratic Flow = 0.70 mL/min; T = 25° C., retention time = 9.70 min, wavelength = 245 nm. |
| 45 | Racemic cis-N-(3-Hydroxytetrahydropyran-4-yl)-4-(2-fluoropyridin-4-ylmethyl)-1-methyl-1H-pyrrolo[2,3-b]pyridine-6-carboxamide | $^1$H-NMR (DMSO-d$_6$, 400 MHz) δ ppm: 1.62 (m, 1H), 1.90 (m, 1H), 3.43-3.43 (m, 2H), 3.57-3.58 (m, 1H), 3.66-3.80 (m, 2H), 3.87 (m, 3H), 4.05 (m, 1H), 4.40 (s, 2H), 5.25-5.27 (d, J = 5.2 Hz, 1H), 6.69-6.70 (d, J = 3.3 Hz, 1H), 7.14 (s, 1H), 7.24-7.25 (m, 1H), 7.71-7.72 (d, J = 3.4 Hz, 1H), 7.75 (s, 1H), 8.11-8.12 (d, J = 5.12 Hz, 1H), 8.37-8.39 (d, J = 8.3 Hz, 1H); Mass (m/z): 385.0 (M + H)$^+$. |
| 46 | cis-N-(3-Hydroxytetrahydropyran-4-yl)-4-(2-fluoropyridin-4-ylmethyl)-1-methyl-1H-pyrrolo[2,3-b]pyridine-6-carboxamide (Isomer-I) | $^1$H-NMR (DMSO-d$_6$, 400 MHz) δ ppm: 1.60-1.62 (m, 1H), 1.88-1.92 (m, 1H), 3.41-3.46 (m, 2H), 3.53 (m, 1H), 3.66-3.78 (m, 2H), 3.87 (s, 3H), 4.05 (m, 1H), 4.40 (s, 2H), 5.27-5.28 (d, J = 4.8 Hz, 1H), 6.69-6.69 (d, J = 3.2 Hz, 1H), 7.14 (s, 1H), 7.24-7.25 (d, J = 4.4 Hz, 1H), 7.70-7.71 (d, J = 3.2 Hz, 1H), 7.74 (s, 1H), 8.11-8.12 (d, J = 5.0 Hz, 1H), 8.37-8.39 (d, J = 8.2 Hz, 1H); Mass (m/z): 385.1 (M + H)$^+$. Chiral HPLC: 99.97%, Method: CHIRAL PAK IC, 250 × 4.6 mm, 5 μm; Solvent A = 60.0% n-Heptane, B = 30.0% Ethanol, C = 10.0% IPA; Isocratic Flow = 0.70 mL/min; T = 25° C., retention time = 16.43 min, wavelength = 245 nm. |

| Example No. | Structure and IUPAC name | Characterization data |
|---|---|---|
| 47 | cis-N-(3-Hydroxytetrahydropyran-4-yl)-4-(2-fluoropyridin-4-ylmethyl)-1-methyl-1H-pyrrolo[2,3-b]pyridine-6-carboxamide (Isomer-II) | $^1$H-NMR (DMSO-$d_6$, 400 MHz) δ ppm: 1.60-1.62 (m, 1H), 1.85-1.94 (m, 1H), 3.48-3.53 (m, 2H), 3.57-3.58 (m, 1H), 3.66-3.82 (m, 2H), 3.87 (s, 3H), 4.05 (m, 1H), 4.40 (s, 2H), 5.27-5.28 (d, J = 4.04 Hz, 1H), 6.69-6.69 (d, J = 3.04 Hz, 1H), 7.14 (s, 1H), 7.24-7.25 (d, J = 3.8 Hz, 1H), 7.70-7.71 (d, J = 3.1 Hz, 1H), 7.74 (s, 1H), 8.11-8.12 (d, J = 5.0 Hz, 1H), 8.37-8.39 (d, J = 8.2 Hz, 1H); Mass (m/z): 385.1 (M + H)$^+$. Chiral HPLC: 98.87%, Method: CHIRAL PAK IC, 250 × 4.6 mm, 5 μm; Solvent A = 60.0% n-Heptane, B = 30.0% Ethanol, C = 10.0% IPA; Isocratic Flow = 0.70 mL/min; T = 25° C., retention time = 18.43 min, wavelength = 245 nm. |
| 48 | Racemic cis-N-(3-Hydroxytetrahydropyran-4-yl)-4-(2-chloropyridin-5-ylmethyl)-1-methyl-1H-pyrrolo[2,3-b]pyridine-6-carboxamide | $^1$H-NMR (DMSO-$d_6$, 400 MHz) δ ppm: 1.58-1.61 (m, 1H), 1.84-1.93 (m, 1H), 3.30-3.44 (m, 1H), 3.49-3.52 (m, 1H), 3.54-3.64 (m, 1H), 3.73-3.81 (m, 2H), 3.85 (s, 3H), 4.01-4.03 (m, 1H), 4.33 (s, 2H), 5.22-5.24 (d, J = 5.1 Hz, 1H), 6.67-6.68 (d, J = 3.4 Hz, 1H), 7.23-7.25 (d, J = 7.8 Hz, 1H), 7.56-7.61 (m, 3H), 8.34-8.36 (d, J = 8.3 Hz, 1H), 8.43 (s, 1H); Mass (m/z): 401.2 (M + H)$^+$. |
| 49 | cis-N-(3-Hydroxytetrahydropyran-4-yl)-4-(2-chloropyridin-5-ylmethyl)-1-methyl-1H-pyrrolo[2,3-b]pyridine-6-carboxamide (Isomer-I) | $^1$H-NMR (DMSO-$d_6$, 400 MHz) δ ppm: 1.59-1.62 (m, 1H), 1.85-1.93 (m, 1H), 3.39-3.45 (m, 1H), 3.50-3.53 (m, 1H), 3.55-3.65 (m, 1H), 3.75-3.82 (m, 2H), 3.87 (s, 3H), 4.05-4.07 (m, 1H), 4.34 (s, 2H), 5.25-5.27 (d, J = 4.7 Hz, 1H), 6.69-6.70 (d, J = 2.5 Hz, 1H), 7.41-7.43 (d, J = 8.1 Hz, 1H), 7.70-7.74 (m, 3H), 8.36-8.38 (d, J = 8.1 Hz, 1H), 8.45 (s, 1H); Mass (m/z): 401.2 (M + H)$^+$. Chiral HPLC: 99.83%, Method: CHIRAL PAK IC, 250 × 4.6 mm, 5 μm; Solvent A = 30.0% n-Heptane, B = 40.0% Ethanol, C = 30.0% IPA; Isocratic Flow = 0.50 mL/min; T = 25° C., retention time = 17.02 min, wavelength = 245 nm. |

| Example No. | Structure and IUPAC name | Characterization data |
|---|---|---|
| 50 | 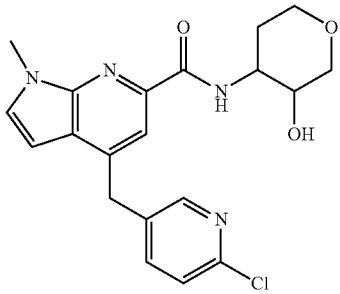<br>cis-N-(3-Hydroxytetrahydropyran-4-yl)-4-(2-chloropyridin-5-ylmethyl)-1-methyl-1H-pyrrolo[2,3-b]pyridine-6-carboxamide (Isomer-II) | $^1$H-NMR (DMSO-d$_6$, 400 MHz) δ ppm: 1.59-1.62 (m, 1H), 1.85-1.91 (m, 1H), 3.40-3.45 (m, 1H), 3.50-3.53 (m, 1H), 3.55-3.65 (m, 1H), 3.75-3.82 (m, 2H), 3.87 (s, 3H), 4.02-4.07 (m, 1H), 4.34 (s, 2H), 5.25-5.27 (d, J = 5.2 Hz, 1H), 6.69-6.70 (d, J = 3.3 Hz, 1H), 7.41-7.43 (d, J = 8.2 Hz, 1H), 7.70-7.75 (m, 3H), 8.36-8.38 (d, J = 8.3 Hz, 1H), 8.45-8.45 (d, J = 1.8 Hz, 1H); Mass (m/z): 401.2 (M + H)$^+$.<br>Chiral HPLC: 93.41%, Method: CHIRAL PAK IC, 250 × 4.6 mm, 5 µm; Solvent A = 30.0% n-Heptane, B = 40.0% Ethanol, C = 30.0% IPA; Isocratic Flow = 0.50 mL/min; T = 25° C., retention time = 22.98 min, wavelength = 245 nm. |
| 51 | 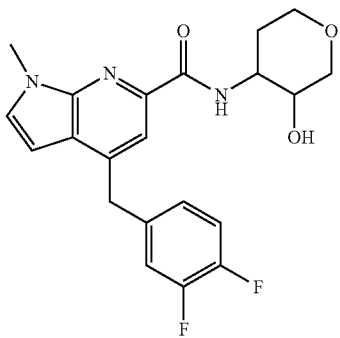<br>trans-N-(3-Hydroxytetrahydropyran-4-yl)-4-(3,4-difluorobenzyl)-1-methyl-1H-pyrrolo[2,3-b]pyridine-6-carboxamide (Isomer-I) | $^1$H-NMR (DMSO-d$_6$, 400 MHz) δ ppm: 1.64-1.68 (m, 1H), 1.87-1.89 (m, 1H), 3.02-3.08 (t, J = 10.4 Hz, 1H), 3.36-3.38 (m, 1H), 3.59-3.63 (m, 1H), 3.80-3.87 (m, 3H), 3.92 (s, 3H), 4.29 (s, 2H), 4.99-5.00 (d, J = 5.72 Hz, 1H), 6.67-6.68 (d, 1H, J = 3.2 Hz), 7.14 (m, 1H), 7.29-7.41 (m, 2H), 7.67 (s, 2H), 8.43-8.45 (m, J = 8.15 Hz, 1H); Mass (m/z): 401.9 (M + H)$^+$.<br>Chiral HPLC: 95.32%, Method: CHIRAL PAK AD-H, 250 × 4.6 mm, 5 µm; Solvent A = 30.0% n-Heptane, B = 40.0% MeOH, C = 30.0% IPA, D = 0.10% DEA; Isocratic Flow = 0.70 mL/min; T = 25° C., retention time = 7.04 min, wavelength = 245 nm. |
| 52 | 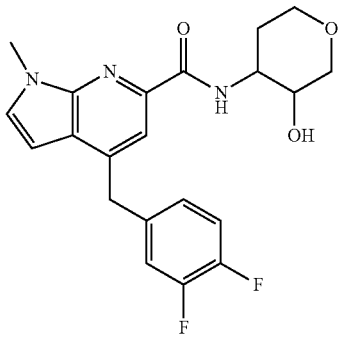<br>trans-N-(3-Hydroxytetrahydropyran-4-yl)-4-(3,4-difluorobenzyl)-1-methyl-1H-pyrrolo[2,3-b]pyridine-6-carboxamide (Isomer-II) | $^1$H-NMR (DMSO-d$_6$, 400 MHz) δ ppm: 1.62-1.68 (m, 1H), 1.70-1.72 (m, 1H), 3.05-3.08 (t, J = 10.4 Hz, 1H), 3.35-3.38 (m, 1H), 3.58-3.64 (m, 1H), 3.79-3.87 (m, 3H), 3.92 (s, 3H), 4.29 (s, 2H), 5.01 (bs, 1H), 6.67-6.68 (d, J = 3.4 Hz, 1H), 7.14-7.15 (m, 1H), 7.29-7.42 (m, 2H), 7.67 (s, 2H), 8.43-8.45 (m, J = 8.2 Hz, 1H); Mass (m/z): 402.0 (M + H)$^+$.<br>Chiral HPLC: 97.10%, Method: CHIRAL PAK AD-H, 250 × 4.6 mm, 5 µm; Solvent A = 30.0% n-Heptane, B = 40.0% MeOH, C = 30.0% IPA, D = 0.10% DEA; Isocratic Flow = 0.70 mL/min; T = 25° C., retention time = 9.40 min, wavelength = 245 nm. |

| Example No. | Structure and IUPAC name | Characterization data |
|---|---|---|
| 53 | 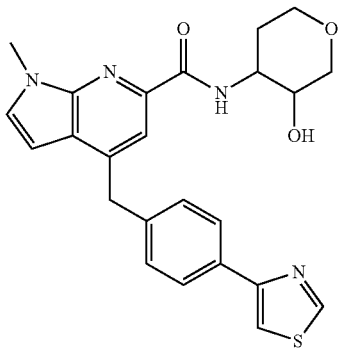<br>Racemic trans-N-(3-Hydroxytetrahydropyran-4-yl)-4-[4-(thiazol-4-yl)benzyl]-1-methyl-1H-pyrrolo[2,3-b]pyridine-6-carboxamide | $^1$H-NMR (DMSO-$d_6$, 400 MHz) δ ppm: 1.64-1.68 (m, 1H), 1.86-1.89 (m, 1H), 3.02-3.07 (m, 1H), 3.34-3.36 (m, 1H), 3.61 (m, 1H), 3.78-3.85 (m, 3H), 3.92 (s, 3H), 4.32 (s, 2H), 4.99-5.01 (d, J = 5.52 Hz, 1H), 6.67-6.69 (m, 1H), 7.36-7.38 (d, J = 8.08 Hz, 2H), 7.66-7.68 (m, 2H), 7.89-7.91 (d, J = 8.04 Hz, 2H), 8.09-8.09 (d, J = 1.40 Hz, 1H), 8.43-8.45 (d, J = 8.16 Hz, 1H), 9.16-9.16 (d, J = 1.48 Hz, 1H); Mass (m/z): 449.3 (M + H)$^+$. |
| 54 | 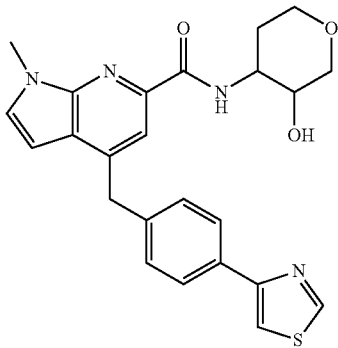<br>trans-N-(3-Hydroxytetrahydropyran-4-yl)-4-[4-(thiazol-4-yl)benzyl]-1-methyl-1H-pyrrolo[2,3-b]pyridine-6-carboxamide (Isomer-I) | $^1$H-NMR (DMSO-$d_6$, 400 MHz) δ ppm: 1.64-1.70 (m, 1H), 1.88-1.90 (m, 1H), 3.02-3.08 (m, 1H), 3.35-3.38 (m, 1H), 3.60-3.64 (m, 1H), 3.81-3.84 (m, 3H), 3.92 (s, 3H), 4.32 (s, 2H), 4.99 (bs, 1H), 6.67-6.68 (d, J = 3.23 Hz, 1H), 7.36-7.38 (d, J = 7.94 Hz, 2H), 7.66-7.67 (d, J = 3.26 Hz, 1H), 7.68 (s, 1H), 7.89-7.91 (d, J = 7.97 Hz, 2H), 8.08-8.09 (d, J = 1.74 Hz, 1H), 8.41-8.43 (d, J = 8.13 Hz, 1H), 9.16-9.16 (d, J = 1.77 Hz, 1H); Mass (m/z): 449.3 (M + H)$^+$.<br>Chiral HPLC: 95.45%, Method: CHIRAL PAK AD-H, 250 × 4.6 mm, 5 μm; Solvent A = 55.0% MeOH, B = 45.0% IPA, C = 0.10% DEA; Isocratic Flow = 0.50 mL/min; T = 25° C., retention time = 19.60 min, wavelength = 250 nm |
| 55 | 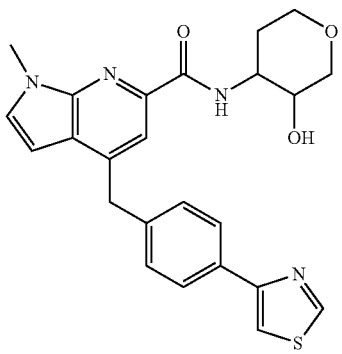<br>trans-N-(3-Hydroxytetrahydropyran-4-yl)-4-[4-(thiazol-4-yl)benzyl]-1-methyl-1H-pyrrolo[2,3-b]pyridine-6-carboxamide (Isomer-II) | $^1$H-NMR (DMSO-$d_6$, 400 MHz) δ ppm: 1.64-1.70 (m, 1H), 1.88-1.90 (m, 1H), 3.02-3.08 (m, 1H), 3.35-3.38 (m, 1H), 3.60-3.64 (m, 1H), 3.81-3.84 (m, 3H), 3.92 (s, 3H), 4.32 (s, 2H), 4.99 (bs, 1H), 6.67-6.68 (d, J = 3.23 Hz, 1H), 7.36-7.38 (d, J = 7.94 Hz, 2H), 7.66-7.67 (d, J = 3.26 Hz, 1H), 7.68 (s, 1H), 7.89-7.91 (d, J = 7.97 Hz, 2H), 8.08-8.09 (d, J = 1.74 Hz, 1H), 8.41-8.43 (d, J = 8.13 Hz, 1H), 9.16-9.16 (d, J = 1.77 Hz, 1H); Mass (m/z): 449.3 (M + H)$^+$.<br>Chiral HPLC: 90.82%, Method: CHIRAL PAK AD-H, 250 × 4.6 mm, 5 μm; Solvent A = 55.0% MeOH, B = 45.0% IPA, C = 0.10% DEA; Isocratic Flow = 0.50 mL/min; T = 25° C., retention time = 28.34 min, wavelength = 250 nm. |

| Example No. | Structure and IUPAC name | Characterization data |
|---|---|---|
| 56 | 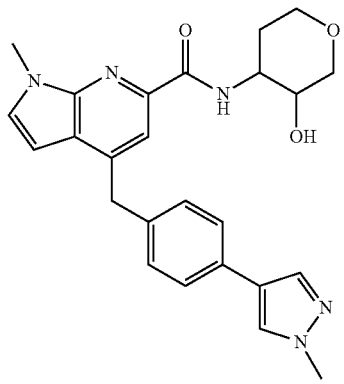<br>Racemic trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide | $^1$H-NMR (DMSO-d$_6$, 400 MHz) δ ppm: 1.64-1.68 (m, 1H), 1.87-1.90 (m, 1H), 3.02-3.07 (m, 2H), 3.59-3.62 (m, 1H), 3.80-3.81 (m, 3H), 3.83 (s, 3H), 3.92 (s, 3H), 4.26 (s, 2H), 4.99-5.01 (d, J = 5.76 Hz, 1H), 6.66-6.68 (m, 1H), 7.25-7.27 (d, J = 7.98 Hz, 2H), 7.44-7.46 (d, J = 8.02 Hz, 2H), 7.66-7.67 (m, 2H), 7.78 (s, 1H), 8.05 (s, 1H), 8.42-8.44 (d, J = 8.17 Hz, 1H); Mass (m/z): 446.3 (M + H)$^+$. |
| 57 | 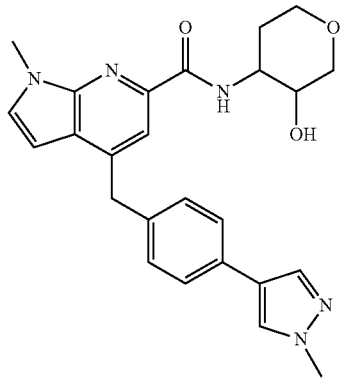<br>trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-I) | $^1$H-NMR (DMSO-d$_6$, 400 MHz) δ ppm: 1.61-1.71 (m, 1H), 1.86-1.89 (m, 1H), 2.89-3.02 (m, 1H), 3.33 (m, 1H), 3.58-3.63 (m, 1H), 3.81 (m, 3H), 3.83 (s, 3H), 3.92 (s, 3H), 4.26 (s, 2H), 5.00-5.01 (d, J = 5.72 Hz, 1H), 6.67-6.67 (d, J = 3.36 Hz, 1H), 7.25-7.27 (d, J = 7.92 Hz, 2H), 7.44-7.46 (d, J = 7.93 Hz, 2H), 7.66 (s, 2H), 7.78 (s, 1H), 8.05 (s, 1H), 8.42-8.44 (d, J = 8.14 Hz, 1H); Mass (m/z): 446.3 (M + H)$^+$. Chiral HPLC: 99.51%, Method: CHIRAL PAK IC, 250 × 4.6 mm, 5 μm; Solvent A = 90.0% MeOH, B = 10.0% IPA, C = 0.10% DEA; Isocratic Flow = 0.80 mL/min; T = 25° C., retention time = 11.61 min, wavelength = 250 nm. |

| Example No. | Structure and IUPAC name | Characterization data |
|---|---|---|
| 58 | trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-II) | $^1$H-NMR (DMSO-d$_6$, 400 MHz) δ ppm: 1.61-1.71 (m, 1H), 1.86-1.89 (m, 1H), 2.89-3.02 (m, 1H), 3.33 (m, 1H), 3.58-3.63 (m, 1H), 3.81 (m, 3H), 3.83 (s, 3H), 3.92 (s, 3H), 4.26 (s, 2H), 5.00-5.01 (d, J = 5.72, 1H), 6.67-6.67 (d, J = 3.36 Hz, 1H), 7.25-7.27 (d, J = 7.92 Hz, 2H), 7.44-7.46 (d, J = 7.93 Hz, 2H), 7.66 (s, 2H), 7.78 (s, 1H), 8.05 (s, 1H), 8.42-8.44 (d, J = 8.14 Hz, 1H); Mass (m/z): 446.3 (M + H)$^+$. Chiral HPLC: 94.53%, Method: CHIRAL PAK IC, 250 × 4.6 mm, 5 μm; Solvent A = 90.0% MeOH, B = 10.0% IPA, C = 0.1% DEA; Isocratic Flow = 0.80 mL/min; T = 25° C., retention time = 13.14 min, wavelength = 250 nm. |
| 59 | Racemic trans-N-(3-Hydroxytetrahydropyran-4-yl)-4-(4-methoxybenzyl)-1-methyl-1H-pyrrolo[2,3-b]pyridine-6-carboxamide | $^1$H-NMR (CDCl$_3$, 400 MHz) δ ppm: 1.73-1.89 (m, 2H), 3.21-3.26 (m, 1H), 3.43-3.52 (m, 2H), 3.65-3.66 (m, 1H), 3.76 (s, 3H), 3.89 (s, 3H), 4.00-4.08 (m, 2H), 4.22 (s, 2H), 4.65 (m, 1H), 6.46-6.47 (d, J = 3.24 Hz, 1H), 6.79-6.81 (d, J = 8.48 Hz, 2H), 7.13-7.15 (d, J = 8.46 Hz, 2H), 7.27 (s, 1H), 8.01 (s, 1H), 8.11-8.12 (d, J = 5.30 Hz, 1H); Mass (m/z): 396.45 (M + H)$^+$. |
| 60 | trans-N-(3-Hydroxytetrahydropyran-4-yl)-4-(4-methoxybenzyl)-1-methyl-1H-pyrrolo[2,3-b]pyridine-6-carboxamide (Isomer-I) | $^1$H-NMR (DMSO-d$_6$, 400 MHz) δ ppm: 1.64-1.68 (m, 1H), 1.86-1.88 (m, 1H), 3.05-3.07 (m, 1H), 3.58-3.64 (m, 1H), 3.69 (s, 3H), 3.81-3.83 (m, 4H), 3.91 (s, 3H), 4.21 (s, 2H), 5.00-5.01 (d, J = 5.73 Hz, 1H), 6.64-6.65 (d, J = 3.31 Hz, 1H), 6.83-6.85 (d, J = 8.46 Hz, 2H), 7.91-7.21 (d, J = 8.53 Hz, 2H), 7.61 (s, 1H), 7.64-7.65 (d, J = 3.34 Hz, 1H), 8.41-8.43 (d, J = 8.18 Hz, 1H); Mass (m/z): 396.2 (M + H)$^+$. Chiral HPLC: 98.31%, Method: CHIRAL PAK AD-H 250 × 4.6 mm 5 μm; Solvent A = 70.0% MeOH, B = 30.0% IPA, C = 0.10% DEA; Isocratic Flow = 0.70 mL/min; T = 25° C., retention time = 8.86 min, wavelength = 245 nm. |

| Example No. | Structure and IUPAC name | Characterization data |
|---|---|---|
| 61 | 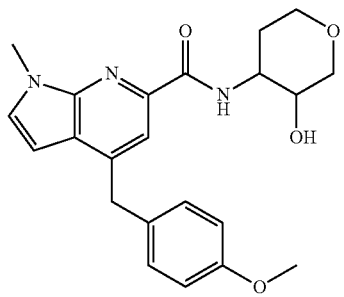<br>trans-N-(3-Hydroxytetrahydropyran-4-yl)-4-(4-methoxybenzyl)-1-methyl-1H-pyrrolo[2,3-b]pyridine-6-carboxamide (Isomer-II) | $^1$H-NMR (DMSO-d$_6$, 400 MHz) δ ppm: 1.64-1.68 (m, 1H), 1.86-1.88 (m, 1H), 3.05-3.07 (m, 1H), 3.58-3.64 (m, 1H), 3.69 (s, 3H), 3.81-3.83 (m, 4H), 3.91 (s, 3H), 4.21 (s, 2H), 5.00-5.01 (d, J = 5.73 Hz, 1H), 6.64-6.65 (d, J = 3.31 Hz, 1H), 6.83-6.85 (d, J = 8.46 Hz, 2H), 7.91-7.21 (d, J = 8.53 Hz, 2H), 7.61 (s, 1H), 7.64-7.65 (d, J = 3.34 Hz, 1H), 8.41-8.43 (d, J = 8.18 Hz, 1H); Mass (m/z): 396.2 (M + H)$^+$.<br>Chiral HPLC: 95.68%, Method: CHIRAL PAK AD-H 250 × 4.6 mm 5 µm; Solvent A = 70.0% MeOH, B = 30.0% IPA, C = 0.10% DEA; Isocratic Flow = 0.70 mL/min; T = 25° C., retention time = 11.36 min, wavelength = 245 nm. |
| 62 | 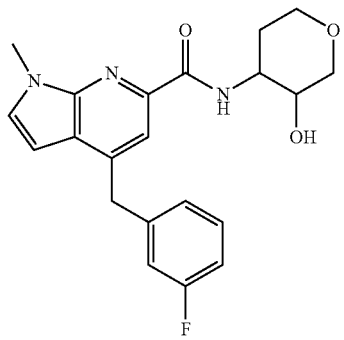<br>trans-N-(3-Hydroxytetrahydropyran-4-yl)-4-(3-fluorobenzyl)-1-methyl-1H-pyrrolo[2,3-b]pyridine-6-carboxamide (Isomer-I) | $^1$H-NMR (DMSO-d$_6$, 400 MHz) δ ppm: 1.64-1.68 (m, 1H), 1.86-1.89 (m, 1H), 3.04-3.07 (m, 1H), 3.50-3.53 (m, 1H), 3.81-3.83 (m, 4H), 3.91 (s, 3H), 4.30 (s, 2H), 5.03-5.04 (d, J = 5.64 Hz, 1H), 6.67-6.68 (d, J = 3.34 Hz, 1H), 7.02-7.04 (m, 1H), 7.12-7.13 (m, 2H), 7.29-7.32 (m, 1H), 7.66 (s, 2H), 8.45-8.47 (d, J = 8.18 Hz, 1H); Mass (m/z): 384.3 (M + H)$^+$.<br>Chiral HPLC: 99.66%, Method: CHIRAL PAK AD-H 250 × 4.6 mm 5 µm; Solvent A = 100.0% MeOH, B = 0.10% DEA; Isocratic Flow = 0.80 mL/min; T = 25° C., retention time = 6.11 min, wavelength = 245 nm. |
| 63 | 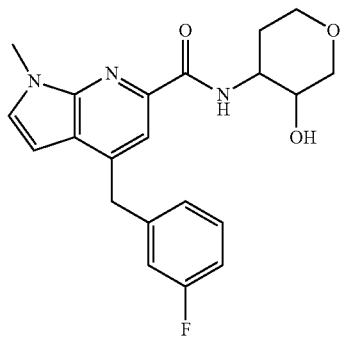<br>trans-N-(3-Hydroxytetrahydropyran-4-yl)-4-(3-fluorobenzyl)-1-methyl-1H-pyrrolo[2,3-b]pyridine-6-carboxamide (Isomer-II) | $^1$H-NMR (DMSO-d$_6$, 400 MHz) δ ppm: 1.64-1.68 (m, 1H), 1.86-1.89 (m, 1H), 3.04-3.07 (m, 1H), 3.50-3.53 (m, 1H), 3.81-3.83 (m, 4H), 3.91 (s, 3H), 4.30 (s, 2H), 5.03-5.04 (d, J = 5.64 Hz, 1H), 6.67-6.68 (d, J = 3.34 Hz, 1H), 7.02-7.04 (m, 1H), 7.12-7.13 (m, 2H), 7.29-7.32 (m, 1H), 7.66 (s, 2H), 8.45-8.47 (d, J = 8.18 Hz, 1H); Mass (m/z): 384.3 (M + H)$^+$.<br>Chiral HPLC: 99.72%, Method: CHIRAL PAK AD-H 250 × 4.6 mm 5 µm; Solvent A = 100.0% MeOH, B = 0.10% DEA; Isocratic Flow = 0.80 mL/min; T = 25° C., retention time = 8.07 min, wavelength = 245 nm. |

Example 64

Racemic cis-N-(4-Hydroxytetrahydropyran-3-yl)-4-(4-fluorobenzyl)-1-methyl-H-pyrrolo[2,3-b]pyridine-6-carboxamide

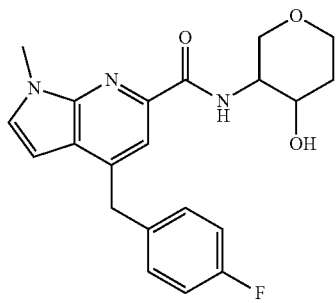 [SMILES: Cn1ccc2c(Cc3ccc(F)cc3)cc(C(=O)NC3COCCC3O)nc21]

The title compound was prepared by the experimental procedure as described in the step 8 of example 1 using cis-3-aminotetrahydropyran-4-ol hydrochloride (I-23).

Yield: 0.11 g; $^1$H-NMR (DMSO-d$_6$, 400 MHz) δ ppm: 1.50-1.52 (m, 1H), 1.88-1.91 (m, 1H), 3.15-3.25 (m, 1H), 3.35-3.50 (m, 1H), 3.65 (m, 1H), 3.75-3.86 (m, 2H), 3.90 (s, 3H), 4.28 (s, 2H), 5.03-5.04 (d, J=4.3 Hz, 1H), 6.66-6.67 (d, J=3.2 Hz, 1H), 7.08-7.12 (m, 2H), 7.31-7.34 (m, 2H), 7.64 (s, 1H), 7.67-7.68 (d, J=3.3 Hz, 2H), 8.31-8.33 (d, J=7.1 Hz, 1H); Mass (m/z): 384.3 (M+H)$^+$.

Example 65 cis-N-(4-Hydroxytetrahydropyran-3-yl)-4-(4-fluorobenzyl)-1-methyl-1H-pyrrolo[2,3-b]pyridine-6-carboxamide (Isomer-I)

Yield: 0.056 g; $^1$H-NMR (DMSO-d$_6$, 400 MHz) δ ppm: 1.50-1.52 (m, 1H), 1.88-1.91 (m, 1H), 3.22-3.24 (m, 1H), 3.31-3.39 (m, 1H), 3.74-3.76 (m, 2H), 3.81-3.87 (m, 2H), 3.90 (s, 3H), 4.28 (s, 2H), 5.03-5.04 (m, 1H), 6.66-6.67 (d, J=3.3 Hz, 1H), 7.08-7.12 (t, 2H), 7.31-7.34 (m, 2H), 7.64 (s, 1H), 7.67-7.68 (d, J=3.4 Hz, 1H), 8.31-8.33 (d, J=7.5 Hz, 1H); Mass (m/z): 384.3 (M+H)$^+$.

Chiral HPLC: 96.53%, Method: CHIRALPAK AD-H, 250×4.6 mm, 5 μm; Solvent A=70.0% MeOH, B=30.0% IPA, D=0.10% DEA; Isocratic Flow=0.6 mL/min; T=25° C., retention time=7.92 min, wavelength=245 nm.

Example 66 cis-N-(4-Hydroxytetrahydropyran-3-yl)-4-(4-fluorobenzyl)-1-methyl-1H-pyrrolo[2,3-b]pyridine-6-carboxamide (Isomer-II)

Yield: 0.046 g; $^1$H-NMR (DMSO-d$_6$, 400 MHz) δ ppm: 1.50-1.52 (m, 1H), 1.88-1.91 (m, 1H), 3.14-3.24 (m, 1H), 3.37-3.42 (m, 1H), 3.75-3.81 (m, 2H), 3.84-3.87 (m, 2H), 3.90 (s, 3H), 4.28 (s, 2H), 5.03-5.04 (d, J=4.3 Hz, 1H), 6.66-6.67 (d, J=3.3 Hz, 1H), 7.08-7.12 (t, 2H), 7.31-7.34 (m, 2H), 7.64 (s, 1H), 7.67-7.68 (d, J=3.3 Hz, 1H), 8.31-8.33 (d, J=7.0 Hz, 1H); Mass (m/z): 384.3 (M+H)$^+$.

Chiral HPLC: 99.19%, Method: CHIRALPAK AD-H, 250×4.6 mm, 5 μm; Solvent A=70.0% MeOH, B=30.0% IPA, D=0.10% DEA; Isocratic Flow=0.6 mL/min; T=25° C., retention time=11.2 min, wavelength=245 nm.

Examples 67 to 68

The compounds of Example 67 to 68 were prepared by following the experimental procedures as described in the Example 64, with some non-critical variations

| Example No. | Structure and IUPAC name | Characterization data |
| --- | --- | --- |
| 67 | Racemic cis-N-(4-Hydroxytetrahydropyran-3-yl)-4-(4-methoxybenzyl)-1-methyl-1H-pyrrolo[2,3-b]pyridine-6-carboxamide | $^1$H-NMR (DMSO-d$_6$, 400 MHz) δ ppm: 1.50-1.52 (m, 1H), 1.88-1.91 (d, J = 11.1, 1H), 3.26-3.27 (m, 1H), 3.38-3.41 (m, 1H), 3.70 (s, 3H), 3.84 (s, 2H), 3.86 (s, 3H), 3.90 (s, 2H), 4.2 (s, 2H), 5.03-5.04 (d, J = 4.43 Hz, 1H), 6.65-6.66 (d, J = 3.19 Hz, 1H), 6.83-6.85 (d, J = 8.33 Hz, 2H), 7.19-7.21 (d, J = 8.33 Hz, 2H), 7.61 (s, 1H), 7.66 (d, J = 3.19 Hz, 1H), 8.30-8.32 (d, J = 7.07 Hz, 1H); Mass (m/z): 396.2 (M + H)$^+$. |

| Example No. | Structure and IUPAC name | Characterization data |
|---|---|---|
| 68 | 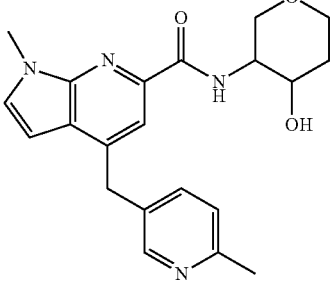<br>Racemic cis-N-(4-Hydroxytetrahydropyran-3-yl)-4-(2-methylpyridin-5-ylmethyl)-1-methyl-1H-pyrrolo[2,3-b]pyridine-6-carboxamide | Mass (m/z): 381.3 (M + H)⁺ |

Example 69

(3S,4S)—N-(4-Hydroxytetrahydropyran-3-yl)-4-(4-fluorobenzyl)-1-methyl-1H-pyrrolo[2,3-b]pyridine-6-carboxamide

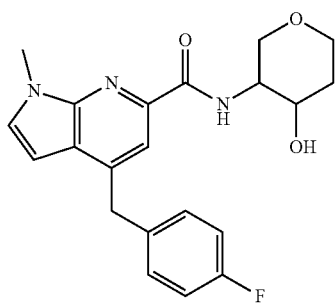 [SMILES: Cn1ccc2c(Cc3ccc(F)cc3)cc(C(=O)NC3COCCC3O)nc21]

The title compound was prepared by the experimental procedure as described in the step 8 of example 1 using commercially available (3S,4S)-3-aminotetrahydro-2H-pyran-4-ol.

¹H-NMR (DMSO-d₆, 400 MHz) δ ppm: 1.50-1.52 (m, 1H), 1.88-1.91 (m, 1H), 3.15-3.25 (m, 1H), 3.35-3.50 (m, 1H), 3.65 (m, 1H), 3.75-3.86 (m, 2H), 3.90 (s, 3H), 4.28 (s, 2H), 5.03-5.04 (d, J=4.3 Hz, 1H), 6.66-6.67 (d, J=3.2 Hz, 1H), 7.08-7.12 (m, 2H), 7.31-7.34 (m, 2H), 7.64 (s, 1H), 7.67-7.68 (d, J=3.3 Hz, 2H), 8.31-8.33 (d, J=7.1 Hz, 1H); Mass (m/z): 384.2 (M+H)⁺.

Examples 70 to 71

The compounds of Example 70 to 71 were prepared by following the experimental procedures as described in the Example 69, with some non-critical variations

| Example No. | Structure and IUPAC name | Characterization data |
|---|---|---|
| 70 | 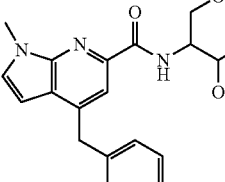<br>(3S,4S)-N-(4-Hydroxytetrahydropyran-3-yl)-4-(4-methoxybenzyl)-1-methyl-1H-pyrrolo[2,3-b]pyridine-6-carboxamide | ¹H-NMR (DMSO-d₆, 400 MHz) δ ppm: 1.48-1.51 (m, 1H), 1.85-1.88 (m, 1H), 3.18-3.26 (m, 1H), 3.38-3.52 (m, 1H), 3.60 (m, 1H), 3.77-3.84 (m, 2H), 3.89 (s, 3H), 3.95 (s, 3H), 4.26 (s, 2H), 5.04-5.05 (d, J = 4.3 Hz, 1H), 6.65-6.66 (d, 1H), 7.26-7.28 (d, 2H), 7.42-7.44 (d, 2H), 7.66 (s, 1H), 7.68-7.69 (d, J = 3.4 Hz, 2H), 8.30-8.32 (d, J = 7.3 Hz, 1H); Mass (m/z): 396.2 (M + H)⁺ |
| 71 | 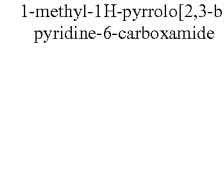<br>(3S,4S)-N-(4-Hydroxytetrahydropyran-3-yl)-4-(2-methylpyridin-5-ylmethyl)-1-methyl-1H-pyrrolo[2,3-b]pyridine-6-carboxamide | ¹H-NMR (DMSO-d₆, 400 MHz) δ ppm: 1.51-1.53 (m, 1H), 1.82-1.86 (m, 1H), 3.16-3.24 (m, 1H), 3.32 (s, 3H), 3.37-3.49 (m, 1H), 3.62 (m, 1H), 3.73-3.80 (m, 2H), 3.86 (s, 3H), 4.32 (s, 2H), 5.01-5.03 (d, J = 4.3 Hz, 1H), 6.61-6.63 (d, 1H), 7.50-7.55 (m, 2H), 7.69 (s, 1H), 7.70-7.71 (d, J = 3.4 Hz, 2H), 7.80 (s, 1H), 8.28-8.30 (d, J = 7.3 Hz, 1H); Mass (m/z): 381.3 (M + H)⁺ |

Example 72

N-[(1S,2S)-2-Hydroxycyclohexyl]-4-(2-chloropyridin-5-ylmethyl)-1-methyl-2,3-dihydro-1H-pyrrolo[2,3-b]pyridine-6-carboxamide

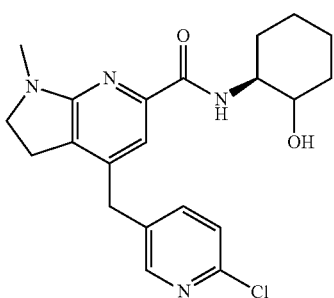 [SMILES: CN1CCc2c(Cc3ccc(Cl)nc3)cc(C(=O)N[C@H]3CCCCC3O)nc21]

To a solution of N-[(1S,2S)-2-hydroxycyclohexyl]-4-(2-chloropyridin-5-ylmethyl)-1-methyl-1H-pyrrolo[2,3-b]pyridine-6-carboxamide (Example 18, 0.38 g, 0.0009 mole) in glacial acetic acid (25 mL) at 25° C., sodium cyanoborohydride (0.73 g, 0.0011 mole) was added in portions at 5-10° C. and warmed to RT and stirred for 48 hours. Reaction mixture was concentrated to obtain a residual mass that was quenched into ice water (50 mL), basified with lye solution pH-9 and extracted with dichloromethane (50 mL×3). The organic layer was washed with brine solution (50 mL), dried over $Na_2SO_4$ and concentrated under vacuum to obtain the crude compound which was further purified by flash chromatography using methanol:dichloromethane (1.5:98.5) to afford the title compound.

Yield: 0.15 g; $^1$H-NMR (DMSO-$d_6$, 400 MHz) δ ppm: 1.22-1.25 (m, 4H), 1.58-1.64 (m, 2H), 1.85-1.88 (m, 2H), 2.91 (s, 3H), 2.94-2.96 (t, 2H), 3.36-3.45 (m, 2H), 3.46-3.50 (t, 2H), 3.88 (s, 2H), 4.68-4.69 (d, J=5.4 Hz, 1H), 6.97 (s, 1H), 7.44-7.46 (d, J=8.1 Hz, 1H), 7.66-7.69 (d, J=2.2, 8.1 Hz, 1H), 8.07-8.09 (d, J=7.8 Hz, 1H), 8.33-8.33 (d, J=2.0 Hz, 1H); Mass (m/z): 400.9 (M+H)$^+$.

Examples 73 to 86

The compounds of Example 73 to 86 were prepared from the appropriate compounds of previous Examples by following the experimental procedures as described in the Example 72, with some non-critical variations.

| Example No. | Structure and IUPAC name | Characterization data |
| --- | --- | --- |
| 73 | N-[(1S,2S)-2-Hydroxycyclohexyl]-4-(2-fluoropyridin-4-ylmethyl)-1-methyl-2,3-dihydro-1H-pyrrolo[2,3-b]pyridine-6-carboxamide | $^1$H-NMR (DMSO-$d_6$, 400 MHz) δ ppm: 1.22-1.24 (m, 4H), 1.58-1.64 (m, 2H), 1.85-1.88 (m, 2H), 2.91 (s, 3H), 2.92-2.96 (t, 2H), 3.36-3.45 (m, 2H), 3.47-3.51 (t, 2H), 3.95 (s, 2H), 4.68-4.69 (d, J = 5.4 Hz, 1H), 7.00 (s, 1H), 7.05 (s, 1H), 7.18-7.19 (d, J = 4.7 Hz, 1H), 8.08-8.10 (d, J = 7.7 Hz, 1H), 8.14-8.15 (d, J = 5.1 Hz, 1H); Mass (m/z): 385.0 (M + H)$^+$. |
| 74 | N-[(1S,2S)-2-Hydroxycyclohexyl]-4-(2-fluoropyridin-5-ylmethyl)-1-methyl-2,3-dihydro-1H-pyrrolo[2,3-b]pyridine-6-carboxamide | $^1$H-NMR (DMSO-$d_6$, 400 MHz) δ ppm: 1.22-1.24 (m, 4H), 1.58-1.64 (m, 2H), 1.85-1.90 (m, 2H), 2.91 (s, 3H), 2.93-2.97 (t, 2H), 3.35-3.45 (m, 2H), 3.46-3.48 (t, 2H), 3.90 (s, 2H), 4.67-4.68 (d, J = 5.3 Hz, 1H), 6.98 (s, 1H), 7.05 (s, 1H), 7.10-7.13 (m, J = 2.7, 8.4 Hz, 1H), 8.07-8.09 (d, J = 7.8 Hz, 1H), 8.15 (s, 1H); Mass (m/z): 385.0 (M + H)$^+$. |

| Example No. | Structure and IUPAC name | Characterization data |
|---|---|---|
| 75 | 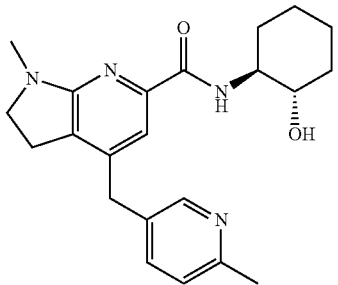 [SMILES: Cc1ccc(Cc2cc(C(=O)N[C@H]3CCCC[C@@H]3O)nc3c2CCN3C)cn1]<br>N-[(1S,2S)-2-Hydroxycyclohexyl]-1-methyl-(6-methylpyridin-3-ylmethyl)-2,3-dihydro-1H-pyrrolo[2,3-b]pyridine-6-carboxamide | $^1$H-NMR (DMSO-$d_6$, 400 MHz) δ ppm: 1.22-1.25 (m, 4H), 1.58-1.64 (m, 2H), 1.85-1.88 (m, 2H), 2.42 (s, 3H), 2.91 (s, 3H), 2.94-2.96 (t, 2H), 3.36-3.45 (m, 2H), 3.46-3.49 (t, 2H), 3.82 (s, 2H), 4.67-4.69 (d, J = 5.4 Hz, 1H), 6.95 (s, 1H), 7.17-7.19 (d, J = 8.0 Hz, 1H), 7.44-7.46 (d, J = 8.1 Hz, 1H), 8.07-8.09 (d, J = 7.8 Hz, 1H), 8.33 (s, 1H); Mass (m/z): 381.0 (M + H)$^+$. |
| 76 | 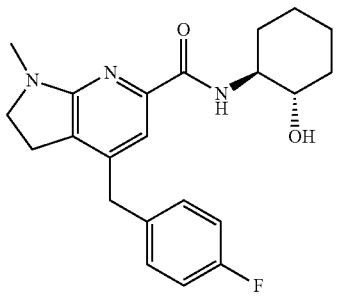 [SMILES: CN1CCc2c(Cc3ccc(F)cc3)cc(C(=O)N[C@H]3CCCC[C@@H]3O)nc21]<br>N-[(1S,2S)-2-Hydroxycyclohexyl]-4-(4-fluorobenzyl)-1-methyl-2,3-dihydro-1H-pyrrolo[2,3-b]pyridine-6-carboxamide | $^1$H-NMR (DMSO-$d_6$, 400 MHz) δ ppm: 1.24-1.27 (m, 4H), 1.58-1.64 (m, 2H), 1.85-1.91 (m, 2H), 2.90-2.95 (m, 5H), 3.45-3.49 (m, 4H), 3.84 (m, 2H), 4.68-4.69 (d, J = 5.3 Hz, 1H), 6.97 (s, 1H), 7.10-7.14 (dd, J = 5.5, 8.0 Hz, 2H), 7.22-7.26 (dd, J = 5.5, 8.0 Hz, 2H), 8.07-8.09 (d, J = 7.7 Hz, 1H); Mass (m/z): 384.2 (M + H)$^+$. |
| 77 | 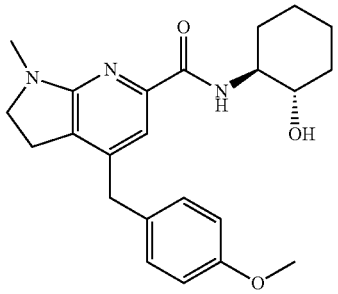 [SMILES: COc1ccc(Cc2cc(C(=O)N[C@H]3CCCC[C@@H]3O)nc3c2CCN3C)cc1]<br>N-[(1S,2S)-2-Hydroxycyclohexyl]-4-(4-methoxybenzyl)-1-methyl-2,3-dihydro-1H-pyrrolo[2,3-b]pyridine-6-carboxamide | $^1$H-NMR (DMSO-$d_6$, 400 MHz) δ ppm: 1.23-1.30 (m, 4H), 1.58-1.64 (m, 2H), 1.85-1.89 (m, 2H), 2.88-2.94 (m, 5H), 3.45-3.49 (m, 4H), 3.71 (s, 3H), 3.77 (s, 2H), 4.68-4.69 (d, J = 5.4 Hz, 1H), 6.84-6.87 (d, J = 8.5 Hz, 2H), 6.98 (s, 1H), 7.10-7.12 (d, J = 8.5 Hz, 2H), 8.06-8.08 (d, J = 7.7 Hz, 1H); Mass (m/z): 396.1 (M + H)$^+$. |

| Example No. | Structure and IUPAC name | Characterization data |
|---|---|---|
| 78 | 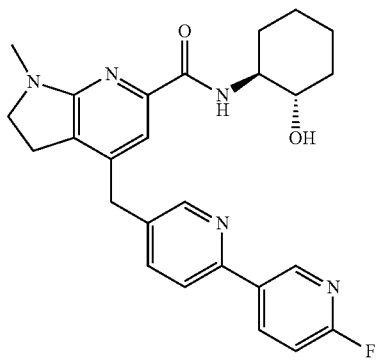 [SMILES: CN1CCc2c(Cc3ccc(-c4ccc(F)nc4)nc3)cc(C(=O)N[C@H]3CCCC[C@@H]3O)nc21]<br>N-[(1S,2S)-2-Hydroxycyclohexyl]-4-(2'-fluoro-[2,5']bipyridinyl-5-ylmethyl)-1-methyl-2,3-dihydro-1H-pyrrolo[2,3-b]pyridine-6-carboxamide | $^1$H-NMR (DMSO-d$_6$, 400 MHz) δ ppm: 1.23-1.30 (m, 4H), 1.58-1.64 (m, 2H), 1.87-1.91 (m, 2H), 2.92 (s, 3H), 2.97-3.01 (t, 2H), 3.33-3.41 (m, 2H), 3.48-3.52 (m, 2H), 3.91 (s, 2H), 4.67-4.69 (d, J = 5.3 Hz, 1H), 7.02 (s, 1H), 7.29-7.31 (dd, J = 2.2, 8.4 Hz, 1H), 7.74-7.76 (d, J = 8.0 Hz, 1H), 7.98-8.00 (d, J = 8.0 Hz, 1H), 8.08-8.09 (d, J = 7.7 Hz, 1H), 8.59-8.61 (d, J = 7.8 Hz, 2H), 8.89 (s, 1H); Mass (m/z): 462.2 (M + H)$^+$. |
| 79 | 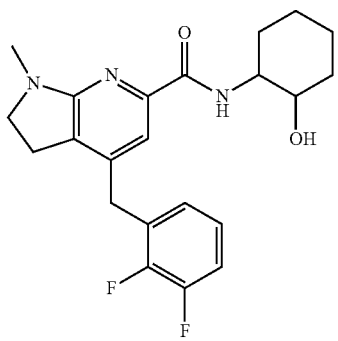 [SMILES: CN1CCc2c(Cc3cccc(F)c3F)cc(C(=O)NC3CCCCC3O)nc21]<br>N-[(1S,2S)-2-Hydroxycyclohexyl]-4-(2,3-difluorobenzyl)-1-methyl-2,3-dihydro-1H-pyrrolo[2,3-b]pyridine-6-carboxamide | $^1$H-NMR (DMSO-d$_6$, 400 MHz) δ ppm: 1.25-1.28 (m, 4H), 1.69-1.75 (m, 2H), 1.96 (m, 2H), 2.98 (s, 3H), 3.26-3.27 (m, 2H), 3.47-3.48 (m, 1H), 3.50-3.52 (m, 1H), 3.70-3.73 (m, 2H), 3.86-3.90 (m, 2H), 4.32 (bs, 1H), 6.89-6.91 (m, 1H), 6.96-7.06 (m, 2H), 7.23-7.26 (s, 1H), 7.97-7.98 (bs, 1H); Mass (m/z): 402.1 (M + H)$^+$. |
| 80 | 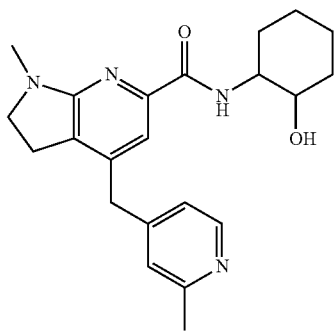 [SMILES: Cc1cc(Cc2cc(C(=O)NC3CCCCC3O)nc3c2CCN3C)ccn1]<br>N-[(1S,2S)-2-Hydroxycyclohexyl]-4-(2-methyl-4-pyridinylmethyl)-1-methyl-2,3-dihydro-1H-pyrrolo[2,3-b]pyridine-6-carboxamide | $^1$H-NMR (DMSO-d$_6$, 400 MHz) δ ppm: 1.23-1.30 (m, 4H), 1.56-1.60 (m, 2H), 1.79-1.87 (m, 2H), 2.33 (s, 3H), 2.67 (s, 3H), 2.91-2.95 (m, 2H), 3.18-3.21 (m, 2H), 3.32-3.35 (m, 1H), 3.48-3.55 (m, 1H), 3.95 (s, 2H), 4.51-4.53 (d, J = 4.7 Hz, 1H), 6.79-6.81 (m, 1H), 7.09-7.14 (m, 2H), 7.61-7.63 (m, 1H), 8.01 (bs, 1H); Mass (m/z): 381.2 (M + H)$^+$. |

| Example No. | Structure and IUPAC name | Characterization data |
|---|---|---|
| 81 | 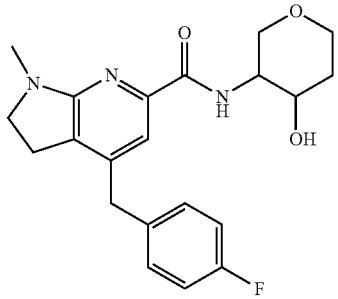 [SMILES: CN1CCc2c(Cc3ccc(F)cc3)cc(C(=O)NC3COCCC3O)nc21]<br>cis-N-(4-Hydroxytetrahydropyran-3-yl)-4-(4-fluorobenzyl)-1-methyl-2,3-dihydro-1H-pyrrolo[2,3-b]pyridine-6-carboxamide (Isomer-I) | $^1$H-NMR (DMSO-$d_6$, 400 MHz) δ ppm: 1.47-1.50 (m, 1H), 1.83-1.87 (m, 1H), 2.91 (s, 3H), 2.92-2.96 (t, 2H), 3.25-3.28 (m, 1H), 3.37-3.39 (m, 1H), 3.48-3.51 (t, 2H), 3.52-3.65 (m, 2H), 3.68-3.79 (m, 2H), 3.90 (s, 2H), 5.00-5.03 (m, 1H), 7.08-7.14 (m, 2H), 7.31-7.34 (m, 2H), 7.64 (s, 1H), 8.31-8.33 (d, J = 6.9 Hz, 1H); Mass (m/z): 386.1 (M + H)$^+$. |
| 82 | 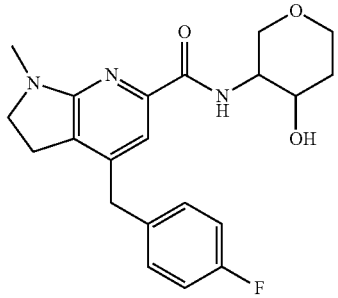 [SMILES: CN1CCc2c(Cc3ccc(F)cc3)cc(C(=O)NC3COCCC3O)nc21]<br>cis-N-(4-Hydroxytetrahydropyran-3-yl)-4-(4-fluorobenzyl)-1-methyl-2,3-dihydro-1H-pyrrolo[2,3-b]pyridine-6-carboxamide (Isomer-II) | $^1$H-NMR (DMSO-$d_6$, 400 MHz) δ ppm: 1.47-1.50 (m, 1H), 1.83-1.91 (m, 1H), 2.91 (s, 3H), 2.92-2.96 (t, 2H), 3.16-3.22 (m, 1H), 3.36-3.42 (m, 1H), 3.46-3.50 (t, 2H), 3.52-3.66 (m, 2H), 3.69-3.78 (m, 2H), 3.90 (s, 2H), 5.00-5.03 (m, 1H), 7.08-7.14 (m, 2H), 7.31-7.34 (m, 2H), 7.64 (s, 1H), 8.31-8.33 (d, J = 6.9 Hz, 1H); Mass (m/z): 386.0 (M + H)$^+$. |
| 83 | 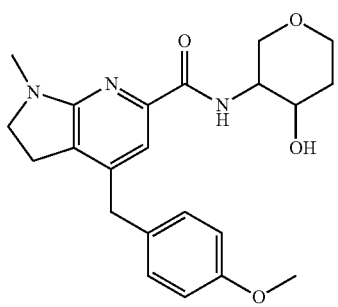 [SMILES: COc1ccc(Cc2cc(C(=O)NC3COCCC3O)nc3c2CCN3C)cc1]<br>Racemic cis-N-(4-Hydroxytetrahydropyran-3-yl)-4-(4-methoxybenzyl)-1-methyl-2,3-dihydro-1H-pyrrolo[2,3-b]pyridine-6-carboxamide | $^1$H-NMR (DMSO, 400 MHz) δ ppm: 1.24-1.27 (m, 2H), 1.49-1.51 (m, 1H), 1.83-1.87 (m, 1H), 3.33-3.37 (m, 1H), 3.38-3.39 (m, 1H), 3.48-3.50 (m, 2H), 3.66-3.68 (m, 2H), 3.71 (s, 3H), 3.77 (s, 3H), 3.80-3.82 (m, 2H), 4.03 (s, 2H), 5.01-5.02 (d, J = 4.8 Hz, 1H), 6.85-6.87 (d, J = 8.4 Hz, 2H), 6.97 (s, 1H), 7.11-7.13 (d, J = 8.2 Hz, 2H), 8.12-8.14 (d, J = 7.5 Hz, 1H); Mass (m/z): 398.3 (M + H)$^+$. |

-continued

| Example No. | Structure and IUPAC name | Characterization data |
|---|---|---|
| 84 | 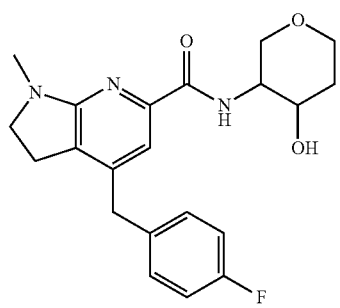 [SMILES: CN1CCc2c(Cc3ccc(F)cc3)cc(C(=O)NC3COCCC3O)nc21]<br>(3S,4S)-N-(4-Hydroxytetrahydropyran-3-yl)-4-(4-fluorobenzyl)-1-methyl-2,3-dihydro-1H-pyrrolo[2,3-b]pyridine-6-carboxamide | Mass (m/z): 386.4 (M + H)$^+$. |
| 85 | 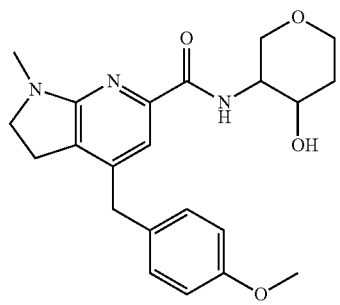 [SMILES: COc1ccc(Cc2cc(C(=O)NC3COCCC3O)nc3c2CCN3C)cc1]<br>(3S,4S)-N-(4-Hydroxytetrahydropyran-3-yl)-4-(4-methoxybenzyl)-1-methyl-2,3-dihydro-1H-pyrrolo[2,3-b]pyridine-6-carboxamide | Mass (m/z): 398.3 (M + H)$^+$. |
| 86 | 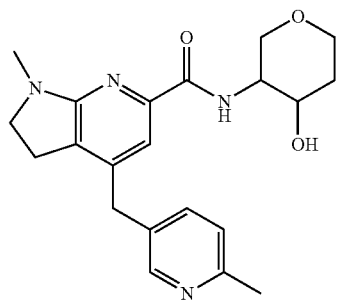 [SMILES: Cc1ccc(Cc2cc(C(=O)NC3COCCC3O)nc3c2CCN3C)cn1]<br>(3S,4S)-N-(4-Hydroxytetrahydropyran-3-yl)-4-(2-methylpyridin-5-ylmethyl)-1-methyl-2,3-dihydro-1H-pyrrolo[2,3-b]pyridine-6-carboxamide | Mass (m/z): 383.3 (M + H)$^+$. |

Example 87

N-[(1S,2S)-2-Hydroxycyclohexyl]-4-(4-fluorobenzyl)-5,6,7,8-tetrahydro[1,7]naphthyridine-2-carboxamide Hydrochloride

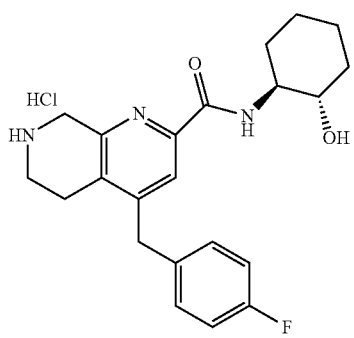 [SMILES: O=C(N[C@H]1CCCC[C@@H]1O)c1cc(Cc2ccc(F)cc2)c2c(n1)CNCC2 ; Cl]

Step-1

Ethyl 7-(tert-butoxycarbonyl)-4-(4-fluorobenzyl)-5,8-dihydro-6H-[1,7]naphthyridine-2-carboxylate

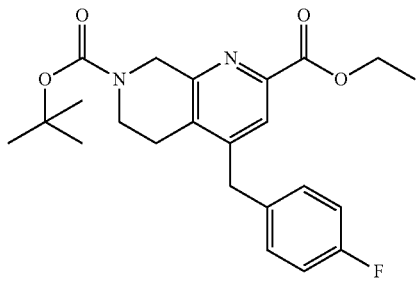 [SMILES: CCOC(=O)c1cc(Cc2ccc(F)cc2)c2c(n1)CN(C(=O)OC(C)(C)C)CC2]

To a solution of Ethyl 7-(tert-butoxycarbonyl)-4-chloro-5,8-dihydro-6H-[1,7]naphthyridine-2-carboxylate (0.2 g, 0.0005 mole, prepared as per patent publication WO2016/029454A1) in dry THF (12 mL) under $N_2$, was added bis(tri-tert-butylphosphine) palladium(0) (0.015 g, 0.000029 mole) and degassed for 5 minutes. 4-fluorobenzyl zinc chloride (1.5 mL, 0.5 M in THF, 0.0007 mole) and stirred for 2 hours, filtered through celite, and washed with ethyl acetate (20 mL×2). The filtrate was concentrated under vacuum to obtain the residue which was diluted with ethyl acetate (50 mL), washed with water (30 mL), brine solution (30 mL) and dried over $Na_2SO_4$ and concentrated under vacuum to obtain the title compound.

Yield: 0.2 g; Mass (m/z): 415.1 (M+H)$^+$.

Step-2: 7-(tert-Butoxycarbonyl)-4-(4-fluorobenzyl)-5,8-dihydro-6H-[1,7]naphthyridine-2-carboxylic acid

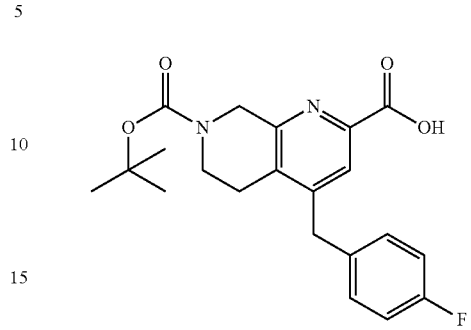

To a solution of tert-butyl 2-ethyl 4-(4-fluorobenzyl)-5,8-dihydro-6H-[1,7]naphthyridine-2,7-dicarboxylate (0.2 g, 0.0004 mole) in 1,4-dioxane (10 mL) at 25° C., was added 10 mL saturated aqueous lithium hydroxide (0.1 g, 0.002 mole) and stirred for 2 hours. Reaction mass was concentrated under vacuum to obtain the residue which was diluted with ice-cold water (50 mL), acidified with 1N HCl and extracted with dichloromethane (50 mL×3). The organic layer was washed with brine solution (50 mL), dried over $Na_2SO_4$ and concentrated under vacuum to obtain the title compound.

Yield: 0.18 g; $^1$H-NMR (DMSO-$d_6$, 400 MHz) δ ppm: 1.42 (s, 9H), 2.84 (m, 2H), 3.67 (m, 2H), 4.13 (s, 2H), 4.84 (m, 2H), 7.13-7.26 (m, 4H), 8.02 (s, 1H); Mass (m/z): 387.0 (M+H)$^+$.

Step-3: tert-Butyl 4-(4-fluorobenzyl)-2-(2-hydroxycyclohexylcarbamoyl)-5,8-dihydro-6H-[1,7]naphthyridine-7-carboxylate

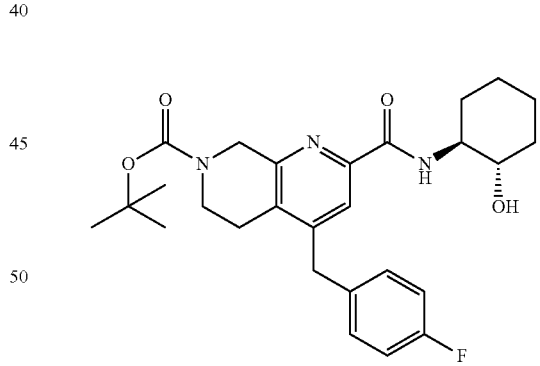

The title compound was synthesized from 7-(tert-butoxycarbonyl)-4-(4-fluorobenzyl)-5,8-dihydro-6H-[1,7]naphthyridine-2-carboxylic acid by the procedure described in step 8 of example 1. The crude compound obtained was further purified by flash chromatography using methanol:dichloromethane (1:99) to afford the title compound.

Yield: 0.2 g; $^1$H-NMR (DMSO; 400 MHz) δ ppm: 1.23-1.32 (m, 4H), 1.42 (s, 9H), 1.60-1.64 (m, 2H), 1.87-1.89 (m, 2H), 2.78 (m, 2H), 3.41-3.53 (m, 2H), 3.61 (m, 2H), 4.05 (s, 2H), 4.60 (m, 2H), 4.66 (m, 1H), 7.12-7.16 (m, 2H), 7.19-7.23 (m, 2H), 7.62 (s, 1H), 8.20-8.22 (d, J=7.6 Hz, 1H); Mass (m/z): 484.3 (M+H)$^+$.

Step-4: N-[(1S,2S)-2-Hydroxycyclohexyl]-4-(4-fluorobenzyl)-5,6,7,8-tetrahydro[1,7]naphthyridine-2-carboxamide Hydrochloride tert-Butyl 4-(4-fluorobenzyl)-2-(2-hydroxycyclohexylcarbamoyl)-5,8-dihydro-6H-[1,7]naphthyridine-7-carboxylate was deprotected with IPA HCl by the procedure as described in step-5 of preparation 21 to obtain the title compound as hydrochloride salt.

Yield: 0.08 g; $^1$H-NMR (DMSO; 400 MHz) δ ppm: 1.23-1.28 (m, 4H), 1.61-1.66 (m, 2H), 1.87-1.89 (m, 2H), 2.96 (t, 2H), 3.39-3.44 (m, 2H), 3.61 (m, 2H), 4.10 (s, 2H), 4.36 (m, 3H), 7.14-7.18 (m, 2H), 7.21-7.24 (m, 2H), 7.78 (s, 1H), 8.19-8.21 (d, J=8.0 Hz, 1H), 9.25 (bs, 2H); Mass (m/z): 384.3 (M+H)$^+$.

Examples 88 to 94

The compounds of Example 88 to 94 were prepared by following the experimental procedures as described in the Example 87, with some non-critical variations.

| Example No. | Structure and IUPAC name | Characterization data |
|---|---|---|
| 88 | 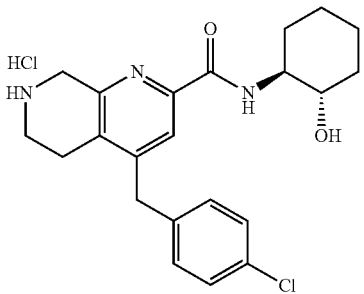 [SMILES: Cl ; O=C(N[C@H]1CCCC[C@@H]1O)c1cc(Cc2ccc(Cl)cc2)c2c(n1)CNCC2]<br>N-[(1S,2S)-2-Hydroxycyclohexyl]-4-(4-chlorobenzyl)-5,6,7,8-tetrahydro[1,7]naphthyridine-2-carboxamide Hydrochloride | $^1$H-NMR (DMSO; 400 MHz) δ ppm: 1.23 1.26 (m, 4H), 1.61-1.66 (m, 2H), 1.87-1.89 (m, 2H), 2.68 (s, 2H), 2.95 (m, 2H), 3.38-3.43 (m, 2H), 4.11 (s, 2H), 4.36-4.39 (m, 3H), 7.20-7.22 (d, J = 8.1 Hz, 2H), 7.38-7.40 (d, J = 8.2 Hz, 2H), 7.80 (s, 1H), 8.20-8.22 (d, J = 7.8 Hz,1H), 9.19 (s, 2H); Mass (m/z): 400.0 (M + H)$^+$. |
| 89 | 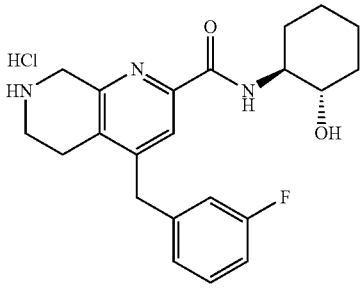 [SMILES: Cl ; O=C(N[C@H]1CCCC[C@@H]1O)c1cc(Cc2cccc(F)c2)c2c(n1)CNCC2]<br>N-[(1S,2S)-2-Hydroxycyclohexyl-4-(3-fluorobenzyl)-5,6,7,8-tetrahydro[1,7]naphthyridine-2-carboxamide Hydrochloride | $^1$H-NMR (DMSO; 400 MHz) δ ppm: 1.24 1.26 (m, 4H), 1.61-1.65 (m, 2H), 1.87-1.89 (m, 2H), 2.98 (s, 2H), 3.44 (m, 2H), 4.14 (m, 2H), 4.11 (s, 2H), 4.36 (m, 3H), 7.02-7.09 (m, 2H), 7.37-7.38 (m, 2H), 7.79 (s, 1H), 8.21-8.23 (d, J = 7.9 Hz, 1H), 9.40 (bs, 2H); Mass (m/z): 384.0 (M + H)$^+$. |
| 90 | 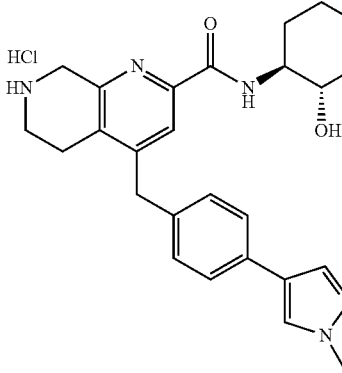<br>N-[(1S,2S)-2-Hydroxycyclohexyl]-4-[4-(1-methyl-1H-pyrazol-4-yl)-benzyl-5,6,7,8-tetrahydro[1,7]naphthyridine-2-carboxamide Hydrochloride | $^1$H-NMR (DMSO; 400 MHz) δ ppm: 1.23-1.27 (m, 4H), 1.59-1.65 (m, 2H), 1.87-1.90 (m, 2H), 3.00-3.01 (m, 2H), 3.39-3.44 (m, 4H), 3.84-3.86 (m, 3H), 4.08 (s, 2H), 4.36-438 (m, 3H), 7.15-7.17 (d, J = 8.0 Hz, 2H), 7.49-7.51 (d, J = 8.0 Hz, 2H), 7.81-7.82 (d, J = 1.2 Hz, 2H), 8.09 (s, 1H), 8.20-8.22 (d, J = 8.0 Hz, 1H), 9.32 (bs, 2H); Mass (m/z): 446.0 (M + H)$^+$. |

| Example No. | Structure and IUPAC name | Characterization data |
|---|---|---|
| 91 | 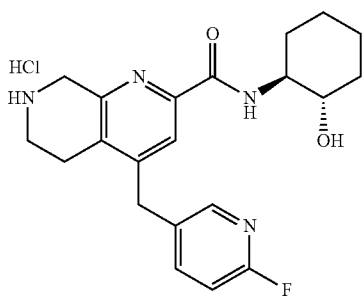 [SMILES: Cl ; O=C(N[C@H]1CCCC[C@@H]1O)c1cc(Cc2ccc(F)nc2)c2c(n1)CNCC2]<br>N-[(1S,2S)-2-Hydroxycyclohexyl]-4-(2-fluoropyridin-5-ylmethyl)-5,6,7,8-tetrahydro[1,7]naphthyridine-2-carboxamide Hydrochloride | $^1$H-NMR (DMSO; 400 MHz) δ ppm: 1.24 1.26 (m, 4H), 1.59-1.66 (m, 2H), 1.87-1.99 (m, 2H), 2.97-3.00 (s, 2H), 3.36-3.44 (m, 2H), 3.52-3.54 (m, 2H), 4.16 (s, 2H), 4.36 (m, 3H), 7.16-7.18 (m, 1H), 7.77-7.81 (m, 2H), 8.12 (s, 1H), 8.21-8.23 (d, J = 7.9 Hz, 1H), 9.29 (bs, 2H); Mass (m/z): 385.0 (M + H)$^+$. |
| 92 | 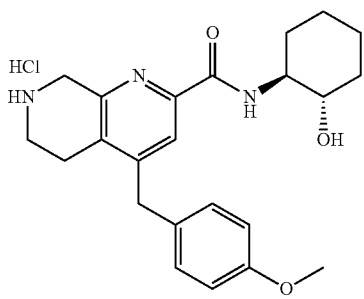 [SMILES: Cl ; COc1ccc(Cc2cc(C(=O)N[C@H]3CCCC[C@@H]3O)nc3c2CCNC3)cc1]<br>N-[(1S,2S)-2-Hydroxycyclohexyl]-4-(4-methoxybenzyl)-5,6,7,8-tetrahydro[1,7]naphthyridine-2-carboxamide Hydrochloride | $^1$H-NMR (DMSO-d$_6$, 400 MHz) δ ppm: 1.22-1.25 (m, 4H), 1.60-1.65 (m, 2H), 1.86-1.88 (m, 2H), 2.98-3.01 (m, 2H), 3.35-3.39 (m, 2H), 3.54-3.56 (m, 2H), 3.72 (s, 3H), 4.01 (s, 2H), 4.32 4.34 (bs, 3H), 6.88-6.90 (d, J = 8.4 Hz, 2H), 7.09-7.11 (d, J = 8.3 Hz, 2H), 7.74 (s, 1H), 8.20-8.22 (d, J = 8.0 Hz, 1H), 9.46 (bs, 2H); Mass (m/z): 396.1 |
| 93 | 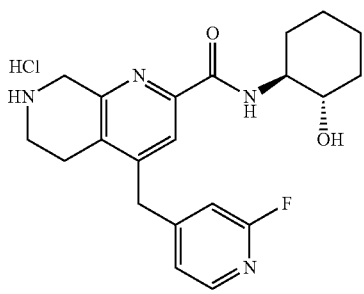 [SMILES: Cl ; O=C(N[C@H]1CCCC[C@@H]1O)c1cc(Cc2ccnc(F)c2)c2c(n1)CNCC2]<br>N-[(1S,2S)-2-Hydroxycyclohexyl-4-(2-fluoropyridin-4-ylmethyl)-5,6,7,8-tetrahydro[1,7]naphthyridine-2-carboxamide Hydrochloride | $^1$H-NMR (DMSO-d$_6$, 400 MHz) δ ppm: 1.23-1.25 (m, 4H), 1.62-1.66 (d, 2H), 1.88-1.91 (d, 2H), 2.93-2.96 (t, 2H), 3.50-3.54 (m, 2H), 3.56-3.58 (m, 2H), 4.24 (s, 2H), 4.37 (m, 3H), 6.98 (s, 1H), 7.15-7.17 (d, J = 4.7 Hz, 1H), 7.87 (s, 1H), 8.18-8.19 (d, J = 5.1 Hz, 1H), 8.23-8.25 (d, J = 8.0 Hz, 1H), 9.33 (bs, 2H); Mass (m/z): 385.2 (M + H)$^+$. |

| Example No. | Structure and IUPAC name | Characterization data |
|---|---|---|
| 94 | 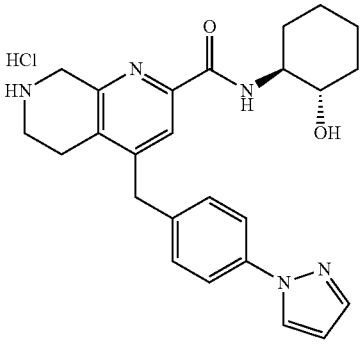 [SMILES: Cl ; O=C(N[C@H]1CCCC[C@@H]1O)c1cc(Cc2ccc(-n3cccn3)cc2)c2c(n1)CNCC2]<br>N-[(1S,2S)-2-Hydroxycyclohexyl]-4-(4-pyrazol-1-ylbenzyl)-5,6,7,8-tetrahydro[1,7]naphthyridine-2-carboxamide Hydrochloride | $^1$H-NMR (DMSO-d$_6$, 400 MHz) δ ppm: 1.24-1.26 (m, 4H), 1.61-1.65 (m, 2H), 1.87-1.89 (m, 2H), 3.00-3.02 (m, 2H), 3.39-3.44 (m, 2H), 4.15 (m, 2H), 4.11 (s, 2H), 4.36 (m, 3H), 6.53 (s, 1H), 7.29-7.31 (d, J = 8.4 Hz, 2H), 7.73 (s, 1H), 7.78-7.80 (d, J = 8.3 Hz, 2H), 7.82 (s, 1H), 8.21-8.23 (d, J = 8.0 Hz, 1H ), 8.47-8.47 (d, J = 2.0 Hz, 1H), 9.35 (bs, 2H); Mass (m/z): 432.5 (M + H)$^+$. |

Example 95

N-[(1S,2S)-2-Hydroxycyclohexyl]-4-(4-fluorobenzyl)-7-methyl-5,6,7,8-tetrahydro[1,7]naphthyridine-2-carboxamide

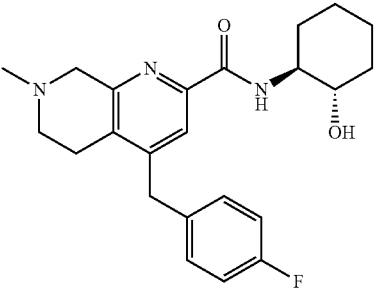 [SMILES: CN1CCc2c(Cc3ccc(F)cc3)cc(C(=O)N[C@H]3CCCC[C@@H]3O)nc2C1]

Step-1

N-[(1S,2S)-2-Hydroxycycloexyl]-4-(4-fluorobenzyl)-5,6,7,8-tetrahydro[1,7]naphthyridine-2-carboxamide tert-Butyl 4-(4-fluorobenzyl)-2-(2-hydroxycyclohexylcarbamoyl)-5,8-dihydro-6H-[1,7]naphthyridine-7-carboxylate was deprotected with IPA HCl by the procedure as described in step-5 of preparation 21, basified with aqueous ammonia pH ~9 and extracted with dichloromethane (50 mL×3). The organic layer was washed with brine solution (50 mL), dried over Na$_2$SO$_4$ and concentrated under vacuum to obtain the title compound.

Yield: 0.05 g; $^1$H-NMR (DMSO-d$_6$, 400 MHz) δ ppm: 1.24-1.27 (m, 4H), 1.59-1.64 (m, 2H), 1.87-1.90 (m, 2H), 2.67-2.68 (m, 2H), 2.98-2.99 (m, 2H), 3.35-3.38 (m, 2H), 3.93 (s, 2H), 4.01 (s, 2H), 4.67-4.68 (d, J=5.5 Hz, 1H), 7.12-7.22 (m, 4H), 7.59 (s, 1H), 8.12-8.14 (d, J=8.0 Hz, 1H); Mass (m/z): 384.1 (M+H)$^+$.

Step-2: N-[(1S,2S)-2-Hydroxycyclohexyl]-4-(4-fluorobenzyl)-7-methyl-5,6,7,8-tetrahydro[1,7]naphthyridine-2-carboxamide To a solution of N-[(1S,2S)-2-hydroxycyclohexyl]-4-(4-fluorobenzyl)-5,6,7,8-tetrahydro[1,7]naphthyridine-2-carboxamide (0.034 g, 0.00008 mole) in 1,2-dichloroethane (5 mL) at 25° C., was added paraformaldehyde (0.0034 g, 0.00001 mole), glacial acetic acid (0.008 mL, 0.00013 mole) and stirred for 2 hours. Sodium triacetoxyborohydride (0.056 g, 0.00026 mole) was added and stirred overnight. Reaction mixture was quenched into saturated sodium bicarbonate solution and extracted with dichloromethane (50 mL×3). The organic layer was washed with brine solution (50 mL), dried over Na$_2$SO$_4$ and concentrated under vacuum to obtain the crude compound which was further purified by flash chromatography using methanol:dichloromethane (5:95) to afford the title compound.

Yield: 0.012 g; $^1$H-NMR (DMSO-d$_6$, 400 MHz) δ ppm: 1.23-1.26 (m, 4H), 1.59-1.64 (m, 2H), 1.88-1.91 (m, 2H), 2.36 (s, 3H), 2.67 (m, 2H), 2.78 (m, 2H), 3.34-3.44 (m, 2H), 3.53 (s, 2H), 4.02-4.16 (m, 2H), 4.67-4.69 (d, J=5.3 Hz, 1H), 7.13-7.24 (m, 4H), 7.59 (s, 1H), 8.12-8.14 (d, J=7.8 Hz, 1H); Mass (m/z): 398.1 (M+H)$^+$.

Example 96

N-[(1S,2S)-2-Hydroxycyclohexyl]-4-(4-fluorobenzyl)-7-ethyl-5,6,7,8-tetrahydro[1,7]naphthyridine-2-carboxamide

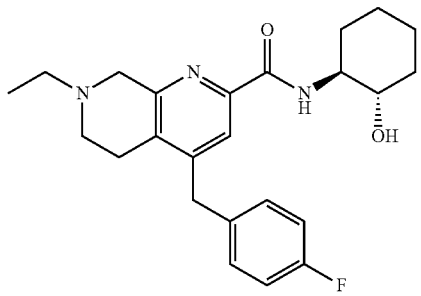 [SMILES: CCN1CCc2c(Cc3ccc(F)cc3)cc(C(=O)N[C@H]3CCCC[C@@H]3O)nc2C1]

The title compound was synthesized from N-[1S,2S)-2-hydroxycyclohexyl]-4-(4-fluorobenzyl)-5,6,7,8-tetrahydro[1,7]naphthyridine-2-carboxamide by the procedure as described in step 2 of example 95 using acetaldehyde in place of paraformaldehyde. The crude compound obtained was further purified by flash chromatography using methanol:dichloromethane (4:96).

Yield: 0.014 g; $^1$H-NMR (DMSO-$d_6$, 400 MHz) δ ppm: 1.23-1.26 (m, 4H), 1.28-1.32 (t, 3H), 1.59-1.64 (m, 2H), 1.87-1.90 (m, 2H), 2.42-2.48 (m, 2H), 2.67 (m, 2H), 2.78 (m, 2H), 3.34-3.43 (m, 2H), 3.51 (s, 2H), 4.35-4.41 (t, 2H), 4.67-4.69 (d, J=5.3 Hz, 1H), 7.12-7.22 (m, 4H), 7.58 (s, 1H), 8.12-8.14 (d, J=7.8 Hz, 1H); Mass (m/z): 412.0 (M+H)$^+$.

Example 97 trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-II)

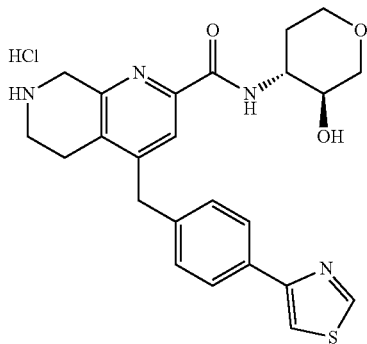 [SMILES: Cl ; O=C(N[C@@H]1CCOC[C@H]1O)c1cc(Cc2ccc(-c3cscn3)cc2)c2c(n1)CNCC2]

Step-1: Ethyl 7-(tert-butoxycarbonyl)-4-(4,4,5,5-tetramethyl-[1,3,2]dioxaborolan-2-yl)-5,8-dihydro-6H[1,7]naphthyridine-2-carboxylate

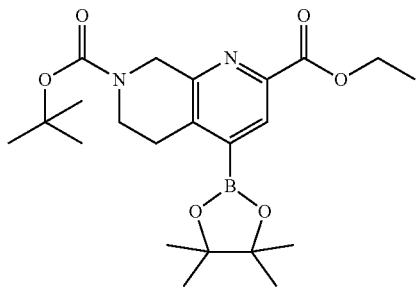 [SMILES: CCOC(=O)c1cc(B2OC(C)(C)C(C)(C)O2)c2c(n1)CN(C(=O)OC(C)(C)C)CC2]

To a solution of ethyl 7-(tert-butoxycarbonyl)-4-chloro-5,8-dihydro-6H-[1,7]naphthyridine-2-carboxylate (1.0 g, 0.003 mole, prepared as per patent WO2016/029454 A1) in 1,4-dioxane (20 mL) in a sealed tube under N$_2$ at 25° C., was added bis (pinacolato)diboron (1.1 g, 0.004 mole) and 1,1-bis(diphenylphosphino)ferrocene palladium(II)dichloride dichloromethane complex (0.24 g, 0.0003 mole) and potassium acetate (1.0 g, 0.011 mole). The reaction mixture was heated at 120° C. for 22 hours, cooled to RT, diluted with ethyl acetate (50 mL), filtered through a pad of celite and washed with ethyl acetate (50 mL×2). The filtrate was concentrated under vacuum to obtain the title compound.

Yield: 2.5 g; $^1$H-NMR (DMSO-$d_6$, 400 MHz) δ ppm: 1.15 (s, 12H), 1.29-1.34 (t, 3H), 1.43 (s, 9H), 3.07 (m, 2H), 3.59-3.60 (m, 2H), 4.34-4.36 (q, 2H), 4.59 (m, 2H), 7.94 (s, 1H); Mass (m/z): 433.1 (M+H)$^+$.

Step-2: Ethyl 7-(tert-butoxycarbonyl)-4-[4-(thiazol-4-yl)benzyl]-5,8-dihydro-6H-[1,7]naphthyridine-2-carboxylate

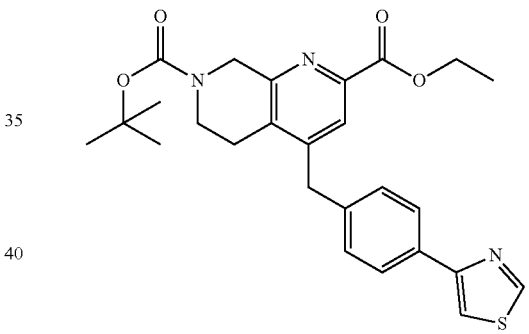

To a solution of ethyl 7-(tert-butoxycarbonyl)$_4$-(4,4,5,5-tetramethyl-[1,3,2]dioxaborolan-2-yl)-5,8-dihydro-6H[1,7]naphthyridine-2-carboxylate (0.4 g, 0.0009 mole) in THF (18 mL) under N$_2$, was added 4-(4-bromomethylphenyl) thiazole (I-14, 0.3 g, 0.0012 mole), cesium carbonate (0.9 g, 0.0027 mole) and degassed for 10 minutes. Then added bis(tri tert-butyl phosphine) palladium(0) (0.094 g, 0.00018 mole). The reaction mixture was slowly warmed to 40° C. for 4 hours, cooled to RT, filtered through celite, and washed with ethyl acetate (20 mL×2). The filtrate was concentrated under vacuum to obtain the crude compound which was further purified by flash chromatography using ethyl acetate: n-hexane (30:70) to obtain the title compound.

Yield: 0.1 g; $^1$H-NMR (DMSO-$d_6$, 400 MHz) δ ppm: 1.29-1.31 (t, 3H), 1.41-1.43 (m, 9H), 2.67 (m, 2H), 2.81 (t, 2H), 4.11 (s, 2H), 4.30-4.32 (q, 2H), 4.58 (m, 2H), 7.25-7.27 (d, J=7.9 Hz, 2H), 7.72 (s, 1H), 7.93-7.95 (d, J=8.0 Hz, 2H), 8.13-8.14 (m, J=1.4 Hz, 1H), 9.24 (m, 1H); Mass (m/z): 480.1 (M+H)$^+$.

Step-3: 7-(tert-Butoxycarbonyl)-4-[4-(thiazol-4-yl)benzyl]-5,8-dihydro-6H-[1,7]naphthyridine-2-carboxylic acid

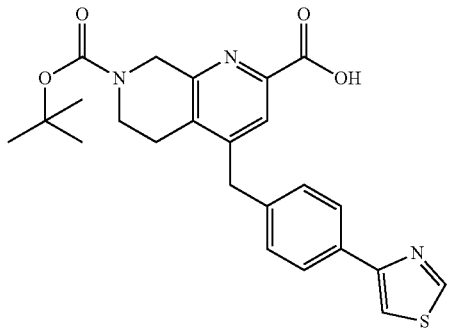 [SMILES: CC(C)(C)OC(=O)N1CCc2c(Cc3ccc(-c4cscn4)cc3)cc(C(=O)O)nc2C1]

Ethyl 7-(tert-butoxycarbonyl)-4-[4-(thiazol-4-yl)benzyl]-5,8-dihydro-6H-[1,7]naphthyridine-2-carboxylate was converted in to 7-(tert-butoxycarbonyl)-4-[4-(thiazol-4-yl) benzyl]-5,8-dihydro-6H-[1,7]naphthyridine-2-carboxylic acid by the procedure described in step-2 of example 87.

Yield: 0.05 g; $^1$H-NMR (DMSO-$d_6$, 400 MHz) δ ppm: 1.41 (s, 9H), 2.81 (m, 2H), 3.62 (m, 2H), 4.09 (s, 2H), 4.58 (m, 2H), 7.26-7.27 (d, J=7.6 Hz, 2H), 7.67 (s, 1H), 7.93-7.95 (d, J=7.8 Hz, 2H), 8.13 (s, 1H), 9.18 (s, 1H).

Step-4: trans tert-Butyl 2-(3-Hydroxytetrahydropyran-4-ylcarbamoyl)-4-[4-(thiazol-4-yl) benzyl]-5,8-dihydro-6H-[1,7]naphthyridine-7-carboxylate (Isomer-II)

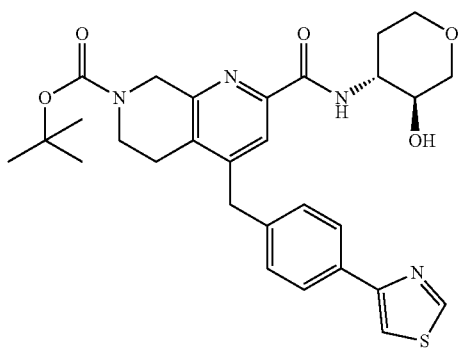 [SMILES: CC(C)(C)OC(=O)N1CCc2c(Cc3ccc(-c4cscn4)cc3)cc(C(=O)N[C@@H]3CCOC[C@H]3O)nc2C1]

The title compound was synthesized from 7-(tert-butoxycarbonyl)-4-[4-(thiazol-4-yl) benzyl]-5,8-dihydro-6H-[1,7] naphthyridine-2-carboxylic acid by the procedure as described in step 3 of example 87 using trans-4-aminotetrahydropyran-3-ol hydrochloride (Isomer-II, 1-22). The crude compound obtained was further purified by flash chromatography using methanol:dichloromethane (3:97).

Yield: 0.05 g; $^1$H-NMR (DMSO-$d_6$, 400 MHz) δ ppm: 1.41-1.43 (s, 9H), 1.55-1.62 (m, 1H), 1.65-1.88 (m, 1H), 2.81 (m, 2H), 3.42-3.62 (m, 4H), 3.78-3.80 (m, 4H), 4.10 (s, 2H), 4.63 (s, 2H), 4.78 (m, 1H), 7.24-7.26 (d, J=8.1 Hz, 2H), 7.69 (s, 1H), 7.93-7.95 (d, J=8.0 Hz, 2H), 8.12-8.13 (m, J=1.7 Hz, 1H), 8.41-8.43 (d, J=8.0 Hz, 1H), 9.18-9.19 (s, J=1.5 Hz, 1H); Mass (m/z): 550.9 (M+H)$^+$.

Step-5: trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-II)

Trans tert-Butyl 2-(3-hydroxytetrahydropyran-4-ylcarbamoyl)-4-[4-(thiazol-4-yl) benzyl]-5,8-dihydro-6H-[1,7] naphthyridine-7-carboxylate (Isomer-II) was deprotected with IPA HCl by the procedure as described in step-4 of example 87 to obtain the title compound.

Yield: 0.04 g; $^1$H-NMR (DMSO-$d_6$, 400 MHz) δ ppm: 1.58-1.62 (m, 1H), 1.65-1.88 (m, 1H), 2.99-3.03 (m, 2H), 3.37-3.57 (m, 4H), 3.78-63.82 (m, 4H), 4.15 (s, 2H), 4.38 (m, 2H), 4.39 (s, 1H), 7.26-7.28 (d, J=8.0 Hz, 2H), 7.85 (s, 1H), 7.94-7.96 (d, J=8.0 Hz, 2H), 8.13-8.14 (d, J=1.7 Hz, 1H), 8.41-8.43 (d, J=8.3 Hz, 1H), 9.18-9.19 (d, J=1.4 Hz, 1H), 9.21 (bs, 2H); Mass (m/z): 450.9 (M+H)$^+$.

Example 98 to 99

The compounds of Example 98 and 99 were prepared by following the experimental procedure as described in the Example 97, with some non-critical variation.

| Example No. | Structure and IUPAC name | Characterization data |
|---|---|---|
| 98 | ![structure] trans-N-(3-Hydroxytetrahydropyran-4-yl)-4-(4-fluorobenzyl)-5,6,7,8-tetrahydro[1,7]naphthyridine-2-carboxamide Hydrochloride (Isomer-II) | $^1$H-NMR (DMSO-$d_6$, 400 MHz) δ ppm: 1.59-1.63 (m, 1H), 1.79-1.83 (m, 1H), 2.96-2.98 (t, 2H), 3.00-3.05 (m, 2H), 3.42-3.59 (m, 2H), 3.78-3.83 (m, 4H), 4.10 (s, 2H), 4.36 (m, 3H), 7.14-7.19 (m, 2H), 7.21-7.24 (m, 2H), 7.79 (s, 1H), 8.40-8.42 (d, J = 8.3 Hz, 1H), 9.26 (bs, 2H); Mass (m/z): 386.0 (M + H)$^+$. |

| Example No. | Structure and IUPAC name | Characterization data |
|---|---|---|
| 99 | 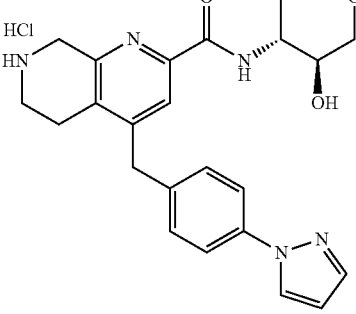<br>trans-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-II) | $^1$H-NMR (DMSO-$d_6$, 400 MHz) δ ppm: 1.58-1.67 (m, 1H), 1.80-1.84 (m, 1H), 3.00-3.05 (m, 2H), 3.30-3.33 (m, 2H), 3.55-3.59 (m, 2H), 3.78-3.83 (m, 4H), 4.15 (s, 2H), 4.35-4.37 (m, 3H), 6.53 (s, 1H), 7.30-7.32 (d, J = 8.3 Hz, 2H), 7.73 (s, 1H), 7.78- 7.83 (d, J = 8.3 Hz, 2H), 7.83 (s, 1H), 8.41-8.43 (d, J = 8.3 Hz, 1H), 8.46-8.47 (d, J = 2.2 Hz, 1H), 9.41 (bs, 2H); Mass (m/z): 434.2 (M + H)$^+$. |

Examples 100 to 102

The compounds of Example 100 and 102 were prepared by the experimental procedure as described in the step 8 of example 1 using cis-3-aminotetrahydropyran-4-ol hydrochloride (I-23) followed by separation by preparative chiral HPLC method.

| Example No. | Structure and IUPAC name | Characterization data |
|---|---|---|
| 100 | 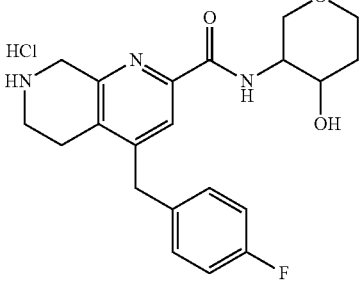<br>cis-N-(4-Hydroxytetrahydropyran-3-yl)-4-(4-fluorobenzyl)-5,6,7,8-tetrahydro[1,7]naphthyridine-2-carboxamide Hydrochloride (Isomer-I) | $^1$H-NMR (DMSO-$d_6$, 400 MHz) δ ppm: 1.48-1.50 (m, 1H), 1.85-1.88 (m, 1H), 2.98 (m, 2H), 3.18-3.20 (m, 2H), 3.43-3.45 (m, 2H), 3.62 (m, 2H), 3.80-3.82 (m, 2H), 4.10 (s, 2H), 4.37 (m, 3H), 7.14-7.24 (m, 4H), 7.79 (s, 1H), 8.28-8.30 (d, J = 6.6 Hz, 1H), 9.24 (bs, 2H); Mass (m/z): 386.1 (M + H)$^+$. |
| 101 | 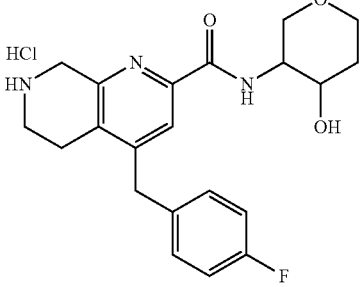<br>cis-N-(4-Hydroxytetrahydropyran-3-yl)-4-(4-fluorobenzyl)-5,6,7,8-tetrahydro[1,7]naphthyridine-2-carboxamide Hydrochloride (Isomer-II) | $^1$H-NMR (DMSO-$d_6$, 400 MHz) δ ppm: 1.47-1.50 (m, 1H), 1.85-1.88 (m, 1H), 2.98 (m, 2H), 3.16-3.20 (m, 2H), 3.42-3.46 (m, 2H), 3.71 (m, 2H), 3.80-3.82 (m, 2H), 4.10 (s, 2H), 4.37 (m, 3H), 7.14-7.24 (m, 4H), 7.79 (s, 1H), 8.28-8.30 (d, J = 6.8 Hz, 1H), 9.21 (bs, 2H); Mass (m/z): 386.1 (M + H)$^+$. |

| Example No. | Structure and IUPAC name | Characterization data |
|---|---|---|
| 102 | 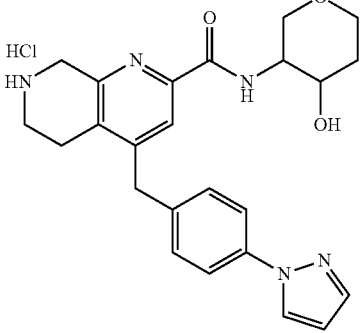<br>Racemic cis-N-(4-Hydroxytetrahydropyran-3-yl)-4-(4-pyrazol-1-ylbenzyl)-5,6,7,8-tetrahydro[1,7]naphthyridine-2-carboxamide Hydrochloride | $^1$H-NMR (DMSO-$d_6$, 400 MHz) δ ppm: 1.41-1.51 (m, 1H), 1.85-1.88 (m, 1H), 2.99-3.00 (m, 2H), 3.14-3.21 (m, 2H), 3.35-3.45 (m, 1H), 3.71 (m, 3H), 3.80-3.82 (m, 2H), 4.16 (s, 2H), 4.36-4.38 (m, 3H), 6.54 (s, 1H), 7.29-7.31 (d, J = 8.3 Hz, 2H), 7.73 (s, 1H), 7.78-7.81 (d, J = 8.3 Hz, 2H), 7.85 (s, 1H), 8.29-8.30 (d, J = 6.9 Hz, 1H), 8.46-8.47 (d, J = 1.8 Hz, 1H), 9.41 (bs, 2H); Mass (m/z): 434.2 (M + H)$^+$. |

Example 103

N-[(1S,2S)-2-Hydroxycyclohexyl]-8-(4-fluorobenzyl)-2,3-dihydro-[1,4]dioxino[2,3-b]pyridine-6-carboxamide

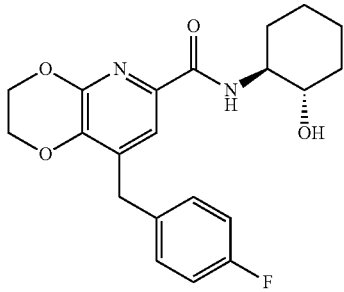 [SMILES: O=C(N[C@H]1CCCC[C@@H]1O)c1cc(Cc2ccc(F)cc2)c2c(n1)OCCO2]

Step-1: 2,3-Dihydro-[1,4]dioxino[2,3-b]pyridine

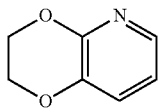

A solution of 2,3-dihydroxy pyridine (10.0 g, 0.09 mole) in acetonitrile (200 mL) under N$_2$ at 25° C., was added potassium carbonate (99.4 g, 0.72 mole), 1-bromo 2-chloro ethane (25.7 g, 0.18 mole), sodium iodide (1.3 g, 0.009 mole) and heated to 100° C. for 20 hours. Reaction mixture was filtered through celite, and washed with ethyl acetate (50 mL×2). The filtrate was concentrated under vacuum to obtain the title compound.

Yield: 6.9 g; $^1$H-NMR (DMSO-$d_6$, 400 MHz) δ ppm: 4.22-4.24 (d, 2H), 4.37-4.39 (d, 2H), 6.90-6.95 (m, 1H), 7.26-7.28 (d, J=0.9, 7.8 Hz, 1H), 7.72-7.73 (d, J=1.0, 4.4 Hz, 1H), Mass (m/z): 137.9 (M+H)$^+$.

Step-2: 2,3-Dihydro-[1,4]dioxino[2,3-b]pyridine-5-oxide

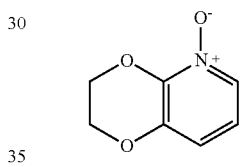

The title compound was synthesized from 2,3-dihydro-[1,4]dioxino[2,3-b]pyridine by the procedure as described in step-1 of example 1.

Yield: 3.6 g; $^1$H-NMR (DMSO-$d_6$, 400 MHz) δ ppm: 4.31-4.33 (dd, J=2.3, 7.9 Hz, 2H), 4.50-4.52 (dd, J=3.6, 7.9 Hz, 2H), 6.85-6.89 (d, J=8.2 Hz, 1H), 6.93-6.95 (d, J=8.3 Hz, 1H), 7.83-7.85 (d, J=6.4 Hz, 1H); Mass (m/z): 154.0 (M+H)$^+$.

Step-3: 8-Chloro-2,3-dihydro-[1,4]dioxino[2,3-b]pyridine

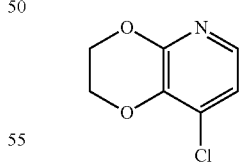

Phosphorusoxychloride (45 mL, 8 vol.) was added to 2,3-dihydro-[1,4]dioxino[2,3-b]pyridine-5-oxide (3.5 g, 0.02 mole) under N$_2$ at 0° C., and then heated to 100° C. for 7 hours. Reaction mixture was concentrated under vacuum to obtain the residual compound, which was neutralized with saturated sodium bicarbonate solution pH ~8 and extracted with dichloromethane (100 mL×3). The filtrate was concentrated under vacuum to obtain the crude compound which was further purified by flash chromatography using ethyl acetate:n-hexane (25:75) to obtain the title compound.

Yield: 1.9 g; $^1$H-NMR (DMSO-d$_6$, 400 MHz) δ ppm: 4.35-4.36 (d, J=2.1, 4.1 Hz, 2H), 4.44-4.45 (d, J=1.4, 4.0 Hz, 2H), 7.12-7.14 (d, J=5.2 Hz, 1H), 7.69-7.70 (d, J=5.2 Hz, 1H), Mass (m/z): 171.9 (M+H)$^+$.

Step-4: 8-Chloro-2,3-dihydro-[1,4]dioxino[2,3-b]pyridine-5-oxide

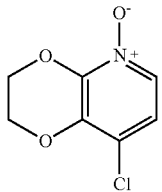

The title compound was synthesized from 8-chloro-2,3-dihydro-[1,4]dioxino[2,3-b]pyridine by the procedure as described in step-1 of example 1.

Yield: 1.9 g; $^1$H-NMR (DMSO-d$_6$, 400 MHz) δ ppm: 4.43-4.44 (d, J=2.0, 4.2 Hz, 2H), 4.55-4.56 (d, J=2.6, 4.1 Hz, 2H), 7.12-7.14 (d, J=7.1 Hz, 1H), 7.87-7.89 (d, J=7.1 Hz, 1H), Mass (m/z): 188.0 (M+H)$^+$.

Step-5: 8-Chloro-2,3-Dihydro-[1,4]dioxino[2,3-b]pyridine-6-carbonitrile

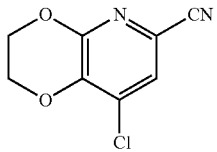 [SMILES: N#Cc1cc(Cl)c2c(n1)OCCO2]

The title compound was synthesized from 8-chloro-2,3-dihydro-[1,4] dioxino[2,3-b]pyridine by the procedure as described in step-2 of example 1.

Yield: 1.6 g; $^1$H-NMR (DMSO-d$_6$, 400 MHz) δ ppm: 4.47-4.54 (m, 4H), 7.97 (s, 1H); Mass (m/z): 197.0 (M+H)$^+$.

Step-6: 8-Chloro-2,3-dihydro-[1,4]dioxino[2,3-b]pyridine-6-carboxylic acid

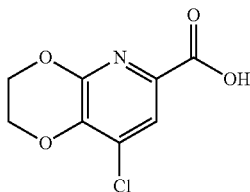 [SMILES: O=C(O)c1cc(Cl)c2c(n1)OCCO2]

The title compound was synthesized from 8-chloro-2,3-dihydro-[1,4] dioxino[2,3-b]pyridine-6-carbonitrile by the procedure as described in step-3 of example 1.

Yield: 1.2 g; $^1$H-NMR (DMSO-d$_6$, 400 MHz) δ ppm: 4.44-4.51 (m, 4H), 7.71 (s, 1H), 13.17 (s, 1H); Mass (m/z): 216.0 (M+H)$^+$.

Step-7: Methyl 8-chloro-2,3-dihydro-[1,4]dioxino[2,3-b]pyridine-6-carboxylate

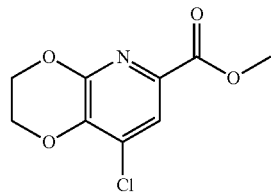

The title compound was synthesized from 8-chloro-2,3-dihydro-[1,4] dioxino[2,3-b]pyridine-6-carboxylic acid by the procedure as described in step-4 of example 1, using potassium carbonate as a base and reaction mixture was stirred for overnight at 25° C.

Yield: 1.2 g; $^1$H-NMR (DMSO-d$_6$, 400 MHz) δ ppm: 3.83 (s, 3H), 4.45-4.52 (m, 4H), 7.76 (s, 1H); Mass (m/z): 230.0 (M+H)$^+$.

Step-8: Methyl 8-(4-fluorobenzyl)-2,3-dihydro-[1,4]dioxino[2,3-b]pyridine-6-carboxylate

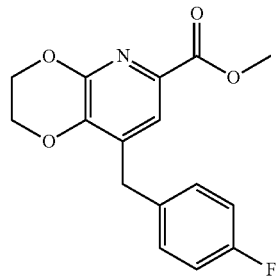 [SMILES: COC(=O)c1cc(Cc2ccc(F)cc2)c2c(n1)OCCO2]

The title compound was synthesized from methyl 8-chloro-2,3-dihydro-[1,4]dioxino[2,3-b]pyridine-6-carboxylate by the procedure as described in step-1 of example 87.

Yield: 0.19 g; $^1$H-NMR (DMSO-d$_6$, 400 MHz) δ ppm: 3.77 (s, 3H), 3.95 (s, 2H), 4.38-4.46 (m, 4H), 7.10-7.15 (t, 2H), 7.27-7.30 (t, 2H), 7.49 (s, 1H); Mass (m/z): 304.0 (M+H)$^+$.

Step-9: 8-(4-Fluorobenzyl)-2,3-dihydro-[1,4]dioxino[2,3-b]pyridine-6-carboxylic acid

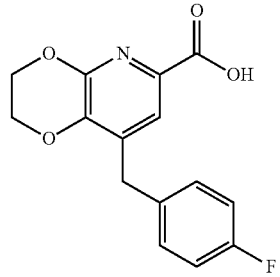 [SMILES: O=C(O)c1cc(Cc2ccc(F)cc2)c2c(n1)OCCO2]

The title compound was synthesized from methyl 8-(4-fluorobenzyl)-2,3-dihydro-[1,4]dioxino[2,3-b]pyridine-6-carboxylate by the procedure as described in step-2 of example 87.

Yield: 0.18 g; $^1$H-NMR (DMSO-d$_6$, 400 MHz) δ ppm: 3.94 (s, 2H), 4.37-4.38 (m, 2H), 4.44-4.45 (m, 2H), 7.11-7.15 (t, 2H), 7.27-7.30 (t, 2H), 7.45 (s, 1H); Mass (m/z): 290.1 (M+H)$^+$.

Step-10: N-[(1S,2S)-2-Hydroxycyclohexyl]-8-(4-fluorobenzyl)-2,3-dihydro-[1,4]dioxino[2,3-b]pyridine-6-carboxamide The title compound was synthesized from 8-(4-fluorobenzyl)-2,3-dihydro-[1,4]dioxino[2,3-b]pyridine-6-carboxylic acid by the procedure described in step 8 of example 1. The crude compound obtained was further purified by flash chromatography using methanol:dichloromethane (1.5:98.5).

Yield: 0.07 g; $^1$H-NMR (DMSO-d$_6$, 400 MHz) δ ppm: 1.21-1.25 (m, 4H), 1.57-1.63 (m, 2H), 1.87-1.89 (m, 2H), 3.35-3.41 (m, 2H), 3.96 (m, 2H), 4.37 (s, 2H), 4.45 (s, 2H), 4.65-4.66 (d, J=5.4 Hz, 1H), 7.10-7.15 (m, 2H), 7.26-7.29 (m, 2H), 7.41 (s, 1H), 7.87-7.89 (d, J=7.7 Hz, 1H); Mass (m/z): 386.8 (M+H)$^+$.

Examples 104 to 105

The compounds of Example 104 to 105 were prepared by following the experimental procedure as described in the Example 103, with some non-critical variation.

Example 106

N-[(1S,2S)-2-Hydroxycyclohexyl]-8-[4-(1-methyl-1H-pyrazol-4-yl)-benzyl]-2,3-dihydro-[1,4]dioxino[2,3-b]pyridine-6-carboxamide

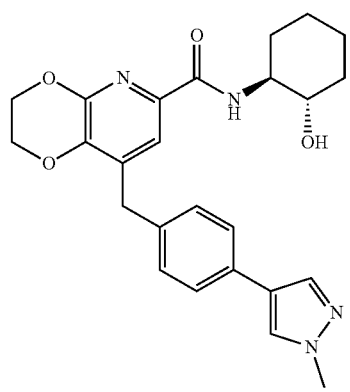 [SMILES: Cn1cc(-c2ccc(Cc3cc(C(=O)N[C@H]4CCCC[C@@H]4O)nc4c3OCCO4)cc2)cn1]

| Example No. | Structure and IUPAC name | Characterization data |
|---|---|---|
| 104 | N-[(1S,2S)-2-Hydroxycyclohexyl]-8-(4-methoxybenzyl)-2,3-dihydro-[1,4]dioxino[2,3-b]pyridine-6-carboxamide | $^1$H-NMR (DMSO, 400 MHz) δ ppm: 1.20-1.23 (m, 4H), 1.57-1.62 (m, 2H), 1.84-1.86 (m, 2H), 2.67-2.69 (m, 1H), 3.41-3.42 (m, 1H), 3.72 (s, 3H), 3.89 (s, 2H), 4.37 (d, 2H, J = 2.59 Hz), 4.45 (d, 2H, J = 2.53 Hz), 4.65-4.67 (d, 1H, J = 5.30 Hz), 6.86-6.88 (d, 2H, J = 8.36 Hz), 7.14-7.16 (d, 2H, J = 8.34 Hz), 7.37 (s, 1H), 7.86-7.88 (d, 1H, J = 7.7 Hz); Mass (m/z): 399.2 (M + H)$^+$. |
| 105 | N-[(1S,2S)-2-Hydroxycyclohexyl]-8-(2-chloropyridin-5-ylmethyl)-2,3-dihydro-[1,4]dioxino[2,3-b]pyridine-6-carboxamide | Mass (m/z): 404.80 (M + H)$^+$ |

Step-1: Methyl 8-(4-chlorobenzyl)-2,3-dihydro-[1,4]dioxino[2,3-b]pyridine-6-carboxylate

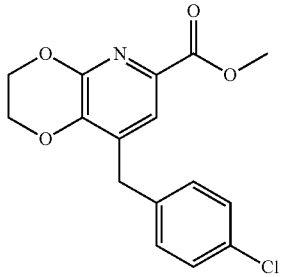 [SMILES: COC(=O)c1cc(Cc2ccc(Cl)cc2)c2c(n1)OCCO2]

The title compound was synthesized by the procedure as described in step-1 of example 87 with some non-critical variations.

Yield: 0.19 g; $^1$H-NMR (DMSO-d$_6$, 400 MHz) δ ppm: 3.78 (s, 3H), 3.96 (s, 2H), 4.36-4.46 (dd, J=3.0, 5.8 Hz, 4H), 7.26-7.28 (d, 2H), 7.35-7.37 (d, 2H), 7.51 (s, 1H); Mass (m/z): 320.1 (M+H)$^+$.

Step-2: Methyl 8-[4-(1-methyl-1H-pyrazol-4-yl)benzyl]-2,3-dihydro-[1,4]dioxino[2,3-b]pyridine-6-carboxylate

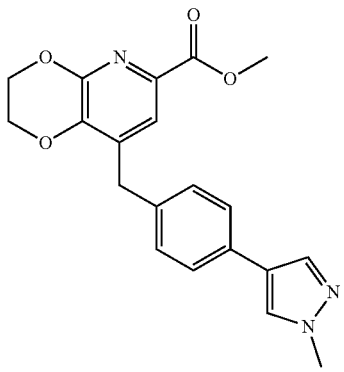 [SMILES: COC(=O)c1cc(Cc2ccc(-c3cnn(C)c3)cc2)c2c(n1)OCCO2]

To a solution of methyl 8-(4-chlorobenzyl)-2,3-dihydro-[1,4]dioxino[2,3-b]pyridine-6-carboxylate (0.05 g, 0.00015 mole) in THF (8 mL) under N$_2$, was added 1-methyl-4-(4,4,5,5-tetramethyl-[1,3,2]dioxaborolan-2-yl)-1H-pyrazole (0.14 g, 0.0007 mole), 1N cesium carbonate (0.4 mL, 0.0007 mole) and degassed for 10 minutes. Then added bis(tri tert-butyl phosphine) palladium(0) (0.016 g, 0.00003 mole). The reaction mixture was slowly warmed to 90° C. for 30 hours, cooled to RT, filtered through celite, and washed with ethyl acetate (30 mL×2). The filtrate was concentrated under vacuum to obtain the crude compound which was further purified by flash chromatography using methanol:ethyl acetate (2:98) to obtain the title compound.

Yield: 0.06 g; $^1$H-NMR (DMSO-d$_6$, 400 MHz) δ ppm: 3.77-3.84 (t, 6H), 3.94 (s, 2H), 4.39-4.46 (d, J=2.6 Hz, 4H), 7.21-7.23 (d, J=7.9 Hz, 1H), 7.47-7.50 (m, 2H), 7.56 (s, 1H), 7.80-7.81 (d, J=4.1 Hz, 2H), 8.08 (s, 1H); Mass (m/z): 366.3 (M+H)$^+$.

Step-3: 8-[4-(1-methyl-1H-pyrazol-4-yl)benzyl]-2,3-dihydro-[1,4]dioxino[2,3-b]pyridine-6-carboxic acid

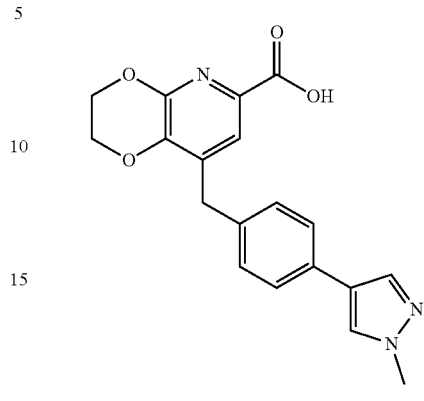

The title compound was synthesized from methyl 8-[4-(1-methyl-1H-pyrazol-4-yl)-benzyl]-2,3-dihydro-[1,4]dioxino[2,3-b]pyridine-6-carboxylate by the procedure as described in step-2 of example 87.

Yield: 0.043 g; $^1$H-NMR (DMSO-d$_6$, 400 MHz) δ ppm: 3.84 (s, 3H), 3.93 (s, 2H), 4.39-4.45 (m, 4H), 7.21-7.23 (m, 2H), 7.43-7.49 (m, 3H), 7.81 (s, 1H), 8.08 (s, 1H), 12.80 (bs, 1H); Mass (m/z): 352.3 (M+H)$^+$.

Step-4: N-[(1S,2S)-2-Hydroxycyclohexyl]-8-[4-(1-methyl-1H-pyrazol-4-yl)benzyl]-2,3-dihydro-[1,4]dioxino[2,3-b]pyridine-6-carboxamide The title compound was synthesized from 8-[4-(1-methyl-1H-pyrazol-4-yl)-benzyl]-2,3-dihydro-[1,4]dioxino[2,3-b]pyridine-6-carboxylic acid by the procedure as described in step 8 of example 1. The crude compound obtained was further purified by flash chromatography using methanol:dichloromethane (3.5:96.5) to afford pure compound.

Yield: 0.03 g; $^1$H-NMR (DMSO-d$_6$, 400 MHz) δ ppm: 1.21-1.23 (m, 4H), 1.57-1.62 (m, 2H), 1.82-1.84 (m, 2H), 3.41-3.50 (m, 2H), 3.84 (s, 3H), 3.94 (s, 2H), 4.38-4.58 (d, 4H), 4.65-4.67 (m, 1H), 7.20-7.22 (d, J=7.8 Hz, 2H), 7.42 (s, 1H), 7.47-7.49 (d, J=7.8 Hz, 2H), 7.80 (s, 1H), 7.87-7.89 (d, J=7.6 Hz, 1H), 8.08 (s, 1H); Mass (m/z): 449.4 (M+H)$^+$.

Example 107

N-[(1S,2S)-2-Hydroxycyclohexyl]-8-(2,3-difluorobenzyl)-2,3-dihydro-[1,4]dioxino[2,3-b]pyridine-6-carboxamide

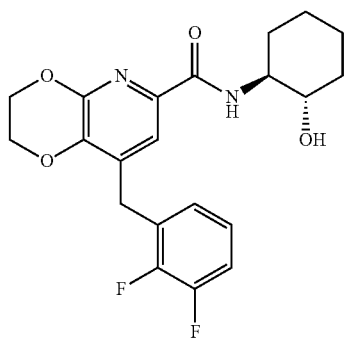 [SMILES: O=C(N[C@H]1CCCC[C@@H]1O)c1cc(Cc2cccc(F)c2F)c2c(n1)OCCO2]

Step-1: Methyl 8-(4,4,5,5-tetramethyl-[1,3,2]dioxaborolan-2-yl)-2,3-dihydro-[1,4]dioxino[2,3-b]pyridine-6-carboxylate

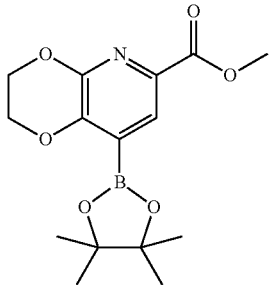 [SMILES: COC(=O)c1cc(B2OC(C)(C)C(C)(C)O2)c2c(n1)OCCO2]

Dichloro[1,1'-bis(diphenylphosphino)ferrocene]palladium((II), complex with dichloromethane (17.75 mg, 0.02 mmol) was added to a stirred mixture of methyl 8-chloro-2,3-dihydro-[1,4]dioxino[2,3-b]pyridine-6-carboxylate (50 mg, 0.21 mmol), Bis(pinacolato)diboron (82.8 mg, 0.32 mmol) and potassium acetate (40.60 mg, 0.43 mmol) in 1,4-dioxane (10 mL), in a sealed tube, and the mixture was heated at 110° C. (oil bath temperature) for 7 h. The mixture was cooled to room temperature, diluted with ethylacetate (30 mL), filtered through celite, washed with brine (10 mL), dried over anhydrous $Na_2SO_4$, filtered and concentrated under vacuum to obtain crude mass of the title compound. Mass (m/z): 322.3 $(M+H)^+$.

Step-2: Methyl 8-(2,3-difluorobenzyl)-2,3-dihydro-[1,4]dioxino[2,3-b]pyridine-6-carboxylate

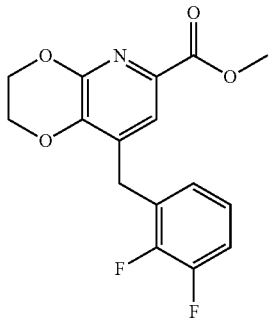 [SMILES: COC(=O)c1cc(Cc2cccc(F)c2F)c2c(n1)OCCO2]

To a solution of methyl 8-(4,4,5,5-tetramethyl-[1,3,2]dioxaborolan-2-yl)-2,3-dihydro-[1,4]dioxino[2,3-b]pyridine-6-carboxylate (50 mg, 0.15 mmole) in a mixture of 8 mL of THF and 0.8 mL of water under $N_2$, was added 2,3-difluorobenzylbromide (38.6 mg, 0.18 mmole), cesium carbonate (152.01 mg, 0.46 mmole) and [1,1'-bis(diphenylphosphino)ferrocene] dichloro-palladium (II), 1:1 complex with dichloromethane (15.26 mg, 0.01 mmole). The mixture was refluxed for 4 h, cooled to RT, filtered through celite, and washed with ethyl acetate (30 mL×2). The filtrate was concentrated under vacuum to obtain the crude compound which was further purified by flash chromatography using ethyl acetate:n-hexane (40:60) to obtain the title compound.

Yield: 56 mg; Mass (m/z): 322.1 $(M+H)^+$.

Step-3: 8-(2,3-Difluorobenzyl)-2,3-dihydro-[1,4]dioxino[2,3-b]pyridine-6-carboxylic acid

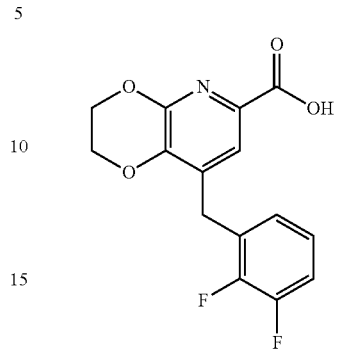

NaOH flakes (62.3 mg, 1.5 mmole) were added in portions to a stirred mixture of 8-(2,3-Difluorobenzyl)-2,3-dihydro-[1,4]dioxino[2,3-b]pyridine-6-carboxylic acid methyl ester (50 mg, 0.15 mmole) in THF:water (10 mL: 1 mL) and then refluxed for 3 h. The reaction mixture was cooled to room temperature and acidified it with conc. HCl (pH-2) and product was extracted with ethyl acetate (10 mL×4). The combined organic layers were washed with brine (15 mL), dried over anhydrous $Na_2SO_4$, filtered and concentrated under vacuum to obtain the title compound.

Yield: 27 mg; Mass (m/z): 308.0 $(M+H)^+$.

Step-4: N-[(1S,2S)-2-Hydroxycyclohexyl]-8-(2,3-difluorobenzyl)-2,3-dihydro-[1,4]dioxino[2,3-b]pyridine-6-carboxamide To a solution of 8-(2,3-difluorobenzyl)-2,3-dihydro-[1,4]dioxino[2,3-b]pyridine-6-carboxylic acid (0.01 g, 0.00003 mole) in DMF (5 mL) at 25° C. under $N_2$, was added HATU (0.016 g, 0.00004 mole) stirred for 10 minutes, followed by addition of (1S,2S)-2-amino cyclohexanol hydrochloride (0.0041 g, 0.00003 mole) and DIPEA (0.023 mL, 0.0001 mole) in 10 minutes of time interval and stirred for 15 hours. Reaction mixture was quenched in to ice water (20 mL) and extracted with ethyl acetate (20 mL×3). Organic layer was washed with brine solution (15 mL) and dried over $Na_2SO_4$. Organic layer was concentrated under vacuum to obtain the title compound.

Yield: 0.007 g; $^1$H-NMR (CDCl$_3$, 400 MHz) δ ppm: 1.25-1.30 (m, 4H), 1.64-1.67 (m, 2H), 2.00-2.04 (m, 2H), 2.77-2.80 (m, 1H), 3.42-3.44 (m, 1H), 4.02 (s, 2H), 4.42-4.43 (d, J=2.52 Hz, 2H), 4.47-4.48 (d, J=2.22 Hz, 2H), 4.40-4.51 (d, J=4.38 Hz, 1H), 6.87-6.90 (m, 1H), 6.91-7.08 (m, 2H), 7.30 (s, 1H), 8.41-8.43 (d, J=8.43 Hz, 1H); Mass (m/z): 405.1 $(M+H)^+$.

Examples 108 to 112

The compounds of Example 108 to 112 were prepared by following the experimental procedure as described in the Example 107, with some non-critical variation.

| Example No. | Structure and IUPAC name | Characterization data |
|---|---|---|
| 108 | 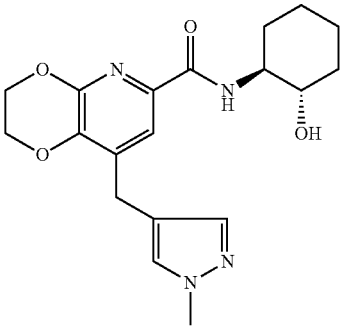 [SMILES: Cn1cc(Cc2cc(C(=O)N[C@H]3CCCC[C@@H]3O)nc3c2OCCO3)cn1]

N-[(1S,2S)-2-Hydroxycyclohexyl]-8-(1-methyl-1H-pyrazol-4-ylmethyl)-2,3-dihydro-[1,4]dioxino[2,3-b]pyridine-6-carboxamide | Mass (m/z): 373.4 (M + H)+ |
| 109 | 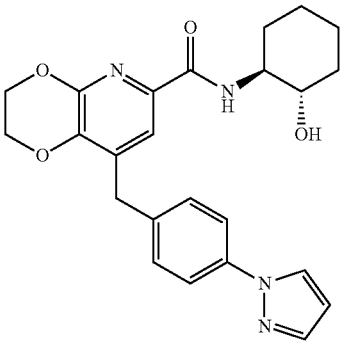 [SMILES: O=C(N[C@H]1CCCC[C@@H]1O)c1cc(Cc2ccc(-n3cccn3)cc2)c2c(n1)OCCO2]

N-[(1S,2S)-2-Hydroxycyclohexyl]-8-[4-(pyrazol-1-yl)benzyl]-2,3-dihydro-[1,4]dioxino[2,3-b]pyridine-6-carboxamide | Mass (m/z): 435.3 (M + H)+ |
| 110 | 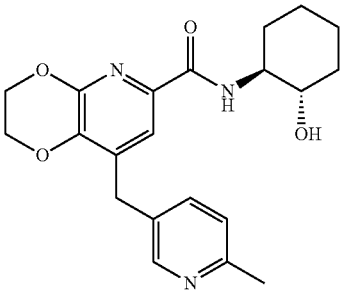 [SMILES: Cc1ccc(Cc2cc(C(=O)N[C@H]3CCCC[C@@H]3O)nc3c2OCCO3)cn1]

N-[(1S,2S)-2-Hydroxycyclohexyl]-8-(2-methylpyridin-5-ylmethyl)-2,3-dihydro-[1,4]dioxino[2,3-b]pyridine-6-carboxamide | Mass (m/z): 384.4 (M + H)+ |
| 111 | 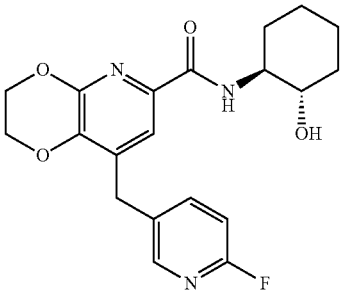

N-[(1S,2S)-2-Hydroxycyclohexyl]-8-(2-fluoropyridin-5-ylmethyl)-2,3-dihydro-[1,4]dioxino[2,3-b]pyridine-6-carboxamide | Mass (m/z): 388.3 (M + H)+ |
| 112 | 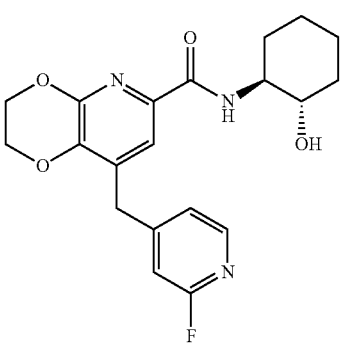 [SMILES: O=C(N[C@H]1CCCC[C@@H]1O)c1cc(Cc2ccnc(F)c2)c2c(n1)OCCO2]

N-[(1S,2S)-2-Hydroxycyclohexyl]-8-(2-fluoropyridin-4-ylmethyl)-2,3-dihydro-[1,4]dioxino[2,3-b]pyridine-6-carboxamide | Mass (m/z): 388.3 (M + H)+ |

Example 113 trans-N-(3-Hydroxytetrahydropyran-4-yl)-8-(4-fluorobenzyl)-2,3-dihydro-[1,4]dioxino[2,3-b]pyridine-6-carboxamide (Isomer-IT)

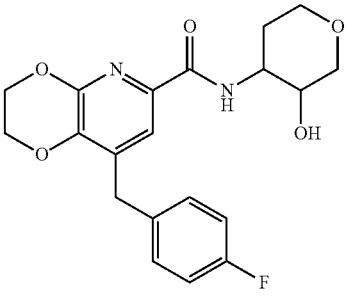 [SMILES: O=C(NC1CCOCC1O)c1cc(Cc2ccc(F)cc2)c2c(n1)OCCO2]

trans-N-(3-Hydroxytetrahydropyran-4-yl)-8-(4-fluorobenzyl)-2,3-dihydro-[1,4]dioxino[2,3-b]pyridine-6-carboxamide was synthesized by the procedure as described in step-10 of example 103 using trans-4-aminotetrahydropyran-3-ol hydrochloride (Isomer-II, 1-22). The crude compound obtained was further purified by flash chromatography using methanol:dichloromethane (2.5:97.5) to afford the title compound.

Yield: 0.06 g; ¹H-NMR (DMSO-$d_6$, 400 MHz) δ ppm: 1.58-1.61 (m, 1H), 1.76-1.89 (m, 1H), 3.36-3.39 (m, 2H), 3.44-3.57 (m, 2H), 3.69-3.78 (m, 2H), 3.96 (s, 2H), 4.37-4.38 (d, J=2.8 Hz, 2H), 4.38-4.46 (d, J=2.9 Hz, 2H), 4.93-4.95 (d, J=5.6 Hz, 1H), 7.10-7.15 (t, 2H), 7.26-7.29 (m, 2H), 7.42 (s, 1H), 8.08-8.10 (d, J=8.1 Hz, 1H); Mass (m/z): 389.0 (M+H)⁺.

Example 114 to 117

The compounds of Example 114 to 117 were prepared by following the experimental procedure as described in the Example 113, with some non-critical variation

| Example No. | Structure and IUPAC name | Characterization data |
|---|---|---|
| 114 | (3S,4S)-N-(4-Hydroxytetrahydropyran-3-yl)-8-(4-methoxybenzyl)-2,3-dihydro-[1,4]dioxino[2,3-b]pyridine-6-carboxamide | Mass (m/z): 401.3 (M + H)⁺. |
| 115 | (3S,4S)-N-(4-Hydroxytetrahydropyran-3-yl)-8-(4-fluorobenzyl)-2,3-dihydro-[1,4]dioxino[2,3-b]pyridine-6-carboxamide | Mass (m/z): 389.3 (M + H)⁺. |
| 116 | (3S,4S)-N-(4-Hydroxytetrahydropyran-3-yl)-8-(2-chloropyridin-5-ylmethyl)-2,3-dihydro-[1,4]dioxino[2,3-b]pyridine-6-carboxamide | Mass (m/z): 406.7 (M + H)⁺. |
| 117 | (3S,4S)-N-(4-Hydroxytetrahydropyran-3-yl)-8-(2-methylpyridin-5-ylmethyl)-2,3-dihydro-[1,4]dioxino[2,3-b]pyridine-6-carboxamide | Mass (m/z): 386.3 (M + H)⁺. |

Example 118

Racemic cis-N-(4-Hydroxytetrahydropyran-3-yl)-8-(4-fluorobenzyl)-2,3-dihydro-[1,4]dioxino[2,3-b]pyridine-6-carboxamide The title compound was prepared by the experimental procedure as described in step 10 of example 103 using the intermediate, cis-3-aminotetrahydropyran-4-ol hydrochloride (I-23) and the intermediate obtained from step 9 of example 103.

¹H-NMR (DMSO-$d_6$, 400 MHz) δ ppm: 1.47-1.57 (m, 1H), 1.81-1.84 (m, 1H), 3.11-3.19 (m, 1H), 3.44-3.50 (m, 1H), 3.61-3.69 (m, 2H), 3.76-3.79 (m, 2H), 3.96 (s, 2H), 4.37 (s, 2H), 4.98-4.99 (d, J=4.3 Hz, 1H), 7.10-7.15 (t, 2H), 7.26-7.30 (m, 2H), 7.42 (s, 1H), 8.09-8.11 (d, J=8.1 Hz, 1H); Mass (m/z): 389.3 (M+H)⁺.

Example 119

Racemic cis-N-(4-Hydroxytetrahydropyran-3-yl)-8-(4-methoxybenzyl)-2,3-dihydro-[1,4]dioxino[2,3-b]pyridine-6-carboxamide

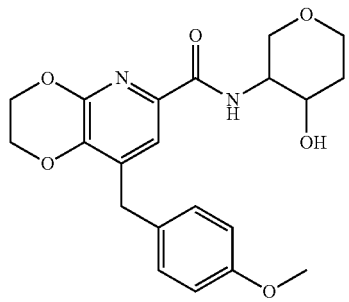 [SMILES: COc1ccc(Cc2cc(C(=O)NC3COCCC3O)nc3c2OCCO3)cc1]

This compound was prepared by following the experimental procedures as described in the Example 118, with some non-critical variations.

¹H-NMR (DMSO, 400 MHz) δ ppm: 1.44-1.49 (m, 1H), 1.82-1.84 (m, 1H), 2.67-2.69 (m, 1H), 3.11-3.16 (m, 1H), 3.60-3.69 (m, 2H), 3.72 (s, 3H), 3.76-3.79 (m, 2H), 3.89 (s, 2H), 4.380-4.385 (d, 2H, J=2.02 Hz), 4.45-4.46 (d, 2H, J=2.30 Hz), 4.98-4.99 (d, 1H, J=4.86 Hz), 6.86-6.88 (d, 2H, J=8.35 Hz), 7.15-7.17 (d, 2H, J=8.26 Hz), 7.38 (s, 1H), 7.96-7.98 (d, 1H, J=7.76 Hz); Mass (m/z): 401.2 (M+H)⁺.

Example 120

N-[(1S,2S)-2-Hydroxycyclohexyl]-8-(4-fluorobenzyl)-4-methyl-2H-pyrido[3,2-b][1,4]oxazine-6-carboxamide

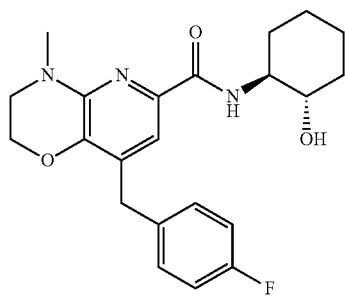 [SMILES: CN1CCOc2c(Cc3ccc(F)cc3)cc(C(=O)N[C@H]3CCCC[C@@H]3O)nc21]

Step-1: 2-Amino-4-bromopyridin-3-ol Hydrobromide

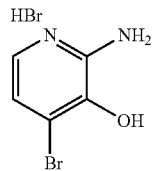

Bromine (11.2 mL, 0.21 mole) was added dropwise to a mechanically stirred suspension of 2-aminopyridin-3-ol (20 g, 0.18 mole) in acetic acid (300 mL) at 5-10° C. and brought to room temperature. The reaction mixture was heated at 120-125° C., maintained for 12 hours and concentrated to get a crude mass that was triturated with diethyl ether (50 mL×3) and dried under vacuum to obtain 2-amino-4-bromopyridin-3-ol hydrobromide as dark brown compound that was used as such without any purification.

Yield: 48.5 g; Mass (m/z): 189.3, 191.1 (M+H)⁺.

Step-2: 4-Bromo-3-(2-chloroethoxy)pyridin-2-ylamine

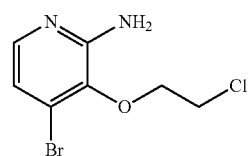 [SMILES: Nc1nccc(Br)c1OCCCl]

Bromochloroethane (63.5 g, 0.44 mole) was added to a stirred suspension of 2-amino-4-bromopyridin-3-ol Hydrobromide (48 g, 0.17 mole), potassium carbonate (85.8 g, 0.62 mole) and sodium iodide (3.9 g, 0.026 mole) in acetonitrile (500 mL) at room temperature and then refluxed the reaction mass for 18 hours. The reaction mixture was concentrated to obtain a residual mass that was diluted with water (250 mL) and extracted with ethyl acetate (250 mL×3). The organic layers were combined, washed with brine solution (100 mL), dried over Na₂SO₄ and concentrated under vacuum to obtain the crude compound which was further purified by flash chromatography using ethyl acetate:n-hexane (20:80) to obtain 4-bromo-3-(2-chloroethoxy)pyridin-2-ylamine.

Yield: 9.3 g; ¹H-NMR (CDCl₃, 400 MHz) δ ppm: 3.84-3.88 (t, J=5.21 Hz, 2H), 4.24-4.27 (t, J=4.99 Hz, 2H), 4.97 (bs, 2H), 6.79-6.81 (d, J=5.32 Hz, 1H), 7.63-7.65 (d, J=5.36 Hz, 1H); (Mass (m/z): 251.0, 253.0 (M+H)⁺.

Step-3: 8-Bromo-3,4-dihydro-2H-pyrido[3,2-b][1,4]oxazine

A solution of 4-bromo-3-(2-chloroethoxy)pyridin-2-ylamine (9.2 g, 0.036 mole) in DMF (50 mL) was added drop wise to a stirred suspension of sodium hydride (2.6 g, 0.065 mole, 60% oil suspension) in DMF (10 mL) at 15-25° C. followed by the addition of sodium iodide (0.5 g, 0.0036 mole) and stirred at room temperature for 4 h. The reaction mixture was added to water (250 mL), extracted with ethyl acetate (250 mL×3). The organic layers were combined, washed with brine solution (100 mL), dried over Na₂SO₄ and concentrated under vacuum to obtain the crude compound which was further purified by flash chromatography using ethyl acetate:n-hexane (60:40) to obtain 8-bromo-3,4-dihydro-2H-pyrido[3,2-b][1,4]oxazine.

Yield: 6.3 g; ¹H-NMR (CDCl₃, 400 MHz) δ ppm: 3.56-3.59 (m, 2H), 4.31-4.33 (m, 2H), 4.96 (bs, 1H), 6.77-6.78 (d, J=5.44 Hz, 1H), 7.46-7.47 (d, J=5.48 Hz, 1H); Mass (m/z): 215.1, 217.0 (M+H)⁺.

Step-4: 8-Bromo-3,4-dihydro-2H-pyrido[3,2-b][1,4]oxazine-5-oxide

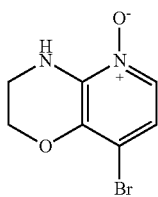

The title compound was synthesized from 8-bromo-3,4-dihydro-2H-pyrido[3,2-b][1,4]oxazine following the procedure as described in step-1 of example 1.

Yield: 5.2 g; ¹H-NMR (DMSO-d₆, 400 MHz) δ ppm: 3.48-3.51 (m, 2H), 4.24-4.26 (m, 2H), 6.77-6.79 (d, J=7.16 Hz, 1H), 7.56 (bs, 1H), 7.66-7.68 (d, J=6.96 Hz, 1H); Mass (m/z): 231.1, 233.0 (M+H)⁺.

Step-5: 8-Bromo-3,4-dihydro-2H-pyrido[3,2-b][1,4]oxazine-6-carbonitrile

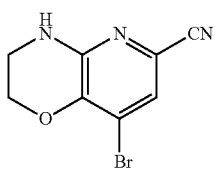

The title compound was synthesized from 8-bromo-3,4-dihydro-2H-pyrido[3,2-b][1,4]oxazine-5-oxide following the procedure as described in step-2 of example 1.

Yield: 1.9 g; ¹H-NMR (CDCl₃, 400 MHz) δ ppm: 3.50-3.52 (t, J=4.16 Hz, 2H), 4.25-4.27 (t, J=4.20 Hz, 2H), 7.17 (s, 1H); Mass (m/z): 240.1, 242.0 (M+H)⁺.

Step-6: 8-Bromo-4-methyl-3,4-dihydro-2H-pyrido[3,2-b][1,4]oxazine-6-carbonitrile

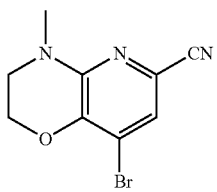

The title compound was synthesized from 8-bromo-3,4-dihydro-2H-pyrido[3,2-b][1,4]oxazine-6-carbonitrile following the procedure as described in step-4 of example 1.

Yield: 0.39 g; ¹H-NMR (CDCl₃, 400 MHz) δ ppm: 3.13 (s, 3H), 3.51-3.53 (t, J=4.34 Hz, 2H), 4.37-4.39 (t, J=4.30 Hz, 2H), 7.12 (s, 1H); Mass (m/z): 254.0, 256.1 (M+H)⁺.

Step-7: 8-Bromo-4-methyl-3,4-dihydro-2H-pyrido[3,2-b][1,4]oxazine-6-carboxylic acid

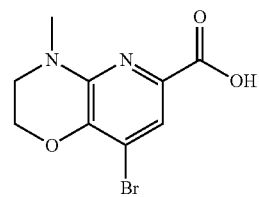

The title compound was synthesized from 8-bromo-4-methyl-3,4-dihydro-2H-pyrido[3,2-b][1,4]oxazine-6-carbonitrile following the procedure as described in step-3 of example 1.

Yield: 0.89 g; ¹H-NMR (DMSO-d₆, 400 MHz) δ ppm: 3.06 (s, 3H), 3.48 (m, 2H), 4.33 (m, 2H), 7.33 (s, 1H); Mass (m/z): 273.0, 275.0 (M+H)⁺.

Step-8: Methyl 8-bromo-4-methyl-3,4-dihydro-2H-pyrido[3,2-b][1,4]oxazine-6-carboxylate

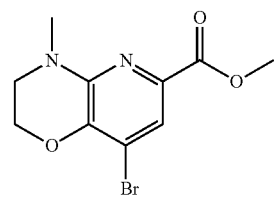 [SMILES: COC(=O)c1cc(Br)c2c(n1)N(C)CCO2]

The title compound was synthesized from 8-bromo-4-methyl-3,4-dihydro-2H-pyrido[3,2-b][1,4]oxazine-6-carboxylic acid following the procedure as described in step-4 of example 1.

Yield: 0.6 g; ¹H-NMR (CDCl₃, 400 MHz) δ ppm: 3.21 (s, 3H), 3.49-3.52 (t, J=4.38 Hz, 2H), 3.91 (s, 3H), 4.37-4.39 (t, J=4.36 Hz, 2H), 7.60 (s, 1H); Mass (m/z): 287.0, 289.0 (M+H)⁺.

Step-9: Methyl 8-(4-fluorobenzyl)-4-methyl-3,4-dihydro-2H-pyrido[3,2-b][1,4]oxazine-6-carboxylate

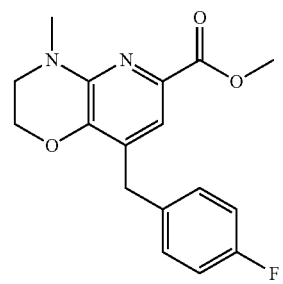 [SMILES: COC(=O)c1cc(Cc2ccc(F)cc2)c2c(n1)N(C)CCO2]

A stirred solution of methyl 8-bromo-4-methyl-3,4-dihydro-2H-pyrido[3,2-b][1,4]oxazine-6-carboxylate (0.39 g, 0.0013 mole) in dry THF (15 mL) was degassed for 2 minutes and back filled with N₂ followed by addition of bis(tri-tert-butylphosphine)palladium (0.034 g, 0.000067 mole) and 4-fluorobenzylzinc chloride solution (4.1 mL, 0.002 mole, 0.5 M in THF). The reaction mixture was refluxed for 3 hours, cooled to room temperature, poured in to water (50 mL) and extracted with ethyl acetate (50 mL×3). The organic layers were combined, washed with brine solution (100 mL), dried over $Na_2SO_4$ and concentrated under vacuum to obtain the crude compound which was further purified by flash chromatography using ethyl acetate:n-hexane (50:50) to obtain methyl 8-(4-fluorobenzyl)-4-methyl-3,4-dihydro-2H-pyrido[3,2-b][1,4]oxazine-6-carboxylate.

Yield: 0.39 g; $^1$H-NMR (CDCl$_3$, 400 MHz) δ ppm: 3.19 (s, 3H), 3.45-3.47 (t, J=4.5 Hz, 2H), 3.84 (s, 3H), 3.87 (s, 2H), 4.28-4.30 (t, J=4.44 Hz, 2H), 6.93-6.97 (m, 2H), 7.13-7.16 (m, 1H), 7.24-7.26 (m, J=7.29 Hz, 2H); Mass (m/z): 317.0 (M+H)$^+$.

Step-10: 8-(4-Fluorobenzyl)-4-methyl-3,4-dihydro-2H-pyrido[3,2-b][1,4]oxazine-6-carboxylic acid

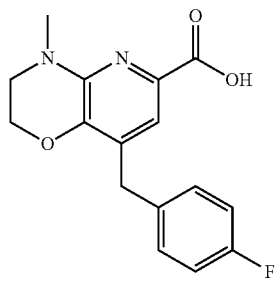 [SMILES: CN1CCOc2c(Cc3ccc(F)cc3)cc(C(=O)O)nc21]

The title compound was synthesized from methyl 8-(4-fluorobenzyl)-4-methyl-3,4-dihydro-2H-pyrido[3,2-b][1,4]oxazine-6-carboxylate following the procedure as described in step-7 of example 1.

Yield: 0.38 g; $^1$H-NMR (DMSO-d$_6$, 400 MHz) δ ppm: 3.04 (s, 3H), 3.42-3.44 (t, J=3.80 Hz, 2H), 3.81 (s, 2H), 4.27-4.29 (t, J=3.84 Hz, 2H), 7.04-7.12 (m, 3H), 7.22-7.25 (m, 2H); Mass (m/z): 303.0 (M+H)$^+$.

Step-11: N-[(1S,2S)-2-Hydroxycyclohexyl]-8-(4-fluorobenzyl)-4-methyl-2H-pyrido[3,2-b][1,4]oxazine-6-carboxamide

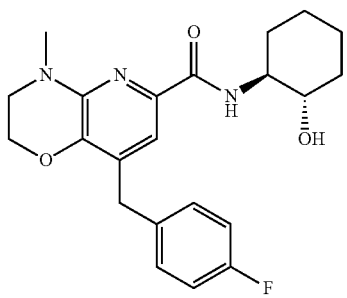 [SMILES: CN1CCOc2c(Cc3ccc(F)cc3)cc(C(=O)N[C@H]3CCCC[C@@H]3O)nc21]

The title compound was synthesized from 8-(4-fluorobenzyl)-4-methyl-3,4-dihydro-2H-pyrido[3,2-b][1,4]oxazine-6-carboxylic acid following the procedure as described in step-8 of example 1.

Yield: 0.40 g; $^1$H-NMR (CDCl$_3$, 400 MHz) δ ppm: 1.25-1.39 (m, 4H), 1.73-1.76 (m, 2H), 2.00-2.02 (m, 1H), 2.07-2.11 (m, 1H), 3.11 (s, 3H), 3.41-3.48 (m, 3H), 3.70-3.72 (m, 1H), 3.85 (s, 2H), 4.01-4.02 (d, J=3.26, 1H), 4.28-4.30 (t, J=4.47 Hz, 2H), 6.90-6.95 (m, 2H), 7.13-7.17 (m, 2H), 7.33 (s, 1H), 7.75-7.77 (d, J=6.68 Hz, 1H); Mass (m/z): 400.2 (M+H)$^+$.

Examples 121 to 128

The compounds of Example 121 to 128 were prepared by following the experimental procedures as described in the Example 120, with some non-critical variations

| Example No. | Structure and IUPAC name | Characterization data |
|---|---|---|
| 121 | ![structure] N-[(1S,2S)-2-Hydroxycyclohexyl]-8-(3-fluorobenzyl)-4-methyl-2H-pyrido[3,2-b][1,4]oxazine-6-carboxamide | $^1$H-NMR (DMSO-d$_6$, 400 MHz) δ ppm: 1.23-1.33 (m, 4H), 1.57-1.64 (m, 2H), 1.84-1.90 (m, 2H), 3.10 (s, 3H), 3.33-3.35 (m, 2H), 3.47-3.48 (m, 2H), 3.88 (s, 2H), 4.29-4.31 (t, J = 4.08, 2H), 4.68-4.69 (d, J = 5.37 Hz, 1H), 7.01-7.06 (m, 4H), 7.29-7.33 (m, 1H), 7.89-7.91 (d, J = 7.72 Hz, 1H); Mass (m/z): 400.1 (M + H)$^+$. |

| Example No. | Structure and IUPAC name | Characterization data |
|---|---|---|
| 122 | 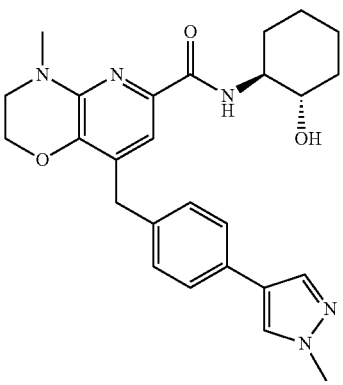 [SMILES: CN1CCOc2c(Cc3ccc(-c4cnn(C)c4)cc3)cc(C(=O)N[C@H]3CCCC[C@@H]3O)nc21]<br><br>N-[(1S,2S)-2-Hydroxycyclohexyl]-8-[4-(1-methyl-1H-pyrazol-4-yl)benzyl]-4-methyl-2H-pyrido[3,2-b][1,4]oxazine-6-carboxamide | $^1$H-NMR (DMSO-d$_6$, 400 MHz) δ ppm: 1.23-1.35 (m, 2H), 1.56-1.57 (m, 2H), 1.83-1.84 (m, 4H), 3.10 (s, 3H), 3.27-3.30 (m, 1H), 3.37-3.47 (m, 3H), 3.84 (s, 5H), 4.29-4.31 (m, 2H), 4.68-4.69 (d, J = 5.40 Hz, 1H), 7.05 (s, 1H), 7.16-7.18 (d, J = 7.90 Hz, 2H), 7.44-7.46 (d, J = 8.01 Hz, 2H), 7.95 (s, 1H), 7.89-7.91 (d, J = 7.71 Hz, 1H), 8.06 (s, 1H); Mass (m/z): 462.4 (M + H)$^+$. |
| 123 | 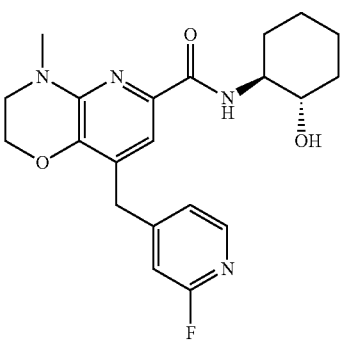 [SMILES: CN1CCOc2c(Cc3ccnc(F)c3)cc(C(=O)N[C@H]3CCCC[C@@H]3O)nc21]<br><br>N-[(1S,2S)-2-Hydroxycyclohexyl]-8-(2-fluoropyridin-4-ylmethyl)-4-methyl-2H-pyrido[3,2-b][1,4]oxazine-6-carboxamide | $^1$H-NMR (DMSO-d$_6$, 400 MHz) δ ppm: 1.58-1.75 (4H, m), 1.84-1.97 (m, 4H). 3.11 (s, 3H), 3.39-3.40 (m, 1H), 3.46-3.50 (m, 3H), 3.96 (s, 2H), 4.27-4.29 (m, 2H), 4.68-4.70 (d, J = 5.48 Hz, 1H), 7.12 (s, 1H), 7.16-7.17 (d, J = 4.79 Hz, 1H), 7.90-7.92 (d, J = 7.7 Hz, 1H), 7.95 (s, 1H), 8.12-8.13 (d, J = 5.09 Hz, 1H); Mass (m/z): 401.0 (M + H)$^+$. |
| 124 | 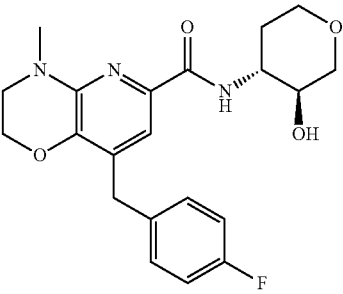 [SMILES: CN1CCOc2c(Cc3ccc(F)cc3)cc(C(=O)N[C@@H]3CCOC[C@H]3O)nc21]<br><br>trans-N-(3-Hydroxytetrahydropyran-4-yl)-8-(4-fluorobenzyl)-4-methyl-2H-pyrido[3,2-b][1,4]oxazine-6-carboxamide (Isomer-II) | $^1$H-NMR (DMSO-d$_6$, 400 MHz) δ ppm: 1.56-1.57 (m, 1H), 1.59-1.60 (m, 1H), 2.99-3.14 (m, 1H), 3.12 (s, 3H), 3.36-3.37 (m, 1H), 3.46-3.53 (m, 3H), 3.74-3.83 (m, 3H), 3.85 (s, 2H), 4.28-4.30 (m, 2H), 4.97-4.98 (d, J = 5.70 Hz, 1H), 7.05-7.12 (m, 3H), 7.22-7.25 (m, 2H), 8.00-8.02 (d, J = 7.98 Hz, 1H); Mass (m/z): 401.9 (M + H)$^+$. |

| Example No. | Structure and IUPAC name | Characterization data |
|---|---|---|
| 125 | 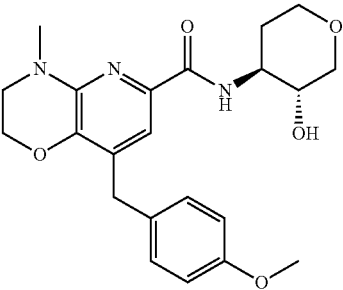 [SMILES: COc1ccc(Cc2cc(C(=O)N[C@H]3CCOC[C@@H]3O)nc3c2OCCN3C)cc1]<br>trans-N-(3-Hydroxytetrahydropyran-4-yl)-8-(4-methoxybenzyl)-4-methyl-2H-pyrido[3,2-b][1,4]oxazine-6-carboxamide (Isomer-II) | Mass (m/z): 414.2 (M + H)+. |
| 126 | 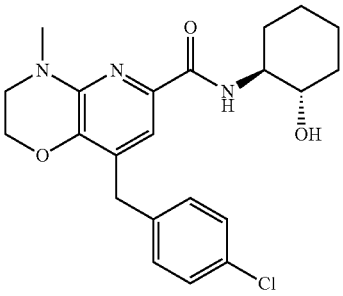 [SMILES: CN1CCOc2c(Cc3ccc(Cl)cc3)cc(C(=O)N[C@H]3CCCC[C@@H]3O)nc21]<br>N-[(1S,2S)-2-Hydroxycyclohexyl]-8-(2-chloropyridin-5-ylmethyl)-4-methyl-2H-pyrido[3,2-b][1,4]oxazine-6-carboxamide | $^1$H-NMR (DMSO-d$_6$, 400 MHz) δ ppm: 1.25-1.33 (m, 2H), 1.57-1.64 (m, 2H), 1.84-1.97 (m, 4H), 3.11 (s, 3H), 3.28-3.29 (m, 1H), 3.37-3.38 (m, 1H), 3.42-3.44 (m, 2H), 3.89 (s, 2H), 4.28-4.29 (m, 2H), 4.68-4.69 (d, J = 5.45 Hz, 1H), 7.10 (s, 1H), 7.41-7.44 (d, J = 8.17 Hz, 1H), 7.65-7.68 (dd, J = 2.09, 8.12 Hz, 1H), 7.89-7.91 (d, J = 7.66 Hz, 1H), 8.30-8.31 (d, J = 1.85 Hz, 1H); Mass (m/z): 417.4, 419.3 (M + H)+. |
| 127 | 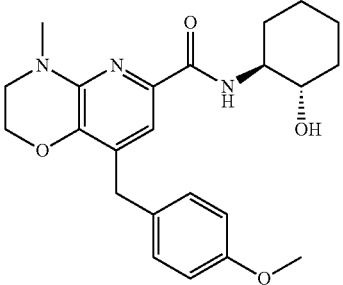 [SMILES: COc1ccc(Cc2cc(C(=O)N[C@H]3CCCC[C@@H]3O)nc3c2OCCN3C)cc1]<br>N-[(1S,2S)-2-Hydroxycyclohexyl]-8-(4-methoxybenzyl)-4-methyl-2H-pyrido[3,2-b][1,4]oxazine-6-carboxamide | $^1$H-NMR (DMSO-d$_6$, 400 MHz) δ ppm: 1.28-1.38 (m, 2H), 1.57-1.64 (m, 2H), 2.33 (m, 1H), 2.67-2.69 (m, 2H), 3.10 (s, 3H), 3.37-3.38 (m, 2H), 3.47 (m, 3H), 3.71 (s, 3H), 3.78 (s, 2H), 4.30 (m, 2H), 4.68-4.69 (d, J = 5.2 Hz, 1H), 6.83-6.85 (d, J = 8.3 Hz, 2H), 7.01 (s, 1H), 7.10-7.12 (d, J = 8.3 Hz, 2H), 7.88-7.90 (d, J = 7.5 Hz, 1H); Mass (m/z): 412.1 (M + H)+. |

| Example No. | Structure and IUPAC name | Characterization data |
|---|---|---|
| 128 | 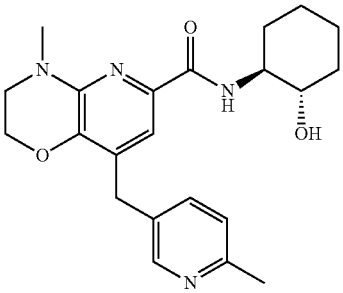 [SMILES: Cc1ccc(Cc2cc(C(=O)N[C@H]3CCCC[C@@H]3O)nc3c2OCCN3C)cn1]<br>N-[(1S,2S)-2-N-Hydroxycyclohexyl]-8-(2-methylpyridin-5-ylmethyl)-4-methyl-2H-pyrido[3,2-b][1,4]oxazine-6-carboxamide | $^1$H-NMR (DMSO-d$_6$, 400 MHz) δ ppm: 1.23-1.30 (m, 4H), 1.57-1.64 (m, 2H), 1.84-1.86 (m, 1H), 1.88-1.97 (m, 2H), 2.41 (s, 3H), 3.10 (s, 3H), 3.46-3.48 (m, 3H), 3.83 (s, 2H), 4.35-4.37 (m, 2H), 4.68-4.69 (d, J = 5.24 Hz, 1H), 7.05 (s, 1H), 7.14-7.16 (m, 1H), 7.46-7.48 (m, 1H), 7.89-7.91 (d, J = 7.56 Hz, 1H), 8.32 (s, 1H); Mass (m/z): 397.1 (M + H)$^+$. |

Example 129

N-[(1S,2S)-2-Hydroxycyclohexyl]-8-[4-pyrazol-1-ylbenzyl]-4-methyl-2H-pyrido[3,2-b][1,4]oxazine-6-carboxamide

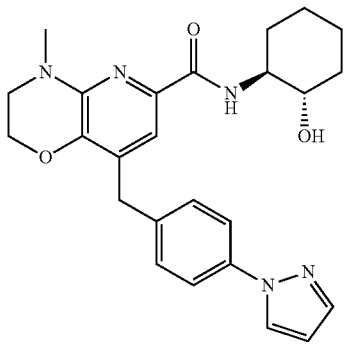 [SMILES: CN1CCOc2c(Cc3ccc(-n4cccn4)cc3)cc(C(=O)N[C@H]3CCCC[C@@H]3O)nc21]

Step-1: Methyl 4-methyl-8-(4,4,5,5-tetramethyl-[1,3,2]dioxaborolan-2-yl)-3,4-dihydro-2H-pyrido[3,2-b][1,4]oxazine-6-carboxylate

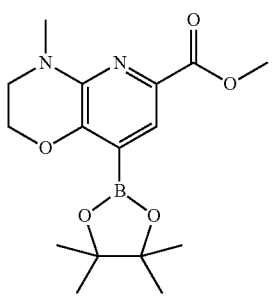

The title compound was synthesized from methyl 8-bromo-4-methyl-3,4-dihydro-2H-pyrido[3,2-b][1,4]oxazine-6-carboxylate following the procedure as described in step-5 of example 1.

$^1$H-NMR (CDCl$_3$, 400 MHz) δ ppm: 1.27 (s, 12H), 3.21 (s, 3H), 3.50-3.52 (m, 2H), 3.91 (s, 3H), 4.37-4.40 (m, 2H), 7.60 (s, 1H); (Mass (m/z): 335.4 (M+H)$^+$.

Step-2: Methyl 8-[4-pyrazol-1-ylbenzyl]-4-methyl-3,4-dihydro-2H-pyrido[3,2-b][1,4]oxazine-6-carboxylate

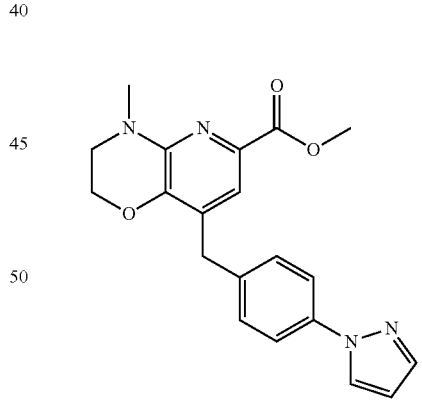

The title compound was synthesized from methyl 4-methyl-8-(4-pyrazol-1-yl-benzyl)-3,4-dihydro-2H-pyrido[3,2-b][1,4]oxazine-6-carboxylate following the procedure as described in step-6 of example 1.

Yield: 0.14 g; $^1$H-NMR (CDCl$_3$, 400 MHz) δ ppm: 3.20 (s, 3H), 3.46-3.48 (t, J=4.5 Hz, 2H), 3.88 (s, 3H), 3.91 (s, 2H), 4.29-4.31 (t, J=4.5 Hz, 2H), 6.44-6.45 (m, 1H), 7.28-7.28 (m, 3H), 7.58-7.60 (m, 2H), 7.70-7.70 (m, 1H), 7.88-7.88 (d, J=2.3 Hz, 1H); (Mass (m/z): 365.1 (M+H)$^+$.

Step-3: 8-[4-Pyrazol-1-ylbenzyl]-4-methyl-3,4-di-hydro-2H-pyrido[3,2-b][1,4]oxazine-6-carboxylic acid

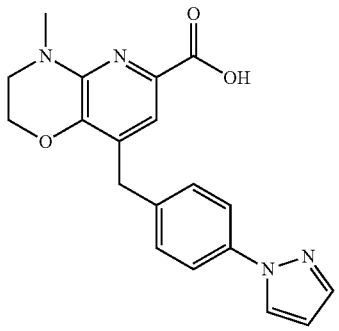 [SMILES: CN1CCOc2c(Cc3ccc(-n4cccn4)cc3)cc(C(=O)O)nc21]

The title compound was synthesized from methyl 4-methyl-8-(4-pyrazol-1-yl-benzyl)-3,4-dihydro-2H-pyrido[3,2-b][1,4]oxazine-6-carboxylate following the procedure as described in step-7 of example 1.

Yield: 0.12 g; $^1$H-NMR (CDCl$_3$, 400 MHz) δ ppm: 3.08 (s, 3H), 3.47-3.49 (m, 2H), 4.02 (s, 2H), 4.32-4.34 (m, 2H), 6.52 (m, 1H), 7.14 (s, 1H), 7.32-7.34 (d, J=8.3 Hz, 2H), 7.20-7.61 (m, 3H), 8.43-8.44 (d, J=2.1 Hz, 1H); (Mass (m/z): 351.2 (M+H)$^+$.

Step-4: N-[(1S,2S)-2-Hydroxycyclohexyl]-8-[4-pyrazol-1-ylbenzyl]-4-methyl-2H-pyrido[3,2-b][1,4]oxazine-6-carboxamide The title compound was synthesized from 4-methyl-8-(4-pyrazol-1-yl-benzyl)-3,4-dihydro-2H-pyrido[3,2-b][1,4]oxazine-6-carboxylic acid following the procedure as described in step-8 of example 1.

Yield: 0.075 g; $^1$H-NMR (DMSO-d$_6$, 400 MHz) δ ppm: 1.23-1.35 (m, 2H), 1.58-1.64 (m, 2H), 1.85-1.99 (m, 3H), 2.33-2.67 (m, 2H), 3.11 (s, 3H), 3.33-3.49 (m, 3H), 3.90 (s, 2H), 4.31 (m, 2H), 4.68-4.70 (d, J=5.0 Hz, 1H), 6.52 (s, 1H) 7.09 (s, 1H), 7.33-7.31 (d, J=7.9 Hz, 2H), 7.75-7.71 (m, 3H), 7.90-7.92 (d, J=7.3 Hz, 1H), 8.44 (s, 1H); Mass (m/z): 448.1 (M+H)$^+$.

Example 130

N-[(1S,2S)-2-Hydroxycyclohexyl]-4-methyl-8-(1-methyl-1H-pyrazol-4-ylmethyl)-2H-pyrido[3,2-b][1,4]oxazine-6-carboxamide

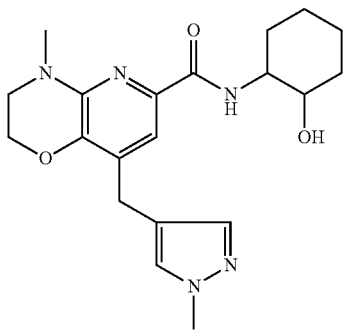 [SMILES: CN1CCOc2c(Cc3cnn(C)c3)cc(C(=O)NC3CCCCC3O)nc21]

The title compound was prepared by following the experimental procedures as described in the Example 129, with some non-critical variations Mass (m/z): 386.3 (M+H)$^+$.

Examples 131 to 136

The compounds of Example 131 to 136 were prepared by following the experimental procedures as described in the Example 120, 125, 120, 125, 129 and 130 respectively, with some non-critical variations

| Example No. | Structure and IUPAC name | Characterization data |
|---|---|---|
| 131 | Racemic cis-N-(4-Hydroxytetrahydropyran-3-yl)-8-(4-fluorobenzyl)-4-methyl-2H-pyrido[3,2-b][1,4]oxazine-6-carboxamide | Mass (m/z): 402.2 (M + H)$^+$. |
| 132 | Racemic cis-N-(4-Hydroxytetrahydropyran-3-yl)-8-(4-methoxybenzyl)-4-methyl-2H-pyrido[3,2-b][1,4]oxazine-6-carboxamide | Mass (m/z): 414.3 (M + H)$^+$. |
| 133 | (3S,4S)-N-(4-Hydroxytetrahydropyran-3-yl)-8-(4-fluorobenzyl)-4-methyl-2H-pyrido[3,2-b][1,4]oxazine-6-carboxamide | Mass (m/z): 402.4 (M + H)$^+$. |

| Example No. | Structure and IUPAC name | Characterization data |
|---|---|---|
| 134 | 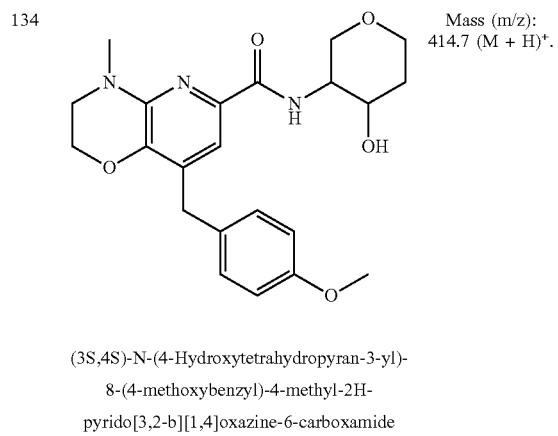<br>(3S,4S)-N-(4-Hydroxytetrahydropyran-3-yl)-8-(4-methoxybenzyl)-4-methyl-2H-pyrido[3,2-b][1,4]oxazine-6-carboxamide | Mass (m/z): 414.7 (M + H)⁺. |
| 135 | 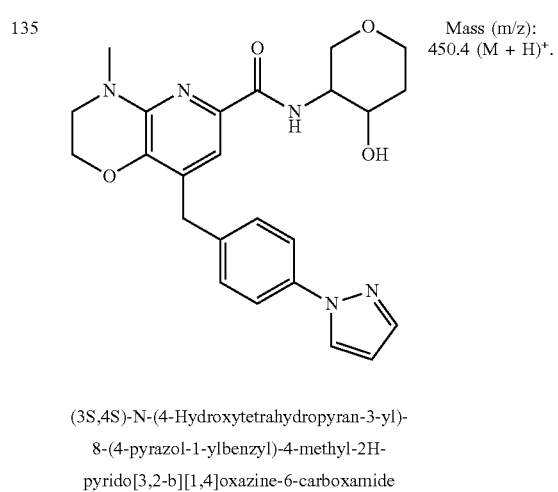<br>(3S,4S)-N-(4-Hydroxytetrahydropyran-3-yl)-8-(4-pyrazol-1-ylbenzyl)-4-methyl-2H-pyrido[3,2-b][1,4]oxazine-6-carboxamide | Mass (m/z): 450.4 (M + H)⁺. |
| 136 | 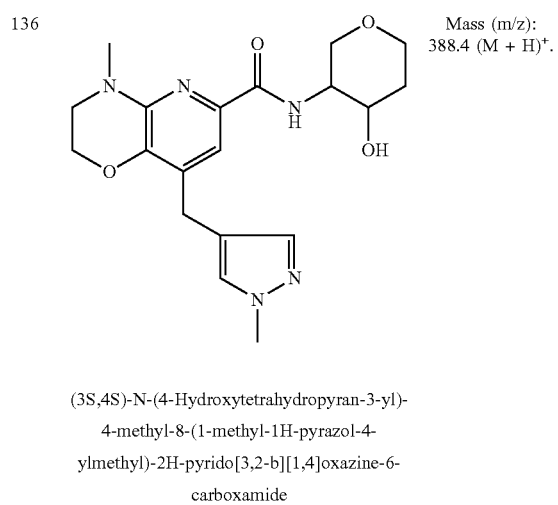<br>(3S,4S)-N-(4-Hydroxytetrahydropyran-3-yl)-4-methyl-8-(1-methyl-1H-pyrazol-4-ylmethyl)-2H-pyrido[3,2-b][1,4]oxazine-6-carboxamide | Mass (m/z): 388.4 (M + H)⁺. |

Example 137

N-[(1S,2S)-2-Hydroxycyclohexyl]-7-(4-fluorobenzyl)-1-methyl-1H-pyrrolo[3,2-b]pyridine-5-carboxamide

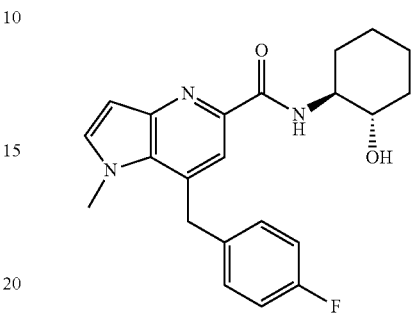

Step-1: 7-Chloro-1H-pyrrolo[3,2-b]pyridine 4-oxide

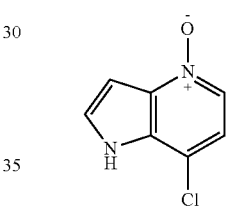

The title compound was synthesized from 7-chloro-4-azaindole following the procedure as described in step-1 of example 1.

Yield: 2.36 g; $^1$H-NMR (DMSO-d$_6$, 400 MHz) δ ppm: 6.74-6.74 (d, J=3.16 Hz, 1H), 7.23-7.25 (d, J=6.6 Hz, 1H), 7.66-7.67 (d, J=3.04 Hz, 1H), 8.03-8.05 (s, J=6.6 Hz, 1H), 12.42 (bs, 1H); Mass (m/z): 169.2 (M+H)⁺.

Step-2: 7-Chloro-1H-pyrrolo[3,2-b]pyridine-5-carbonitrile

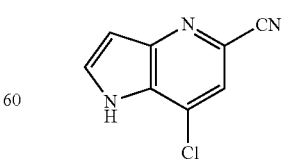

The title compound was synthesized from 7-chloro-1H-pyrrolo[3,2-b]pyridine 4-oxide following the procedure as described in step-2 of example 1.

Yield: 1.65 g; $^1$H-NMR (DMSO-d$_6$, 400 MHz) δ ppm: 6.83-6.83 (m, 1H), 7.99-8.01 (m, 2H), 12.52 (bs, 1H); Mass (m/z): 178.3, 180.2 (M+H)$^+$.

Step-3: 7-Chloro-1-methyl-1H-pyrrolo[3,2-b]pyridine-5-carbonitrile

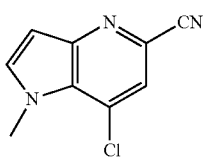

The title compound was synthesized from 7-chloro-1H-pyrrolo[3,2-b]pyridine-5-carbonitrile following the procedure as described in step-4 of example 1.

Yield: 0.2 g; $^1$H-NMR (CDCl$_3$, 400 MHz) δ ppm: 4.17 (s, 3H), 6.77-6.78 (d, J=3.38 Hz, 1H), 7.40-7.41 (d, J=3.25 Hz, 1H), 7.47 (s, 1H); Mass (m/z): 192.1, 194.1 (H)$^+$.

Step-4: 7-(4-Fluorobenzyl)-1-methyl-1H-pyrrolo[3,2-b]pyridine-5-carbonitrile

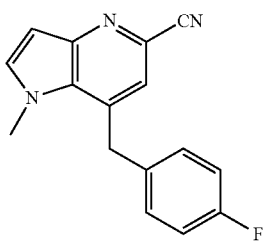 [SMILES: Cn1ccc2nc(C#N)cc(Cc3ccc(F)cc3)c21]

The title compound was synthesized from 7-chloro-1-methyl-1H-pyrrolo[3,2-b]pyridine-5-carbonitrile following the procedure as described in step 9 of example 79.

Yield: 0.13 g; $^1$H-NMR (CDCl$_3$, 400 MHz) δ ppm: 3.90 (s, 3H), 4.45 (s, 2H), 6.76-6.77 (d, J=3.17 Hz, 1H), 7.02-7.03 (m, 4H), 7.17 (s, 1H), 7.32-7.32 (d, J=3.01 Hz, 1H); Mass (m/z): 266.1, 267.2 (M+H)$^+$.

Step-5: 7-(4-Fluorobenzyl)-1-methyl-1H-pyrrolo[3,2-b]pyridine-5-carboxylic acid

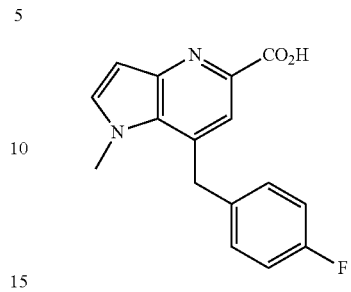

The title compound was synthesized from 7-(4-fluorobenzyl)-1-methyl-1H-pyrrolo[3,2-b]pyridine-5-carbonitrile following the procedure as described in step-7 of example 1.

Yield: 0.066 g; $^1$H-NMR (DMSO-d$_6$, 400 MHz) δ ppm: 3.89 (s, 3H), 4.51 (s, 2H), 6.60-6.61 (d, J=2.31 Hz, 1H), 7.14-7.18 (m, 4H), 7.49-7.51 (m, 2H); Mass (m/z): 285.1 (M+H)$^+$.

Step-6: N-[(1S,2S)-2-Hydroxycyclohexyl]-7-(4-fluorobenzyl)-1-methyl-1H-pyrrolo[3,2-b]pyridine-5-carboxamide

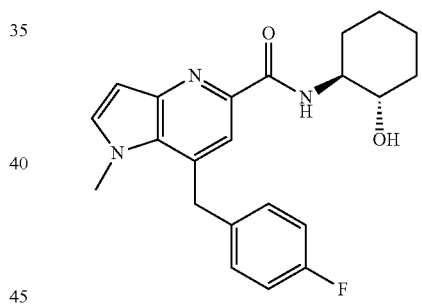

The title compound was synthesized from 7-(4-fluorobenzyl)-1-methyl-1H-pyrrolo[3,2-b]pyridine-5-carboxylic acid following the procedure as described in step-8 of example 1.

Yield: 0.034 g; $^1$H-NMR (DMSO-d$_6$, 400 MHz) δ ppm: 1.25-1.31 (m, 4H), 1.60-1.65 (m, 2H), 1.88-1.93 (m, 2H), 3.38-3.44 (m, 1H), 3.45-3.50 (m, 1H), 3.95 (s, 3H), 4.59 (s, 2H), 4.70-4.71 (d, J=5.32 Hz, 1H), 6.64-6.65 (d, J=3.04 Hz, 1H), 7.16-7.17 (m, 4H), 7.53 (s, 1H), 7.65-7.66 (d, J=2.9 Hz, 1H), 8.25-8.27 (d, J=7.6 Hz, 1H); Mass (m/z): 382.3 (M+H)$^+$.

Examples 138 to 142

The compounds of Example 138 to 142 were prepared by following the experimental procedures as described in the Example 137, with some non-critical variations

| Example No. | Structure and IUPAC name | Characterization data |
|---|---|---|
| 138 | 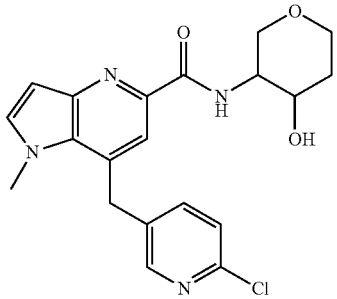 [SMILES: Cn1ccc2nc(C(=O)NC3COCCC3O)cc(Cc3ccc(Cl)nc3)c21]<br><br>Racemic cis-N-(3-Hydroxytetrahydropyran-4-yl)-7-(2-chloropyridin-5-ylmethyl)-1-methyl-1H-pyrrolo[3,2-b]pyridine-5-carboxamide | $^1$H-NMR (DMSO-d$_6$, 400 MHz) δ ppm: 1.54-1.60 (m, 1H), 1.62-1.64 (m, 1H), 3.34 (s, 3H), 3.58-3.61 (m, 1H), 3.74-3.83 (m, 5H), 3.99 (s, 2H), 4.97-4.98 (d, J = 5.71 Hz, 1H), 6.66-6.67 (d, J = 3.14 Hz, 1H), 7.47-7.50 (2H, m), 7.58-7.60 (dd, J = 1.86, 8.3 Hz, 1H), 7.69-7.70 (d, J = 3.14 Hz, 1H), 8.32-8.32 (d, J = 1.46 Hz, 1H), 8.44-8.46 (d, J = 8.0 Hz, 1H); Mass (m/z): 401.2, 403.2 (M + H)$^+$. |
| 139 | 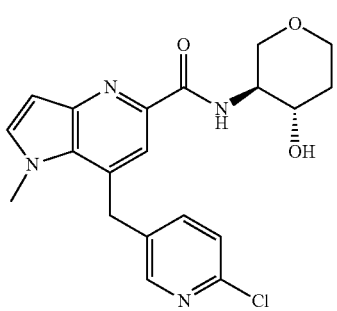 [SMILES: Cn1ccc2nc(C(=O)N[C@H]3COCC[C@@H]3O)cc(Cc3ccc(Cl)nc3)c21]<br><br>N-[(1S,2S)-2-Hydroxycyclohexyl]-7-(2-chloropyridin-5-ylmethyl)-1-methyl-1H-pyrrolo[3,2-b]pyridine-5-carboxamide | $^1$H-NMR (DMSO-d$_6$, 400 MHz) δ ppm: 1.23-1.27 (m, 2H), 1.65-1.74 (m, 2H), 1.88-1.97 (m, 4H), 3.42-3.46 (m, 1H), 3.50-3.54 (m, 1H), 3.99 (s, 3H), 4.66 (s, 2H), 4.69-4.70 (d, J = 5.36 Hz, 1H), 6.66-6.66 (d, J = 3.09 Hz, 1H), 7.47-7.50 (m, 2H), 7.58-7.60 (dd, J = 2.07, 8.16 Hz, 1H), 7.68-7.69 (d, J = 3.24 Hz, 1H), 8.25-8.27 (d, J = 7.71 Hz, 1H), 8.31-8.32 (d, J = 1.71 Hz, 1H); Mass (m/z): 399.3, 401.2 (M + H)$^+$. |
| 140 | 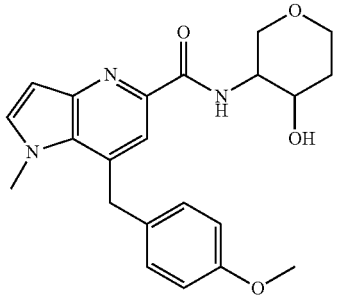 [SMILES: COc1ccc(Cc2cc(C(=O)NC3COCCC3O)nc3ccn(C)c23)cc1]<br><br>Racemic cis-N-(4-Hydroxytetrahydropyran-3-yl)-7-(4-methoxybenzyl)-1-methyl-1H-pyrrolo[3,2-b]pyridine-5-carboxamide | Mass (m/z): 396.2 (M + H)$^+$. |

-continued

| Example No. | Structure and IUPAC name | Characterization data |
|---|---|---|
| 141 | 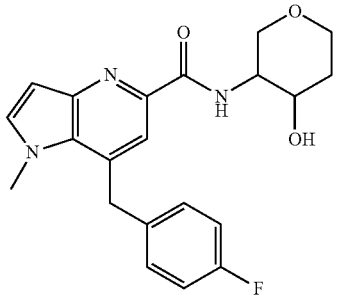 [SMILES: Cn1ccc2nc(C(=O)NC3COCCC3O)cc(Cc3ccc(F)cc3)c21]<br>(3S,4S)-N-(4-Hydroxytetrahydropyran-3-yl)-7-(4-fluorobenzyl)-1-methyl-1H-pyrrolo[3,2-b]pyridine-5-carboxamide | Mass (m/z): 384.4 (M + H)$^+$. |
| 142 | 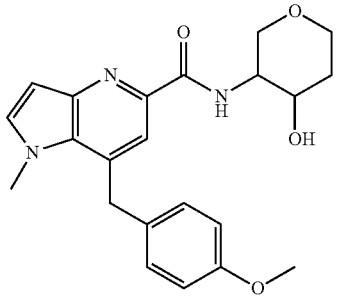 [SMILES: COc1ccc(Cc2cc(C(=O)NC3COCCC3O)nc3ccn(C)c23)cc1]<br>(3S,4S)-N-(4-Hydroxytetrahydropyran-3-yl)-7-(4-methoxybenzyl)-1-methyl-1H-pyrrolo[3,2-b]pyridine-5-carboxamide | Mass (m/z): 396.4 (M + H)$^+$. |

Example 143

Determination of Allosteric Potency $EC_{50}$ Values for Muscarinic M1 Receptor:

A stable CHO cell line expressing recombinant human Muscarinic M1 receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cyclic AMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added along with $EC_{20}$ of acetylcholine in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50% in presence of $EC_{20}$ of acetylcholine and the results are provided in table 1.

TABLE 1

$EC_{50}$ values of the test compounds

| Example No. | $EC_{50}$ (nM) |
|---|---|
| 1 | 1479 |
| 2 | 1083 |
| 3 | 977 |
| 4 | 811 |
| 5 | 130 |
| 6 | 15 |
| 7 | 8 |
| 8 | 17 |
| 9 | 1574 |
| 10 | 570 |
| 11 | 1723 |
| 12 | 306 |
| 13 | 617 |
| 14 | 891 |
| 15 | 38 |
| 16 | 1292 |
| 17 | 1626 |
| 18 | 38 |
| 19 | 1113 |
| 20 | 315 |
| 21 | 1053 |
| 23 | 727 |
| 24 | 834 |
| 25 | 362 |

TABLE 1-continued

EC$_{50}$ values of the test compounds

| Example No. | EC$_{50}$ (nM) |
|---|---|
| 26 | 221 |
| 27 | 234 |
| 32 | 486 |
| 35 | 1469 |
| 36 | 3167 |
| 37 | 1251 |
| 38 | 983 |
| 39 | 968 |
| 40 | 755 |
| 41 | 1227 |
| 42 | 2289 |
| 43 | 2531 |
| 44 | 748 |
| 45 | 3148 |
| 46 | 2963 |
| 49 | 1414 |
| 50 | 2916 |
| 51 | 1821 |
| 53 | 31 |
| 54 | 764 |
| 55 | 32 |
| 56 | 38 |
| 61 | 222 |
| 72 | 494 |
| 73 | 786 |
| 76 | 380 |
| 77 | 342 |
| 87 | 241 |
| 90 | 18 |
| 97 | 6 |
| 98 | 109 |
| 103 | 131 |
| 104 | 231 |
| 106 | 14 |
| 113 | 136 |
| 120 | 407 |
| 122 | 85 |
| 127 | 946 |
| 129 | 15 |
| 137 | 641 |
| 138 | 278 |

Example 144

Rodent Pharmacokinetic Study

Male Wistar rats (260±50 grams) were used as experimental animals. Animals were housed individually in polypropylene cage. Two days prior to study, male Wistar rats were anesthetized with isoflurane for surgical placement of jugular vein catheter. Rats were randomly divided for oral (3 mg/kg) and intravenous (1 mg/kg) dosing (n=3/group) and fasted overnight before oral dosing (p.o.). However, rats allocated to intravenous dosing food and water was provided ad libitum.

At pre-determined point, blood was collected through jugular vein and replenished with an equivalent volume of normal saline. Collected blood was transferred into a labeled eppendorf tube containing 10 µL of heparin as an anticoagulant. Typically blood samples were collected at following time points: 0.08, 0.25, 0.5, 1, 2, 4, 6, 8, and 24 hours post dose. Blood was centrifuged at 4000 rpm for 10 minutes. Plasma was separated and stored frozen at −80° C. until analysis. The concentrations of the test compounds were quantified in plasma by qualified LC-MS/MS method using suitable extraction technique. The test compounds were quantified in the calibration range around 1-1000 ng/mL in plasma. Study samples were analyzed using calibration samples in the batch and quality control samples spread across the batch.

Pharmacokinetic parameters $C_{max}$, $AUC_t$, $T_{1/2}$, Clearance and Bioavailability (F) were calculated by non-compartmental model using standard non-compartmental model by using Phoenix WinNonlin 6.0.4 version Software package.

TABLE 2

Pharmacokinetic profile of the test compounds

| Example No. | ROA | $C_{max}$ (ng/mL) | AUC$_{0-t}$ (ng · hr/mL) | $T_{1/2}$ (hr) | Clearance (mL/min/kg) | F (%) |
|---|---|---|---|---|---|---|
| 1 | oral (gavage) | 373 ± 53 | 875 ± 215 | 1.3 ± 0.2 | — | 59 ± 14 |
| | intravenous (bolus) | — | 796 ± 41 | 1.3 ± 0.3 | 34 ± 3 | |
| 18 | oral (gavage) | 887 ± 74 | 2713 ± 769 | 3.6 ± 0.1 | — | 106 ± 30 |
| | intravenous (bolus) | — | 853 ± 109 | 1.3 ± 0.2 | 20 ± 3 | |
| 73 | oral (gavage) | 1097 ± 85 | 1737 ± 296 | 1.2 ± 0.1 | — | 78 ± 13 |
| | intravenous (bolus) | — | 742 ± 40 | 1.1 ± 0.3 | 22 ± 1.0 | |
| 87 | oral (gavage) | 97 ± 39 | 219 ± 70 | 0.7 ± 0.3 | — | 32 ± 10 |
| | intravenous (bolus) | — | 224 ± 66 | 1.5 ± 0.1 | 79 ± 27 | |
| 103 | oral (gavage) | 825 ± 41 | 1093 ± 102 | 0.5 ± 0.2 | — | 46 ± 4 |
| | intravenous (bolus) | — | 791 ± 11 | 0.7 ± 0.1 | 21 ± 0 | |
| 120 | oral (gavage) | 69 ± 12 | 234 ± 76 | 3.5 ± 3.3 | — | 13 ± 4 |
| | intravenous (bolus) | — | 593 ± 79 | 1.2 ± 0.3 | 28 ± 4 | |

TABLE 2-continued

Pharmacokinetic profile of the test compounds

| Example No. | ROA | $C_{max}$ (ng/mL) | $AUC_{0-t}$ (ng · hr/mL) | $T_{1/2}$ (hr) | Clearance (mL/min/kg) | F (%) |
|---|---|---|---|---|---|---|
| 124 | oral (gavage) | 306 ± 66 | 526 ± 126 | 0.50 ± 0.0 | — | 22 ± 5 |
|  | intravenous (bolus) | — | 787 ± 130 | 1.1 ± 0.1 | 21 ± 3 |  |

Example 145

Rodent Brain Penetration Study

Male Wistar rats (260±40 grams) were used as experimental animals. Three animals were housed in each cage. Animals were given water and food ad libitum throughout the experiment and maintained on a 12 hours light/dark cycle.

Brain penetration was determined in discrete manner in rats. One day prior to dosing day, male Wistar rats were acclimatized and randomly grouped according to their weight. At each time point (0.50, 1 and 2 hours) n=3 animals were used.

The test compounds were suitably preformulated and administered orally at (free base equivalent) 3 mg/kg. Blood samples were removed via cardiac puncture by using isoflurane anesthesia. The animals were sacrificed to collect brain tissue. Plasma was separated and brain samples were homogenized and stored frozen at −20° C. until analysis. The concentrations of the test compounds in plasma and brain were determined using LC-MS/MS method.

The test compounds were quantified in plasma and brain homogenate by qualified LC-MS/MS method using suitable extraction technique. The test compounds were quantified in the calibration range of 1-500 ng/mL in plasma and brain homogenate. Study samples were analyzed using calibration samples in the batch and quality control samples spread across the batch. Extent of brain-plasma ratio (Cb/Cp) was calculated

TABLE 3

Blood Brain Penetration data of the test compounds

| Example No. | Single dose Rat Brain Penetration (Cb/Cp) at 3 mg/kg, p.o. |
|---|---|
| 1 | 0.33 ± 0.02 |
| 18 | 0.27 ± 0.06 |
| 65 | 0.32 ± 0.0 |
| 87 | 0.15 ± 0.01 |
| 103 | 0.63 ± 0.05 |
| 120 | 1.37 ± 0.1 |
| 124 | 0.52 ± 0.05 |

Example 146

Object Recognition Task Model

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an circular or square arena made up of acrylic. Rats were habituated to individual arenas for up to 1 hour in the absence of any objects on day 1.

One group of 12 rats received vehicle and another set of animals received test compounds, before familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 hours after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects ($a_1+a_2$).

$T_2$ is the total time spent exploring the familiar object and novel object ($a_3+b$).

The object recognition test was performed as described in *Behav. Brain Res.*, 1988, 31, 47-59.

TABLE 4

Novel objection recognition data of test compounds

| Example No. | Dose | Exploration time mean ± S.E.M (sec) | | Inference |
|---|---|---|---|---|
| | | Familiar object | Novel object | |
| 1 | 3 mg/kg, p.o. | 12.67 ± 0.95 | 17.98 ± 1.77 | Active |
| 18 | 10 mg/kg, p.o. | 8.00 ± 2.88 | 14.38 ± 1.62 | Active |
| 103 | 3 mg/kg, p.o. | 12.20 ± 1.59 | 19.17 ± 3.01 | Active |
| 120 | 10 mg/kg, p.o. | 10.48 ± 1.02 | 15.43 ± 1.23 | Active |

Example 147

Object Recognition Task Model (Combination Study)

The cognition enhancing properties of compounds of this invention were estimated by using this model.

Male Wistar rats (8-10 weeks old) were used as experimental animals. Four animals were housed in each cage. Animals were kept on 20% food deprivation from a day prior to experimentation. Water was provided ad libitum throughout the experiment. Animals were maintained on a 12 hours light/dark cycle in temperature and humidity controlled room. The experiment was carried out in an open field made up of acrylic. Rats were habituated to individual arenas (open field) for 20 minutes in the absence of any objects on day 1.

One group of 12 rats received vehicle and another set of animals received compound of the formula (I) or Donepezil or compound of formula (I) and Donepezil, before the familiar ($T_1$) and choice ($T_2$) trials. During the familiarization phase, ($T_1$), the rats were placed individually in the arena for 3 minutes, in which two identical objects ($a_1$ and $a_2$) were positioned 10 cm from the wall. 24 hours after $T_1$, trial for long-term memory test was performed. The same rats were placed in the same arena as they were placed in $T_1$ trial. During the choice phase ($T_2$) rats were allowed to explore the arena for 3 minutes in presence of a copy of familiar object ($a_3$) and one novel object (b). During the $T_1$ and $T_2$ trial, explorations of each object (defined as sniffing, licking, chewing or having moving vibrissae whilst directing the nose towards the object at a distance of less than 1 cm) were recorded using stopwatch.

$T_1$ is the total time spent exploring the familiar objects (a1+a2).

$T_2$ is the total time spent exploring the familiar object and novel object (a3+b).

Discriminative index=Time spent with novel object/
(time spent with novel and familiar object).

The object recognition test was performed as described by in *Behav. Brain Res.*, 1988, 31, 47-59.

Procognitive effects were observed with combination of Example 1 and donepezil. The results of this study are provided in FIG. 1.

What is claimed is:
1. A compound of formula (I),

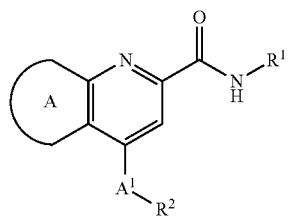

(I)

wherein:
ring A is selected from:

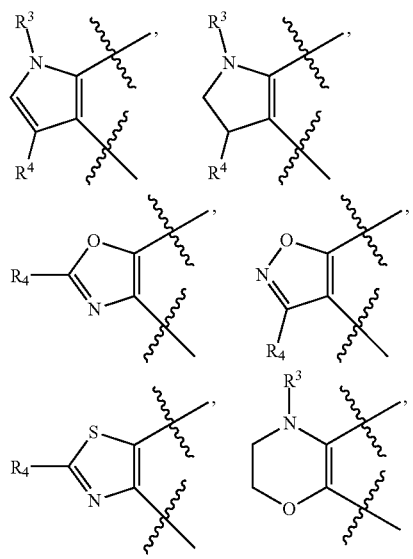

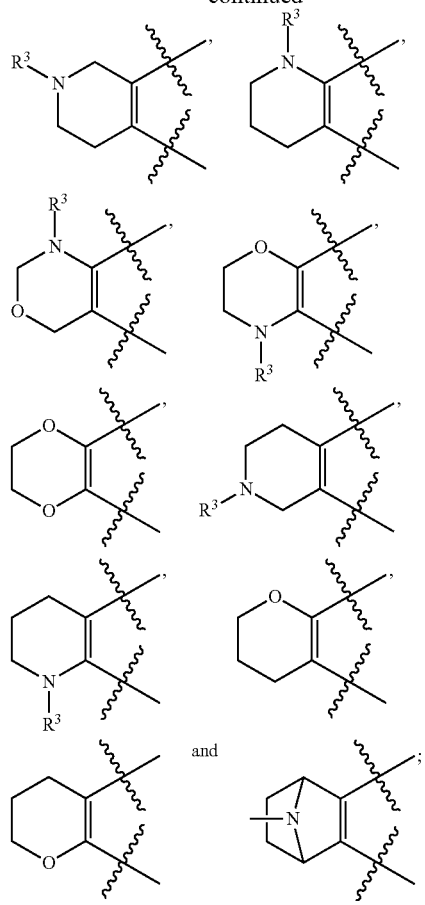

$A^1$ is $CH_2$, CHF or $CF_2$;
$R^1$ is selected from the group consisting of:

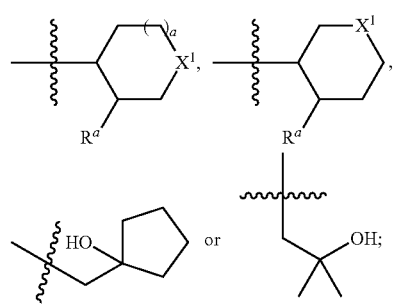

$R^a$ is OH;
$X^1$ is independently selected from $CH_2$ or O;
a is 0 or 1;
$R^2$ is ($C_{6-10}$)-aryl or ($C_{5-10}$)-heteroaryl; each of which is optionally substituted with one or more substituents selected from halogen, —O—($C_{1-4}$)-alkyl, —S—($C_{1-4}$)-alkyl, —N(CH$_3$)$_2$, —($C_{1-4}$)-alkyl, —($C_{3-6}$)-cycloalkyl, halo($C_{1-4}$)-alkyl, —OH, —NH$_2$, —CN or $R^{2a}$;
$R^{2a}$ is —($C_{6-10}$)-aryl or ($C_{5-10}$)-heteroaryl; each of which is optionally substituted with one or more substituents selected from the group consisting of halogen, —OH, —NH$_2$, —CN, —O—($C_{1-2}$)-alkyl, —S—($C_{1-2}$)-alkyl, —($C_{1-2}$)-alkyl or ($C_{3-6}$)-cycloalkyl;

"  " represents point of attachment;
R³ is —(C₁₋₄)-alkyl, —(C₃₋₆)-cycloalkyl, —(C₁₋₄)-alkyl-(C₃₋₆)-cycloalkyl, halo(C₁₋₄)-alkyl and hydrogen; and
R⁴ is hydrogen, —(C₁₋₄)-alkyl and halo(C₁₋₄)-alkyl;
or an isotopic form, a stereoisomer, a tautomer or a pharmaceutically acceptable salt thereof.

2. The compound of formula (I) as claimed in claim 1, wherein:
R² is selected from the grouping consisting of:

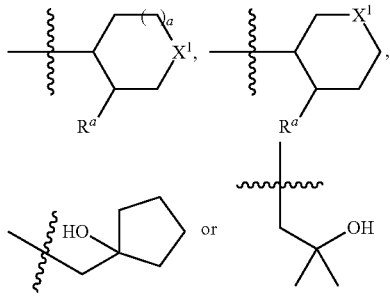

A³ is N or CH;
A⁴ is CH or CF;
R$^b$ at each occurrence is independently selected from halogen, —O—(C₁₋₄)-alkyl, —S—(C₁₋₄)-alkyl, —(C₁₋₄)-alkyl, —(C₃₋₆)-cycloalkyl, halo(C₁₋₄)-alkyl, —OH, —NH₂, —CN, phenyl, pyridyl, pyrazolyl, thiazolyl and oxazolyl; wherein phenyl, pyridyl, pyrazolyl, thiazolyl and oxazolyl are optionally substituted with one or more substituents selected from the group consisting of halogen, —OH, —NH₂, —CN, —O—(C₁₋₂)—O-alkyl, —S—(C₁₋₂)-alkyl, —(C₁₋₂)-alkyl or —(C₃₋₆)-cycloalkyl;
R$^c$ is hydrogen or —(C₁₋₄)-alkyl;
X² is independently selected from NH, —N—(C₁₋₂)-alkyl, O or S;
X³ is independently selected from CH or N;
b is 0, 1 or 2;
"  " represents point of attachment;
or an isotopic form, a stereoisomer, a tautomer or a pharmaceutically acceptable salt thereof.

3. The compound of formula (I) as claimed in claim 1, wherein:
ring A is selected from,

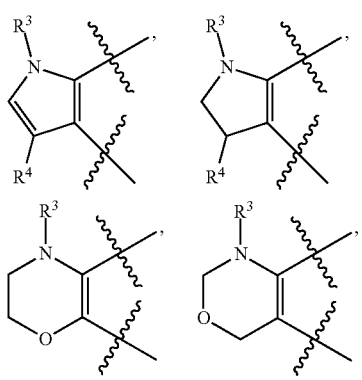

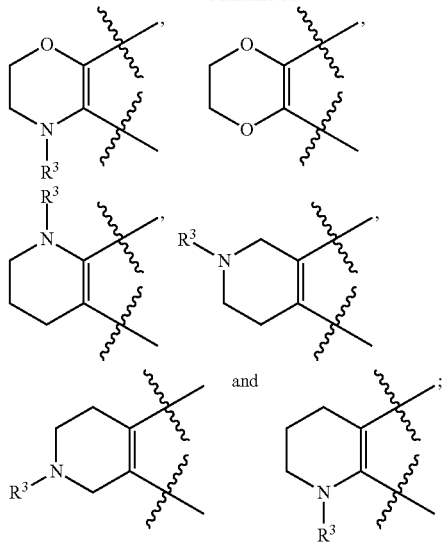

A¹ is CH₂;
R¹ is selected from the grouping consisting of:

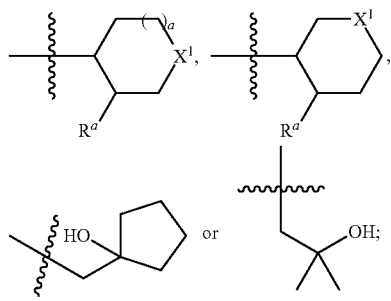

R$^a$ is OH;
X¹ is independently selected from CH₂ or O;
R² is selected from the grouping consisting of:

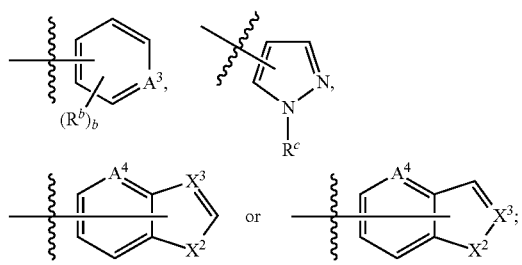

A³ is N or CH;
A⁴ is CH or CF;
R$^b$ at each occurrence is independently selected from halogen, —O—(C₁₋₄)-alkyl, —S—(C₁₋₄)-alkyl, —N(CH₃)₂, —(C₁₋₄)-alkyl, —(C₃₋₆)-cycloalkyl, halo (C₁₋₄)-alkyl,
—OH, —NH₂, —CN, phenyl, pyridyl, pyrazolyl, thiazolyl and oxazolyl; wherein phenyl, pyridyl, pyrazolyl, thiazolyl and oxazolyl are optionally substituted with one or more substituents selected from the group consisting of halogen, —OH, —NH₂, —CN, —O—($C_{1-2}$)-alkyl, —S—($C_{1-2}$)-alkyl, —($C_{1-2}$)-alkyl, or —($C_{3-6}$)-cycloalkyl;

$R^c$ is hydrogen or —($C_{1-4}$)-alkyl;

$X^2$ is independently selected from NH, —N—($C_{1-2}$)-alkyl, O or S;

$X^3$ is independently selected from CH or N;

b is 0, 1 or 2;

"∿∿∿" represents point of attachment;

$R^3$ is —($C_{1-4}$)-alkyl, halo($C_{1-4}$)-alkyl or hydrogen; and $R^4$ is hydrogen, —($C_{1-4}$)-alkyl and halo($C_{1-4}$)-alkyl;

or an isotopic form, a stereoisomer, a tautomer or a pharmaceutically acceptable salt thereof.

4. The compound as claimed in claim 1, wherein the compound is selected from the group consisting of:

N-[(1S,2S)-2-Hydroxycyclohexyl]-4-(2-fluoropyridin-4-ylmethyl)-1-methyl-1H-pyrrolo[2,3-b]pyridine-6-carboxamide;

N-[(1S,2S)-2-Hydroxycyclohexyl]-4-(2-methoxypyridin-5-ylmethyl)-1-methyl-1H-pyrrolo[2,3-b]pyridine-6-carboxamide;

N-[(1S,2S)-2-Hydroxycyclohexyl]-4-(2-fluoropyridin-5-ylmethyl)-1-methyl-1H-pyrrolo[2,3-b]pyridine-6-carboxamide;

N-[(1S,2S)-2-Hydroxycyclohexyl]-4-(4-fluorobenzyl)-1-methyl-H-pyrrolo[2,3-b]pyridine-6-carboxamide;

N-[(1S,2S)-2-Hydroxycyclohexyl]-4-(4-thiazol-4-ylbenzyl)-1-methyl-1H-pyrrolo[2,3-b]pyridine-6-carboxamide;

N-[(1S,2S)-2-Hydroxycyclohexyl]-4-(4-pyrazol-1-ylbenzyl)-1-methyl-1H-pyrrolo[2,3-b]pyridine-6-carboxamide;

N-[(1S,2S)-2-Hydroxycyclohexyl]-4-[4-(1-methyl-1H-pyrazol-4-yl)benzyl]-1-methyl-1H-pyrrolo[2,3-b]pyridine-6-carboxamide;

N-[(1S,2S)-2-Hydroxycyclohexyl]-4-[2-fluoro-4-(1-methyl-1H-pyrazol-4-yl)benzyl]-1-methyl-1H-pyrrolo[2,3-b]pyridine-6-carboxamide;

N-[(1S,2S)-2-Hydroxycyclohexyl]-4-(2-methylpyridin-5-ylmethyl)-1-methyl-H-pyrrolo[2,3-b]pyridine-6-carboxamide;

N-[(1S,2S)-2-Hydroxycyclohexyl]-4-(2-chloropyridin-4-ylmethyl)-1-methyl-1H-pyrrolo[2,3-b]pyridine-6-carboxamide;

N-[(1S,2S)-2-Hydroxycyclohexyl]-4-(2,5-difluoropyridin-4-ylmethyl)-1-methyl-1H-pyrrolo[2,3-b]pyridine-6-carboxamide;

N-[(1S,2S)-2-Hydroxycyclohexyl]-4-(benzothiazol-6-ylmethyl)-1-methyl-H-pyrrolo[2,3-b]pyridine-6-carboxamide;

N-[(1S,2S)-2-Hydroxycyclohexyl]-4-(2'-fluoro-[2,5']bipyridinyl-5-ylmethyl)-1-methyl-1H-pyrrolo[2,3-b]pyridine-6-carboxamide;

N-[(1S,2S)-2-Hydroxycyclohexyl]-4-(pyridin-4-ylmethyl)-1-methyl-H-pyrrolo[2,3-b]pyridine-6-carboxamide;

N-[(1S,2S)-2-Hydroxycyclohexyl]-4-[2-(1-methyl-1H-pyrazol-4-yl)pyridin-5-ylmethyl]-1-methyl-1H-pyrrolo[2,3-b]pyridine-6-carboxamide;

N-[(1S,2S)-2-Hydroxycyclohexyl]-4-(2,3-difluorobenzyl)-1-methyl-1H-pyrrolo[2,3-b]pyridine-6-carboxamide;

N-[(1S,2S)-2-Hydroxycyclohexyl]-4-(2-methylpyridin-4-ylmethyl)-1-methyl-1H-pyrrolo[2,3-b]pyridine-6-carboxamide;

N-[(1S,2S)-2-Hydroxycyclohexyl]-4-(2-chloropyridin-5-ylmethyl)-1-methyl-1H-pyrrolo[2,3-b]pyridine-6-carboxamide;

N-[(1S,2S)-2-Hydroxycyclohexyl]-4-(4-methoxybenzyl)-1-methyl-H-pyrrolo[2,3-b]pyridine-6-carboxamide;

N-[(1S,2S)-2-Hydroxycyclohexyl]-4-(2-methylsulfanylpyridin-5-ylmethyl)-1-methyl-1H-pyrrolo[2,3-b]pyridine-6-carboxamide;

N-[(1S,2S)-2-Hydroxycyclohexyl]-4-[4-(2-methylpyridin-3-yl)benzyl]-1-methyl-1H-pyrrolo[2,3-b]pyridine-6-carboxamide;

N-[(1S,2S)-2-Hydroxycyclohexyl]-4-(1-methyl-1H-benzimidazol-4-ylmethyl)-1-methyl-1H-pyrrolo[2,3-b]pyridine-6-carboxamide;

N-[(1S,2S)-2-Hydroxycyclohexyl]-4-(2-chloropyridin-5-ylmethyl)-1-(2-fluoroethyl)-1H-pyrrolo[2,3-b]pyridine-6-carboxamide;

N-(2-Hydroxy-2-methylpropyl)-4-[4-(thiazol-4-yl)benzyl]-1-methyl-1H-pyrrolo[2,3-b]pyridine-6-carboxamide;

N-[(1S,2S)-2-Hydroxycyclohexyl]-4-(3-fluorobenzyl)-1-methyl-H-pyrrolo[2,3-b]pyridine-6-carboxamide;

N-(1-Hydroxycyclopentylmethyl)-4-[4-(thiazol-4-yl)benzyl]-1-methyl-1H-pyrrolo[2,3-b]pyridine-6-carboxamide;

N-[(1S,2S)-2-Hydroxycyclohexyl]-4-(pyridin-3-ylmethyl)-1-methyl-H-pyrrolo[2,3-b]pyridine-6-carboxamide;

N-[(1S,2S)-2-Hydroxycyclohexyl]-4-(2-cyclopropylpyridin-5-ylmethyl)-1-methyl-H-pyrrolo[2,3-b]pyridine-6-carboxamide;

N-[(1S,2S)-2-Hydroxycyclohexyl]-4-(2-fluoropyridin-4-ylmethyl)-1-ethyl-1H-pyrrolo[2,3-b]pyridine-6-carboxamide;

N-[(1S,2S)-2-Hydroxycyclohexyl]-4-(2-fluoropyridin-4-ylmethyl)-1-isopropyl-1H-pyrrolo[2,3-b]pyridine-6-carboxamide;

N-[(1S,2S)-2-Hydroxycyclohexyl]-4-(2,3-difluorophenylmethyl)-1,3-dimethyl-1H-pyrrolo[2,3-b]pyridine-6-carboxamide;

Racemic trans-N-(3-Hydroxytetrahydropyran-4-yl)-4-(4-fluorobenzyl)-1-methyl-1H-pyrrolo[2,3-b]pyridine-6-carboxamide;

trans-N-(3-Hydroxytetrahydropyran-4-yl)-4-(4-fluorobenzyl)-1-methyl-1H-pyrrolo[2,3-b]pyridine-6-carboxamide (Isomer-I);

trans-N-(3-Hydroxytetrahydropyran-4-yl)-4-(4-fluorobenzyl)-1-methyl-1H-pyrrolo[2,3-b]pyridine-6-carboxamide (Isomer-II);

Racemic cis-N-(3-Hydroxytetrahydropyran-4-yl)-4-(4-fluorobenzyl)-1-methyl-H-pyrrolo[2,3-b]pyridine-6-carboxamide;

cis-N-(3-Hydroxytetrahydropyran-4-yl)-4-(4-fluorobenzyl)-1-methyl-1H-pyrrolo[2,3-b]pyridine-6-carboxamide (Isomer-I);

cis-N-(3-Hydroxytetrahydropyran-4-yl)-4-(4-fluorobenzyl)-1-methyl-1H-pyrrolo[2,3-b]pyridine-6-carboxamide (Isomer-II);

Racemic trans-N-(3-Hydroxytetrahydropyran-4-yl)-4-(2-fluoropyridin-4-ylmethyl)-1-methyl-1H-pyrrolo[2,3-b]pyridine-6-carboxamide;

trans-N-(3-Hydroxytetrahydropyran-4-yl)-4-(2-fluoropyridin-4-ylmethyl)-1-methyl-1H-pyrrolo[2,3-b]pyridine-6-carboxamide (Isomer-I);

trans-N-(3-Hydroxytetrahydropyran-4-yl)-4-(2-fluoro-pyridin-4-ylmethyl)-1-methyl-1H-pyrrolo[2,3-b]pyridine-6-carboxamide (Isomer-II);

Racemic cis-N-(3-Hydroxytetrahydropyran-4-yl)-4-(3,4-difluorobenzyl)-1-methyl-1H-pyrrolo[2,3-b]pyridine-6-carboxamide;

cis-N-(3-Hydroxytetrahydropyran-4-yl)-4-(3,4-difluorobenzyl)-1-methyl-1H-pyrrolo[2,3-b]pyridine-6-carboxamide (Isomer-I);

cis-N-(3-Hydroxytetrahydropyran-4-yl)-4-(3,4-difluorobenzyl)-1-methyl-1H-pyrrolo[2,3-b]pyridine-6-carboxamide (Isomer-II);

Racemic trans-N-(3-Hydroxytetrahydropyran-4-yl)-4-(2,3-difluorobenzyl)-1-methyl-1H-pyrrolo[2,3-b]pyridine-6-carboxamide;

trans-N-(3-Hydroxytetrahydropyran-4-yl)-4-(2,3-difluorobenzyl)-1-methyl-1H-pyrrolo[2,3-b]pyridine-6-carboxamide (Isomer-I);

trans-N-(3-Hydroxytetrahydropyran-4-yl)-4-(2,3-difluorobenzyl)-1-methyl-1H-pyrrolo[2,3-b]pyridine-6-carboxamide (Isomer-II);

Racemic cis-N-(3-Hydroxytetrahydropyran-4-yl)-4-(2,3-difluorobenzyl)-1-methyl-1H-pyrrolo[2,3-b]pyridine-6-carboxamide;

cis-N-(3-Hydroxytetrahydropyran-4-yl)-4-(2,3-difluorobenzyl)-1-methyl-1H-pyrrolo[2,3-b]pyridine-6-carboxamide (Isomer-I);

cis-N-(3-Hydroxytetrahydropyran-4-yl)-4-(2,3-difluorobenzyl)-1-methyl-1H-pyrrolo[2,3-b]pyridine-6-carboxamide (Isomer-II);

Racemic cis-N-(3-Hydroxytetrahydropyran-4-yl)-4-(2-fluoropyridin-4-ylmethyl)-1-methyl-1H-pyrrolo[2,3-b]pyridine-6-carboxamide;

cis-N-(3-Hydroxytetrahydropyran-4-yl)-4-(2-fluoropyridin-4-ylmethyl)-1-methyl-1H-pyrrolo[2,3-b]pyridine-6-carboxamide (Isomer-I);

cis-N-(3-Hydroxytetrahydropyran-4-yl)-4-(2-fluoropyridin-4-ylmethyl)-1-methyl-1H-pyrrolo[2,3-b]pyridine-6-carboxamide (Isomer-II);

Racemic cis-N-(3-Hydroxytetrahydropyran-4-yl)-4-(2-chloropyridin-5-ylmethyl)-1-methyl-1H-pyrrolo[2,3-b]pyridine-6-carboxamide;

cis-N-(3-Hydroxytetrahydropyran-4-yl)-4-(2-chloropyridin-5-ylmethyl)-1-methyl-1H-pyrrolo[2,3-b]pyridine-6-carboxamide (Isomer-I);

cis-N-(3-Hydroxytetrahydropyran-4-yl)-4-(2-chloropyridin-5-ylmethyl)-1-methyl-1H-pyrrolo[2,3-b]pyridine-6-carboxamide (Isomer-II);

Racemic trans-N-(3-Hydroxytetrahydropyran-4-yl)-4-(2-chloropyridin-5-ylmethyl)-1-methyl-1H-pyrrolo[2,3-b]pyridine-6-carboxamide;

trans-N-(3-Hydroxytetrahydropyran-4-yl)-4-(2-chloropyridin-5-ylmethyl)-1-methyl-1H-pyrrolo[2,3-b]pyridine-6-carboxamide (Isomer-I);

trans-N-(3-Hydroxytetrahydropyran-4-yl)-4-(2-chloropyridin-5-ylmethyl)-1-methyl-1H-pyrrolo[2,3-b]pyridine-6-carboxamide (Isomer-II);

Racemic trans-N-(3-Hydroxytetrahydropyran-4-yl)-4-(3,4-difluorobenzyl)-1-methyl-1H-pyrrolo[2,3-b]pyridine-6-carboxamide;

trans-N-(3-Hydroxytetrahydropyran-4-yl)-4-(3,4-difluorobenzyl)-1-methyl-1H-pyrrolo[2,3-b]pyridine-6-carboxamide (Isomer-I);

trans-N-(3-Hydroxytetrahydropyran-4-yl)-4-(3,4-difluorobenzyl)-1-methyl-1H-pyrrolo[2,3-b]pyridine-6-carboxamide (Isomer-II);

Racemic trans-N-(3-Hydroxytetrahydropyran-4-yl)-4-[4-(thiazol-4-yl)benzyl]-1-methyl-1H-pyrrolo[2,3-b]pyridine-6-carboxamide;

trans-N-(3-Hydroxytetrahydropyran-4-yl)-4-[4-(thiazol-4-yl)benzyl]-1-methyl-1H-pyrrolo[2,3-b]pyridine-6-carboxamide (Isomer-I);

trans-N-(3-Hydroxytetrahydropyran-4-yl)-4-[4-(thiazol-4-yl)benzyl]-1-methyl-1H-pyrrolo[2,3-b]pyridine-6-carboxamide (Isomer-II);

Racemic cis-N-(3-Hydroxytetrahydropyran-4-yl)-4-[4-(thiazol-4-yl)benzyl]-1-methyl-1H-pyrrolo[2,3-b]pyridine-6-carboxamide;

cis-N-(3-Hydroxytetrahydropyran-4-yl)-4-[4-(thiazol-4-yl)benzyl]-1-methyl-1H-pyrrolo[2,3-b]pyridine-6-carboxamide (Isomer-I);

cis-N-(3-Hydroxytetrahydropyran-4-yl)-4-[4-(thiazol-4-yl)benzyl]-1-methyl-1H-pyrrolo[2,3-b]pyridine-6-carboxamide (Isomer-II);

Racemic trans-N-(3-Hydroxytetrahydropyran-4-yl)-4-[4-(1-methyl-H-pyrazol-4-yl)benzyl]-1-methyl-1H-pyrrolo[2,3-b]pyridine-6-carboxamide;

trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-I);

trans-N-(3-Hydroxytetrahydropyran-4-yl)-4-[4-(1-methyl-1H-pyrazol-4-yl)benzyl]-1-methyl-1H-pyrrolo[2,3-b]pyridine-6-carboxamide (Isomer-II);

Racemic cis-N-(3-Hydroxytetrahydropyran-4-yl)-4-[4-(1-methyl-H-pyrazol-4-yl)benzyl]-1-methyl-1H-pyrrolo[2,3-b]pyridine-6-carboxamide;

cis-N-(3-Hydroxytetrahydropyran-4-yl)-4-[4-(1-methyl-1H-pyrazol-4-yl)benzyl]-1-methyl-H-pyrrolo[2,3-b]pyridine-6-carboxamide (Isomer-I);

cis-N-(3-Hydroxytetrahydropyran-4-yl)-4-[4-(1-methyl-1H-pyrazol-4-yl)benzyl]-1-methyl-H-pyrrolo[2,3-b]pyridine-6-carboxamide (Isomer-II);

Racemic trans-N-(3-Hydroxytetrahydropyran-4-yl)-4-(4-methoxybenzyl)-1-methyl-1H-pyrrolo[2,3-b]pyridine-6-carboxamide;

trans-N-(3-Hydroxytetrahydropyran-4-yl)-4-(4-methoxybenzyl)-1-methyl-1H-pyrrolo[2,3-b]pyridine-6-carboxamide (Isomer-I);

trans-N-(3-Hydroxytetrahydropyran-4-yl)-4-(4-methoxybenzyl)-1-methyl-1H-pyrrolo[2,3-b]pyridine-6-carboxamide (Isomer-II);

Racemic cis-N-(3-Hydroxytetrahydropyran-4-yl)-4-(4-methoxybenzyl)-1-methyl-1H-pyrrolo[2,3-b]pyridine-6-carboxamide;

cis-N-(3-Hydroxytetrahydropyran-4-yl)-4-(4-methoxybenzyl)-1-methyl-1H-pyrrolo[2,3-b]pyridine-6-carboxamide (Isomer-I);

cis-N-(3-Hydroxytetrahydropyran-4-yl)-4-(4-methoxybenzyl)-1-methyl-1H-pyrrolo[2,3-b]pyridine-6-carboxamide (Isomer-II);

Racemic trans-N-(3-Hydroxytetrahydropyran-4-yl)-4-(3-fluorobenzyl)-1-methyl-H-pyrrolo[2,3-b]pyridine-6-carboxamide;

trans-N-(3-Hydroxytetrahydropyran-4-yl)-4-(3-fluorobenzyl)-1-methyl-1H-pyrrolo[2,3-b]pyridine-6-carboxamide (Isomer-I);

trans-N-(3-Hydroxytetrahydropyran-4-yl)-4-(3-fluorobenzyl)-1-methyl-1H-pyrrolo[2,3-b]pyridine-6-carboxamide (Isomer-II);

Racemic cis-N-(3-Hydroxytetrahydropyran-4-yl)-4-(3-fluorobenzyl)-1-methyl-H-pyrrolo[2,3-b]pyridine-6-carboxamide;

cis-N-(3-Hydroxytetrahydropyran-4-yl)-4-(3-fluorobenzyl)-1-methyl-1H-pyrrolo[2,3-b]pyridine-6-carboxamide (Isomer-I);
cis-N-(3-Hydroxytetrahydropyran-4-yl)-4-(3-fluorobenzyl)-1-methyl-1H-pyrrolo[2,3-b]pyridine-6-carboxamide (Isomer-II);
Racemic cis-N-(4-Hydroxytetrahydropyran-3-yl)-4-(4-fluorobenzyl)-1-methyl-1H-pyrrolo[2,3-b]pyridine-6-carboxamide;
cis-N-(4-Hydroxytetrahydropyran-3-yl)-4-(4-fluorobenzyl)-1-methyl-1H-pyrrolo[2,3-b]pyridine-6-carboxamide (Isomer-I);
cis-N-(4-Hydroxytetrahydropyran-3-yl)-4-(4-fluorobenzyl)-1-methyl-1H-pyrrolo[2,3-b]pyridine-6-carboxamide (Isomer-II);
Racemic trans-N-(4-Hydroxytetrahydropyran-3-yl)-4-(4-fluorobenzyl)-1-methyl-H-pyrrolo[2,3-b]pyridine-6-carboxamide;
trans-N-(4-Hydroxytetrahydropyran-3-yl)-4-(4-fluorobenzyl)-1-methyl-1H-pyrrolo[2,3-b]pyridine-6-carboxamide (Isomer-I);
trans-N-(4-Hydroxytetrahydropyran-3-yl)-4-(4-fluorobenzyl)-1-methyl-1H-pyrrolo[2,3-b]pyridine-6-carboxamide (Isomer-II);
Racemic cis-N-(4-Hydroxytetrahydropyran-3-yl)-4-(4-methoxybenzyl)-1-methyl-1H-pyrrolo[2,3-b]pyridine-6-carboxamide;
cis-N-(4-Hydroxytetrahydropyran-3-yl)-4-(4-methoxybenzyl)-1-methyl-1H-pyrrolo[2,3-b]pyridine-6-carboxamide (Isomer-I);
cis-N-(4-Hydroxytetrahydropyran-3-yl)-4-(4-methoxybenzyl)-1-methyl-1H-pyrrolo[2,3-b]pyridine-6-carboxamide (Isomer-II);
Racemic trans-N-(4-Hydroxytetrahydropyran-3-yl)-4-(4-methoxybenzyl)-1-methyl-1H-pyrrolo[2,3-b]pyridine-6-carboxamide;
trans-N-(4-Hydroxytetrahydropyran-3-yl)-4-(4-methoxybenzyl)-1-methyl-1H-pyrrolo[2,3-b]pyridine-6-carboxamide (Isomer-I);
trans-N-(4-Hydroxytetrahydropyran-3-yl)-4-(4-methoxybenzyl)-1-methyl-1H-pyrrolo[2,3-b]pyridine-6-carboxamide (Isomer-II);
Racemic cis-N-(4-Hydroxytetrahydropyran-3-yl)-4-(2-methylpyridin-5-ylmethyl)-1-methyl-1H-pyrrolo[2,3-b]pyridine-6-carboxamide;
cis-N-(4-Hydroxytetrahydropyran-3-yl)-4-(2-methylpyridin-5-ylmethyl)-1-methyl-1H-pyrrolo[2,3-b]pyridine-6-carboxamide (Isomer-I);
cis-N-(4-Hydroxytetrahydropyran-3-yl)-4-(2-methylpyridin-5-ylmethyl)-1-methyl-1H-pyrrolo[2,3-b]pyridine-6-carboxamide (Isomer-II);
Racemic trans-N-(4-Hydroxytetrahydropyran-3-yl)-4-(2-methylpyridin-5-ylmethyl)-1-methyl-1H-pyrrolo[2,3-b]pyridine-6-carboxamide;
trans-N-(4-Hydroxytetrahydropyran-3-yl)-4-(2-methylpyridin-5-ylmethyl)-1-methyl-1H-pyrrolo[2,3-b]pyridine-6-carboxamide (Isomer-I);
trans-N-(4-Hydroxytetrahydropyran-3-yl)-4-(2-methylpyridin-5-ylmethyl)-1-methyl-1H-pyrrolo[2,3-b]pyridine-6-carboxamide (Isomer-II);
(3S,4S)—N-(4-Hydroxytetrahydropyran-3-yl)-4-(4-fluorobenzyl)-1-methyl-1H-pyrrolo[2,3-b]pyridine-6-carboxamide;
(3S,4S)—N-(4-Hydroxytetrahydropyran-3-yl)-4-(4-methoxybenzyl)-1-methyl-1H-pyrrolo[2,3-b]pyridine-6-carboxamide;
(3S,4S)—N-(4-Hydroxytetrahydropyran-3-yl)-4-(2-methylpyridin-5-ylmethyl)-1-methyl-1H-pyrrolo[2,3-b]pyridine-6-carboxamide;
N-[(1S,2S)-2-Hydroxycyclohexyl]-4-(2-chloropyridin-5-ylmethyl)-1-methyl-2,3-dihydro-1H-pyrrolo[2,3-b]pyridine-6-carboxamide;
N-[(1S,2S)-2-Hydroxycyclohexyl]-4-(2-fluoropyridin-4-ylmethyl)-1-methyl-2,3-dihydro-1H-pyrrolo[2,3-b]pyridine-6-carboxamide;
N-[(1S,2S)-2-Hydroxycyclohexyl]-4-(2-fluoropyridin-5-ylmethyl)-1-methyl-2,3-dihydro-1H-pyrrolo[2,3-b]pyridine-6-carboxamide;
N-[(1S,2S)-2-Hydroxycyclohexyl]-1-methyl-(6-methylpyridin-3-ylmethyl)-2,3-dihydro-1H-pyrrolo[2,3-b]pyridine-6-carboxamide;
N-[(1S,2S)-2-Hydroxycyclohexyl]-4-(4-fluorobenzyl)-1-methyl-2,3-dihydro-1H-pyrrolo[2,3-b]pyridine-6-carboxamide;
N-[(1S,2S)-2-Hydroxycyclohexyl]-4-(4-methoxybenzyl)-1-methyl-2,3-dihydro-1H-pyrrolo[2,3-b]pyridine-6-carboxamide;
N-[(1S,2S)-2-Hydroxycyclohexyl]-4-(2'-fluoro-[2,5']bipyridinyl-5-ylmethyl)-1-methyl-2,3-dihydro-1H-pyrrolo[2,3-b]pyridine-6-carboxamide;
N-[(1S,2S)-2-Hydroxycyclohexyl]-4-(2,3-difluorobenzyl)-1-methyl-2,3-dihydro-1H-pyrrolo[2,3-b]pyridine-6-carboxamide;
N-[(1S,2S)-2-Hydroxycyclohexyl]-4-(2-methyl-4-pyridinylmethyl)-1-methyl-2,3-dihydro-1H-pyrrolo[2,3-b]pyridine-6-carboxamide;
cis-N-(4-Hydroxytetrahydropyran-3-yl)-4-(4-fluorobenzyl)-1-methyl-2,3-dihydro-1H-pyrrolo[2,3-b]pyridine-6-carboxamide (Isomer-I);
cis-N-(4-Hydroxytetrahydropyran-3-yl)-4-(4-fluorobenzyl)-1-methyl-2,3-dihydro-1H-pyrrolo[2,3-b]pyridine-6-carboxamide (Isomer-II);
Racemic cis-N-(4-Hydroxytetrahydropyran-3-yl)-4-(4-methoxybenzyl)-1-methyl-2,3-dihydro-1H-pyrrolo[2,3-b]pyridine-6-carboxamide;
(3S,4S)—N-(4-Hydroxytetrahydropyran-3-yl)-4-(4-fluorobenzyl)-1-methyl-2,3-dihydro-1H-pyrrolo[2,3-b]pyridine-6-carboxamide;
(3S,4S)—N-(4-Hydroxytetrahydropyran-3-yl)-4-(4-methoxybenzyl)-1-methyl-2,3-dihydro-1H-pyrrolo[2,3-b]pyridine-6-carboxamide;
(3S,4S)—N-(4-Hydroxytetrahydropyran-3-yl)-4-(2-methylpyridin-5-ylmethyl)-1-methyl-2,3-dihydro-1H-pyrrolo[2,3-b]pyridine-6-carboxamide;
N-[(1S,2S)-2-Hydroxycyclohexyl]-4-(4-fluorobenzyl)-5,6,7,8-tetrahydro[1,7]naphthyridine-2-carboxamide Hydrochloride;
N-[(1S,2S)-2-Hydroxycyclohexyl]-4-(4-fluorobenzyl)-5,6,7,8-tetrahydro[1,7]naphthyridine-2-carboxamide;
N-[(1S,2S)-2-Hydroxycyclohexyl]-4-(4-chlorobenzyl)-5,6,7,8-tetrahydro[1,7]naphthyridine-2-carboxamide Hydrochloride;
N-[(1S,2S)-2-Hydroxycyclohexyl]-4-(4-chlorobenzyl)-5,6,7,8-tetrahydro[1,7]naphthyridine-2-carboxamide;
N-[(1S,2S)-2-Hydroxycyclohexyl]-4-(3-fluorobenzyl)-5,6,7,8-tetrahydro[1,7]naphthyridine-2-carboxamide Hydrochloride;
N-[(1S,2S)-2-Hydroxycyclohexyl]-4-(3-fluorobenzyl)-5,6,7,8-tetrahydro[1,7]naphthyridine-2-carboxamide;
N-[(1S,2S)-2-Hydroxycyclohexyl]-4-[4-(1-methyl-1H-pyrazol-4-yl)-benzyl]-5,6,7,8-tetrahydro[1,7]naphthyridine-2-carboxamide Hydrochloride;

N-[(1S,2S)-2-Hydroxycyclohexyl]-4-[4-(1-methyl-1H-pyrazol-4-yl)-benzyl]-5,6,7,8-tetrahydro[1,7]naphthyridine-2-carboxamide;

N-[(1S,2S)-2-Hydroxycyclohexyl]-4-(2-fluoropyridin-5-ylmethyl)-5,6,7,8-tetrahydro[1,7]naphthyridine-2-carboxamide Hydrochloride;

N-[(1S,2S)-2-Hydroxycyclohexyl]-4-(2-fluoropyridin-5-ylmethyl)-5,6,7,8-tetrahydro[1,7]naphthyridine-2-carboxamide;

N-[(1S,2S)-2-Hydroxycyclohexyl]-4-(4-methoxybenzyl)-5,6,7,8-tetrahydro[1,7]naphthyridine-2-carboxamide Hydrochloride;

N-[(1S,2S)-2-Hydroxycyclohexyl]-4-(4-methoxybenzyl)-5,6,7,8-tetrahydro[1,7]naphthyridine-2-carboxamide;

N-[(1S,2S)-2-Hydroxycyclohexyl]-4-(2-fluoropyridin-4-ylmethyl)-5,6,7,8-tetrahydro[1,7]naphthyridine-2-carboxamide Hydrochloride;

N-[(1S,2S)-2-Hydroxycyclohexyl]-4-(2-fluoropyridin-4-ylmethyl)-5,6,7,8-tetrahydro[1,7]naphthyridine-2-carboxamide;

N-[(1S,2S)-2-Hydroxycyclohexyl]-4-(4-pyrazol-1-ylbenzyl)-5,6,7,8-tetrahydro[1,7]naphthyridine-2-carboxamide Hydrochloride;

N-[(1S,2S)-2-Hydroxycyclohexyl]-4-(4-pyrazol-1-ylbenzyl)-5,6,7,8-tetrahydro[1,7]naphthyridine-2-carboxamide;

N-[(1S,2S)-2-Hydroxycyclohexyl]-4-(4-fluorobenzyl)-7-methyl-5,6,7,8-tetrahydro[1,7]naphthyridine-2-carboxamide;

N-[(1S,2S)-2-Hydroxycyclohexyl]-4-(4-fluorobenzyl)-7-ethyl-5,6,7,8-tetrahydro[1,7]naphthyridine-2-carboxamide;

trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-II);

Racemic cis-N-(3-Hydroxytetrahydropyran-4-yl)-4-[4-(thiazol-4-yl)benzyl]-5,6,7,8-tetrahydro[1,7]naphthyridine-2-carboxamide Hydrochloride;

cis-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-I);

cis-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-II);

Racemic trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride;

trans-N-(3-Hydroxytetrahydropyran-4-yl)-4-[4-(thiazol-4-yl)benzyl]-5,6,7,8-tetrahydro[1,7]naphthyridine-2-carboxamide Hydrochloride (Isomer-I);

Racemic cis-N-(3-Hydroxytetrahydropyran-4-yl)-4-[4-(thiazol-4-yl)benzyl]-5,6,7,8-tetrahydro[1,7]naphthyridine-2-carboxamide;

cis-N-(3-Hydroxytetrahydropyran-4-yl)-4-[4-(thiazol-4-yl)benzyl]-5,6,7,8-tetrahydro[1,7]naphthyridine-2-carboxamide (Isomer-I);

cis-N-(3-Hydroxytetrahydropyran-4-yl)-4-[4-(thiazol-4-yl)benzyl]-5,6,7,8-tetrahydro[1,7]naphthyridine-2-carboxamide (Isomer-II);

Racemic trans-N-(3-Hydroxytetrahydropyran-4-yl)-4-[4-(thiazol-4-yl)benzyl]-5,6,7,8-tetrahydro[1,7]naphthyridine-2-carboxamide;

trans-N-(3-Hydroxytetrahydropyran-4-yl)-4-[4-(thiazol-4-yl)benzyl]-5,6,7,8-tetrahydro[1,7]naphthyridine-2-carboxamide (Isomer-I);

trans-N-(3-Hydroxytetrahydropyran-4-yl)-4-[4-(thiazol-4-yl)benzyl]-5,6,7,8-tetrahydro[1,7]naphthyridine-2-carboxamide (Isomer-II);

trans-N-(3-Hydroxytetrahydropyran-4-yl)-4-(4-fluorobenzyl)-5,6,7,8-tetrahydro[1,7]naphthyridine-2-carboxamide Hydrochloride (Isomer-II);

Racemic cis-N-(3-Hydroxytetrahydropyran-4-yl)-4-(4-fluorobenzyl)-5,6,7,8-tetrahydro[1,7]naphthyridine-2-carboxamide Hydrochloride;

cis-N-(3-Hydroxytetrahydropyran-4-yl)-4-(4-fluorobenzyl)-5,6,7,8-tetrahydro[1,7]naphthyridine-2-carboxamide Hydrochloride (Isomer-I);

cis-N-(3-Hydroxytetrahydropyran-4-yl)-4-(4-fluorobenzyl)-5,6,7,8-tetrahydro[1,7]naphthyridine-2-carboxamide Hydrochloride (Isomer-II);

Racemic trans-N-(3-Hydroxytetrahydropyran-4-yl)-4-(4-fluorobenzyl)-5,6,7,8-tetrahydro[1,7]naphthyridine-2-carboxamide Hydrochloride;

trans-N-(3-Hydroxytetrahydropyran-4-yl)-4-(4-fluorobenzyl)-5,6,7,8-tetrahydro[1,7]naphthyridine-2-carboxamide Hydrochloride (Isomer-I);

Racemic cis-N-(3-Hydroxytetrahydropyran-4-yl)-4-(4-fluorobenzyl)-5,6,7,8-tetrahydro[1,7]naphthyridine-2-carboxamide;

cis-N-(3-Hydroxytetrahydropyran-4-yl)-4-(4-fluorobenzyl)-5,6,7,8-tetrahydro[1,7]naphthyridine-2-carboxamide (Isomer-I);

cis-N-(3-Hydroxytetrahydropyran-4-yl)-4-(4-fluorobenzyl)-5,6,7,8-tetrahydro[1,7]naphthyridine-2-carboxamide (Isomer-II);

Racemic trans-N-(3-Hydroxytetrahydropyran-4-yl)-4-(4-fluorobenzyl)-5,6,7,8-tetrahydro[1,7]naphthyridine-2-carboxamide;

trans-N-(3-Hydroxytetrahydropyran-4-yl)-4-(4-fluorobenzyl)-5,6,7,8-tetrahydro[1,7]naphthyridine-2-carboxamide (Isomer-I);

trans-N-(3-Hydroxytetrahydropyran-4-yl)-4-(4-fluorobenzyl)-5,6,7,8-tetrahydro[1,7]naphthyridine-2-carboxamide (Isomer-II);

trans-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-II);

Racemic trans-N-(3-Hydroxytetrahydropyran-4-yl)-4-(4-pyrazol-1-ylbenzyl)-5,6,7,8-tetrahydro[1,7]naphthyridine-2-carboxamide Hydrochloride;

trans-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-I);

Racemic cis-N-(3-Hydroxytetrahydropyran-4-yl)-4-(4-pyrazol-1-ylbenzyl)-5,6,7,8-tetrahydro[1,7]naphthyridine-2-carboxamide Hydrochloride;

cis-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-I);

cis-N-(3-Hydroxytetrahydropyran-4-yl)-4-(4-pyrazol-1-ylbenzyl)-5,6,7,8-tetrahydro[1,7]naphthyridine-2-carboxamide Hydrochloride (Isomer-II);

Racemic trans-N-(3-Hydroxytetrahydropyran-4-yl)-4-(4-pyrazol-1-ylbenzyl)-5,6,7,8-tetrahydro[1,7]naphthyridine-2-carboxamide;

trans-N-(3-Hydroxytetrahydropyran-4-yl)-4-(4-pyrazol-1-ylbenzyl)-5,6,7,8-tetrahydro[1,7]naphthyridine-2-carboxamide (Isomer-I);

trans-N-(3-Hydroxytetrahydropyran-4-yl)-4-(4-pyrazol-1-ylbenzyl)-5,6,7,8-tetrahydro[1,7]naphthyridine-2-carboxamide (Isomer-II);

Racemic cis-N-(3-Hydroxytetrahydropyran-4-yl)-4-(4-pyrazol-1-ylbenzyl)-5,6,7,8-tetrahydro[1,7]naphthyridine-2-carboxamide;
cis-N-(3-Hydroxytetrahydropyran-4-yl)-4-(4-pyrazol-1-ylbenzyl)-5,6,7,8-tetrahydro[1,7]naphthyridine-2-carboxamide (Isomer-I);
cis-N-(3-Hydroxytetrahydropyran-4-yl)-4-(4-pyrazol-1-ylbenzyl)-5,6,7,8-tetrahydro[1,7]naphthyridine-2-carboxamide (Isomer-II);
cis-N-(4-Hydroxytetrahydropyran-3-yl)-4-(4-fluorobenzyl)-5,6,7,8-tetrahydro[1,7]naphthyridine-2-carboxamide Hydrochloride (Isomer-I);
cis-N-(4-Hydroxytetrahydropyran-3-yl)-4-(4-fluorobenzyl)-5,6,7,8-tetrahydro[1,7]naphthyridine-2-carboxamide Hydrochloride (Isomer-II);
Racemic cis-N-(4-Hydroxytetrahydropyran-3-yl)-4-(4-fluorobenzyl)-5,6,7,8-tetrahydro[1,7]naphthyridine-2-carboxamide Hydrochloride;
Racemic trans-N-(4-Hydroxytetrahydropyran-3-yl)-4-(4-fluorobenzyl)-5,6,7,8-tetrahydro[1,7]naphthyridine-2-carboxamide Hydrochloride;
trans-N-(4-Hydroxytetrahydropyran-3-yl)-4-(4-fluorobenzyl)-5,6,7,8-tetrahydro[1,7]naphthyridine-2-carboxamide Hydrochloride (Isomer-I);
trans-N-(4-Hydroxytetrahydropyran-3-yl)-4-(4-fluorobenzyl)-5,6,7,8-tetrahydro[1,7]naphthyridine-2-carboxamide Hydrochloride (Isomer-II);
Racemic cis-N-(4-Hydroxytetrahydropyran-3-yl)-4-(4-fluorobenzyl)-5,6,7,8-tetrahydro[1,7]naphthyridine-2-carboxamide;
cis-N-(4-Hydroxytetrahydropyran-3-yl)-4-(4-fluorobenzyl)-5,6,7,8-tetrahydro[1,7]naphthyridine-2-carboxamide (Isomer-I);
cis-N-(4-Hydroxytetrahydropyran-3-yl)-4-(4-fluorobenzyl)-5,6,7,8-tetrahydro[1,7]naphthyridine-2-carboxamide (Isomer-II);
Racemic trans-N-(4-Hydroxytetrahydropyran-3-yl)-4-(4-fluorobenzyl)-5,6,7,8-tetrahydro[1,7]naphthyridine-2-carboxamide;
trans-N-(4-Hydroxytetrahydropyran-3-yl)-4-(4-fluorobenzyl)-5,6,7,8-tetrahydro[1,7]naphthyridine-2-carboxamide (Isomer-I);
trans-N-(4-Hydroxytetrahydropyran-3-yl)-4-(4-fluorobenzyl)-5,6,7,8-tetrahydro[1,7]naphthyridine-2-carboxamide (Isomer-II);
Racemic cis-N-(4-Hydroxytetrahydropyran-3-yl)-4-(4-pyrazol-1-ylbenzyl)-5,6,7,8-tetrahydro[1,7]naphthyridine-2-carboxamide Hydrochloride;
cis-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-I);
cis-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-II);
Racemic trans-N-(4-Hydroxytetrahydropyran-3-yl)-4-(4-pyrazol-1-ylbenzyl)-5,6,7,8-tetrahydro[1,7]naphthyridine-2-carboxamide Hydrochloride;
trans-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-I);
trans-N-(4-Hydroxytetrahydropyran-3-yl)-4-(4-pyrazol-1-ylbenzyl)-5,6,7,8-tetrahydro[1,7]naphthyridine-2-carboxamide Hydrochloride (Isomer-II);
Racemic cis-N-(4-Hydroxytetrahydropyran-3-yl)-4-(4-pyrazol-1-ylbenzyl)-5,6,7,8-tetrahydro[1,7]naphthyridine-2-carboxamide;
cis-N-(4-Hydroxytetrahydropyran-3-yl)-4-(4-pyrazol-1-ylbenzyl)-5,6,7,8-tetrahydro[1,7]naphthyridine-2-carboxamide (Isomer-I);
cis-N-(4-Hydroxytetrahydropyran-3-yl)-4-(4-pyrazol-1-ylbenzyl)-5,6,7,8-tetrahydro[1,7]naphthyridine-2-carboxamide (Isomer-II);
Racemic trans-N-(4-Hydroxytetrahydropyran-3-yl)-4-(4-pyrazol-1-ylbenzyl)-5,6,7,8-tetrahydro[1,7]naphthyridine-2-carboxamide;
trans-N-(4-Hydroxytetrahydropyran-3-yl)-4-(4-pyrazol-1-ylbenzyl)-5,6,7,8-tetrahydro[1,7]naphthyridine-2-carboxamide (Isomer-I);
trans-N-(4-Hydroxytetrahydropyran-3-yl)-4-(4-pyrazol-1-ylbenzyl)-5,6,7,8-tetrahydro[1,7]naphthyridine-2-carboxamide (Isomer-II);
N-[(1S,2S)-2-Hydroxycyclohexyl]-8-(4-fluorobenzyl)-2,3-dihydro-[1,4]dioxino[2,3-b]pyridine-6-carboxamide;
N-[(1S,2S)-2-Hydroxycyclohexyl]-8-(4-methoxybenzyl)-2,3-dihydro-[1,4]dioxino[2,3-b]pyridine-6-carboxamide;
N-[(1S,2S)-2-Hydroxycyclohexyl]-8-(2-chloropyridin-5-ylmethyl)-2,3-dihydro-[1,4]dioxino[2,3-b]pyridine-6-carboxamide;
N-[(1S,2S)-2-Hydroxycyclohexyl]-8-[4-(1-methyl-1H-pyrazol-4-yl)-benzyl]-2,3-dihydro-[1,4]dioxino[2,3-b]pyridine-6-carboxamide;
N-[(1S,2S)-2-Hydroxycyclohexyl]-8-(2,3-difluorobenzyl)-2,3-dihydro-[1,4]dioxino[2,3-b]pyridine-6-carboxamide;
N-[(1S,2S)-2-Hydroxycyclohexyl]-8-(1-methyl-1H-pyrazol-4-ylmethyl)-2,3-dihydro-[1,4]dioxino[2,3-b]pyridine-6-carboxamide;
N-[(1S,2S)-2-Hydroxycyclohexyl]-8-[4-(pyrazol-1-yl)benzyl]-2,3-dihydro-[1,4]dioxino[2,3-b]pyridine-6-carboxamide;
N-[(1S,2S)-2-Hydroxycyclohexyl]-8-(2-methylpyridin-5-ylmethyl)-2,3-dihydro-[1,4]dioxino[2,3-b]pyridine-6-carboxamide;
N-[(1S,2S)-2-Hydroxycyclohexyl]-8-(2-fluoropyridin-5-ylmethyl)-2,3-dihydro-[1,4]dioxino[2,3-b]pyridine-6-carboxamide;
N-[(1S,2S)-2-Hydroxycyclohexyl]-8-(2-fluoropyridin-4-ylmethyl)-2,3-dihydro-[1,4]dioxino[2,3-b]pyridine-6-carboxamide;
trans-N-(3-Hydroxytetrahydropyran-4-yl)-8-(4-fluorobenzyl)-2,3-dihydro-[1,4]dioxino[2,3-b]pyridine-6-carboxamide (Isomer-II);
cis-N-(3-Hydroxytetrahydropyran-4-yl)-8-(4-fluorobenzyl)-2,3-dihydro-[1,4]dioxino[2,3-b]pyridine-6-carboxamide (Isomer-II);
Racemic cis-N-(3-Hydroxytetrahydropyran-4-yl)-8-(4-fluorobenzyl)-2,3-dihydro-[1,4]dioxino[2,3-b]pyridine-6-carboxamide;
cis-N-(3-Hydroxytetrahydropyran-4-yl)-8-(4-fluorobenzyl)-2,3-dihydro-[1,4]dioxino[2,3-b]pyridine-6-carboxamide (Isomer-I);
Racemic trans-N-(3-Hydroxytetrahydropyran-4-yl)-8-(4-fluorobenzyl)-2,3-dihydro-[1,4]dioxino[2,3-b]pyridine-6-carboxamide;
trans-N-(3-Hydroxytetrahydropyran-4-yl)-8-(4-fluorobenzyl)-2,3-dihydro-[1,4]dioxino[2,3-b]pyridine-6-carboxamide (Isomer-I);
(3S,4S)—N-(4-Hydroxytetrahydropyran-3-yl)-8-(4-methoxybenzyl)-2,3-dihydro-[1,4]dioxino[2,3-b]pyridine-6-carboxamide;

(3S,4S)—N-(4-Hydroxytetrahydropyran-3-yl)-8-(4-fluorobenzyl)-2,3-dihydro-[1,4]dioxino[2,3-b]pyridine-6-carboxamide;
(3S,4S)—N-(4-Hydroxytetrahydropyran-3-yl)-8-(2-chloropyridin-5-ylmethyl)-2,3-dihydro-[1,4]dioxino[2,3-b]pyridine-6-carboxamide;
(3S,4S)—N-(4-Hydroxytetrahydropyran-3-yl)-8-(2-methylpyridin-5-ylmethyl)-2,3-dihydro-[1,4]dioxino[2,3-b]pyridine-6-carboxamide;
Racemic cis-N-(4-Hydroxytetrahydropyran-3-yl)-8-(4-fluorobenzyl)-2,3-dihydro-[1,4]dioxino[2,3-b]pyridine-6-carboxamide;
Racemic cis-N-(4-Hydroxytetrahydropyran-3-yl)-8-(4-methoxybenzyl)-2,3-dihydro-[1,4]dioxino[2,3-b]pyridine-6-carboxamide;
N-[(1S,2S)-2-Hydroxycyclohexyl]-8-(4-fluorobenzyl)-4-methyl-2H-pyrido[3,2-b][1,4]oxazine-6-carboxamide;
N-[(1S,2S)-2-Hydroxycyclohexyl]-8-(3-fluorobenzyl)-4-methyl-2H-pyrido[3,2-b][1,4]oxazine-6-carboxamide;
N-[(1S,2S)-2-Hydroxycyclohexyl]-8-[4-(1-methyl-1H-pyrazol-4-yl)benzyl]-4-methyl-2H-pyrido[3,2-b][1,4]oxazine-6-carboxamide;
N-[(1S,2S)-2-Hydroxycyclohexyl]-8-(2-fluoropyridin-4-ylmethyl)-4-methyl-2H-pyrido[3,2-b][1,4]oxazine-6-carboxamide;
trans-N-(3-Hydroxytetrahydropyran-4-yl)-8-(4-fluorobenzyl)-4-methyl-2H-pyrido[3,2-b][1,4]oxazine-6-carboxamide (Isomer-II);
Racemic cis-N-(3-Hydroxytetrahydropyran-4-yl)-8-(4-fluorobenzyl)-4-methyl-2H-pyrido[3,2-b][1,4]oxazine-6-carboxamide;
cis-N-(3-Hydroxytetrahydropyran-4-yl)-8-(4-fluorobenzyl)-4-methyl-2H-pyrido[3,2-b][1,4]oxazine-6-carboxamide (Isomer-I);
Racemic trans-N-(3-Hydroxytetrahydropyran-4-yl)-8-(4-fluorobenzyl)-4-methyl-2H-pyrido[3,2-b][1,4]oxazine-6-carboxamide;
trans-N-(3-Hydroxytetrahydropyran-4-yl)-8-(4-fluorobenzyl)-4-methyl-2H-pyrido[3,2-b][1,4]oxazine-6-carboxamide (Isomer-I);
trans-N-(3-Hydroxytetrahydropyran-4-yl)-8-(4-fluorobenzyl)-4-methyl-2H-pyrido[3,2-b][1,4]oxazine-6-carboxamide (Isomer-II);
trans-N-(3-Hydroxytetrahydropyran-4-yl)-8-(4-methoxybenzyl)-4-methyl-2H-pyrido[3,2-b][1,4]oxazine-6-carboxamide (Isomer-II);
Racemic trans-N-(3-Hydroxytetrahydropyran-4-yl)-8-(4-methoxybenzyl)-4-methyl-2H-pyrido[3,2-b][1,4]oxazine-6-carboxamide;
trans-N-(3-Hydroxytetrahydropyran-4-yl)-8-(4-methoxybenzyl)-4-methyl-2H-pyrido[3,2-b][1,4]oxazine-6-carboxamide (Isomer-I);
Racemic cis-N-(3-Hydroxytetrahydropyran-4-yl)-8-(4-methoxybenzyl)-4-methyl-2H-pyrido[3,2-b][1,4]oxazine-6-carboxamide;
cis-N-(3-Hydroxytetrahydropyran-4-yl)-8-(4-methoxybenzyl)-4-methyl-2H-pyrido[3,2-b][1,4]oxazine-6-carboxamide (Isomer-I);
cis-N-(3-Hydroxytetrahydropyran-4-yl)-8-(4-methoxybenzyl)-4-methyl-2H-pyrido[3,2-b][1,4]oxazine-6-carboxamide (Isomer-II);
N-[(1S,2S)-2-Hydroxycyclohexyl]-8-(2-chloropyridin-5-ylmethyl)-4-methyl-2H-pyrido[3,2-b][1,4]oxazine-6-carboxamide;
N-[(1S,2S)-2-Hydroxycyclohexyl]-8-(4-methoxybenzyl)-4-methyl-2H-pyrido[3,2-b][1,4]oxazine-6-carboxamide;
N-[(1S,2S)-2-Hydroxycyclohexyl]-8-(2-methylpyridin-5-ylmethyl)-4-methyl-2H-pyrido[3,2-b][1,4]oxazine-6-carboxamide;
N-[(1S,2S)-2-Hydroxycyclohexyl]-8-[4-pyrazol-1-ylbenzyl]-4-methyl-2H-pyrido[3,2-b][1,4]oxazine-6-carboxamide;
N-[(1S,2S)-2-Hydroxycyclohexyl]-4-methyl-8-(1-methyl-1H-pyrazol-4-ylmethyl)-2H-pyrido[3,2-b][1,4]oxazine-6-carboxamide;
Racemic cis-N-(4-Hydroxytetrahydropyran-3-yl)-8-(4-fluorobenzyl)-4-methyl-2H-pyrido[3,2-b][1,4]oxazine-6-carboxamide;
Racemic cis-N-(4-Hydroxytetrahydropyran-3-yl)-8-(4-methoxybenzyl)-4-methyl-2H-pyrido[3,2-b][1,4]oxazine-6-carboxamide;
(3S,4S)—N-(4-Hydroxytetrahydropyran-3-yl)-8-(4-fluorobenzyl)-4-methyl-2H-pyrido[3,2-b][1,4]oxazine-6-carboxamide;
(3S,4S)—N-(4-Hydroxytetrahydropyran-3-yl)-8-(4-methoxybenzyl)-4-methyl-2H-pyrido[3,2-b][1,4]oxazine-6-carboxamide;
(3S,4S)—N-(4-Hydroxytetrahydropyran-3-yl)-8-(4-pyrazol-1-ylbenzyl)-4-methyl-2H-pyrido[3,2-b][1,4]oxazine-6-carboxamide; and
(3S,4S)—N-(4-Hydroxytetrahydropyran-3-yl)-4-methyl-8-(1-methyl-1H-pyrazol-4-ylmethyl)-2H-pyrido[3,2-b][1,4]oxazine-6-carboxamide;
or a pharmaceutically acceptable salt thereof.

5. A pharmaceutical composition comprising the compound of formula (I) or a pharmaceutically acceptable salt thereof as claimed in claim 1 and pharmaceutically acceptable excipients.

6. The pharmaceutical composition as claimed in claim 5, for the treatment of disease or disorder mediated by muscarinic M1 receptor, wherein said disease or disorder is selected from the group consisting of cognitive disorders, pain and sleep disorder.

7. A combination comprising the compound as claimed in claim 1, with one or more therapeutic agents selected from acetylcholinesterase inhibitors and NMDA receptor antagonist.

8. The combination as claimed in claim 7, wherein the therapeutic agents are selected from galantamine, rivastigmine, donepezil, tacrine and memantine.

9. A pharmaceutical composition comprising the compound of formula (I) or a pharmaceutically acceptable salt thereof as claimed in claim 4 and pharmaceutically acceptable excipients.

10. The pharmaceutical composition as claimed in claim 9, for the treatment of disease or disorder mediated by muscarinic M1 receptor, wherein said disease or disorder is selected from the group consisting of cognitive disorders, pain and sleep disorder.

11. A combination comprising the compound as claimed in claim 4, with one or more therapeutic agents selected from acetylcholinesterase inhibitors and NMDA receptor antagonist.

12. The combination as claimed in claim 11, wherein the therapeutic agents are selected from galantamine, rivastigmine, donepezil, tacrine and memantine.

13. A method of treatment of disease or disorder mediated by muscarinic M1 receptor, wherein the disease or disorder is selected from the group consisting of cognitive disorders, pain and sleep disorder comprising the step of administering to a patient in need thereof, a therapeutically effective amount of the compound of formula (I) or a pharmaceutically acceptable salt thereof as claimed in claim 1.

14. The method of treating disease or disorder as claimed in claim 13, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, and senile dementia.

15. A method of treatment of disease or disorder mediated by muscarinic M1 receptor, wherein the disease or disorder is selected from the group consisting of cognitive disorders, pain and sleep disorder comprising the step of administering to a patient in need thereof, a therapeutically effective amount of the compound of formula (I) or a pharmaceutically acceptable salt thereof as claimed in claim 4.

16. The method of treating disease or disorder as claimed in claim 15, wherein the cognitive disorder is selected from the group consisting of dementia in Alzheimer's disease, dementia in Parkinson's disease, dementia in Huntington's disease, dementia associated with Down syndrome, dementia associated with Tourette's syndrome, dementia associated with post menopause, frontotemporal dementia, Lewy body dementia, Vascular dementia, dementia in HIV, dementia in Creutzfeldt-Jakob disease, substance-induced persisting dementia, dementia in Pick's disease, dementia in schizophrenia, and senile dementia.

\* \* \* \* \*

UNITED STATES PATENT AND TRADEMARK OFFICE
CERTIFICATE OF CORRECTION

PATENT NO. : 11,040,026 B2
APPLICATION NO. : 16/327742
DATED : June 22, 2021
INVENTOR(S) : Ramakrishna Nirogi et al.

It is certified that error appears in the above-identified patent and that said Letters Patent is hereby corrected as shown below:

In the Specification

Column 9, Lines 27 and 41: The phase "Ra is" incorrectly appears above the four R1 groups. The phrase should be "Ra is OH;" and appear directly below the four R1 groups.
Column 11, Line 6: The phrase "R2 is" is missing above the first group of two ring structures on that page.
Column 12, Line 51: "pyrrolo" should be "pyrrol".
Column 15, Lines 39 and 42: "1-methyl-H-pyrrolo" should be "1-methyl-1H-pyrrolo".
Column 16, Line 16: A ";" is missing after "carboxamide" and "trans-N-...." should appear on a new line.
Column 36, Line 27: "difluoropyridine-7)" should be "difluoropyridine (I-7)".
Column 23, Scheme-1: The left most ring structure A is missing the definition "X is halogen".
Column 59, Example 10: The structure is incorrect, namely, the N in the lowest ring should be in the lower right corner of the ring, not the bottom corner.
Column 80, Example 35, Line 14: "1-methyl-H-pyrrolo" should be "1-methyl-1H-pyrrolo".
Column 99, Example 64, Line 4: "1-methyl-H-pyrrolo" should be "1-methyl-1H-pyrrolo".
Column 122, Line 45: "7-(tert-butoxycarbonyl)$_4$-(4,4,5,5-" should be "7-(tert-butoxycarbonyl)4-(4,4,5,5-".
Column 138, Example 113, Line 44: "Isomer-IT" should be "Isomer-II".
Column 139, Example 114: The structure is incorrect, namely, there is an extra N in the bottom most ring.
Column 149, Example 126: The structure is incorrect, namely, there is an N missing from the bottom most ring.

In the Claims

Claim 2, Column 169, Line 35: "-O-(C1-2)-O-alkyl" should be "-O-(C1-2)-alkyl".
Claim 4, Column 171, Lines 27, 42, 51, 57: "1-methyl-H-pyrrolo" should be "1-methyl-1H-pyrrolo".
Claim 4, Column 172, Lines 29, 33, 54: "1-methyl-H-pyrrolo" should be "1-methyl-1H-pyrrolo".
Claim 4, Column 174, Lines 33, 36, 57: "1-methyl-H-pyrrolo" should be "1-methyl-1H-pyrrolo".

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*

Claim 4, Column 175, Lines 18: "1-methyl-H-pyrrolo" should be "1-methyl-1H-pyrrolo".
Claim 4, Column 174, Lines 21, 30: "1-methyl-H-pyrazol" should be "1-methyl-1H- pyrazol".